United States Patent
Jakobi et al.

(10) Patent No.: US 8,298,994 B2
(45) Date of Patent: Oct. 30, 2012

(54) SUBSTITUTED 1-(DIAZINYL)PYRAZOL-4-YLACETIC ACIDS, PROCESSES FOR THEIR PREPARATION AND THEIR USE AS HERBICIDES AND PLANT GROWTH REGULATORS

(75) Inventors: Harald Jakobi, Frankfurt (DE); Arianna Martelletti, Sulzbach (DE); Joerg Tiebes, Frankfurt (DE); Jan Dittgen, Frankfurt (DE); Dieter Feucht, Eschborn (DE); Isolde Haeuser-Hahn, Leverkusen (DE); Heinz Kehne, Hofheim (DE); Christopher Hugh Rosinger, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 278 days.

(21) Appl. No.: 12/485,999

(22) Filed: Jun. 17, 2009

(65) Prior Publication Data
US 2010/0160164 A1 Jun. 24, 2010

(30) Foreign Application Priority Data

Jun. 17, 2008 (EP) .................................... 08010947

(51) Int. Cl.
- *A01N 43/54* (2006.01)
- *A01N 43/58* (2006.01)
- *A01N 43/60* (2006.01)
- *C07D 403/04* (2006.01)
- *A01P 13/00* (2006.01)

(52) U.S. Cl. ........ 504/237; 504/239; 544/238; 544/331; 544/405

(58) Field of Classification Search ........................ None
See application file for complete search history.

(56) References Cited

FOREIGN PATENT DOCUMENTS

| EP | 1 938 686 | 7/2008 |
| WO | WO 02/068413 | 9/2002 |
| WO | WO 2004/089931 | 10/2004 |
| WO | WO 2005/089551 | 9/2005 |
| WO | WO 2006/029867 | 3/2006 |

*Primary Examiner* — Kamal Saeed
(74) *Attorney, Agent, or Firm* — Frommer Lawrence & Haug LLP

(57) ABSTRACT

The invention relates to 1-(3-diazinyl)pyrazol-4-ylacetic acid derivatives of the general formula (I) and salts thereof

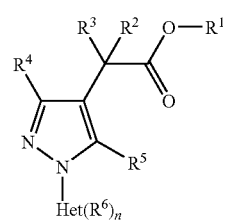

in which Het, $R^1$, $R^2$, $R^3$, $R^4$, $R^5$, $R^6$ and n are as defined in the specification. The compounds (I) and their salts are suitable as herbicides and plant growth regulators, in particular as herbicides for the selective control of harmful plants in crops of useful plants, and can be prepared by processes as described in the specification.

14 Claims, No Drawings

SUBSTITUTED 1-(DIAZINYL)PYRAZOL-4-YLACETIC ACIDS, PROCESSES FOR THEIR PREPARATION AND THEIR USE AS HERBICIDES AND PLANT GROWTH REGULATORS

Any foregoing applications, including EP 08010947.3, filed on 17 Jun. 2008, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

DESCRIPTION

The invention relates to the technical field of the herbicides and plant growth regulators, for example the herbicides for controlling broad-leaved weeds and weed grasses in crops of useful plants or the plant growth regulators which can be used for influencing the growth of crop plants.

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low or that they have a toxicologically unfavorable profile. Other active compounds which can be used as plant growth regulators for a number of useful plants cause unwanted reduced harvest yields in other useful plants or are not compatible with the crop plant, or only within a narrow application rate range. Other known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

Herbicidal 3-(hetero)aryl-4-[(hetero)arylcarbonyl]pyrazole compounds are known from EP-A-0822187 (U.S. Pat. No. 5,939,559) and the literature cited therein.

U.S. Pat. No. 4,146,721 discloses pyrazolylacetic acids as analgesics, antipyretics and antiinflammatory agents; however, a use as pesticides, in particular herbicides, has not been described.

U.S. Pat. No. 4,095,025 describes 1,3-diarylpyrazole-4-acrylic acids and derivatives thereof for pharmaceutical (for example anti inflammatory) purposes.

WO 2004/089931 (US 2006-264419) describes substituted pyrazoles having optionally substituted phenyl or pyrid-3-yl radicals at the nitrogen atom in position 1 of the pyrazole for the treatment and prophylaxis of diseases modulated by binding of the compounds to 5 HT receptors.

For the reasons mentioned, there is still a need for alternative, highly active herbicides for the selective application in plant crops and use on non-crop land. It is also desirable to prepare alternative chemically active compounds which, if appropriate, can be used advantageously as herbicides or plant growth regulators.

The present invention provides compounds of the formula (I) or salts thereof

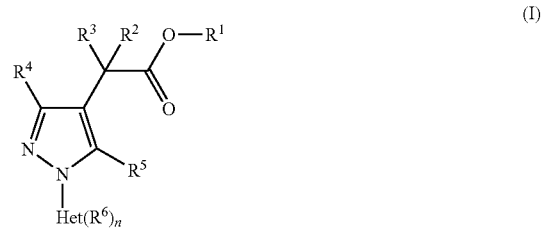

in which

Het is a six-membered heteroaromatic radical having two heteroatoms as ring atoms, where the heteroatoms in the ring are nitrogen atoms and at least one nitrogen atom in the ring is located in the 1,3-position to the ring carbon atom which is attached to the pyrazole radical, $R^1$ is hydrogen or a hydrolyzable radical, preferably hydrogen or an optionally substituted hydrocarbon radical or an optionally substituted heterocyclyl radical, where each of the two last-mentioned carbon-containing radicals has, including substituents, 1 to 30 carbon atoms, preferably 1 to 24 carbon atoms, in particular 1 to 20 carbon atoms, or a radical of the formula $SiR^a R^b R^c$, $-NR^a R^b$ or $-N=CR^c R^d$, where in the 3 last-mentioned formulae each of the radicals $R^a$, $R^b$, $R^c$ and $R^d$ independently of the others is hydrogen or an optionally substituted hydrocarbon radical or $R^a$ and $R^b$ together with the nitrogen atom are a 3- to 9-membered heterocycle which, in addition to the nitrogen atom, may contain one or two further ring heteroatoms selected from the group consisting of N, O and S and which is unsubstituted or substituted, or $R^c$ and $R^d$ together with the carbon atom are a 3- to 9-membered carbocyclic radical or a heterocyclic radical which may contain 1 to 3 ring heteroatoms selected from the group consisting of N, O and S, where the carbocyclic or heterocyclic radical is unsubstituted or substituted, where each of the radicals $R^a$, $R^b$, $R^c$ and $R^d$ including substituents has up to 30 carbon atoms, preferably up to 24 carbon atoms, in particular up to 20 carbon atoms, $R^2$ is hydrogen, halogen or $(C_1-C_6)$-alkyl which is unsubstituted or substituted by one or more radicals selected from the group consisting of halogen, $(C_1-C_4)$-alkoxy, $(C_1-C_4)$-alkylthio and $(C_1-C_4)$-haloalkoxy, $R^3$ is hydrogen, halogen or $(C_1-C_6)$-alkyl which is unsubstituted or substituted by one or more radicals selected from the group consisting of halogen, $(C_1-C_4)$-alkoxy, $(C_1-C_4)$-alkylthio and $(C_1-C_4)$-haloalkoxy, or $R^2$ and $R^3$ together with the carbon atom to which they are attached are a carbocyclic saturated or partially unsaturated ring having 3 to 6 carbon atoms which is unsubstituted or substituted by one or more radicals selected from the group consisting of halogen and $(C_1-C_4)$-alkyl, and $R^4$ is hydrogen, halogen, cyano, $(C_1-C_6)$-alkyl, $(C_2-C_6)$-alkenyl or $(C_2-C_6)$-alkynyl, where each of the three last-mentioned radicals is unsubstituted or substituted by one or more radicals selected from the group consisting of halogen, cyano, hydroxyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_9)$-cycloalkyl, or preferably unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_9)$-cycloalkyl, or $(C_3-C_9)$-cycloalkyl, $(C_5-C_9)$-cycloalkenyl or $(C_5-C_9)$-cycloalkynyl, where each of the 3 last-mentioned radicals is unsubstituted or substituted by one or more radicals selected from the group consisting of halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy and $(C_1-C_4)$-alkylthio, or phenyl which is unsubstituted or substituted by one or more radicals selected from the group consisting of halogen, cyano, nitro, carboxy, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_1-C_4)$-alkanoyl, $(C_1-C_4)$-haloalkanoyl, [$(C_1-C_4)$-alkoxy]carbonyl and [$(C_1-C_4)$-haloalkoxy]carbonyl, or $(C_1-C_6)$-alkanoyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_6)$-cycloalkyl, or

[$(C_1-C_4)$-alkoxy]carbonyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl- or $(C_1-C_4)$-haloalkyl-substituted $(C_3-C_6)$-cycloalkyl, or

[$(C_3-C_9)$-cycloalkoxy]carbonyl which is unsubstituted or substituted by one or more radicals selected from the group consisting of halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy and $(C_1-C_4)$-alkylthio, $R^5$ is an aryl radical which is unsubstituted or substituted and, including substituents, has 6 to 30 carbon atoms, preferably 6 to 24 carbon atoms, in particular 6 to 20 carbon atoms, or a heteroaromatic radical having 1 to 4 ring heteroatoms selected from the group consisting of N, O and S which is unsubstituted or substituted and, including substituents, has 1 to 30 carbon atoms, preferably 1 to 24 carbon atoms, in particular 1 to 20 carbon atoms, and $(R^6)_n$ are n substituents $R^6$, where $R^6$, in the case that n=1, or each of the substituents $R^6$ independently of the others, in the case that n is greater than 1, is a radical halogen, hydroxyl, amino, nitro, carboxy, cyano, carbamoyl, $(C_1-C_6)$-alkyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- or di-[$(C_1-C_4)$-alkyl]aminoalkyl, hydroxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $(C_1-C_6)$-haloalkylthio, [$(C_1-C_6)$-alkoxy]carbonyl, [$(C_1-C_6)$-haloalkoxy]carbonyl, $(C_1-C_6)$-alkanoyl, $(C_1-C_6)$-haloalkanoyl, mono- or di-[$(C_1-C_4)$-alkyl]aminocarbonyl, mono- or di-[$(C_1-C_6)$-acyl]amino, mono- or di-[$(C_1-C_6)$-alkyl]amino, N—[$(C_1-C_6)$-acyl]-N—[$(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_3-C_9)$-cycloalkyl or $(C_5-C_9)$-cycloalkenyl, where each of the two last-mentioned radicals is unsubstituted or substituted by one or more radicals selected from the group consisting of halogen, $(C_1-C_4)$-alkyl and $(C_1-C_4)$-haloalkyl, and n is 0, 1, 2 or 3.

By addition of a suitable inorganic or organic acid, such as, for example, HCl, HBr, $H_2SO_4$ or $HNO_3$, but also oxalic acid or sulfonic acids, onto a basic group, such as, for example, amino or alkylamino, the compounds of the formula (I) may form salts. Suitable substituents present in deprotonated form, such as, for example, sulfonic acids or carboxylic acids, may form inner salts with groups which for their part can be protonated, such as amino groups. Salts may also be formed by replacing the hydrogen of suitable substituents, such as, for example, sulfonic acids or carboxylic acids, by an agriculturally suitable cation. These salts are, for example, metal salts, in particular alkali metal salts or alkaline earth metal salts, especially sodium salts and potassium salts, or else ammonium salts, salts with organic amines or quaternary ammonium salts.

In the formula (I) and all subsequent formulae, terms for chemical radicals are used which have in particular the meanings illustrated below.

A hydrolyzable radical (see definition of $R^1$) is a radical which can be hydrolyzed under application conditions, for example a radical which can be hydrolyzed even in the spray liquor or in particular under the physiological conditions in plants, where a compound of the formula (I) having the carboxylic ester group —CO—$OR^1$ ($R^1$ is not hydrogen) is hydrolyzed to the compound of the formula (I) having the carboxylic acid group —CO—OH (i.e. the compound (I) where $R^1$=H). Expressly, the definition of the hydrolyzable radicals also includes radicals where $R^1$=hydrocarbon radical or heterocyclyl radical, the two last-mentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, for example "$(C_1-C_6)$-alkyl", correspondingly also include straight-chain or branched alkyl radicals having a larger number of carbon atoms, i.e., according to the example, also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in combined radicals. Alkyl radicals, including in the combined definitions such as alkoxy, haloalkyl, etc., are, for example, methyl, ethyl, n- or isopropyl, n-, iso-, t- or 2-butyl, pentyls, hexyls such as n-hexyl, isohexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methyl-prop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl(1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl.

$(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not yet being fixed. In the case of a branched alkane, of course, only positions at which two hydrogen atoms may be replaced by the double bond are possible; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are, respectively, alkyl, alkenyl and alkynyl substituted partly or fully by identical or different halogen atoms, preferably from the group of fluorine, chlorine and bromine, in particular from the group of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluoroenyl and the like, preferably phenyl.

Optionally substituted aryl also includes polycyclic systems such as tetrahydronaphthyl, indenyl, indanyl, fluorenyl, biphenylyl, where the point of attachment is at the aromatic system.

A heterocyclic radical (heterocyclyl) contains at least one heterocyclic ring (=carbocyclic ring in which at least one carbon atom is replaced by a heteroatom, preferably by a heteroatom from the group consisting of N, O, S, P, B, Si, Se) which is saturated, unsaturated or heteroaromatic and which may be unsubstituted or substituted, where the point of attachment is located at a ring atom.

Unless defined otherwise, it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical can, for example, be a heteroaromatic radical or ring (heteroaryl), such as, for example, a mono-, bi- or polycyclic aromatic system in which at least 1 ring contains one or more heteroatoms.

If the heterocyclyl radical or the heterocyclic ring is optionally substituted, it may be fused to other carbocyclic or heterocyclic rings. Preference is given to benzo-fused heterocyclic or heteroaromatic rings.

Optionally substituted heterocyclyl also includes polycyclic systems, such as, for example, 8-azabicyclo[3.2.1]octanyl or 1-azabicyclo[2.2.1]heptyl.

Optionally substituted heterocyclyl also includes spirocyclic systems, such as, for example, 1-oxa-5-aza-spiro[2.3]hexyl.

Preferred is a radical of a heteroaromatic ring having a heteroatom from the group consisting of N, O and S, for example the radical of a five- or six-membered ring, such as pyridyl, pyrrolyl, thienyl or furyl;

preference is furthermore given to a radical of a corresponding heteroaromatic ring having 2, 3 or 4 heteroatoms, for example pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl;

more preference is also given to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;

more preference is also given to heteroaromatic radicals of five-membered heterocycles having 2 nitrogen atoms and 1 oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, more preference is also given to heteroaromatic radicals of five-membered heterocycles having two nitrogen atoms and one sulfur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl;

more preference is also given to heteroaromatic radicals of five-membered heterocycles having four nitrogen atoms, such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl;

more preference is also given to heteroaromatic radicals of six-membered heterocycles, such as 1,2,4,5-tetrazin-3-yl;

more preference is also given to heteroaromatic radicals of five-membered heterocycles having three nitrogen atoms and one oxygen or sulfur atom, such as 1,2,3,4-oxatriazol-5-yl; 1,2,3,5-oxatriazol-4-yl; 1,2,3,4-thiatriazol-5-yl; 1,2,3,5-thiatriazol-4-yl;

more preference is also given to heteroaromatic radicals of six-membered heterocycles, such as, for example, 1,2,4,6-thiatriazin-1-yl; 1,2,4,6-thiatriazin-3-yl; 1,2,4,6-thiatriazin-5-yl.

Preference is furthermore given to the heterocyclic radical or ring of a partially or fully hydrogenated heterocyclic radical having a heteroatom from the group consisting of N, O and S, for example oxiranyl, oxetanyl, oxolanyl (=tetrahydrofuryl), oxanyl, pyrrolinyl, pyrrolidyl or piperidyl.

Preference is furthermore also given to a partially or fully hydrogenated heterocyclic radical having 2 heteroatoms selected from the group consisting of N, O and S, for example piperazinyl, dioxolanyl, oxazolinyl, isoxazolinyl, oxazolidinyl, isoxazolidinyl and morpholinyl. Suitable substituents for a substituted heterocyclic radical are furthermore the substituents mentioned further below, and additionally also oxo. The oxo group can also be present at the ring heteroatoms which may exist in various oxidation states, for example at N and S.

Preferred examples of heterocyclyl are a heterocyclic radical having 3 to 6 ring atoms from the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, in particular oxiranyl, 2-oxetanyl, 3-oxetanyl or oxolanyl, or a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals also include benzo-condensed or benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl(isoquinolinyl), cinnolinyl, phthalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl, and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals selected from the group of halogen, alkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated aliphatic and aromatic radicals, such as optionally substituted alkenyl, alkynyl, alkenyloxy, alkynyloxy, phenyl, phenoxy, etc. In the case of substituted cylic radicals having aliphatic moieties in the ring, cyclic systems with those substituents which are bonded on the ring by a double bond are also included, for example substituted by an alkylidene group such as methylidene or ethylidene.

The substituents mentioned by way of example ("first substituent level") may, when they contain hydrocarbon moieties; optionally be further substituted there ("second substituent level"), for example by one of the substituents as defined for the first substituent level. Corresponding further substituent levels are possible. The term "substituted radical" preferably includes only one or two substituent levels.

"Base radical" refers to the respective base structure of a radical to which substituents of a substituent level are attached.

Preferred substituents for the substituent levels are, for example, amino, hydroxyl, halogen, nitro, cyano, mercapto, carboxy, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino. It is also possible for two substituents together to form a saturated or unsaturated hydrocarbon bridge or a corresponding bridge in which carbon atoms, CH groups or $CH_2$ groups are replaced by heteroatoms, thus forming a condensed or fused-on cycle. Preference is given here to benzo-fused systems on the basis of the base structure.

Optionally substituted phenyl is preferably phenyl or phenyl which is unsubstituted or substituted by one or more radicals selected from the group consisting of halogen, cyano, $(C_1-C_4)$-alkyl, $(C_1-C_4)$-haloalkyl, $(C_1-C_4)$-alkoxy-$(C_1-C_4)$-alkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and nitro, in particular phenyl which is optionally substituted by one or more radicals selected from the group consisting of halogen, $(C_1-C_4)$-alkyl, $(C_1-C_4)$-haloalkyl and $(C_1-C_4)$-alkoxy.

In the case of radicals with carbon atoms, preference is given to those having from 1 to 6 carbon atoms, preferably from 1 to 4 carbon atoms, in particular 1 or 2 carbon atoms. In general, preferred substituents are those from the group of halogen, e.g. fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given to the substituents methyl, methoxy, fluorine and chlorine.

Substituted amino, such as mono- or disubstituted amino, is a radical from the group of the substituted amino radicals which are N-substituted, for example, by one or two identical or different radicals selected from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1-C_4)$-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids. Acyl is, for example, formyl, alkylcarbonyl such as [$(C_1-C_4)$-alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may each be substituted further in the alkyl or phenyl moiety, for example in the alkyl moiety by one or more radicals selected from the group of halogen, alkoxy, phenyl and phenoxy; examples of substituents in the phenyl moiety are the substituents already mentioned above in general for substituted phenyl. Acyl is preferably an acyl radical in the narrower sense, i.e. a radical of an organic acid in which the acid group is bonded directly to the carbon atom of an organic radical, for example formyl, alkylcarbonyl such as acetyl or [$(C_1-C_4)$-alkyl]carbonyl, phenylcarbonyl, alkylsulfonyl, alkylsulfinyl and other radicals of organic acids. More preferably, acyl is an alkanoyl radical having 1 to 6 carbon atoms, in particular 1 to 4 carbon atoms. Here, $(C_1-C_4)$-alkanoyl is the radical of an alkanoic acid having 1 to 4 carbon atoms after removal of the OH group of the acid group, i.e. formyl, acetyl, n-propionyl, isopropionyl or n-, iso-, sec- or tert-butanoyl.

The "yl position" of a radical denotes the carbon atom having the free bond. Compounds of the formula (I) according to the invention and compounds of the formula (I) used according to the invention (and, if appropriate, salts thereof) are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated specifically in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The invention also provides all the tautomers of the compounds of the formula (I) which can be formed be shifting a hydrogen atom (for example keto/enol tautomers). The tautomers are also included in the compound of the formula (I), even if formally the formula (I) describes only one of the tautomers in the equilibrium or only one of the interconvertible tautomers correctly.

The compounds of the formula (I) also include all physical forms in which these may be present as the pure substance or optionally as a mixture with other compounds, in particular also polymorphic crystalline forms of the compounds of the formula (I) or their salts or solvates (for example hydrates).

For reasons of higher herbicidal action, better selectivity and/or better preparability in particular, inventive compounds of the formula (I) mentioned or salts thereof and their use according to the invention where individual radicals have one of the preferred definitions already mentioned or mentioned hereinafter, or especially those in which one or more of the preferred definitions already mentioned or mentioned hereinafter occur in combination are of particular interest.

Irrespective of the other radicals selected from the group of $R^1$, $R^2$, $R^3$, $R^4$, $R^5$ and $(R^6)_n$ in each case and the subdefinitions corresponding to the general radicals, and preferably in combination with preferred definitions of one or more of these radicals, inventive compounds or inventive uses of compounds of particular interest are those with the preferred definitions of the radicals in question listed below.

Preference is given to the compounds of the formula (I) according to the invention or salts thereof in which
$R^1$ is hydrogen, alkyl, alkenyl, alkynyl, cycloalkyl, cycloalkenyl, cycloalkynyl or aryl, where each of the 7 last-mentioned radicals is unsubstituted or substituted and, including substituents, has up to 30 carbon atoms, preferably up to 24 carbon atoms, in particular up to 20 carbon atoms, or a heterocyclyl radical having 3 to 9 ring atoms which contains 1 to 4 heteroatoms selected from the group consisting of N, O and S, which is unsubstituted or substituted and which, including substituents, has 1 to 30 carbon atoms, preferably 1 to 24 carbon atoms, in particular 1 to 20 carbon atoms.

Here, more preference is also given to compounds (I) or salts thereof in which
$R^1$ is hydrogen.

Here, more preference is also given to compounds (I) or salts thereof in which
$R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl or phenyl, where each of the 7 last-mentioned radicals is unsubstituted or substituted and, including substituents, has up to 30 carbon atoms, preferably up to 24 carbon atoms, in particular up to 20 carbon atoms.

Here, more preference is also given to compounds (I) or salts thereof in which
$R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl or phenyl,
where each of the 7 last-mentioned radicals is unsubstituted or substituted by one or more radicals selected from the group consisting of
halogen, cyano, thio, nitro, hydroxyl, also carboxy, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $(C_2-C_8)$-haloalkynyl, the 7 last-mentioned radicals only in the case of cyclic base radicals, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio, radicals of the formulae —NR*R**, —CO—NR*R** and —O—CO—NR*R**,
where each of the radicals R* and R** in the 3 last-mentioned formulae independently of the others is H, $(C_1-C_8)$-alkyl, $(C_2-C_8)$-alkenyl, $(C_2-C_8)$-alkynyl, benzyl, substituted benzyl, phenyl or substituted phenyl, or together with the nitrogen atom is a 3- to 8-membered heterocycle which, in addition to the nitrogen atom, may contain one or two further ring heteroatoms selected from the group consisting of N, O and S and which is unsubstituted or substituted by one or more radicals selected from the group consisting of $(C_1-C_4)$-alkyl and $(C_1-C_4)$-haloalkyl, and [$(C_1-C_8)$-alkoxy]carbonyl, [$(C_1-C_8)$-alkoxy]thiocarbonyl, [$(C_2-C_8)$-alkenyloxy]carbonyl, [$(C_2-C_8)$-alkynyloxy]carbonyl, [$(C_1-C_8)$-alkylthio]carbonyl, [$(C_2-C_8)$-alkenylthio]carbonyl, [$(C_2-C_8)$-alkynylthio]carbonyl, $(C_1-C_8)$-alkanoyl, [$(C_2-C_8)$-alkenyl]carbonyl, [$(C_2-C_8)$-alkynyl]carbonyl, $(C_1-C_4)$-alkylimino, $(C_1-C_4)$-alkoxyimino, [$(C_1-C_8)$-alkyl]carbonylamino, [$(C_2-C_8)$-alkenyl]carbonylamino, [$(C_2-C_8)$-alkynyl]carbonylamino, [$(C_1-C_8)$-alkoxy]carbonylamino, [$(C_2-C_8)$-alkenyloxy]carbonylamino, [$(C_2-C_8)$-alkynyloxy]carbonylamino, [$(C_1-C_8)$-alkylamino]carbonylamino, [$(C_1-C_6)$-alkyl]carbonyloxy, [$(C_2-C_6)$-alkenyl]carbonyloxy, [$(C_2-C_6)$-alkynyl]carbonyloxy, [$(C_1-C_8)$-alkoxy]carbonyloxy, [$(C_2-C_8)$-alkenyloxy]carbonyloxy, [$(C_2-C_8)$-alkynyloxy]carbonyloxy, $(C_1-C_8)$-alkylsulfinyl and $(C_1-C_8)$-alkylsulfonyl, where each of the 27 last-mentioned radicals is unsubstituted or substituted by one or more radicals selected from the group consisting of halogen, $NO_2$, $(C_1-C_4)$-alkoxy and optionally substituted phenyl, and phenyl, phenyl-$(C_1-C_6)$-alkoxy, phenyl-[$(C_1-C_6)$-alkoxy]carbonyl, phenoxy, phenoxy-$(C_1-C_6)$-alkoxy, phenoxy-[$(C_1-C_6)$-alkoxy]carbonyl, phenoxycarbonyl, phenylcarbonyloxy, also phenoxycarbonyloxy, phenylcarbonylamino, phenyl-[$(C_1-C_6)$-alkyl]carbonylamino, phenyl-[$(C_1-C_6)$-alkyl]carbonyloxy, also phenyl-[$(C_1-C_6)$-alkoxy]carbonyloxy, $(C_3-C_7)$-cycloalkyl, $(C_3-C_7)$-cycloalkoxy, also $(C_3-C_6)$-cycloalkyl-$(C_1-C_6)$-alkoxy, also $(C_3-C_6)$-cycloalkyl-[$(C_1-C_6)$-alkoxy]carbonyl, also $(C_3-C_6)$-cycloalkoxy-$(C_1-C_6)$-alkoxy, also $(C_3-C_6)$-cycloalkoxy-[$(C_1-C_6)$-alkoxy]carbonyl, also $(C_3-C_6)$-cycloalkoxycarbonyl, also $(C_3-C_6)$-cycloalkylcarbonyloxy, also $(C_3-C_6)$-cycloalkoxycarbonyloxy, also $(C_3-C_6)$-cycloalkyl-[$(C_1-C_6)$-alkoxy]carbonyloxy, also $(C_3-C_6)$-cycloalkylcarbonylamino, also $(C_3-C_6)$-cycloalkyl-[$(C_1-C_6)$-alkyl]carbonylamino and also $(C_3-C_6)$-cycloalkyl-[$(C_1-C_6)$-alkyl]carbonyloxy, where each of the 26 last-mentioned radicals is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms selected from the group consisting of N, O and S, preferably benzo-fused, and is, in the ring or in the polycyclic system, unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae —$SiR'_3$, —O—$SiR'_3$, $(R')_3$Si—$(C_1-C_6)$-alkoxy, —CO—O—$NR'_2$, —O—N=$CR'_2$, —N=$CR'_2$, —O—$NR'_2$, —CH$(OR')_2$ and —O—$(CH_2)_m$—CH$(OR')_2$, in which each of the radicals R' independently of the others is H, $(C_1-C_4)$-alkyl or phenyl which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro or substituted in two adjacent positions by a $(C_2-C_6)$-alkylene bridge, and m is an integer of from 0 to 6, and radicals of the formula R"O—CHR'''CH(OR")—$(C_1-C_6)$-alkoxy, in which each of the radicals R" independently of the others is H or $(C_1-C_4)$-alkyl or the radicals R" together are a $(C_1-C_6)$-alkylene group and R''' is H or $(C_1-C_4)$-alkyl, and also radicals of the formula $Het^1$, where $Het^1$ is in each case independently of the others a saturated, partially unsaturated or heteroaromatic heterocyclyl radical having 3 to 9 ring atoms, preferably having 5 or 6 ring atoms, where the heterocyclic radical in question contains 1 to 4 heteroatoms, preferably 1 to 3 ring heteroatoms, from the group consisting of N, O and S and is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms selected from the group consisting of N, O and S, preferably benzo-fused, and is, in the ring or in the polycyclic system, unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo, or $R^1$ is a polycyclic radical based on $(C_3-C_9)$-cycloalkyl, $(C_5-C_9)$-cycloalkenyl, $(C_5-C_9)$-cycloalkynyl or phenyl, where the base ring is fused to a carbocyclic or heterocyclic ring, preferably a 5- or 6-membered ring having 0 or 1 to 3 ring heteroatoms selected from the group consisting of N, O and S, preferably benzo-fused, and where the base ring or the polycyclic system is unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo, or $R^1$ is a saturated, partially unsaturated or heteroaromatic heterocyclyl radical having 3 to 9 ring atoms, preferably having 5 or 6 ring atoms, which contains 1 to 4 heteroatoms, preferably 1 to 3 ring heteroatoms selected from the group consisting of N, O and S, and is optionally also fused to a carbocyclic or heterocyclic ring, preferably a 5- or 6-membered ring having 0 or 1 to 3 ring heteroatoms selected from the group consisting of N, O and S, preferably benzo-fused, and which is, in the ring or in the polycyclic system, unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo.

Here, more preference is also given to compounds (I) or salts thereof in which $R^1$ is H, $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl or phenyl, where each of the 7 last-mentioned radicals is unsubstituted or substituted by one or more radicals selected from the group consisting of halogen, cyano, thio, nitro, hydroxyl, also carboxy, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $(C_2-C_8)$-haloalkynyl, the 7 last-mentioned radicals only in the case of cyclic base radicals, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, $(C_2-C_8)$-alkynylthio, radicals of the formulae —NR*R**, —CO—NR*R** and —O—CO—NR*R**, where each of the radicals R* and R** in the 3 last-mentioned formulae independently of the others is H, $(C_1-C_8)$-alkyl, $(C_2-C_8)$-alkenyl, $(C_2-C_8)$-alkynyl, benzyl, substituted benzyl, phenyl or substituted phenyl, or together with the nitrogen atom is a 3- to 8-membered heterocycle which, in addition to the nitrogen atom, may contain one or two further ring heteroatoms selected from the group consisting of N, O and S and which is unsubstituted or substituted by one or more radicals selected from the group consisting of $(C_1-C_4)$-alkyl and $(C_1-C_4)$-haloalkyl, and $[(C_1-C_8)$-alkoxy]carbonyl, $[(C_1-C_8)$-alkoxy]thiocarbonyl, $[(C_2-C_8)$-alkenyloxy]carbonyl, $[(C_2-C_8)$-alkynyloxy]carbonyl, $[(C_1-C_8)$-alkylthio]carbonyl, $[(C_2-C_8)$-alkenylthio]carbonyl, $[(C_2-C_8)$-alkynylthio]carbonyl, $(C_1-C_8)$-alkanoyl, $[(C_2-C_8)$-alkenyl]carbonyl, $[(C_2-C_8)$-alkynyl]carbonyl, $(C_1-C_4)$-alkylimino, $(C_1-C_4)$-alkoxyimino, $[(C_1-C_8)$-alkyl]carbonylamino, $[(C_2-C_8)$-alkenyl]carbonylamino, $[(C_2-C_8)$-alkynyl]carbonylamino, $[(C_1-C_8)$-alkoxy]carbonylamino, $[(C_2-C_8)$-alkenyloxy]carbonylamino, $[(C_2-C_8)$-alkynyloxy]carbonylamino, $[(C_1-C_8)$-alkylamino]carbonylamino, $[(C_1-C_6)$-alkyl]carbonyloxy, $[(C_2-C_6)$-alkenyl]carbonyloxy, $[(C_2-C_6)$-alkynyl]carbonyloxy, $[(C_1-C_8)$-alkoxy]carbonyloxy, $[(C_2-C_8)$-alkenyloxy]carbonyloxy, $[(C_2-C_8)$-alkynyloxy]carbonyloxy, $(C_1-C_8)$-alkylsulfinyl and $(C_1-C_8)$-alkylsulfonyl, where each of the 27 last-mentioned radicals is unsubstituted or substituted by one or more radicals selected from the group consisting of halogen, $NO_2$, $(C_1-C_4)$-alkoxy and optionally substituted phenyl, and phenyl, phenyl-$(C_1-C_6)$-alkoxy, phenyl-$[(C_1-C_6)$-alkoxy]carbonyl, phenoxy, phenoxy-$(C_1-C_6)$-alkoxy, phenoxy-$[(C_1-C_6)$-alkoxy]carbonyl, phenoxycarbonyl, phenylcarbonyloxy, also phenoxycarbonyloxy, also phenyl-$[(C_1-C_6)$-alkoxy]carbonyloxy, phenylcarbonylamino, phenyl-$[(C_1-C_6)$-alkyl]carbonylamino, phenyl-$[(C_1-C_6)$-alkyl]carbonyloxy, $(C_3-C_7)$-cycloalkyl and $(C_3-C_7)$-cycloalkoxy, also $(C_3-C_6)$-cycloalkoxycarbonyl, also $(C_3-C_6)$-cycloalkylcarbonyloxy, also $(C_3-C_6)$-cycloalkoxycarbonyloxy, also $(C_3-C_6)$-cycloalkyl-$[(C_1-C_6)$-alkyl]carbonyloxy and also $(C_3-C_6)$-cycloalkyl-$[(C_1-C_6)$-alkoxy]carbonyloxy, where each of the 20 last-mentioned radicals is, in the ring, unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae —SiR'$_3$, —O—SiR'$_3$, (R')$_3$Si—$(C_1-C_6)$-alkoxy, —CO—O—NR'$_2$, —O—N=CR'$_2$, —N=CR'$_2$, —O—NR'$_2$, —CH(OR')$_2$ and —O—$(CH_2)_m$—CH(OR')$_2$, in which each of the radicals R' independently of the others is H, $(C_1-C_4)$-alkyl or phenyl which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro or substituted at two adjacent positions by a $(C_2-C_6)$-alkylene bridge, and m is an integer from 0 to 6, and radicals of the formula R"O—CHR'"CH(OR")—$(C_1-C_6)$-alkoxy, in which each of the radicals R" independently of the others is H or $(C_1-C_4)$-alkyl or together they are a $(C_1-C_6)$-alkylene group and R'" is H or $(C_1-C_4)$-alkyl, and also radicals of the formula Het$^1$, where Het$^1$ is in each case independently of the others a saturated, partially unsaturated or heteroaromatic heterocyclyl radical having 5 or 6 ring atoms, where the respective heterocyclic radical contains 1 to 3 ring heteroatoms selected from the group consisting of N, O and S and is optionally also fused to a carbocyclic or heterocyclic ring, preferably a 5- or 6-membered ring having 0 or 1 to 3 ring heteroatoms selected from the group consisting of N, O and S, preferably benzo-fused, and, in the ring or in the polycyclic system, is unsubstituted or substituted by one or more radicals selected from the group consisting of halogen, hydroxyl, $(C_1-C_4)$-alkyl, $(C_1-C_4)$-alkoxy, $(C_1-C_4)$-haloalkyl and $(C_1-C_4)$-haloalkoxy.

Here, more preference is also given to compounds (I) or salts thereof and their use in which $R^1$ is H, $(C_1-C_{12})$-alkyl, $(C_2-C_{12})$-alkenyl, $(C_2-C_{12})$-alkynyl, $(C_3-C_6)$-cycloalkyl, $(C_5-C_6)$-cycloalkenyl, $(C_5-C_6)$-cycloalkynyl or phenyl, where each of the 7 last-mentioned radicals is unsubstituted or substituted by one or more radicals selected from the group consisting of halogen, cyano, thio, nitro, hydroxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, the 7 last-mentioned radicals only in the case of cyclic base radicals, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, radicals of the formulae —NR*R**, —CO—NR*R** and —O—CO—NR*R**, where each of the radicals R* and R** in the 3 last-mentioned formulae independently of the others is H, $(C_1-C_4)$-alkyl, $(C_2-C_4)$-alkenyl, $(C_2-C_4)$-alkynyl, benzyl, phenyl which is unsubstituted or substituted by one or more radicals selected from the group consisting of halogen, $(C_1-C_4)$-alkyl, $(C_1-C_4)$-haloalkyl and $(C_1-C_4)$-alkoxy, or together with the nitrogen atom is a piperidine, piperazine, pyrrolidine, pyrazolidine, piperazolidine or morpholine radical which is unsubstituted or substituted by one or more radicals selected from the group consisting of $(C_1-C_4)$-alkyl and $(C_1-C_4)$-haloalkyl, and $[(C_1-C_4)$-alkoxy]carbonyl, $[(C_1-C_4)$-alkyl]carbonylamino, $[(C_1-C_4)$-alkoxy]carbonylamino, $[(C_1-C_4$-alkylamino]carbonylamino, $[(C_1-C_4)$-alkyl]carbonyloxy, $[(C_1-C_4)$-alkoxy]carbonyloxy and $(C_1-C_4)$-alkylsulfonyl, where each of the 7 last-mentioned radicals is unsubstituted or substituted by one or more radicals selected from the group consisting of halogen, $NO_2$, $(C_1-C_4)$-alkoxy and phenyl, which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and phenyl, phenyl-$(C_1-C_4)$-alkoxy, phenyl-[$(C_1-C_4)$-alkoxy]carbonyl, phenoxy, phenoxy-$(C_1-C_4)$-alkoxy, phenoxy-[$(C_1-C_4)$-alkoxy]carbonyl, phenoxycarbonyl, phenylcarbonyloxy, phenylcarbonylamino, phenyl-[$(C_1-C_4)$-alkyl]carbonylamino, phenyl-[$(C_1-C_4)$-alkyl]carbonyloxy, $(C_3-C_6)$-cycloalkyl and $(C_3-C_6)$-cycloalkoxy, where each of the 13 last-mentioned radicals is unsubstituted in the ring or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and radicals of the formulae —CO—O—NR'$_2$, —O—N=CR'$_2$, —N=CR'$_2$, —O—NR'$_2$, —CH(OR')$_2$ and —O—(CH$_2$)$_m$—CH(OR')$_2$, in which each of the radicals R' independently of the others is H, $(C_1-C_4)$-alkyl or phenyl which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro or is substituted in two adjacent positions by a $(C_2-C_6)$-alkylene bridge, and m is an integer of from 0 to 6, and radicals of the formula R"O—CHR'"CH(OR")—$(C_1-C_6)$-alkoxy, in which each of the radicals R" independently of the others is H or $(C_1-C_4)$-alkyl or the radicals R" together are a $(C_1-C_4)$-alkylene group and R'" is H or $(C_1-C_2)$-alkyl.

Here, more preference is also given to compounds (I) or salts thereof in which $R^1$ is H, $(C_1-C_6)$-alkyl, $(C_2-C_6)$-alkenyl, $(C_2-C_6)$-alkynyl or $(C_3-C_6)$-cycloalkyl, where each of the 4 last-mentioned radicals is unsubstituted or substituted by one or more radicals selected from the group consisting of halogen, $(C_1-C_6)$-alkyl, the latter only a substituent in the case of cyclic base radicals, $(C_1-C_4)$-alkoxy, $(C_1-C_4)$-alkylthio, $(C_3-C_6)$-cycloalkyl which is unsubstituted or substituted by one or more radicals selected from the group consisting of halogen and $(C_1-C_4)$-alkyl, and phenyl which is unsubstituted or substituted by one or more radicals selected from the group consisting of halogen, $(C_1-C_4)$-alkyl, $(C_1-C_4)$-alkoxy and $(C_1-C_4)$-haloalkyl.

Here, particular preference is also given to compounds (I) or salts thereof in which $R^1$ is H, $(C_1-C_4)$-alkyl, $(C_2-C_4)$-alkenyl or $(C_2-C_4)$-alkynyl, where each of the 3 last-mentioned radicals is unsubstituted or substituted by one or more radicals selected from the group consisting of halogen, $(C_1-C_4)$-alkoxy, $(C_1-C_4)$-alkylthio, cyclopropyl, cyclobutyl, where each of the two last-mentioned radicals is unsubstituted or substituted by one or more radicals selected from the group consisting of halogen and $(C_1-C_4)$-alkyl, and phenyl which is unsubstituted or substituted by one or more radicals selected from the group consisting of halogen, $(C_1-C_4)$-alkyl, $(C_1-C_4)$-alkoxy and $(C_1-C_4)$-haloalkyl.

Here, more preferably $R^1$ is also a polycyclic radical based on $(C_3-C_9)$-cycloalkyl, $(C_5-C_9)$-cycloalkenyl, $(C_5-C_9)$-cycloalkynyl or phenyl, where the base ring is fused to a carbocyclic or heterocyclic ring, preferably a 5- or 6-membered ring having 0 or 1 to 3 ring heteroatoms selected from the group consisting of N, O and S, preferably benzo-fused, and where the base ring or the polycyclic system is unsubstituted or substituted by one or more radicals selected from the group consisting of halogen, cyano, nitro, $(C_1-C_6)$-alkyl, $(C_1-C_6)$-haloalkyl, $(C_1-C_4)$-alkoxy-$(C_1-C_4)$-alkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_3-C_6)$-cycloalkyl, $(C_3-C_6)$-cycloalkoxy, [$(C_1-C_4)$-alkoxy]carbonyl and [$(C_1-C_4)$-haloalkoxy]carbonyl.

Preference is also given to compounds (I) or salts thereof in which $R^1$ is a saturated, partially unsaturated or heteroaromatic heterocyclyl radical having 3 to 9 ring atoms, preferably 5 or 6 ring atoms, which contains 1 to 4 heteroatoms, preferably 1 to 3 ring heteroatoms, from the group consisting of N, O and S and which is unsubstituted or substituted by one or more radicals selected from the group consisting of halogen, cyano, thio, nitro, hydroxyl, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl and oxo.

Preference is also given to compounds (I) or salts thereof in which $R^1$ is a radical of the formula SiR$^a$R$^b$R$^c$, —NR$^a$R$^b$ or —N=CR$^c$R$^d$, preferably of the formula —NR$^a$R$^b$ or —N=CR$^c$R$^d$, where in the 5 last-mentioned formulae each of the radicals R$^a$, R$^b$, R$^c$ and R$^d$ independently of the others is hydrogen, $(C_1-C_4)$-alkyl, $(C_2-C_4)$-alkenyl, $(C_2-C_4)$-alkynyl, benzyl, substituted benzyl, phenyl or substituted phenyl or R$^a$ and R$^b$ together with the nitrogen atom are a 3- to 8-membered heterocycle which, in addition to the nitrogen atom, may contain one or two further ring heteroatoms selected from the group consisting of N, O and S and which is unsubstituted or substituted by one or more radicals selected from the group consisting of $(C_1-C_4)$-alkyl and $(C_1-C_4)$-haloalkyl, or R$^c$ and R$^d$ together with the carbon atom are a 3- to 8-membered carbocyclic radical or heterocyclic radical which may contain 1 to 3 ring heteroatoms selected from the group consisting of N, O and S, where the carbocyclic or heterocyclic radical is unsubstituted or substituted by one or more radicals selected from the group consisting of $(C_1-C_4)$-alkyl and $(C_1-C_4)$-haloalkyl.

Here, particular preference is also given to compounds (I) or salts thereof in which $R^1$ is H, methyl, ethyl, n-propyl, iso-propyl, n-butyl, s-butyl, isobutyl, t-butyl, allyl, propargyl (prop-2-yn-1-yl), but-2-yn-1-yl, but-3-yn-1-yl, 2-chloroprop-2-en-1-yl, 3-phenyl-prop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, phenyl, 2-carboxyphenyl, 2-chlorophenyl, 3-chlorophenyl, 4-chlorophenyl, 2-fluorophenyl, 3-fluorophenyl, 4-fluorophenyl, 3-methoxyphenyl, 4-methoxyphenyl, 2-methoxyphenyl, 3-methoxyphenyl, 4-methoxyphenyl, benzyl, 2-phenylethyl, 1-phenylethyl, (4-chlorophenyl)methyl [i.e. =CH$_2$(4-Cl-Ph)], (4-fluorophenyl)methyl [i.e. =CH$_2$(4-F-Ph)], (4-methoxyphenyl)

methyl [i.e. =CH₂(4-OMe-Ph)], 2-methoxyethyl, 2,2,2-trifluoroethyl, 1,1,1-trifluoroprop-2-yl, 2,2-difluoroethyl, 1,3-difluoroprop-2-yl, 2,3-dimethoxypropyl, 2,3-dimethoxyprop-2-yl, 2,2-dimethoxyeth-2-yl, 2-(2,2,2-trifluoroethoxy)ethyl, 2-fluoroethyl, 2-chloroethyl, 2-bromoethyl, 2-iodoethyl, 2,2,3,3,3-pentafluoropropyl, 1-hydroxyprop-2-yl, 2-hydroxyprop-2-yl, 2-hydroxyprop-1-yl, 3-hydroxypropyl, 3-hydroxyprop-2-yl, (2-methoxyethoxy)methyl; 2-(2-methoxyethoxy)ethyl; (2-ethoxyethoxy)methyl; 2-(2-ethoxyethoxy)ethyl, (acetoxy)methyl, (propanoyloxy)methyl, (2-methylpropanoyloxy)methyl, (2,2-dimethylpropanoyloxy)methyl, 1-(acetoxy)ethyl, 2-(acetoxy)ethyl, 2-(propanoyloxy)ethyl, 1-(propanoyloxy)ethyl, 1-(2-methylpropanoyloxy)eth-1-yl, 2-(2-methylpropanoyloxy)eth-1-yl, 2-(2,2-dimethylpropanoyloxy)ethyl [i.e. 1-(t-butylcarbonyloxy)ethyl], 2-(2,2-dimethylpropanoyloxy)ethyl;

1-(2,2-dimethylpropanoyloxy)-2-methylprop-1-yl, 1-(t-butylcarbonyloxy)-2-methylprop-1-yl, (methoxycarbonyl)methyl, (ethoxycarbonyl)methyl, (n-propoxycarbonyl)methyl, (isopropoxycarbonyl)methyl, (n-butoxycarbonyl)methyl, (s-butoxycarbonyl)methyl, (isobutoxycarbonyl)methyl, (t-butoxycarbonyl)methyl, 1-(methoxycarbonyl)ethyl, 2-(methoxycarbonyl)ethyl, 1-(ethoxycarbonyl)ethyl, 2-(ethoxycarbonyl)ethyl, 1-(n-propoxycarbonyl)ethyl, 2-(n-propoxycarbonyl)ethyl, 1-(isopropoxycarbonyl)ethyl, 2-(isopropoxycarbonyl)ethyl, 1-(n-butoxycarbonyl)ethyl, 2-(n-butoxycarbonyl)ethyl, 1-(s-butoxycarbonyl)ethyl, 2-(s-butoxycarbonyl)ethyl, 1-(isobutoxycarbonyl)ethyl, 2-(isobutoxycarbonyl)ethyl, 1-(t-butoxycarbonyl)ethyl, 2-(t-butoxycarbonyl)ethyl, (methoxycarbonyloxy)methyl, (ethoxycarbonyloxy)methyl, (n-propoxycarbonyloxy)methyl, (isopropoxycarbonyloxy)methyl, (n-butoxycarbonyloxy)methyl, (s-butoxycarbonyloxy)methyl, (isobutoxycarbonyloxy)methyl, (t-butoxycarbonyloxy)methyl, 1-(methoxycarbonyloxy)ethyl, 2-(methoxycarbonyloxy)ethyl, 1-(ethoxycarbonyloxy)ethyl, 2-(ethoxycarbonyloxy)ethyl, 1-(n-propoxycarbonyloxy)ethyl, 2-(n-propoxycarbonyloxy)ethyl, 1-(isopropoxycarbonyloxy)ethyl, 2-(isopropoxycarbonyloxy)ethyl, 1-(n-butoxycarbonyloxy)ethyl, 2-(n-butoxycarbonyloxy)ethyl, 1-(s-butoxycarbonyloxy)ethyl, 2-(s-butoxycarbonyloxy)ethyl, 1-(isobutoxycarbonyloxy)ethyl, 2-(isobutoxycarbonyloxy)ethyl, 1-(t-butoxycarbonyloxy)ethyl, 2-(t-butoxycarbonyloxy)ethyl, (cyclohexoxycarbonyloxy)methyl, 1-(cyclohexoxycarbonyloxy)eth-1-yl, 2-(cyclohexoxycarbonyloxy)eth-1-yl, (acetyl)methyl, 1-(acetyl)ethyl, 2-(acetyl)ethyl, 1-(acetyl)propyl, 2-(acetyl)-propyl, 3-(acetyl)propyl, (propanoyl)methyl, 1-(propanoyl)ethyl, 2-(propanoyl)ethyl, 1-(propanoyl)propyl, 2-(propanoyl)propyl, 3-(propanoyl)-propyl, 1-(propanoyl)-2-methylpropyl, 2-(ethylideneaminooxy)ethyl, 2-(prop-2-ylideneaminooxy)ethyl, 2-(but-2-ylideneaminooxy)ethyl, 2-(pent-3-ylideneaminooxy)ethyl, (N,N-dimethylamino)methyl, 2-(N,N-dimethylamino)eth-1-yl, 1-(N,N-dimethylamino)eth-1-yl, 2-(N,N-diethylamino)eth-1-yl, 1-(N,N-diethylamino)eth-1-yl, (N,N-diethylamino)methyl, (N,N-dimethylaminocarbonyl)methyl, 1-(N,N-dimethylaminocarbonyl)ethyl, 2-(N,N-dimethylaminocarbonyl)ethyl, (N,N-diethylaminocarbonyl)methyl, 1-(N,N-diethylaminocarbonyl)ethyl, 2-(N,N-diethylaminocarbonyl)ethyl, 1-(dimethylamino)prop-2-yl [i.e. 2-(dimethylamino)-1-methylethyl], 1-(diethylamino)prop-2-yl, trimethylsilylmethyl, 1-(trimethylsilyl)ethyl, 2-(trimethylsilyl)ethyl, triethylsilylmethyl, 1-(triethylsilyl)ethyl, 2-(triethylsilyl)ethyl, cyclopropyl, cyclopropylmethyl, 1-cyclopropylethyl, 2-cyclopropylethyl, (1-methylcyclopropyl)methyl, 1-(1-methylcyclopropyl)ethyl, 2-(1-methylcyclopropyl)ethyl, (2,2-dichlorocyclopropyl)methyl, 1-(2,2-dichlorocyclopropyl)ethyl, 2-(2,2-dichlorocyclopropyl)ethyl, (2,2-dimethylcyclopropyl)methyl, 1-(2,2-dimethylcyclopropyl)ethyl, 2-(2,2-dimethylcyclopropyl)ethyl, cyclobutylmethyl, cyclopentylmethyl, cyclohexylmethyl or pyrid-2-yl, pyrid-3-yl, pyrid-4-yl, 2-chloropyrid-3-yl, 3-chloropyrid-2-yl, thien-2-yl, thien-3-yl, 2-chlorothien-3-yl, 3-chlorothien-2-yl, 4-chlorothien-2-yl, (1-ethyl-5-methyl-1H-pyrazol-4-yl)methyl, 1-(1-ethyl-5-methyl-1H-pyrazol-4-yl)ethyl, 2-(1-ethyl-5-methyl-1H-pyrazol-4-yl)ethyl (1-ethyl-3-methyl-1H-pyrazol-4-yl)methyl, 1-(1-ethyl-3-methyl-1H-pyrazol-4-yl)ethyl, 2-(1-ethyl-3-methyl-1H-pyrazol-4-yl)ethyl, tetrahydrofuran-2-yl, tetrahydrofuran-3-yl, tetrahydrofuran-2-ylmethyl, tetrahydrofuran-3-ylmethyl, (5-methyl-2-oxo-1,3-dioxol-4-yl)methyl;

oxetan-3-yl, (oxetan-3-yl)methyl, (oxetan-2-yl)methyl, (1,3-dioxolan-2-yl)methyl, (1,3-dioxolan-4-yl)methyl, 5-methyl-2-oxo-1,3-dioxolan-4-yl)methyl, (morpholin-4-yl)methyl; 1-(morpholin-4-yl)ethyl, 2-(morpholin-4-yl)ethyl, 2,3-dihydro-1H-inden-2-yl, dihydro-1H-inden-3-yl, dihydro-1H-inden-4-yl, dihydro-1H-inden-5-yl, 1H-inden-2-yl, 1H-inden-3-yl, 1H-inden-4-yl, 1H-inden-5-yl, 1H-inden-6-yl or 1H-inden-7-yl.

Here, very particular preference is also given to compounds (I) or salts thereof in which $R^1$ is H, methyl, ethyl, n-propyl, isopropyl, phenyl, benzyl, (4-chlorophenyl)methyl [i.e. =CH₂(4-Cl-Ph)], (4-fluorophenyl)methyl [i.e. =CH₂(4-F-Ph)], (4-methoxyphenyl)methyl [i.e. =CH₂(4-OMe-Ph)], 2-methoxyethyl, tetrahydrofuran-2-ylmethyl, 2-(dimethylamino)methyl, oxetan-3-yl, (3-methyloxetan-3-yl)methyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, allyl, propargyl (prop-2-yn-1-yl), 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or (1-ethyl-5-methyl-1H-pyrazol-4-yl)methyl.

Preference is also given to compounds of the formula (I) or salts thereof in which $R^2$ is hydrogen, halogen or $(C_1-C_4)$-alkyl which is unsubstituted or substituted by one or more radicals selected from the group consisting of halogen, such as fluorine or chlorine, preferably hydrogen or $(C_1-C_4)$-alkyl, in particular hydrogen, methyl or ethyl, very particularly hydrogen or methyl.

Preference is also given to the compounds of the formula (I) or salts thereof in which
$R^3$ is hydrogen, halogen or $(C_1-C_4)$-alkyl which is unsubstituted or substituted by one or more radicals selected from the group consisting of halogen, such as fluorine or chlorine, preferably hydrogen or $(C_1-C_4)$-alkyl, in particular hydrogen or methyl, very particularly hydrogen.

Preference is also given to the compounds of the formula (I) or salts thereof in which $R^2$ and $R^3$ together with the carbon atom to which they are attached are $(C_3-C_6)$-cycloalkyl or $(C_5-C_6)$-cycloalkenyl, preferably $(C_3-C_6)$-cycloalkyl, where each of the 3 last-mentioned radicals is unsubstituted or substituted by one or more radicals selected from the group consisting of halogen and $(C_1-C_4)$-alkyl.

Here, preferably, $R^2$ and $R^3$ together with the carbon atom to which they are attached are cyclopropyl, cyclobutyl, cyclopentyl or cyclohexyl, in particular cyclopropyl, where each of the 4 last-mentioned radicals is unsubstituted or substituted by one or more radicals selected from the group consisting of halogen and methyl, preferably fluorine, chlorine and methyl.

Preference is also given to the use of compounds of the formula (I) or salts thereof in which
$R^4$ is hydrogen, halogen, cyano, $(C_1-C_4)$-alkyl, $(C_2-C_4)$-alkenyl or $(C_2-C_4)$-alkynyl,
  where each of the three last-mentioned radicals is unsubstituted or substituted by one or more radicals selected from the group consisting of halogen and hydroxyl, preferably unsubstituted or substituted by one or more radicals selected from the group consisting of halogen, such as fluorine and chlorine, or
  $(C_3-C_6)$-cycloalkyl which is unsubstituted or substituted by one or more radicals selected from the group consisting of halogen and $(C_1-C_4)$-alkyl, or
  phenyl which is unsubstituted or substituted by one or more radicals selected from the group consisting of halogen, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $[(C_1-C_4)$-alkoxy]carbonyl and $[(C_1-C_4)$-haloalkoxy]carbonyl, or
  $(C_1-C_4)$-alkanoyl which is unsubstituted or substituted by one or more radicals selected from the group consisting of halogen, such as fluorine and chlorine, cyano, $(C_1-C_4)$-alkoxy, $(C_1-C_4)$-haloalkoxy and $(C_1-C_2)$-alkoxy-$(C_1-C_2)$-alkoxy, preferably formyl, or
  $[(C_1-C_4)$-alkoxy]carbonyl which is unsubstituted or substituted by one or more radicals selected from the group consisting of halogen, such as fluorine and chlorine, or
  $[(C_3-C_6)$-cycloalkoxy]carbonyl which is unsubstituted or substituted by one or more radicals selected from the group consisting of halogen and $(C_1-C_4)$-alkyl.

More preference is also given to compounds of the formula (I) or salts thereof in which
$R^4$ is hydrogen, halogen, such as fluorine or chlorine, cyano, $(C_1-C_4)$-alkyl which is optionally substituted by hydroxyl [=$(C_1-C_4)$-hydroxyalkyl], $(C_1-C_4)$-haloalkyl, cyclopropyl or cyclobutyl, where each of the two last-mentioned radicals is unsubstituted or substituted by one or more radicals selected from the group consisting of halogen, such as fluorine and chlorine, and $(C_1-C_4)$-alkyl, or
  phenyl which is unsubstituted or substituted by one or more radicals selected from the group consisting of halogen, $(C_1-C_4)$-alkyl, $(C_1-C_4)$-haloalkyl, $(C_1-C_4)$-alkoxy and $(C_1-C_4)$-alkylthio, or
  $(C_1-C_4)$-alkanoyl which is unsubstituted or substituted by one or more radicals selected from the group consisting of halogen, such as fluorine and chlorine, preferably formyl, or
  $[(C_1-C_4)$-alkoxy]carbonyl or $[(C_1-C_4)$-haloalkoxy]carbonyl,
preferably
$R^4$ is hydrogen, halogen, such as fluorine or chlorine, cyano, methyl, ethyl, n-propyl, isopropyl, $CH_2Cl$, $CHCl_2$, $CCl_3$, $CH_2F$, $CHF_2$, $CF_3$ or formyl.

Here, more preference is given to the abovementioned preferred or particularly preferred compounds (I) or salts thereof in which $R^4$ is cyano or in which $R^4$ has one of the other meanings mentioned, other than cyano or formyl.

More preferably, $R^4$ is one of the radicals mentioned for $R^4$ and is different from hydrogen.

More preferably, $R^4$ is hydrogen.

Preference is also given to compounds of the formula (I) or salts thereof in which
$R^5$ is phenyl which is unsubstituted or substituted and, including substituents, has 6 to 24 carbon atoms, in particular 6 to 20 carbon atoms, or
  a 5- or 6-membered heteroaromatic radical having 1 to 3 ring heteroatoms selected from the group consisting of N, O and S which is unsubstituted or substituted and, including substituents, has 1 to 24 carbon atoms, in particular 1 to 20 carbon atoms.

Furthermore preferably,
$R^5$ is a phenyl radical or a 5- or 6-membered heteroaromatic radical having 1 to 3 ring heteroatoms selected from the group consisting of N, O and S, where the phenyl radical or the heterocyclic radical is unsubstituted or substituted by one or more radicals selected from the group consisting of the radicals
(a) halogen, hydroxyl, amino, nitro, carboxy, cyano and carbamoyl,
(b) $(C_1-C_6)$-alkyl, $(C_2-C_6)$-alkenyl, $(C_2-C_6)$-alkynyl, $(C_1-C_6)$-alkoxy, $(C_1-C_6)$-alkenyloxy and $(C_1-C_6)$-alkynyloxy, where each of the 6 last-mentioned radicals is unsubstituted or substituted by one or more radicals selected from the group consisting of halogen, $(C_1-C_4)$-alkoxy, $(C_1-C_6)$-haloalkoxy, $(C_1-C_4)$-alkylthio, mono- and di-$[(C_1-C_4)$-alkyl]amino, hydroxyl, carboxy, $[(C_1-C_4)$-alkoxy]carbonyl, $[(C_1-C_4)$-haloalkoxy]carbonyl, mono- and di-$[(C_1-C_4)$-alkyl]aminocarbonyl and cyano,
(c) $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkylsulfinyloxy, $(C_1-C_6)$-haloalkylsulfinyloxy, $(C_1-C_6)$-alkylsulfonyloxy, $(C_1-C_6)$-haloalkylsulfonyloxy, $(C_1-C_6)$-alkylsulfato, $(C_1-C_6)$-haloalkylsulfato and
(d) $(C_3-C_6)$-cycloalkyl, $(C_3-C_6)$-cycloalkyloxy, phenyl and phenoxy,
  where each of the 4 last-mentioned radicals is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio,
and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio.

Furthermore preferably,

R⁵ is phenyl,
which is unsubstituted or substituted by one or more radicals selected from the group consisting of the radicals
(a) halogen, hydroxyl, amino, nitro, carboxy, cyano and carbamoyl,
(b) $(C_1-C_6)$-alkyl, $(C_2-C_6)$-alkenyl, $(C_2-C_6)$-alkynyl and $(C_1-C_6)$-alkoxy, where each of the 4 last-mentioned radicals is unsubstituted or substituted by one or more radicals selected from the group consisting of halogen, $(C_1-C_4)$-alkoxy, $(C_1-C_6)$-haloalkoxy, $(C_1-C_4)$-alkylthio, hydroxyl, carboxy, $[(C_1-C_4)$-alkoxy]carbonyl and cyano,
(c) $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkylsulfinyloxy, $(C_1-C_6)$-alkylsulfonyloxy and $(C_1-C_6)$-haloalkylsulfonyloxy and
(d) $(C_3-C_6)$-cycloalkyl, $(C_3-C_6)$-cycloalkyloxy, phenyl and phenoxy, where each of the 4 last-mentioned radicals is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio,
and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio, or R⁵ is a 5- or 6-membered heteroaromatic radical having 1 to 3 ring heteroatoms selected from the group consisting of N, O and S which is unsubstituted or substituted by one or more radicals selected from the group consisting of the radicals
(a) halogen, hydroxyl, amino, nitro, carboxy, cyano and carbamoyl,
(b) $(C_1-C_6)$-alkyl, $(C_2-C_6)$-alkenyl, $(C_2-C_6)$-alkynyl and $(C_1-C_6)$-alkoxy, where each of the 6 last-mentioned radicals is unsubstituted or substituted by one or more radicals selected from the group consisting of halogen, $(C_1-C_4)$-alkoxy, $(C_1-C_6)$-haloalkoxy, $(C_1-C_4)$-alkylthio, mono- and di-$[(C_1-C_4)$-alkyl]amino, hydroxyl, carboxy, $[(C_1-C_4)$-alkoxy]carbonyl and cyano,
(c) $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, $(C_1-C_6)$-alkylsulfinyloxy, $(C_1-C_6)$-alkylsulfonyloxy and $(C_1-C_6)$-haloalkylsulfonyloxy and
(d) $(C_3-C_6)$-cycloalkyl, $(C_3-C_6)$-cycloalkyloxy, phenyl and phenoxy, where each of the 4 last-mentioned radicals is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio,
and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen, $(C_1-C_4)$-alkyl, $(C_1-C_4)$-haloalkyl, $(C_1-C_4)$-alkoxy, $(C_1-C_6)$-haloalkoxy and $(C_1-C_4)$-alkylthio.

More preference is given to using compounds of the formula (I) or salts thereof in which R⁵ is phenyl
which is unsubstituted or preferably substituted by one or more radicals selected from the group consisting of halogen, hydroxyl, amino, nitro, carboxy, cyano, carbamoyl, $(C_1-C_6)$-alkyl, also $(C_2-C_4)$-alkenyl, also $(C_2-C_4)$-alkynyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- and di-$[(C_1-C_4)$-alkyl]amino-$(C_1-C_4)$-alkyl, hydroxy-$(C_1-C_4)$-alkyl, carboxy-$(C_1-C_4)$-alkyl, cyano-$(C_1-C_4)$-alkyl, $(C_1-C_6)$-alkoxy, which may optionally also be halogenated [=$(C_1-C_6)$-haloalkoxy], $(C_1-C_4)$-alkoxy-$(C_1-C_4)$-alkoxy, $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, also $(C_1-C_4)$-alkylsulfonyloxy, $(C_3-C_6)$cycloalkyl, $(C_3-C_6)$cycloalkyloxy, phenyl and phenoxy,
where each of the 4 last-mentioned radicals is unsubstituted or substituted by one or more radicals selected from the group consisting of halogen, $(C_1-C_4)$-alkyl and $(C_1-C_4)$-haloalkyl,
and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen and $(C_1-C_6)$-alkyl, or R⁵ is a 5- or 6-membered heteroaromatic radical having 1 to 3 ring heteroatoms selected from the group consisting of N, O and S
which is unsubstituted or substituted by one or more radicals selected from the group consisting of halogen, hydroxyl, amino, nitro, carboxy, cyano, carbamoyl, $(C_1-C_6)$-alkyl, also $(C_2-C_4)$-alkenyl, also $(C_2-C_4)$-alkynyl, $(C_1-C_6)$-haloalkyl, $(C_1-C_4)$-alkoxy-$(C_1-C_4)$-alkyl, $(C_1-C_4)$-alkylthio-$(C_1-C_4)$-alkyl, mono- and di-$[(C_1-C_4)$-alkyl]amino-$(C_1-C_4)$-alkyl, hydroxy-$(C_1-C_4)$-alkyl, carboxy-$(C_1-C_4)$-alkyl, cyano-$(C_1-C_4)$-alkyl, $(C_1-C_6)$-alkoxy, which may optionally also be halogenated [=$(C_1-C_6)$-haloalkoxy], $(C_1-C_4)$-alkoxy-$(C_1-C_4)$-alkoxy, $(C_1-C_6)$-alkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- and di-$[(C_1-C_4)$-alkyl]aminocarbonyl, mono- and di-$[(C_1-C_6)$-acyl]amino, mono- and di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, $(C_1-C_6)$-haloalkylsulfonyl, also $(C_1-C_4)$-alkylsulfonyloxy, $(C_3-C_6)$cycloalkyl, $(C_3-C_6)$cycloalkyloxy, phenyl and phenoxy, where each of the 4 last-mentioned radicals is unsubstituted or substituted by one or more radicals selected from the group consisting of halogen, $(C_1-C_4)$-alkyl and $(C_1-C_4)$-haloalkyl, and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen and $(C_1-C_6)$-alkyl.

Here, more preference is also given to the compounds of the formula (I) or salts thereof in which $R^5$ is phenyl which is unsubstituted or preferably substituted by one or more radicals selected from the group consisting of halogen, hydroxyl, nitro, carboxy, cyano, $(C_1-C_4)$-haloalkyl, $(C_1-C_4)$-alkoxy-$(C_1-C_4)$-alkyl, $(C_1-C_4)$-alkylthio-$(C_1-C_4)$-alkyl, hydroxy-$(C_1-C_4)$-alkyl, $(C_1-C_4)$-alkoxy, which may optionally also be halogenated [=$(C_1-C_4)$-haloalkoxy], $(C_1-C_4)$-alkoxy-$(C_1-C_4)$-alkoxy, $(C_1-C_4)$-alkylthio, [$(C_1-C_4)$-alkoxy]carbonyl, [$(C_1-C_6)$-haloalkoxy]carbonyl, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, $(C_3-C_6)$cycloalkyl, $(C_3-C_6)$cycloalkyloxy, phenyl and phenoxy, where each of the 4 last-mentioned radicals is unsubstituted or substituted by one or more radicals selected from the group consisting of halogen, $(C_1-C_4)$-alkyl and $(C_1-C_4)$-haloalkyl, and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen and $(C_1-C_4)$-alkyl, or $R^5$ is a 5- or 6-membered heteroaromatic radical having 1 to 3 ring heteroatoms selected from the group consisting of N, O and S which is unsubstituted or substituted by one or more radicals selected from the group consisting of halogen, hydroxyl, carboxy, cyano, also amino, $(C_1-C_4)$-alkyl, also $(C_2-C_4)$-alkenyl, also $(C_2-C_4)$-alkynyl, $(C_1-C_4)$-haloalkyl, $(C_1-C_4)$-alkoxy-$(C_1-C_4)$-alkyl, $(C_1-C_4)$-alkylthio-$(C_1-C_4)$-alkyl, hydroxy-$(C_1-C_4)$-alkyl, $(C_1-C_4)$-alkoxy, which may optionally also be halogenated [=$(C_1-C_4)$-haloalkoxy], $(C_1-C_4)$-alkoxy-$(C_1-C_4)$-alkoxy, $(C_1-C_4)$-alkylthio, [$(C_1-C_6)$-alkoxy]carbonyl, [$(C_1-C_6)$-haloalkoxy]carbonyl, $(C_1-C_4)$-alkylsulfinyl, $(C_1-C_4)$-haloalkylsulfinyl, $(C_1-C_4)$-alkylsulfonyl, $(C_1-C_4)$-haloalkylsulfonyl, also $(C_1-C_4)$-alkylsulfonyloxy, also mono- and di-[$(C_1-C_4)$-alkyl]amino, also phenyl and $(C_3-C_6)$-cycloalkyl, which is unsubstituted or substituted by one or more radicals selected from the group consisting of halogen, $(C_1-C_4)$-alkyl and $(C_1-C_4)$-haloalkyl, and where two adjacent substituents may form a fused-on 5- or 6-membered ring which is carbocyclic or may contain another 1 to 3 ring heteroatoms selected from the group consisting of N, O and S and which is unsubstituted or substituted by one or more radicals selected from the group consisting of halogen and $(C_1-C_4)$-alkyl.

Here, even more preference is also given to the compounds of the formula (I) or salts thereof in which $R^5$ is phenyl which is unsubstituted or preferably substituted by one or more radicals selected from the group consisting of halogen, cyano, $(C_1-C_4)$-alkyl, $(C_1-C_4)$-haloalkyl, $(C_1-C_4)$-alkoxy and $(C_1-C_4)$-alkylthio and optionally benzo-fused, or $R^5$ is a 5- or 6-membered heteroaromatic radical having 1 to 3 ring heteroatoms selected from the group consisting of N, O and S which is unsubstituted or substituted by one or more radicals selected from the group consisting of halogen, hydroxyl, $(C_1-C_4)$-alkyl, $(C_1-C_4)$-haloalkyl, $(C_1-C_4)$-alkoxy and $(C_1-C_4)$-alkylthio and also $(C_2-C_4)$-alkenyl, $(C_2-C_4)$-alkynyl, $(C_3-C_6)$-cycloalkyl, phenyl, amino, mono- and di-[$(C_1-C_4)$-alkyl]amino and $(C_1-C_4)$-alkylsulfonyloxy and is optionally benzo-condensed or benzo-fused.

Particular preference is given here to compounds of the formula (I) or salts thereof in which $R^5$ is phenyl which is unsubstituted or preferably substituted by one or more radicals selected from the group consisting of halogen, such as fluorine, chlorine, bromine and iodine, cyano, methyl, ethyl, n-propyl, isopropyl, n-butyl, sec-butyl, isobutyl, t-butyl, trifluoromethyl, trichloromethyl, methoxy and ethoxy and optionally benzo-fused, preferably $R^5$ is phenyl, 2-fluorophenyl, 2-chlorophenyl, 2-bromophenyl, 2-iodophenyl, 2-methylphenyl, 4-(tert-butyl)phenyl, 2-trifluoromethylphenyl, 2-methoxyphenyl or also 2-cyanophenyl or also 2-nitrophenyl or also 4-nitrophenyl, 3-fluorophenyl, 3-chlorophenyl, 3-bromophenyl, 3-iodophenyl, 3-methylphenyl, 3-trifluoromethylphenyl, 3-methoxyphenyl, 4-carboxyphenyl, 4-fluorophenyl, 4-chlorophenyl, 4-bromophenyl, 4-iodophenyl, 4-methylphenyl, 4-trifluoromethylphenyl, 4-methoxyphenyl, 2,3-dichlorophenyl, 2,3-dimethylphenyl, 2,4-dichlorophenyl, 2,4-dimethylphenyl, 2,5-dichlorophenyl, 2,5-dimethylphenyl, 2,6-dichlorophenyl or also 2,4-difluorophenyl, 2,6-dimethylphenyl, 3,4-dichlorophenyl or also 3,4-difluorophenyl, 3,4-dimethylphenyl, 3,5-dichlorophenyl, 3,5-dimethylphenyl, 2-chloro-3-methylphenyl, 2-chloro-4-methylphenyl, 2-chloro-5-methylphenyl, 2-chloro-6-methylphenyl, 3-chloro-4-methylphenyl, 3-chloro-5-methylphenyl, 3-chloro-2-methylphenyl, 4-chloro-2-methylphenyl, 4-chloro-3-methylphenyl or 5-chloro-2-methylphenyl, 4-phenylphenyl, 3-trifluoromethyl-4-chlorophenyl, 4-phenoxy-phenyl, 4-carboxymethylphenyl, 4-acetylphenyl (=4-methylcarbonylphenyl) or 1,3-benzodioxol-5-yl.

Here, preference is also given to compounds of the formula (I) or salts thereof in which $R^5$ is 2-pyridyl, 3-pyridyl, 4-pyridyl, 2-thienyl, 3-thienyl, 2-furyl, 3-furyl, 2-pyrrolyl, 3-pyrrolyl, 2-pyrimidinyl, 4-pyrimidinyl, 5-pyrimidinyl, 3-pyridazinyl, 4-pyridazinyl, 2-pyrazinyl, 3-pyrazinyl, 2-imidazolinyl, 4-imidazolinyl, 1-pyrazolyl, 3-pyrazolyl, 4-pyrazolyl, 5-pyrazolyl, 1,3,5-triazin-2-yl, 1,2,4-triazin-3-yl, 1,2,4-triazin-5-yl, 2-thiazolyl, 1,3-benzothiazol-2-yl, 4-thiazolyl, 5-thiazolyl, 3-isothiazolyl, 4-isothiazolyl, 5-isothiazolyl, 2-oxazolyl, 4-oxazolyl, 5-oxazolyl, 3-isoxazolyl, 4-isoxazolyl, 5-isoxazolyl, thiadiazolyl or triazolyl or also 3-isoquinolinyl, 2-quinolinyl, 1,3-benzthiazol-2-yl or 1,3-benzoxazol-2-yl, preferably 2-pyridyl, 3-pyridyl, 4-pyridyl, 2-pyrimidinyl, 2-pyrazinyl, 2-thienyl, 3-thienyl, 2-furyl or 2-thiazolyl or also 3-isoquinolinyl or 2-quinolinyl, where each of the heteroaromatic radicals mentioned above is unsubstituted or substituted, preferably substituted by the preferred radicals already mentioned above, in particular substituted by one or more radicals selected from the group consisting of halogen, hydroxyl, $(C_1-C_4)$-alkyl, $(C_1-C_4)$-haloalkyl, $(C_1-C_4)$-alkoxy and $(C_1-C_4)$-alkylthio and also $(C_2-C_4)$-alkenyl, $(C_2-C_4)$-alkynyl, $(C_1-C_4)$-alkylamino, di-$[(C_1-C_4)$-alkyl]amino and $(C_1-C_4)$-alkylsulfonyloxy.

Here, particular preference is also given to compounds of the formula (I) or salts thereof in which $R^5$ is 2-pyridyl, 3-fluoropyrid-2-yl, 3-chloropyrid-2-yl, 3-bromopyrid-2-yl, 3-methylpyrid-2-yl, 3-methoxypyrid-2-yl, 3-trifluoromethylpyrid-2-yl, 4-fluoropyrid-2-yl, 4-chloropyrid-2-yl, 4-bromopyrid-2-yl, 4-methylpyrid-2-yl, 4-methoxypyrid-2-yl, 4-trifluoromethylpyrid-2-yl, 5-fluoropyrid-2-yl, 5-chloropyrid-2-yl, 5-bromopyrid-2-yl, 5-methylpyrid-2-yl, 5-methoxypyrid-2-yl, 5-trifluoromethylpyrid-2-yl, 6-fluoropyrid-2-yl, 6-chloropyrid-2-yl, 6-bromopyrid-2-yl, 6-methylpyrid-2-yl, 6-methoxypyrid-2-yl, 6-trifluoromethylpyrid-2-yl, 4,6-dimethylpyridin-2-yl, 3-pyridyl, 2-fluoropyrid-3-yl, 2-chloropyrid-3-yl, 2-bromopyrid-3-yl, 2-methylpyrid-3-yl, 2-methoxypyrid-3-yl, 2-trifluoromethylpyrid-3-yl, 4-fluoropyrid-3-yl, 4-chloropyrid-3-yl, 4-bromopyrid-3-yl, 4-methylpyrid-3-yl, 4-methoxypyrid-3-yl, 4-trifluoromethylpyrid-3-yl, 5-fluoropyrid-3-yl, 5-chloropyrid-3-yl, 5-bromopyrid-3-yl, 5-methylpyrid-3-yl, 5-methoxypyrid-3-yl, 5-trifluoromethylpyrid-3-yl, 6-fluoropyrid-3-yl, 6-chloropyrid-3-yl, 6-bromopyrid-3-yl, 6-methylpyrid-3-yl, 6-methoxypyrid-3-yl, 6-trifluoromethylpyrid-3-yl, 6-hydroxypyridin-3-yl, 4-pyridyl, 2-fluoropyrid-4-yl, 2-chloropyrid-4-yl, 2-bromopyrid-4-yl, 2-methylpyrid-4-yl, 2-methoxypyrid-4-yl, 2-trifluoromethylpyrid-4-yl, 3-fluoropyrid-4-yl, 3-chloropyrid-4-yl, 3-bromopyrid-4-yl, 3-methylpyrid-3-yl, 3-methoxypyrid-4-yl, 3-trifluoromethylpyrid-4-yl or also 5-iodopyrid-2-yl, 5-dimethylaminopyrid-2-yl, 5-methylaminopyrid-2-yl, 5-methylthiopyrid-2-yl, 5-methoxypyrid-2-yl, 5-difluoromethoxypyrid-2-yl, 5-hydroxypyrid-2-yl, 5-ethynylpyrid-2-yl, 5-cyclopropylpyrid-2-yl, 5-allylpyrid-2-yl, 5-phenylpyrid-2-yl, 5-aminopyrid-2-yl or 5-methylsulfonyloxypyrid-2-yl, 2-thienyl, 3-fluorothien-2-yl, 3-chlorothien-2-yl, 3-bromothien-2-yl, 3-methylthien-2-yl, 3-methoxythien-2-yl, 3-trifluoromethylthien-2-yl, 4-fluorothien-2-yl, 4-chlorothien-2-yl, 4-bromothien-2-yl, 4-methylthien-2-yl, 4-methoxythien-2-yl, 4-trifluoromethylthien-2-yl, 5-fluorothien-2-yl, 5-chlorothien-2-yl, 5-bromothien-2-yl, 5-iodo-2-thienyl, 5-methylthien-2-yl, 5-methoxythien-2-yl, 5-trifluoromethylthien-2-yl or also 5-allylpyrid-2-yl, 5-ethynylpyridin-2-yl, 5-(methylsulfonyloxy)pyridin-2-yl or 5-methylthiopyridin-2-yl, 3-thienyl, 2-fluorothien-3-yl, 2-chlorothien-3-yl, 2-bromothien-3-yl, 2-methylthien-3-yl, 2-methoxythien-3-yl, 2-trifluoromethylthien-3-yl, 4-fluorothien-3-yl, 4-chlorothien-3-yl, 4-bromothien-3-yl, 4-methylthien-3-yl, 4-methoxythien-3-yl, 4-trifluoromethylthien-3-yl, 5-fluorothien-3-yl, 5-chlorothien-3-yl, 5-bromothien-3-yl, 5-methylthien-3-yl, 5-methoxythien-3-yl, 5-trifluoromethylthien-3-yl or 2-furyl, 3-fluorofur-2-yl, 3-chlorofur-2-yl, 3-bromofur-2-yl, 3-methylfur-2-yl, 3-methoxyfur-2-yl, 3-trifluoromethylfur-2-yl, 4-fluorofur-2-yl, 4-chlorofur-2-yl, 4-bromofur-2-yl, 4-methylfur-2-yl, 4-methoxyfur-2-yl, 4-trifluoromethylfur-2-yl, 5-fluorofur-2-yl, 5-chlorofur-2-yl, 5-bromofur-2-yl, 5-methylfur-2-yl, 5-methoxyfur-2-yl or 5-trifluoromethylfur-2-yl, 2-thiazolyl, 4-Me-thiazol-2-yl, 5-methylthiazol-2-yl, 5-bromothiazol-2-yl, 5-chlorothiazol-2-yl, 4,5-dimethylthiazol-2-yl, 4,5-dichlorothiazol-2-yl, 1,3-benzothiazol-2-yl, 7-chloro-1,3-benzothiazol-2-yl or also 2-bromothiazol-4-yl, 2-chlorothiazol-4-yl, 4-thiazolyl, 6-chloro-1,3-benzothiazol-2-yl, 7-bromo-1,3-benzothiazol-2-yl, 6-bromo-1,3-benzothiazol-2-yl, 1,3-benzoxazol-2-yl, 7-chloro-1,3-benzoxazol-2-yl, 6-chloro-1,3-benzoxazol-2-yl, 7-bromo-1,3-benzoxazol-2-yl, 6-bromo-1,3-benzoxazol-2-yl, 2-pyrazinyl, 5-methylpyrazin-2-yl, 1,5-dimethylpyrazol-3-yl or also 1-methylpyrazol-3-yl or also 1-methylpyrazol-5-yl, 2-pyrimidinyl, 5-fluoropyrimidin-2-yl, 5-chloropyrimidin-2-yl, 5-bromopyrimidin-2-yl, or also 5-iodopyrimidin-2-yl or 5-methylpyrimidin-2-yl, 4,6-dimethylpyrimidin-2-yl, 3-pyridazinyl, 6-methylpyridazin-3-yl, 1,2,4-triazin-3-yl or 6-methyl-1,2,4-triazin-3-yl or also 3-isoquinolinyl or 2-quinolinyl, preferably $R^5$ is 2-pyridyl, 5-fluoropyrid-2-yl, 5-chloropyrid-2-yl, 5-bromopyrid-2-yl, 5-methylpyrid-2-yl, 5-methoxypyrid-2-yl, 5-trifluoromethylpyrid-2-yl, 3-pyridyl, 6-fluoropyrid-3-yl, 6-chloropyrid-3-yl, 6-bromopyrid-3-yl, 6-methylpyrid-3-yl, 6-methoxypyrid-3-yl or 6-trifluoromethylpyrid-3-yl, 4,6-Me$_2$-pyridin-2-yl, 2-thienyl, 3-chlorothien-2-yl, 3-methylthien-2-yl, 4-chlorothien-2-yl, 4-methylthien-2-yl, 5-chlorothien-2-yl, 5-bromothien-2-yl, 5-iodo-2-thienyl, 5-methylthien-2-yl, 2-thiazolyl, 5-bromothiazol-2-yl, 5-chlorothiazol-2-yl, 4,5-dimethylthiazol-2-yl, 4,5-dichlorothiazol-2-yl, 1,3-benzothiazol-2-yl, 2-pyrazinyl, 5-methylpyrazin-2-yl, 1,5-dimethylpyrazol-3-yl, 2-pyrimidinyl, 5-bromopyrimidin-2-yl, 5-methylpyrimidin-2-yl, 4,6-dimethylpyrimidin-2-yl, 3-pyridazinyl or 6-methylpyridazin-3-yl, 4-fluoropyrid-2-yl, 4-chloropyrid-2-yl, 4-bromopyrid-2-yl, 4-methylpyrid-2-yl or 4-trifluoropyrid-2-yl or also 3-isoquinolinyl or 2-quinolinyl.

Preference is also given to the compounds of the formula (I) or salts thereof in which $(R^6)_n$ is n substituents $R^6$, where $R^6$, if n=1, or each of the substituents $R^6$ independently of the others, if n is greater than 1, is a radical halogen, cyano, $(C_1-C_4)$-alkyl, $(C_1-C_4)$-haloalkyl, $(C_1-C_4)$-alkoxy, $(C_1-C_4)$-alkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl, and n is 0, 1, 2 or 3, preferably 0, 1 or 2.

Here, preference is also given to the compounds of the formula (I) or salts thereof in which $(R^6)_n$ is n substituents $R^6$, where $R^6$, if n=1, or each of the substituents $R^6$ independently of the others, if n is greater than 1, is a radical halogen, such as fluorine, chlorine, bromine or iodine, methyl, ethyl, trifluoromethyl, methoxy, ethoxy, methylthio, ethylthio, methylsulfinyl, ethylsulfinyl, methylsulfonyl or ethylsulfonyl, and n is 0, 1, 2 or 3, preferably 0, 1 or 2.

Preference is given to compounds of the formula (I) or salts thereof in which Het is a radical of the formula (Het-a), (Het-b), (Het-c) or (Het-d)

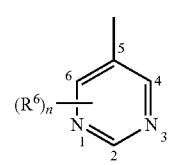

(Het-a)

-continued

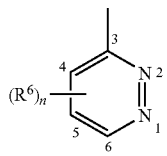
(Het-b)

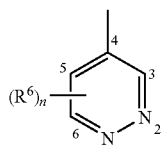
(Het-c)

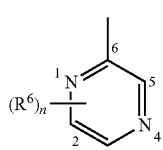
(Het-d)

wherein $(R^6)_n$ has the meaning mentioned or mentioned as being preferred.

More preference is given to compounds of the formula (I) or salts thereof in which Het is the radical (Het-a) mentioned in which n is 0 (=the number zero, i.e. no substituents $R^6$ are present, i.e. all free bonds at the ring are occupied by hydrogen) or $(R^6)_n$ is 2-chloro, 2-fluoro, 2-cyano, 2-methyl, 2-ethyl, 2-$CF_3$, 2-methoxy, 2-ethoxy, 2-methylthio, 2-methylsulfinyl, 2-methylsulfonyl, 4-fluoro, 4-chloro, 4-bromo, 4-cyano, 4-methyl, 4-ethyl, 4-$CF_3$, 4-methoxy, 4-ethoxy, 4-methylthio, 4-methylsulfinyl, 4-methylsulfonyl, 2,4-dimethyl, 2,4-difluoro, 2,4-dichloro, 4,6-dimethyl, 4,6-difluoro or 4,6-dichloro, where the numbering of the radicals refers to the position of the radical at the pyrimidin-5-yl radical in which the nitrogen ring atoms are located in the 1- and 3-position of the ring.

Here, particular preference is given to compounds of the formula (I) or salts thereof in which Het is the radical (Het-a) mentioned in which n=0 or $(R^6)_n$ is 4-fluoro, 4-chloro, 4-methyl, 4-trifluoromethyl, 4-methoxy, 4-methylsulfonyl, 4-methylsulfinyl or 4-methylthio, preferably 4-methyl.

More preference is given to compounds of the formula (I) or salts thereof in which Het is the radical (Het-b) mentioned
in which n is 0 (=the number zero, i.e. no substituents $R^6$ are present, i.e. all free bonds at the ring are occupied by hydrogen) or $(R^6)_n$ is 4-fluoro, 4-chloro, 4-bromo, 4-cyano, 4-methyl, 4-ethyl, 4-trifluoromethyl, 4-methoxy, 4-ethoxy, 4-methylthio, 4-methylsulfinyl, 4-methylsulfonyl, 6-chloro, 6-fluor, 6-cyano, 6-methyl, 6-ethyl, 6-trifluoromethyl, 6-methoxy, 6-ethoxy, 6-methylthio, 6-methylsulfinyl, 6-methylsulfonyl, 4,6-dimethyl, 4,6-difluoro or 4,6-dichloro, where the numbering of the radicals refers to the position of the radical at the pyridazin-3-yl radical in which the nitrogen ring atoms are located in the 1- and 2-position of the ring.

Here, particular preference is given to compounds of the formula (I) or salts thereof in which Het is the radical (Het-b) mentioned in which n=0 or $(R^6)_n$ is 4-fluoro, 4-chloro, 4-methyl, 4-trifluoromethyl, 4-methoxy, 4-methylsulfonyl, 4-methylsulfinyl or 4-methylthio, preferably 4-methyl.

More preference is given to compounds of the formula (I) or salts thereof in which Het is the radical (Het-c) mentioned in which n is 0 (=the number zero, i.e. no substituents $R^6$ are present, i.e. all free bonds at the ring are occupied by hydrogen) or $(R^6)_n$ is 5-fluoro, 5-chloro, 5-bromo, 5-cyano, 5-methyl, 5-ethyl, 5-trifluoromethyl, 5-methoxy, 5-ethoxy, 5-methylthio, 5-methylsulfinyl, 5-methylsulfonyl, 3,5-dimethyl, 3,5-difluoro or 3,5-dichloro, where the numbering of the radicals refers to the position of the radical at the 4-pyridazinyl in which the nitrogen ring atoms are located in the 1- and 2-position of the ring.

Here, particular preference is given to compounds of the formula (I) or salts thereof in which Het is the radical (Het-c) mentioned in which n=0 or in which $(R^6)_n$ is 5-fluoro, 5-chloro, 5-methyl, 5-trifluoromethyl, 5-methoxy, 5-methylsulfonyl, 5-methylsulfinyl or 5-methylthio, preferably 5-methyl.

More preference is given to compounds of the formula (I) or salts thereof in which Het is the radical (Het-d) mentioned in which n is 0 (=the number zero, i.e. no substituents $R^6$ are present, i.e. all free bonds at the ring are occupied by hydrogen) or $(R^6)_n$ is 3-chloro, 3-fluoro, 3-cyano, 3-methyl, 3-ethyl, 3-$CF_3$, 3-methoxy, 3-ethoxy, 3-methylthio, 3-methylsulfinyl, 3-methylsulfonyl, 5-fluoro, 5-chloro, 5-bromo, 5-cyano, 5-methyl, 5-ethyl, 5-$CF_3$, 5-methoxy, 5-ethoxy, 5-methylthio, 5-methylsulfinyl, 5-methylsulfonyl, 3,5-dimethyl, 3,5-difluoro, 3,5-dichloro, where the numbering of the radicals refers to the position of the radical at the 6-pyrazinyl in which the nitrogen ring atoms are located in the 1- and 4-position of the ring.

Particular preference is given here to the compounds of the formula (I) or salts thereof in which Het is the radical (Het-d) mentioned in which n=0 or in which $(R^6)_n$ is 5-fluoro, 5-chloro, 5-methyl, 5-trifluoromethyl, 5-methoxy, 5-methylsulfonyl, 5-methylsulfinyl or 5-methylthio, preferably 5-methyl.

Preference is also given to the compounds of the formula (I) or salts thereof in which Het is the radical (Het-a), (Het-b), (Het-c) or (Het-d) mentioned, in which in each case n=0.

Preference is also given to the compounds of the formula (I) or salts thereof in which the radicals Het, $R^1$, $R^2$, $R^3$, $R^4$, $R^5$, $R^6$ and n have been selected according to two or more of the preferred meanings mentioned.

Preferred as compounds of the formula (I) or salts thereof are the compounds of the formulae (Ia), (Ib), (Ic) and (Id) and their salts,

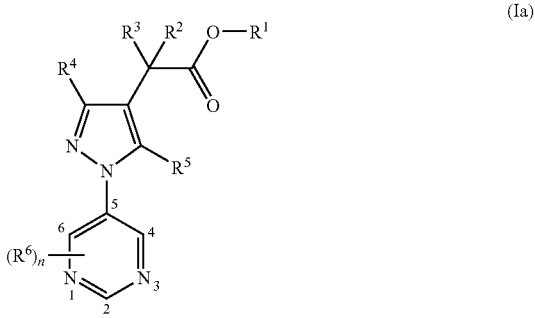
(Ia)

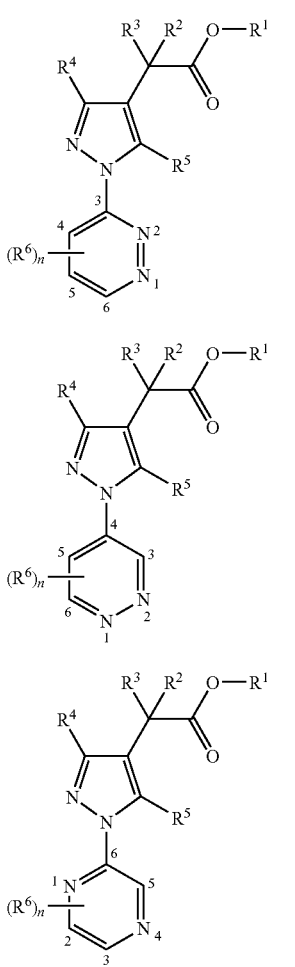

in which $R^1$, $R^2$, $R^3$, $R^4$, $R^5$, $R^6$ and n are defined as for formula (I) or according to the preferred meanings mentioned.

Particular preference is given to the compounds of the general formula (Ia) or salts thereof in which
$R^1$ is hydrogen and $R^2$, $R^3$, $R^4$, $R^5$, $R^6$ and n are as defined for formula (I) [=compounds of the formula (Ia")] or
$R^1$ is methyl and $R^2$, $R^3$, $R^4$, $R^5$, $R^6$ and n are as defined for formula (I), [=compounds of the formula (Ia''')] or
$R^2$ and $R^3$ are each hydrogen and $R^1$, $R^4$, $R^5$, $R^6$ and n are as defined for formula (I) [=compounds of the formula (Ia'''')].

Particular preference is also given to the compounds of the general formula (Ib) or salts thereof in which
$R^1$ is hydrogen and $R^2$, $R^3$, $R^4$, $R^5$, $R^6$ and n are as defined for formula (I) [=compounds of the formula (Ib")] or
$R^1$ is methyl and $R^2$, $R^3$, $R^4$, $R^5$, $R^6$ and n are as defined for formula (I), [=compounds of the formula (Ib''')] or
$R^2$ and $R^3$ are each hydrogen and $R^1$, $R^4$, $R^5$, $R^6$ and n are as defined for formula (I) [=compounds of the formula (Ib'''')].

Particular preference is given to the compounds of the general formula (Ic) or salts thereof in which
$R^1$ is hydrogen and $R^2$, $R^3$, $R^4$, $R^5$, $R^6$ and n are as defined for formula (I) [=compounds of the formula (Ic")] or
$R^1$ is methyl and $R^2$, $R^3$, $R^4$, $R^5$, $R^6$ and n are as defined for formula (I), [=compounds of the formula (Ic''')] or
$R^2$ and $R^3$ are each hydrogen and $R^1$, $R^4$, $R^5$, $R^6$ and n are as defined for formula (I) [=compounds of the formula (Ic'''')].

Particular preference is given to the compounds of the general formula (Id) or salts thereof in which
$R^1$ is hydrogen and $R^2$, $R^3$, $R^4$, $R^5$, $R^6$ and n are as defined for formula (I) [=compounds of the formula (Id")] or
$R^1$ is methyl and $R^2$, $R^3$, $R^4$, $R^5$, $R^6$ and n are as defined for formula (I), [=compounds of the formula (Id''')] or
$R^2$ and $R^3$ are each hydrogen and $R^1$, $R^4$, $R^5$, $R^6$ and n are as defined for formula (I) [=compounds of the formula (Id'''')].

Here, particular preference is given to the compounds of the formulae (I), (Ia), (Ib), (Ic) and (Id) and salts thereof in which one or more of the radicals $R^1$ to $R^6$ has the radical meanings used in the example tables.

Here, particular preference is given to the compounds of the formula (I) and salts thereof in which one or more of the radicals $R^1$ to $R^6$ have the radical meanings used in the example tables.

The compounds of the formula (I) according to the invention include all stereoisomers which can occur on the basis of the centers of asymmetry or double bonds in the molecule whose configuration is not designated specifically in the formula or which are not specified explicitly, and mixtures thereof, including the racemic compounds and the mixtures enriched partly with particular stereoisomers.

The invention also includes all tautomers, such as keto and enol tautomers, and their mixtures and salts, if appropriate functional groups are present.

The invention also provides processes for preparing the compounds of the general formula (I) and/or their salts.

The compounds of the formula (I) according to the invention can be prepared by various alternative processes.

In the processes below, in some cases solvents are employed. In this context, "inert solvents" refers in each case to solvents which are inert under the particular reaction conditions, but which do not have to be inert under any reaction conditions.

(a) To prepare compounds of the general formula (I) or salts thereof in which Het, $R^1$, $R^2$, $R^3$, $R^4$, $R^5$, $R^6$ have the meanings indicated above for formula (I), a compound of the formula (II)

in which Het and $(R^6)_n$ are as defined for formula (I) is reacted with a compound of the formula (III),

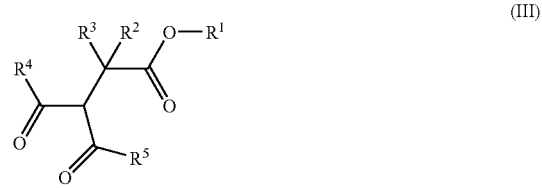

in which $R^1$, $R^2$, $R^3$, $R^4$ and $R^5$ are as defined for formula (I),
to give the compound of the formula (I) or its salt.

Process (a) is preferred for compounds of the formulae (I) and (II) in which Het is a group of the formula (Het-a) mentioned (=pyrimidin-5-yl) and n is not 0 or in which Het is a group of the formula (Het-b) mentioned (=pyrazin-3-yl) and n is not 0 or in which Het is a group of the formula (Het-c)

mentioned (=pyrazin-4-yl) or in which Het is a group of the formula (Het-d) mentioned (=pyridazin-6-yl).

The substituted 1,3-dicarbonyl compounds of the formula (III) used as starting materials in the process (a) according to the invention for preparing compounds of the formula (I) are preferably those where the radicals $R^1$, $R^2$, $R^3$, $R^4$ and $R^5$ have the preferred meanings already indicated above in connection with the description of the compounds of the formula (I) according to the invention as being preferred.

Accordingly, the substituted heteroarylhydrazines of the formula (II) used as starting materials in the process (a) according to the invention for preparing compounds of the formula (I) preferably also have those meanings for $(R^6)_n$ which have already been indicated above in connection with the description of the compounds of the formula (I) according to the invention as being preferred for $(R^6)_n$, and in particular preferred as a function of the radicals Het.

Hydrazines of the formula (II) or salts thereof as starting materials are known and/or can be prepared by known processes (cf., for example, *Methoden der organischen Chemie* (Houben-Weyl, D. Klamann, Ed.) volume E16a, part 1, p. 421 ff., Georg Thieme Verlag, Stuttgart 1990 and the literature cited therein; *J. Am. Chem. Soc.*, 1954, 76, 596; *Monatshefte für Chemie* 1988, 119, 333; *J. Heterocyclic Chem.* 1988, 25, 1055; *J. Heterocyclic Chem.* 1989, 26, 475; *Heterocycles* 1994, 37, 379).

The reaction of the compounds of the formulae (II) and (III) can be carried out without catalyst or in the presence of catalysts, for example of an acid as catalyst, preferably in an organic solvent, such as tetrahydrofuran (THF), dioxane, acetonitrile, dimethylformamide (DMF), methanol and ethanol, at temperatures between 20° C. and the boiling point of the solvent, preferably at from 50° C. to 150° C. If acid addition salts of the formula (II) are used, these are generally liberated in situ with the aid of a base. Suitable bases or basic catalysts are alkali metal hydroxides, alkali metal hydrides, alkali metal carbonates, alkali metal bicarbonates, alkali metal alkoxides, alkaline earth metal hydroxides, alkaline earth metal hydrides, alkaline earth metal carbonates or organic bases, such as triethylamine, diisopropylethylamine or 1,8-diazabicyclo[5.4.0]undec-7-ene (DBU).

Analogous processes have been described in the literature, for example in WO 2004/037793.

(b) If $R^1$ in formula (I) is different from hydrogen, a compound of the formula (I')

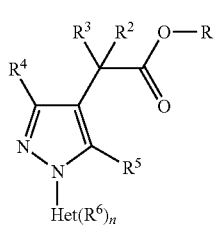

(I')

in which Het, $R^2$, $R^3$, $R^4$, $R^5$ and $R^6$ are as defined for formula (I) and R is a radical which is different from the radical $R^1$ and different from hydrogen selected from the group of radicals as defined for $R^1$, or an anhydride, acid halide or an activated ester of the compound of the formula (I') in which R=H, is reacted with a compound of the formula (IV)

$R^1$—OH (IV)

in which $R^1$ is as defined for formula (I)

to give the compound of the formula (I) or (c) if $R^1$ in formula (I) is different from hydrogen, a compound of the formula (I")

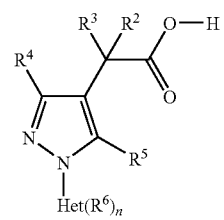

(I")

in which Het, $R^2$, $R^3$, $R^4$, $R^5$ and $R^6$ are as defined for formula (I), is, if appropriate after activation of the acid group, reacted (esterified) with a compound of the formula (IV)

$R^1$—OH (IV)

in which $R^1$ is as defined for formula (I)

to give the compound of the formula (I) or (d) if the compound of the formula (I) in which R=H or its salt is prepared, a compound of the formula (I') [see definition in variant (b)] is hydrolyzed to give the compound of the formula (I) or its salt.

The starting materials of the formulae (II), (III) and (IV) are generally known or can be prepared analogously to known processes.

The reaction of the compounds of the formulae (I') and (IV) can be carried out using standard methods of transesterification or esterification via activated carboxylic acids.

The reaction of the compounds of the formulae (I") and (IV) can be carried out using standard methods of esterification or, if appropriate, via activated carboxylic acids.

The preparation of compounds of the formula (I") from compounds (I') can be carried out using standard methods of hydrolysis.

e) The compounds of the formula (III) can be prepared, for example, by reacting a dicarbonyl compound of the formula (V)

$R^4$—CO—$CH_2$—CO—$R^5$ (V)

with a compound of the formula (VI), $R^2R^3C(Hal)$-CO—$OR^1$ (VI)

where $R^1$, $R^2$, $R^3$, $R^4$ and $R^5$ are defined as for formula (III) and $R^1$ is preferably methyl or ethyl, and Hal is a leaving group, preferably a reactive halogen, such as a chlorine atom or, in particular, a bromine atom, or else p-toluenesulfonyl(tosyl) or methylsulfonyl(mesyl).

The compounds of the formula (I) according to the invention can be prepared by known methods analogously to the processes a) to e) mentioned, as described, for example, in *Methoden der organischen Chemie* [Methods of Organic Chemistry] (Houben-Weyl, E. Schaumann, Ed.) volume E8b, Hetarenes III, part 2, pp. 399-710, Georg Thieme Verlag, Stuttgart 1994 and the literature cited therein, where the syntheses according to *Methoden der organischen Chemie* (Houben-Weyl, E. Schaumann, Ed.) volume E8b, Hetarenes III, part 2, p. 420 ff., Georg Thieme Verlag, Stuttgart 1994 and the literature cited therein; *Synthesis*, 1986, 409; *J. Chinese Chem. Soc.*, 2001, 48, 45 and in particular U.S. Pat. No. 4,146,721, DE2141124, DOS 1946370 and *Justus Liebigs Ann. Chem.* 1973, 1919 are of particular interest.

f) The compounds of the formula (V) can also be prepared, for example, by reacting a compound of the formula (VII)

R$^5$—CO—OR$^7$ (VII)

with a compound of the formula (VIII),

CH$_3$—CO—R$^4$ (VIII)

where R$^4$ and R$^5$ are as defined for formula (I), R$^7$ is (C$_1$-C$_6$)-alkyl, preferably methyl or ethyl, in the presence of a suitable organic base, such as, for example, sodium methoxide or sodium ethoxide, in a suitable solvent, for example methanol, ethanol or, preferably, tetrahydrofuran, in a temperature range between −10 and 50° C., preferably 0° C., and, if appropriate, under an atmosphere of inert gas, for example nitrogen.

Reactions analogous to the reaction have been described in the literature, for example Supramolecular Chemistry (2003), 15(7-8), 529-547; J. Am. Chem. Soc. (1951), 73 5614-16; J. of Med. Chem. (1990), 33(7), 1859-65; WO 00/08002.

Alternatively, compounds of the formula (V) can also be obtained by reacting a compound of the formula (IX)

R$^4$—CO—OR$^7$ (IX)

with a compound of the formula (X),

CH$_3$—CO—R$^5$ (X)

under conditions analogous to those described above under f), where R$^4$ and R$^5$ are as defined for formula (I), R$^7$ is (C$_1$-C$_6$)-alkyl, preferably methyl or ethyl.

Reactions analogous to the reaction have been described in the literature, for example in J. Am. Chem. Soc. (1950), 72 1352-6.

g) To prepare a compound of the general formula (I),

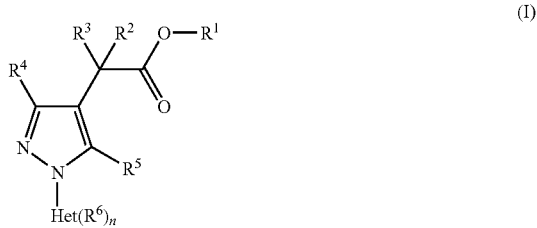

in which Het, R$^1$, R$^2$, R$^3$, R$^4$, R$^5$ and R$^6$ are as defined for formula (I), it is also possible, for example, to react a compound of the general formula (XI) with a boron derivative of the formula (XII) in the presence of a suitable Cu(I) or Cu(II) salt and an organic base, if appropriate in a solvent, as shown in the scheme below:

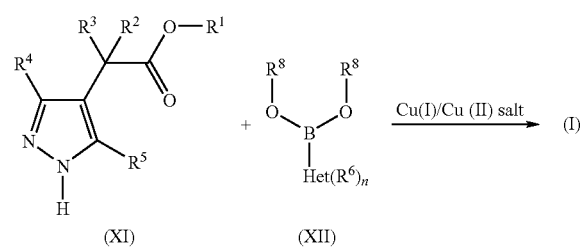

in which Het, R$^1$, R$^2$, R$^3$, R$^4$, R$^5$, R$^6$ have the meanings given above for formula (I) and R$^8$ is H or (C$_1$-C$_6$)-alkyl, preferably methyl, or the two alkyl radicals R$^8$ are linked cyclically.

The reaction is carried out in the presence of a suitable inorganic or organic copper(I) or copper(II) salt, preferably CuI, Cu$_2$O, particularly preferably Cu(OAc)$_2$, using more than one equivalent of boron derivative (XII), preferably between 1.5 and 2 equivalents.

To this end, a suitable organic base such as, for example, pyridine or potassium tert-butoxide is added and, to make the transmetallation more efficient, a source of fluoride anions, preferably cesium fluoride.

The reaction is carried out in a suitable solvent, preferably a halogenated solvent, for example trichloromethane or, preferably, dichloromethane, in a temperature range between 0 and 40° C., preferably between 20 and 30° C., and, if appropriate, under an atmosphere of inert gas, for example nitrogen, until the reaction has gone to completion, which may in some cases require long reaction times.

Analogous methods for copper-induced C—N couplings have been described in the literature, for example in Tet. Lett. 1998, 39, 2941; Tet. Lett. 1998, 39, 2933; Tet. Lett. 44 (2003) 3863-3865; J. Comb. Chem. 2004, 6, 385-390; Tet. Lett. 41 (2000) 9053 to 9057.

Analogous methods for copper-induced C—N couplings in the presence of fluoride anions have been described in the literature, for example in Eur. J. Org. Chem. 2007, 1318-1323 and Org. Lett. 2007, 9 (5), 761.

Compounds of the general formula (XI) can be prepared by processes known to the person skilled in the art, for example by reacting a compound of the general formula (III), in which R$^1$, R$^2$, R$^3$, R$^4$ and R$^5$ are as defined for formula (I), with hydrazine (hydrate) as described in Can. J. Chem. 2001, 79 (2), 183-194.

Compounds of the general formula (XII) are known to the person skilled in the art, and some are commercially available or can be prepared by processes known to the person skilled in the art, for example as described in a) Science of Synthesis, Houben-Weyl (Methods of Molecular Transformations), Category 2, Volume 6, Ed. E. Schaumann; b) Houben-Weyl (Methoden der organische Chemie [Methods of Organic Chemistry]), Volume 13, Organoborverbindungen [Organoboron Compounds] I-Part 3a, Ed. E. Schaumann.

h) A suitable starting material for preparing a compound of the formula (I) mentioned in which Het, R$^1$, R$^2$, R$^3$, R$^4$, R$^5$ and R$^6$ are as defined for formula (I) can also be, for example, a compound of the general formula (XV), which is prepared by reacting a compound of the formula (XIII) in which R$^6$ has the meaning given above for formula (I) with benzophenone hydrazone (XIV) in the presence of a suitable catalyst/ligand system with a suitable base and in a suitable solvent.

Compounds of the general formula (XV) give, with a compound of the general formula (III) in the presence of an acid, if appropriate in a solvent, the compound of the general formula (I), as shown in the scheme below:

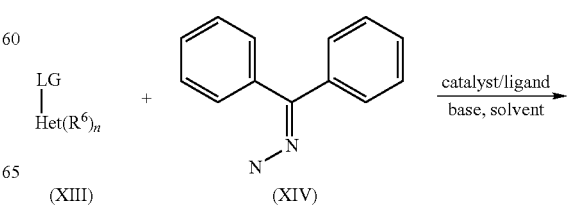

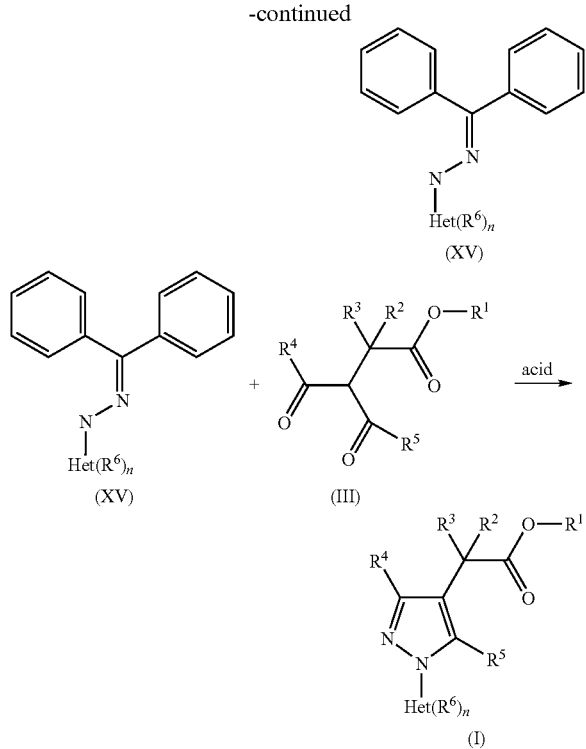

Here, Het, $R^1$, $R^2$, $R^3$, $R^4$, $R^5$, $R^6$ have the meanings given above for formula (I), LG is a leaving group, suitable leaving groups being chlorine, bromine, iodine, phenylsulfonate, tosylate and triflate, inter alia.

Compounds of the formula (XIII) can be reacted with benzophenone hydrazone (XIV) in the presence of a catalyst and a suitable catalyst/ligand system to give compounds of the formula (XV). The reaction is preferably carried out using a palladium catalyst, for example palladium(II) acetate, using a phosphine ligand, such as, for example, 2,2'-bis(diphenylphosphino)-1,1'-binaphthyl (BINAP), 1,1'-diphenylphosphinoferrocene (DPPF), 2-di-tert-butylphosphinobiphenyl (JohnPhos), 2-dicyclohexylphosphino-2'-dimethylaminobiphenyl (DavePhos), 2-dicyclohexylphosphino-2',4',6'-triisopropylbiphenyl (XPhos), 2-dicyclohexylphosphino-2'-methylbiphenyl (MePhos), 4,5-bis(diphenylphosphino)xanthene (XANTPHOS). The use of a base, for example sodium tert-butoxide, is advantageous. The reaction is carried out under an atmosphere of inert gas, for example nitrogen, with exclusion of water in a suitable solvent, for example toluene.

Benzophenone hydrazone is commercially available.

Compounds of the formula (XV) can directly be reated further with compounds of the formula (III) to give compounds of the formula (I). The reaction is carried out in the presence of a suitable inorganic or organic (non)aqueous acid, preferably p-toluenesulfonic acid, sulfuric acid, particularly preferably hydrochloric acid, where between 1 and 10, particularly preferably 5, equivalents of the acid are used.

The reaction is carried out in a suitable solvent, for example diethyl ether, dioxane or, preferably, tetrahydrofuran, in a temperature range between 0 and 80° C., preferably 50° C., and, if appropriate, under an atmosphere of inert gas, for example nitrogen.

Analogous cyclization reactions of a hydrazone with a 1,3-diketone to give a pyrazole have been described in the literature, for example in WO2001/32627; Angew. Chem. 110 (1998) 2249-2252; Tet. Lett. 43 (2002) 2171-2173; J. Am. Chem. Soc. 1981, 103, 7743-7752; Organic Process Research and Development 2004, 8, 1065-1071; Tet. Lett. 45 (2004) 5935-5937; WO2007/064872, U.S. Pat. No. 6,489, 512, WO2006/114213.

Compounds of the formula (XV) can also be converted into compounds of the formula (II) using processes known to the person skilled in the art, in the presence of acid, preferably under partially aqueous conditions. The compounds of the formula (II) can furthermore be reacted according to process a) mentioned above to give compounds of the formula (I).

Compounds of the general formula (XIII) are known to the person skilled in the art, and some of them are commercially available or can be prepared by processes known to the person skilled in the art, for example as described in Science of Synthesis, Houben-Weyl (Methods of Molecular Transformations), Category 2, Volume 16, Ed. E. Schaumann.

Compounds of the general formula (XV) can be prepared as described, for example, in Tet. Lett. 45 (2004) 5935-5937; Angew. Chem. Int. Ed. 2006, 45, 6523-6527; J. Am. Chem. Soc. (2003) 125, 13978-13980; J. Am. Chem. Soc. (2003), 125, 6653-6655; Org. Lett. 3 (9) (2001) 1351; Tet. Lett. 45 (2004) 5935-5937; Tetr. Lett. 43 (2002) 2171-2173; Angew. Chem. Int. Ed. 1998, 37 (15) 2090; WO2001/32627; J. Am. Chem. Soc. (1998) 120, 6621; WO2007/064872; U.S. Pat. No. 6,489,512; WO2006/114213; US2005/0192294, J. Am. Chem. Soc. 2003, 125, 6653-6655; Org. Lett. 2001, 3 (9), 1351-1354.

i) To prepare a compound of the formula (I) mentioned in which Het, $R^1$, $R^2$, $R^3$, $R^4$, $R^5$ and $R^6$ are as defined for formula (I), it is also possible, for example, to react a compound of the general formula (XVI) where $R^6$ is as defined for formula (I) with di-tert-butyl azodicarboxylate (DBAD, XVII) in the presence of a suitable copper salt in a suitable solvent to give a compound of the general formula (XVIII) in which $R^6$ is as defined for formula (I). This gives compounds of the formula (II) or salts thereof in which $R^6$ is as defined for formula (I) which, according to process a), can be converted into compounds of the formula (I) in which $R^1$, $R^2$, $R^3$, $R^4$, $R^5$ and $R^6$ are as defined for formula (I), as shown in the scheme below:

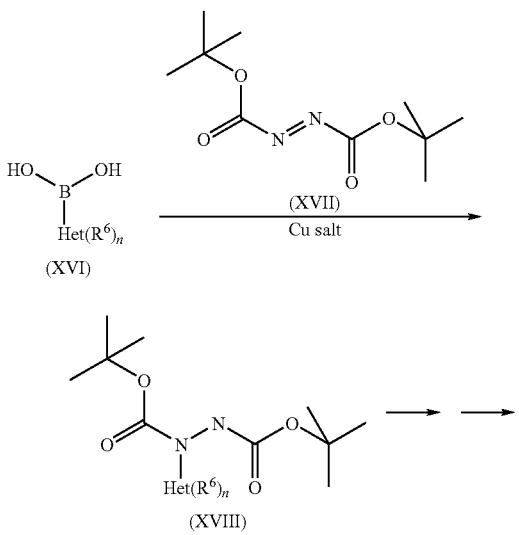

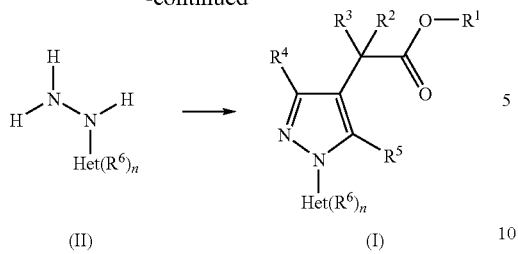

The reaction is carried out, for example, in the presence of a suitable inorganic copper salt, for example $Cu(OAc)_2$ or $Cu(OAc)_2 \cdot H_2O$, in a suitable solvent, for example in an alcohol such as methanol, in a temperature range between 0 and 40° C., preferably 20-25° C., and, if appropriate, under an atmosphere of inert gas, for example nitrogen.

Analogous reactions using commercially available di-tert-butyl(E)-diazene-1,2-dicarboxylate (DTBAD) have been described in the literature, for example Org. Lett. (2006) 8 (1), 43-45; J. Org. Chem. 2005, 70, 8631-8634.

Compounds of the general formula (XVI) are commercially available and/or can be prepared by processes known to the person skilled in the art, for example as described in a) Science of Synthesis, Houben-Weyl (Methods of Molecular Transformations), Category 2, Volume 6, Ed. E. Schaumann; b) Houben-Weyl (Methoden der organische Chemie [Methods of Organic Chemistry]), Volume 13, Organoborverbindungen [Organoboron Compounds] I-Part 3a, Ed. E. Schaumann. Compounds of the general formula (XVIII) can be converted into compounds of the general formula (II) using processes known to the person skilled in the art, for example as described in J. Med. Chem. 1998, 41, 2858-2871; Tetrahedron 44 (17), 5525 (1988); J. Med. Chem. 1996, 39, 1172-1188; J. Org. Chem. 2004, 69, 5778-5781.

Compounds of the general formula (II) or their salts can be converted by the abovementioned process a) into compounds of the formula (I).

j) To prepare a compound of the formula (I) mentioned in which Het, $R^1$, $R^2$, $R^3$, $R^4$, $R^5$ and $R^6$ are as defined for formula (I), it is also possible, for example, to react a compound of the general formula (XIX) in which $R^6$ is as defined for formula (I) and LG' is a suitable group, where suitable groups are boron and iodine, inter alia, with a suitable metal or a suitable transmetallation reagent to give a compound of the formula (XX) which for its part is reacted with di-tert-butyl(E)-diazene-1,2-dicarboxylate (DTBAD, XVII) in the presence of a suitable solvent to give a compound of the general formula (XVIII) in which $R^6$ is as defined for formula (I). This gives compounds of the formula (II) or salts thereof in which $R^6$ is as defined for formula (I) which, according to process a), can be converted into compounds of the formula (I) where $R^1$, $R^2$, $R^3$, $R^4$, $R^5$ and $R^6$ are as defined for formula (I), as shown in the scheme below:

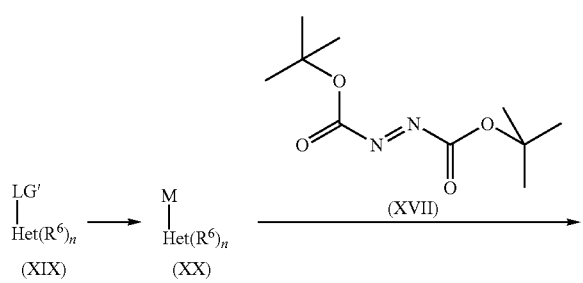

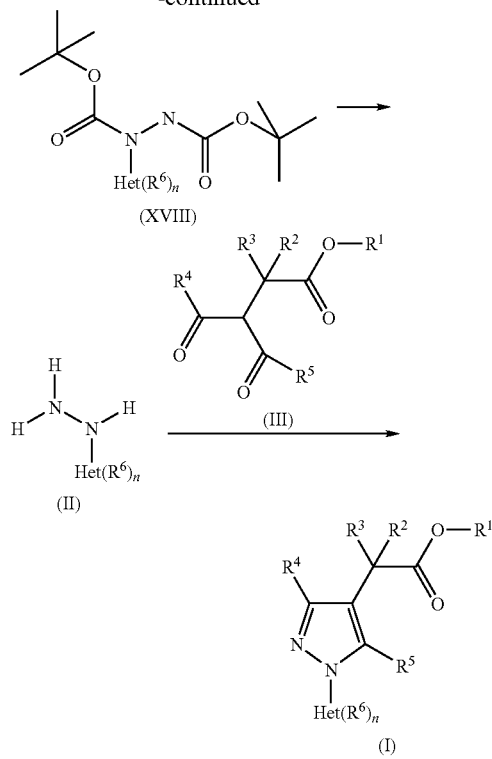

The conversion into a compound of the general formula (XX) is carried out, for example, in the presence of a suitable transmetallation reagent, for example an alkyllithium base, preferably BuLi; or a metal, preferably Li, Mg or Zn. The nucleophile formed in this manner is reacted further with di-tert-butyl(E)-diazene-1,2-dicarboxylate (DTBAD, XVIII) to give a compound of the general formula (XVIII). Analogous reactions using commercially available di-tert-butyl azodicarboxylate (DBAD) have been described in the literature, for example Tet. Lett. 1987, 28 (42), 4933; Tet. Lett. 39 (1998) 9157-9160.

Compounds of the general formula (XIX) are commercially available and/or can be prepared by processes known to the person skilled in the art, for example as described in Science of Synthesis, Houben-Weyl (Methods of Molecular Transformations), Category 2, Volume 16, Ed. E. Schaumann.

Compounds of the general formula (XVIII) can be converted into compounds of the general formula (II) by processes known to the person skilled in the art, for example as described in J. Med. Chem. 1998, 41, 2858-2871; Tetrahedron 44 (17), 5525 (1988); J. Med. Chem. 1996, 39, 1172-1188; J. Org. Chem. 2004, 69, 5778-5781.

Compounds of the general formula (II) or their salts can be converted by the abovementioned process a) into compounds of the formula (I).

The starting materials of the general formula (III) can be obtained via generally known processes by alkylation of corresponding 1,3-diketones with 2-halogenated acetic acid derivatives, for example bromoacetic acid derivatives (cf., for example, DE-OS 1946370, p. 13). The 1,3-diketones (V) required as starting materials for this purpose can be prepared by the abovementioned process f) or are commercially available or known and/or can be prepared by known processes (see, for example, U.S. Pat. No. 4,146,721, DE2141124, DOS1946370 or *J. Am. Chem. Soc.,* 1948, 70, 4023; *Justus Liebigs Ann. Chem.* 1973, 1919; *Justus Liebigs Ann. Chem.*

1976, 13; *J. Chem. Soc. Perkin Trans.* 2, 1993, 6, 1067; *Heteroatom Chemistry,* 1997, 8, 147).

Also possible for preparing enantiomers of the compounds (I) are customary methods for optical resolution (cf. textbooks of stereochemistry), for example following processes for separating mixtures into diastereomers, for example physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the compounds (I) using optically active acids and, if appropriate, provided that acidic groups are present, using optically active bases.

Optically active acids which are suitable for optical resolution by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-phenylethylamine and other analogous bases. The crystallizations are then in most cases carried out in aqueous or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

The following acids are suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulfonic acids, such as p-toluenesulfonic acid and 1,5-naphthalenedisulfonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R"R'"]$^+$ OH$^-$.

What is meant by the "inert solvents" referred to in the above process variants are in each case solvents which are inert under the particular reaction conditions but need not be inert under any reaction conditions.

Collections of compounds of the formula (I) and/or their salts which can be synthesized in accordance with the above-mentioned reactions can also be prepared in a parallelized manner, which can be effected manually or in a partly or fully automated manner. Here, it is possible for example to automate the procedure of the reaction, the work-up or the purification of the products or intermediates. In total, this is understood as meaning a procedure as described for example by D. Tiebes in Combinatorial Chemistry—Synthesis, Analysis, Screening (Editor Günther Jung), Wiley 1999, on pages 1 to 34.

A number of commercially available apparatuses can be used for the parallelized reaction procedure and work-up, for example Calpyso reaction blocks from Barnstead International, Dubuque, Iowa 52004-0797, USA, or reaction stations from Radleys, Shirehill, Saffron Walden, Essex, CB 11 3AZ, England or MultiPROBE Automated Workstations from Perkin Elmar, Waltham, Mass. 02451, USA. Chromatographic apparatuses, for example from ISCO, Inc., 4700 Superior Street, Lincoln, Nebr. 68504, USA, are available, inter alia, for the parallelized purification of compounds of the formula (I) and their salts or of intermediates generated in the course of the preparation.

The apparatuses listed lead to a modular procedure in which the individual passes are automated, but manual operations must be carried out between the passes. This can be circumvented by the use of partly or fully integrated automation systems, where the relevant automation modules are operated by, for example, robots. Such automation systems can be obtained for example from Caliper, Hopkinton, Mass. 01748, USA.

The performance of individual, or a plurality of, synthesis steps can be aided by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Besides the methods described herein, the preparation of compounds of the formula (I) and their salts can be effected fully or in part by solid-phase-supported methods. For this purpose, individual intermediates, or all intermediates, of the synthesis or of a synthesis adapted to the relevant procedure are bound to a synthesis resin. Solid-phase-supported synthesis methods are described sufficiently in the specialist literature, for example Barry A. Bunin in "The Combinatorial Index", Academic Press, 1998 and Combinatorial Chemistry—Synthesis, Analysis, Screening (Editor Günther Jung), Wiley, 1999. The use of solid-phase-supported synthesis methods permits a series of protocols known from the literature, which, again, can be carried out manually or in an automated manner. For example, the reactions can be carried out by means of IRORI technology in microreactors from Nexus Biosystems, 12140 Community Road, Poway, Calif. 92064, USA.

Carrying out individual or a plurality of synthesis steps, both on a solid and in the liquid phase, can be aided by the use of microwave technology. A series of experimental protocols are described in the specialist literature, for example in Microwaves in Organic and Medicinal Chemistry (Editors C. O. Kappe and A. Stadler), Wiley, 2005.

The preparation by the processes described here affords compounds of the formula (I) and their salts in the form of substance collections referred to as libraries. The present invention therefore also provides libraries comprising at least two compounds of the formula (I) and/or salts thereof.

The compounds of the formula (I) according to the invention and/or their salts, hereinbelow together referred to as "compounds (I) according to the invention" or in short "compounds (I)", have an outstanding herbicidal activity against a broad spectrum of economically important monocotyledonous and dicotyledonous annual harmful plants. The active compounds also act efficiently on perennial harmful plants which produce shoots from rhizomes, rootstocks or other perennial organs and which are difficult to control.

The present invention therefore also relates to a method of controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seeds (for example grains, seeds or vegetative propagules such as tubers or shoot parts with buds) or to the area on which the plants grow (for example the area under cultivation). In this context, the compounds according to the invention can be applied for example pre-planting (if appropriate also by incorporation into the soil), pre-emergence or post-emergence. Examples of individual representatives of the monocotyledonous and dicotyledonous weed flora which can be controlled by the compounds according to the invention shall be mentioned, without the mention being intended as a limitation to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

If the compounds according to the invention are applied to the soil surface before germination, either the emergence of the weed seedlings is prevented completely or the weeds grow until they have reached the cotyledon stage, but then stop their growth and, finally, die completely after three to four weeks have elapsed.

When the active compounds are applied post-emergence to the green plant parts, growth stops after the treatment, and the harmful plants remain in the growth stage of the time of application or die fully after a certain period of time, so that competition by weeds, which is harmful to the crop plants, is thus eliminated at an early point in time and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, in particular *Zea* and *Triticum*, are damaged only to an insignificant extent, or not at all, depending on the structure of the respective compound according to the invention and its application rate. This is why the present compounds are highly suitable for the selective control of undesired plant growth in plant crops such as agriculturally useful plants or ornamentals.

Moreover, the compounds according to the invention (depending on their respective structure and the application rate applied) have outstanding growth-regulatory properties in crop plants. They engage in the plant metabolism in a regulatory fashion and can therefore be employed for the influencing, in a targeted manner, of plant constituents and for facilitating harvesting, such as, for example, by triggering desiccation and stunted growth. Moreover, they are also suitable for generally controlling and inhibiting undesired vegetative growth without destroying the plants in the process. Inhibiting the vegetative growth plays an important role in many monocotyledonous and dicotyledonous crops since for example lodging can be reduced, or prevented completely, hereby.

Owing to their herbicidal and plant-growth-regulatory properties, the active compounds can also be employed for controlling harmful plants in crops of genetically modified plants or plants which have been modified by conventional mutagenesis. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known.

With regards to transgenic crops, it is preferred to use the compounds according to the invention in economically important transgenic crops of useful plants and ornamentals, for example of cereals such as wheat, barley, rye, oats, sorghum and millet, rice and maize or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

Owing to their herbicidal and plant-growth-regulatory properties, the active compounds can also be employed for controlling harmful plants in crops of known genetically modified plants or those which have still to be developed. As a rule, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other special properties relate for example to the harvested material with regard to quantity, quality, storability, composition and specific constituents. Thus, transgenic plants with an increased starch content or a modified starch quality or those with a different fatty acid composition of the harvested material are known. Other particular properties may be tolerance or resistance to abiotic stressors, for example heat, cold, drought, salt and ultraviolet radiation.

It is preferred to use the compounds of the formula (I) according to the invention or their salts in economically important transgenic crops of useful plants and ornamentals, for example of cereals such as wheat, barley, rye, oats, sorghum and millet, rice, cassava and maize or else crops of sugar beet, cotton, soybean, oilseed rape, potato, tomato, peas and other vegetables.

It is preferred to employ the compounds of the formula (I) and/or their salts as herbicides in crops of useful plants which are resistant, or have been made resistant by recombinant means, to the phytotoxic effects of the herbicides.

Conventional ways of generating novel plants which, in comparison with existing plants, have modified properties are, for example, traditional breeding methods and the generation of mutants. Alternatively, novel plants with modified properties can be generated with the aid of recombinant methods (see, for example, EP-A-0221044, EP-A-0131624). For example, the following have been described in several cases:

recombinant modifications of crop plants for the purposes of modifying the starch synthesized in the plants (for example-WO 92/11376, WO 92/14827, WO 91/19806), transgenic crop plants which are resistant to certain herbicides of the glufosinate type (cf., for example, EP-A-0242236, EP-A-242246) or of the glyphosate type (WO 92/00377) or of the sulfonylurea type (EP-A-0257993, U.S. Pat. No. 5,013,659), transgenic crop plants, for example cotton, which is capable of producing *Bacillus thuringiensis* toxins (Bt toxins), which make the plants resistant to certain pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431).

To carry out such recombinant manipulations, it is possible to introduce nucleic acid molecules into plasmids, which permit a mutagenesis or sequence modification by recombination of DNA sequences. For example, base substitutions can be carried out, part-sequences can be removed, or natural or synthetic sequences may be added with the aid of standard methods. To link the DNA fragments with one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone [Genes and Clones]", VCH Weinheim 2nd ed., 1996

The generation of plant cells with a reduced activity for a gene product can be achieved for example by the expression of at least one corresponding antisense RNA, a sense RNA for achieving a cosuppression effect or by the expression of at least one correspondingly constructed ribozyme, which specifically cleaves transcripts of the abovementioned gene product.

To do this, it is possible firstly to use DNA molecules which comprise all of the coding sequence of a gene product, including any flanking sequences which may be present, or else DNA molecules which only comprise parts of the coding sequence, it being necessary for these parts to be long enough to bring about an antisense effect in the cells. It is also possible to use DNA sequences which have a high degree of homology with the coding sequences of a gene product, but which are not entirely identical.

When expressing nucleic acid molecules in plants, the protein synthesized may be localized in any compartment of the plant cell. In order to achieve localization in a particular compartment, however, it is possible for example to link the coding region to DNA sequences which ensure the localization in a specific compartment. Such sequences are known to the skilled worker (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give intact plants. In principle, the transgenic plants may be plants of any plant species, that is to say both monocotyledonous and dicotyledonous plants.

Thus, transgenic plants can be obtained which feature modified properties as the result of overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active compounds.

When the active compounds according to the invention are used in transgenic crops, in addition to the effects on harmful plants observed in other crops, effects specific to the application in the particular transgenic crop often occur, for example an altered or specifically extended weed spectrum which can be controlled, altered application rates which can be used for the application, preferably good combinability with the herbicides toward which the transgenic crop is resistant, and influencing of growth and yield of the transgenic crop plants.

The invention therefore also relates to the use of the compounds of the formula (I) according to the invention and/or their salts as herbicides for controlling harmful plants in transgenic crop plants.

The use according to the invention for the control of harmful plants or for growth regulation of plants also includes the case in which the active compound of the formula (I) or its salt is not formed from a precursor substance ("prodrug") until after application on the plant, in the plant or in the soil.

The compounds (I) according to the invention can be employed in the customary preparations in the form of wettable powders, emulsifiable concentrates, sprayable solutions, dusts or granules. The invention therefore also relates to herbicidal and plant-growth-regulating compositions which comprise the compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for scattering and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and further additives, are also known and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active ethylene oxide adducts], Wiss. Verlagsgesell., Stuttgart 1976; Winnacker-Küchler, "Chemische Technologie" [Chemical technology], volume 7, C. Hanser Verlag Munich, 4th Ed. 1986.

Wettable powders are preparations which are uniformly dispersible in water and which, in addition to the active substance, also comprise ionic and/or nonionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, besides a diluent or inert substance. To prepare the wettable powders, the herbicidally active substances are ground finely, for example in customary apparatuses such as hammer mills, blower mills and air-jet mills, and mixed with the formulation auxiliaries, either simultaneously or subsequently.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylarylpolyglycol ethers, fatty alcohol polyglycol ethers, propylene oxide/ethylene oxide condensates, alkyl polyethers, sorbitan esters such as, for example, sorbitan fatty acid esters or polyoxyethylene sorbitan esters such as, for example, polyoxyethylene sorbitan fatty acid esters.

Dusts are obtained by grinding the active substance with finely divided solid materials such as, for example, talc, natural clays such as kaolin, bentonite and pyrophyllite, or diatomaceous earth.

Suspension concentrates can be water- or oil-based. They can be prepared for example by wet-grinding by means of commercially available bead mills, if appropriate with addition of surfactants as already listed above for example in the case of the other formulation types. Emulsions, for example oil-in-water emulsions (EW), can be prepared for example by means of stirrers, colloid mills and/or static mixers using aqueous organic solvents and, if appropriate, surfactants, as have already been mentioned for example above for the other formulation types.

Granules can be prepared either by spraying the active substance onto adsorptive, granulated inert material, or by applying active substance concentrates to the surface of carriers such as sand, kaolinites or granulated inert material with the aid of stickers, for example polyvinyl alcohol, sodium polyacrylate or else mineral oils. Suitable active substances can also be granulated in the manner which is customary for the production of fertilizer granules, if desired as a mixture with fertilizers.

Water-dispersible granules are generally prepared by customary methods such as spray drying, fluidized-bed granulation, disk granulation, mixing with high-speed stirrers, and extrusion without solid inert material. To prepare disk granules, fluidized-bed granules, extruder granules and spray granules, see, for example, methods in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57.

For further details of the formulation of crop protection products see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally from 0.1 to 99% by weight, in particular from 0.1 to 95% by weight, of active compound of the formula (I) and/or its salts.

In wettable powders, the active compound concentration is, for example, from about 10 to 90% by weight; the remainder to 100% by weight consists of customary formulation constituents. In the case of emulsifiable concentrates, the active compound concentration may be from about 1 to 90% by weight, preferably from 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In water-dispersible granules, the active compound content depends partly on whether the active compound is present in solid or liquid form-and which granulation assistants, fillers, etc. are used. In the granules dispersible in water, the content of active compound is, for example, between 1 and 95% by weight, preferably between 10 and 80% by weight.

In addition, the active compound formulations mentioned optionally comprise the respective customary adhesives, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the formula (I) or salts thereof may be used as such or in the form of their preparations (formulations) combined with other pesticidally active substances, for example insecticides, acaricides, nematicides, herbicides, fungicides, safeners, fertilizers and/or growth regulators, for example as a finished formulation or as tank mixes. The combination formulations can be prepared on the basis of the abovementioned formulations, while taking account of the physical properties and stabilities of the active compounds to be combined.

Active substances which can be employed in combination with the compounds according to the invention in mixed formulations or in the tank mix are, for example, known active substances which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 14th edition, The British Crop Protection Council and the Royal Soc. of Chemistry, 2003 and the literature cited therein. Known herbicides or plant growth regulators which can be combined with the compounds according to the invention are, for example, the following active substances (the compounds are either designated by the common name according to the International Organization for-Standardization (ISO) or by the chemical name or the code number) and always comprise all use forms such as acids, salts, esters and isomers such as stereoisomers and optical isomers. In this context, one and in some cases also several use forms are mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, BAH-043, BAS-140H, BAS-693H, BAS-714H, BAS-762H, BAS-776H, BAS-800H, beflubutamid, benazolin, benazolin-ethyl, bencarbazone, benfluralin, benfuresate, bensulide, bensulfuron-methyl, bentazone, benzfendizone, benzobicyclon, benzofenap, benzofluor, benzoylprop, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPIC, esprocarb, ethalfluralin, ethamethsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, fenoprop, fenoxaprop, fenoxaprop-P, fenoxaprop-ethyl, fenoxaprop-P-ethyl, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchioralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, L-glufosinate (glufosinate-P), L-glufosinate-ammonium, glufosinate-ammonium, glufosinate-P-sodium, glyphosate, glyphosate-isopropylammonium, H-9201, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HNPC-9908, HOK-201, HW-02, imazamethabenz, imazamethabenz-methyl, imazamox, imazamox-ammonium, imazapic, imazapyr, imazapyr-isopropylammonium, imazaquin, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, KUH-071, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, methazole, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogen sulfate, monolinuron, monosulfuron, monosulfuron ester, monuron, MT 128, MT-5950, i.e. N-[3-chloro-4-(1-methylethyl)phenyl]-2-methylpentanamide, NGGC-011, naproanilide, napropamide, naptalam, NC-620, NC-310, i.e. 4-(2,4-dichlorobenzoyl)-1-methyl-5-benzyloxypyrazole, neburon, nicosulfuron, nipyraclofen, nitralin, nitrofen, nitrophenolat-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazol, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, sulcotrione, sulf-allate (CDEC), sulfentrazone, sulfometuron, sulfometuron-methyl, sulfosate (glyphosate-trimesium), sulfosulfuron, SYN-449, SYN-523, SYP-249, SYP-298, SYP-300, tebutam, tebuthiuron, tecnazene, tefuryltrione, tembotrione, tepraloxydim, terbacil, terbucarb, terbuchlor, terbumeton, terbuthylazine, terbutryne, TH-547, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0166, ZJ-0270, ZJ-0543, ZJ-0862 and the following compounds

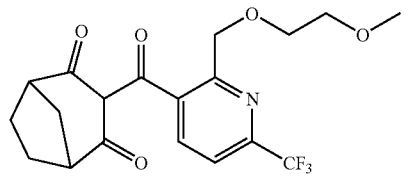

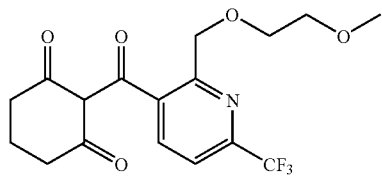

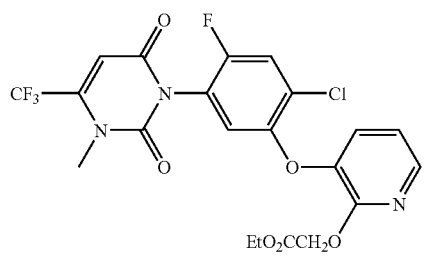

SYN-523

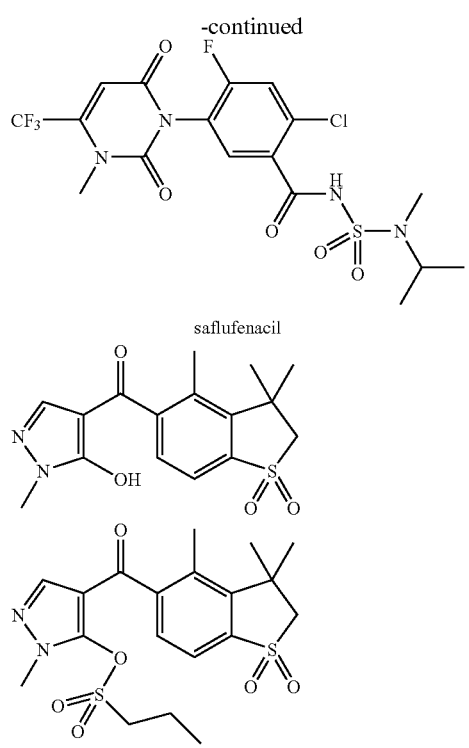

saflufenacil

The selective control of harmful plants in crops of useful plants and ornamentals is of particular interest. Although the compounds (I) according to the invention already feature a very good sufficient selectivity in many crops, it is possible, in principle, that phytotoxicities on the crop plants occur in some crops and mainly also in the case of mixtures with other herbicides which are less selective. In this respect, combinations of compounds (I) according to the invention which comprise the compounds (I) or their combinations with other herbicides or pesticides and safeners are of particular interest. The safeners, which are employed in such a proportion that they act as antidotes, reduce the phytotoxic side effects of the herbicides/pesticides employed, for example in economically important crops such as cereals (wheat, barley, rye, maize, rice, sorghum/millet), sugarbeet, sugar cane, oilseed rape, cotton and soya, preferably cereals. For example, the following groups of compounds are suitable as safeners for the compounds (I) and their combinations with further pesticides:

A) Compounds of the formula (S-I),

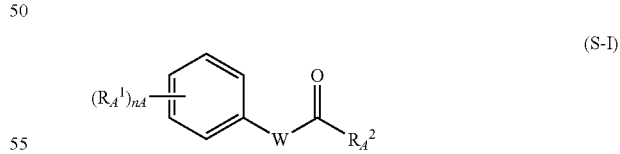

(S-I)

where the symbols and indices have the following meanings:
$n_A$ is a natural number from 0 to 5, preferably 0 to 3;
$R_A^1$ is halogen, $(C_1$-$C_4)$-alkyl, $(C_1$-$C_4)$-alkoxy, nitro or $(C_1$-$C_4)$-haloalkyl;
$W_A$ is an unsubstituted or substituted divalent heterocyclic radical from the group consisting of partially unsaturated or aromatic five-membered heterocycles having 1 to 3 ring heteroatoms of the type N or O, where at least one nitrogen atom and at most one oxygen atom is present in the ring, preferably a radical from the group consisting of $(W_A^1)$ to $(W_A^4)$,

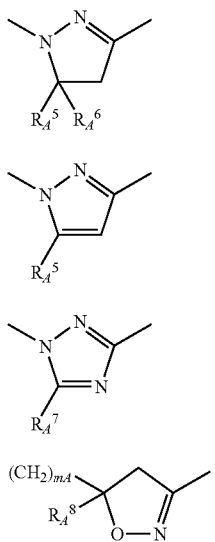

(W$_A^1$)

(W$_A^2$)

(W$_A^3$)

(W$_A^4$)

m$_A$ is 0 or 1;

R$_A^2$ is OR$_A^3$, SR$_A^3$ or NR$_A^3$R$_A^4$ or a saturated
or unsaturated 3- to 7-membered heterocycle having at least one nitrogen atom and up to 3 heteroatoms, preferably from the group consisting of O and S, which is attached via the nitrogen atom to the carbonyl group in (S-I) and which is unsubstituted or substituted by radicals selected from the group consisting of (C$_1$-C$_4$)-alkyl, (C$_1$-C$_4$)-alkoxy and optionally substituted phenyl, preferably a radical of the formula OR$_A^3$, NHR$_A^4$ or N(CH$_3$)$_2$, in particular of the formula OR$_A^3$;

R$_A^3$ is hydrogen or an unsubstituted or substituted aliphatic hydrocarbon radical, preferably having a total of 1 to 18 carbon atoms;

R$_A^4$ is hydrogen, (C$_1$-C$_6$)-alkyl, (C$_1$-C$_6$)-alkoxy or substituted or unsubstituted phenyl;

R$_A^5$ is H, (C$_1$-C$_8$)-alkyl, (C$_1$-C$_8$)-haloalkyl, (C$_1$-C$_4$)-alkoxy-(C$_1$-C$_8$)-alkyl, cyano or COOR$_A^9$ where R$_A^9$ is hydrogen, (C$_1$-C$_8$)-alkyl, (C$_1$-C$_8$)-haloalkyl, (C$_1$-C$_4$)-alkoxy-(C$_1$-C$_4$)-alkyl, (C$_1$-C$_6$)-hydroxyalkyl, (C$_3$-C$_{12}$)-cycloalkyl or tri-(C$_1$-C$_4$)-alkylsilyl;

R$_A^6$, R$_A^7$, R$_A^8$ are identical or different and are hydrogen, (C$_1$-C$_8$)-alkyl, (C$_1$-C$_8$)-haloalkyl, (C$_3$-C$_{12}$)-cycloalkyl or substituted or unsubstituted phenyl;

preferably:
a) compounds of the type of the dichlorophenylpyrazoline-3-carboxylic acid, preferably compounds such as ethyl 1-(2,4-dichlorophenyl)-5-(ethoxycarbonyl)-5-methyl-2-pyrazoline-3-carboxylate (S1-1) ("mefenpyr-diethyl", see Pestic. Man.), and related compounds, as described in WO 91/07874;
b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds, as described in EP-A-333 131 and EP-A-269 806;
c) compounds of the type of the triazolecarboxylic acids, preferably compounds such as fenchlorazole(-ethyl ester), i.e. ethyl 1-(2,4-dichlorophenyl)-5-trichloromethyl-(1H)-1,2,4-triazole-3-carboxylate (S1-6), and related compounds, as described in EP-A-174 562 and EP-A-346 620;
d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II),

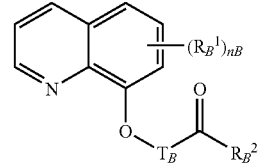

(S-II)

where the symbols and indices have the following meanings:
R$_B^1$ is halogen, (C$_1$-C$_4$)-alkyl, (C$_1$-C$_4$)-alkoxy, nitro or (C$_1$-C$_4$)-haloalkyl;
n$_B$ is a natural number from 0 to 5, preferably from 0 to 3;
R$_B^2$ OR$_B^3$, SR$_B^3$ or NR$_B^3$R$_B^4$ or a saturated or unsaturated 3- to 7-membered heterocycle having at least one nitrogen atom and up to 3 heteroatoms, preferably from the group consisting of O and S, which is attached via the nitrogen atom to the carbonyl group in (S-II) and is unsubstituted or substituted by radicals selected from the group consisting of (C$_1$-C$_4$)-alkyl, (C$_1$-C$_4$)-alkoxy or optionally substituted phenyl, preferably a radical of the formula OR$_B^3$, NHR$_B^4$ or N(CH$_3$)$_2$, in particular of the formula OR$_B^3$;
R$_B^3$ is hydrogen or an unsubstituted or substituted aliphatic hydrocarbon radical having preferably a total of 1 to 18 carbon atoms;
R$_B^4$ is hydrogen, (C$_1$-C$_6$)-alkyl, (C$_1$-C$_6$)-alkoxy or substituted or unsubstituted phenyl;
T$_B$ is a (C$_1$- or C$_2$)-alkanediyl chain which is unsubstituted or substituted by one or two (C$_1$-C$_4$)-alkyl radicals or by [(C$_1$-C$_3$)-alkoxy]carbonyl;

preferably:
a) compounds of the type of the 8-quinolinoxyacetic acid (S2), preferably 1-methylhexyl(5-chloro-8-quinolinoxy) acetate (common name "cloquintocet-mexyl" (S2-1) (see Pestic. Man.), 1,3-dimethylbut-1-yl(5-chloro-8-quinolinoxy)acetate (S2-2), 4-allyloxybutyl(5-chloro-8-quinolinoxy)acetate (S2-3), 1-allyloxyprop-2-yl(5-chloro-8-quinolinoxy)acetate (S2-4), ethyl(5-chloro-8-quinolinoxy)acetate (S2-5), methyl(5-chloro-8-quinolinoxy)acetate (S2-6), allyl(5-chloro-8-quinolinoxy) acetate (S2-7), 2-(2-propylideneiminoxy)-1-ethyl(5-chloro-8-quinolinoxy)acetate (S2-8), 2-oxoprop-1-yl(5-chloro-8-quinolinoxy)acetate (S2-9) and related compounds, as described in EP-A-86 750, EP-A-94 349 and EP-A-191 736 or EP-A-0 492 366, and also their hydrates and salts, as described in WO-A-2002/034048.
b) Compounds of the type of the (5-chloro-8-quinolinoxy) malonic acid, preferably compounds such as diethyl(5-chloro-8-quinolinoxy)malonate, diallyl(5-chloro-8-quinolinoxy)malonate, methyl ethyl(5-chloro-8- quinolinoxy)malonate and related compounds, as described in EP-A-0 582 198.

C) Compounds of the formula (S-III)

(S-III)

where the symbols and indices have the following meanings:

$R_C^1$ is $(C_1$-$C_4)$-alkyl, $(C_1$-$C_4)$-haloalkyl, $(C_2$-$C_4)$-alkenyl, $(C_2$-$C_4)$-haloalkenyl, $(C_3$-$C_7)$-cycloalkyl, preferably dichloromethyl;

$R_C^2$, $R_C^3$ are identical or different and are hydrogen, $(C_1$-$C_4)$-alkyl, $(C_2$-$C_4)$-alkenyl, $(C_2$-$C_4)$-alkynyl, $(C_1$-$C_4)$-haloalkyl, $(C_2$-$C_4)$-haloalkenyl, $(C_1$-$C_4)$-alkylcarbamoyl-$(C_1$-$C_4)$-alkyl, $(C_2$-$C_4)$-alkenylcarbamoyl-$(C_1$-$C_4)$-alkyl, $(C_1$-$C_4)$-alkoxy-$(C_1$-$C_4)$-alkyl, dioxolanyl-$(C_1$-$C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the type of the dichloroacetamides which are frequently used as pre-emergence safeners (soil-acting safeners), such as, for example, "dichlormid" (see Pestic.Man.) (=N,N-diallyl-2,2-dichloroacetamide), "R-29148" (=3-dichloroacetyl-2,2,5-trimethyl-1,3-oxazolidine from Stauffer), "R-28725" (=3-dichloroacetyl-2,2-dimethyl-1,3-oxazolidine from Stauffer), "benoxacor" (see Pestic. Man.) (=4-dichloroacetyl-3,4-dihydro-3-methyl-2H-1,4-benzoxazine), "PPG-1292" (=N-allyl-N-[(1,3-dioxolan-2-yl)methyl] dichloroacetamide from PPG Industries), "DKA-24" (=N-allyl-N-[(allylaminocarbonyl)methyl] dichloroacetamide from Sagro-Chem), "AD-67" or "MON 4660" (=3-dichloroacetyl-1-oxa-3-azaspiro[4,5]decane from Nitrokemia or Monsanto), "TI-35" (=1-dichloroacetylazepane from TRI-Chemical RT)

"diclonon" (dicyclonone) or "BAS145138" or "LAB145138" (=3-dichloroacetyl-2,5,5-trimethyl-1,3-diazabicyclo[4.3.0]nonane from BASF) and "furilazole" or "MON 13900" (see Pestic. Man.) (=(RS)-3-dichloroacetyl-5-(2-furyl)-2,2-dimethyloxazolidine).

D) N-Acylsulfonamides of the formula (S-IV) and their salts,

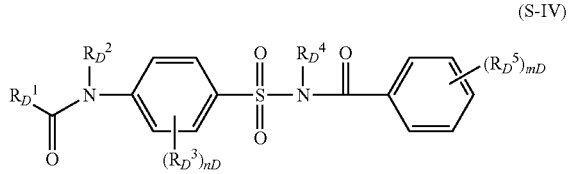

(S-IV)

in which $R_D^1$ is hydrogen, a hydrocarbon radical, a hydrocarbonoxy radical, a hydrocarbonthio radical or a heterocyclyl radical which is preferably attached via a carbon atom, where each of the 4 last-mentioned radicals are unsubstituted or substituted by one or more identical or different radicals selected from the group consisting of halogen, cyano, nitro, amino, hydroxyl, carboxy, formyl, carbonamide, sulfonamide and radicals of the formula —$Z^a$—$R^a$, where each hydrocarbon moiety has preferably 1 to 20 carbon atoms and a carbon-containing radical $R_D^1$ including substituents has preferably 1 to 30 carbon atoms;

$R_D^2$ is hydrogen or $(C_1$-$C_4)$-alkyl, preferably hydrogen, or $R_D^1$ and $R_D^2$ together with the group of the formula —CO—N— are the radical of a 3- to 8-membered saturated or unsaturated ring;

$R_D^3$ are identical or different and are halogen, cyano, nitro, amino, hydroxyl, carboxy, formyl, $CONH_2$, $SO_2NH_2$ or a radical of the formula —$Z^b$—$R^b$;

$R_D^4$ is hydrogen or $(C_1$-$C_4)$-alkyl, preferably H;

$R_D^5$ are identical or different and are halogen, cyano, nitro, amino, hydroxyl, carboxy, CHO, $CONH_2$, $SO_2NH_2$ or a radical of the formula —$Z^c$—$R^c$;

$R^a$ is a hydrocarbon radical or a heterocyclyl radical, where each of the two last-mentioned radicals is unsubstituted or substituted by one or more identical or different radicals selected from the group consisting of halogen, cyano, nitro, amino, hydroxyl, mono- and di-[$(C_1$-$C_4)$-alkyl]amino, or an alkyl radical in which a plurality, preferably 2 or 3, non-adjacent $CH_2$ groups are in each case replaced by an oxygen atom;

$R^b$, $R^c$ are identical or different and are a hydrocarbon radical or a heterocyclyl radical, where each of the two last-mentioned radicals is unsubstituted or substituted by one or more identical or different radicals selected from the group consisting of halogen, cyano, nitro, amino, hydroxyl, phosphoryl, halo-$(C_1$-$C_4)$-alkoxy, mono- and di-[$(C_1$-$C_4)$-alkyl]amino, or an alkyl radical in which a plurality, preferably 2 or 3, non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond indicated on the right-hand side of the respective divalent group is the bond to the radical $R^a$ and where the R* in the 5 last-mentioned radicals independently of one another are in each case H, $(C_1$-$C_4)$-alkyl or halo-$(C_1$-$C_4)$-alkyl;

$Z^b$,$Z^c$ independently of one another are a direct bond or a divalent group of the formula —O—, —S—, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*— or —NR*—CO—, where the bond indicated on the right-hand side of the respective divalent group is the bond to the radical $R^b$ or $R^c$ and where the R* in the 5 last-mentioned radicals independently of one another are in each case H, $(C_1$-$C_4)$-alkyl or halo-$(C_1$-$C_4)$-alkyl;

$n_D$ is an integer from 0 to 4, preferably 0, 1 or 2, in particular 0 or 1, and $m_D$ is an integer from 0 to 5, preferably 0, 1, 2 or 3, in particular 0, 1 or 2.

E) Acylsulfamoylbenzamides of the general formula (S-V), if appropriate also in salt form,

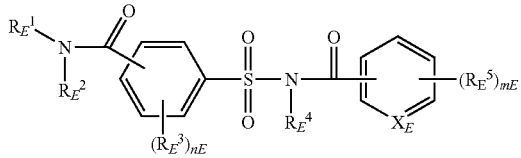

(S-V)

in which
$X_E$ is CH or N;
$R_E^1$ is hydrogen, heterocyclyl or a hydrocarbon radical, where the two last-mentioned radicals are optionally substituted by one or more, identical or different radicals selected from the group consisting of halogen, cyano, nitro, amino, hydroxyl, carboxy, CHO, CONH$_2$, SO$_2$NH$_2$ and $Z^a$—$R^a$;
$R_E^2$ is hydrogen, hydroxyl, (C$_1$-C$_6$)-alkyl, (C$_2$-C$_6$)-alkenyl, (C$_2$-C$_6$)-alkynyl, (C$_1$-C$_6$)-alkoxy, (C$_2$-C$_6$)-alkenyloxy, where the five last-mentioned radicals are optionally substituted by one or more identical or different radicals selected from the group consisting of halogen, hydroxyl, (C$_1$-C$_4$)-alkyl, (C$_1$-C$_4$)-alkoxy and (C$_1$-C$_4$)-alkylthio, or
$R_E^1$ and $R_E^2$ together with the nitrogen atom carrying them are a 3- to 8-membered saturated or unsaturated ring;
$R_E^3$ is halogen, cyano, nitro, amino, hydroxyl, carboxy, CHO, CONH$_2$, SO$_2$NH$_2$ or $Z^b$—$R^b$;
$R_E^4$ is hydrogen, (C$_1$-C$_4$)-alkyl, (C$_2$-C$_4$)-alkenyl or (C$_2$-C$_4$)-alkynyl;
$R_E^5$ is halogen, cyano, nitro, amino, hydroxyl, carboxy, phosphoryl, CHO, CONH$_2$, SO$_2$NH$_2$ or $Z^c$—$R^c$;
$R^a$ is a (C$_2$-C$_{20}$)-alkyl radical whose carbon chain is interrupted once or more than once by oxygen atoms, heterocyclyl or a hydrocarbon radical, where the two last-mentioned radicals are optionally substituted by one or more identical or different radicals selected from the group consisting of halogen, cyano, nitro, amino, hydroxyl, mono- and di-[(C$_1$-C$_4$)-alkyl]amino;
$R^b$, $R^c$ are identical or different and are a (C$_2$-C$_{20}$)-alkyl radical whose carbon chain is interrupted once or more than once by oxygen atoms, heterocyclyl or a hydrocarbon radical, where the two last-mentioned radicals are optionally substituted by one or more identical or different radicals selected from the group consisting of halogen, cyano, nitro, amino, hydroxyl, phosphoryl, (C$_1$-C$_4$)-haloalkoxy, mono- and di-[(C$_1$-C$_4$)-alkyl]amino;
$Z^a$ is a divalent moiety from the group consisting of O, S, CO, CS, C(O)O, C(O)S, SO, SO$_2$, NR$^d$, C(O)NR$^d$ and SO$_2$NR$^d$;
$Z^b$, $Z^c$ are identical or different and are a direct bond or a divalent moiety selected from the group consisting of O, S, CO, CS, C(O)O, C(O)S, SO, SO$_2$, NR$^d$, SO$_2$NR$^d$ and C(O)NR$^d$;
$R^d$ is hydrogen, (C$_1$-C$_4$)-alkyl or (C$_1$-C$_4$)-haloalkyl;
$n_E$ is an integer from 0 to 4, and
$m_E$ if X is CH, is an integer from 0 to 5, and if X is N, is an integer from 0 to 4;
from among these preference is given to compounds (also in the form of their salts) of the type of the acylsulfamoylbenzamides, for example of the formula (S-VI) below, which are known, for example, from WO 99/16744,

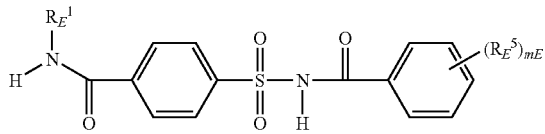

(S-VI)

for example those in which
$R_E^1$=cyclopropyl and $R_E^5$=2-OMe ("cyprosulfamide", S3-1),
$R_E^1$=cyclopropyl and $R_E^5$=5-Cl-2-OMe (S3-2),
$R_E^1$=ethyl and $R_E^5$=2-OMe (S3-3),
$R_E^1$=isopropyl and $R_E^5$=5-Cl-2-OMe (S3-4) and
$R_E^1$=isopropyl and $R_E^5$=2-OMe (S3-5);

F) Compounds of the type of the N-acylsulfamoylphenylureas of the formula (S-VII) known, for example, from EP-A-365484,

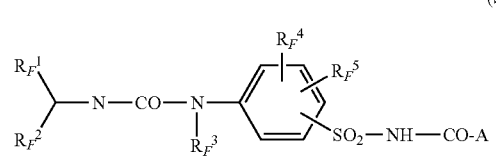

(S-VII)

in which
A is a radical from the group consisting of

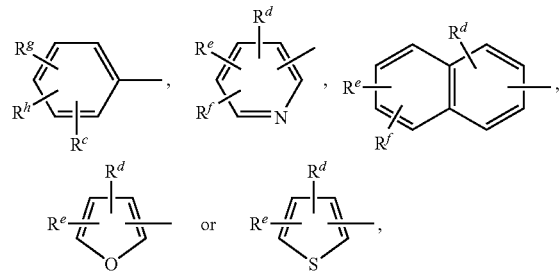

$R_F^1$ and $R_F^2$ independently of one another are hydrogen, (C$_1$-C$_8$)-alkyl, (C$_3$-C$_8$)-cycloalkyl, (C$_3$-C$_6$)-alkenyl, (C$_3$-C$_6$)-alkynyl,

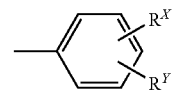

or (C$_1$-C$_4$)-alkoxy which is substituted by (C$_1$-C$_4$)-alkoxy

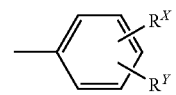

or
$R_F^1$ and $R_F^2$ together are a (C$_4$-C$_6$)-alkylene bridge or a (C$_4$-C$_6$)-alkylene bridge interrupted by oxygen, sulfur, SO, SO$_2$, NH or —N(C$_1$-C$_4$-alkyl)-,
$R_F^3$ is hydrogen or (C$_1$-C$_4$)-alkyl, $R_F^4$ and $R_F^5$ independently of one another are hydrogen, halogen, cyano, nitro, trifluoromethyl, $C_1$-$C_4$-alkyl, $C_1$-$C_4$-alkoxy, $C_1$-$C_4$-alkylthio, $C_1$-$C_4$-alkylsulfinyl, $C_1$-$C_4$-alkylsulfonyl, —COOR$^j$, —CONR$^k$R$^m$, —COR$^n$, —SO$_2$NR$^k$R$^m$ or —OSO$_2$—C$_1$-C$_4$-alkyl, or R$^a$ and R$^b$ together are a (C$_3$-C$_4$)-alkylene bridge which may be substituted by halogen or C$_1$-C$_4$-alkyl, or a (C$_3$-C$_4$)-alkenylene bridge which may be substituted by halogen or (C$_1$-C$_4$)-alkyl, or a C$_4$-alkadienylene bridge which may be substituted by halogen or (C$_1$-C$_4$)-alkyl, and $R^g$ and $R^h$ independently of one another are hydrogen, halogen, $C_1$-$C_4$-alkyl, trifluoromethyl, methoxy, methylthio or —COOR$^j$, where $R^c$ is hydrogen, halogen, ($C_1$-$C_4$)-alkyl or methoxy, $R^d$ is hydrogen, halogen, nitro, ($C_1$-$C_4$)-alkyl, ($C_1$-$C_4$)-alkoxy, ($C_1$-$C_4$)-alkylthio, ($C_1$-$C_4$)-alkylsulfinyl, ($C_1$-$C_4$)-alkylsulfonyl, —COOR$^j$ or —CONR$^k$R$^m$, $R^e$ is hydrogen, halogen, $C_1$-$C_4$-alkyl, —COOR$^j$, trifluoromethyl or methoxy, or R$^d$ and R$^e$ together are a ($C_3$-$C_4$)-alkylene bridge, $R^f$ is hydrogen, halogen or ($C_1$-$C_4$)-alkyl, $R^X$ and $R^Y$ independently of one another are hydrogen, halogen, ($C_1$-$C_4$)-alkyl, ($C_1$-$C_4$)-alkoxy, ($C_1$-$C_4$)-alkylthio, —COOR$^4$, trifluoromethyl, nitro or cyano, $R^j$, $R^k$ and $R^m$ independently of one another are hydrogen or ($C_1$-$C_4$)-alkyl, $R^k$ and $R^m$ together are a ($C_4$-$C_6$)-alkylene bridge or a $C_4$-$C_6$-alkylene bridge which is interrupted by oxygen, NH or —N($C_1$-$C_4$-alkyl), and $R^n$ is ($C_1$-$C_4$)-alkyl, phenyl or halogen-, ($C_1$-$C_4$)-alkyl-, methoxy-, nitro- or trifluoromethyl-substituted phenyl, from among these preference is given to:

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea,

1-[4-(N-naphthoylsulfamoyl)phenyl]-3,3-dimethylurea, including the stereoisomers, and the salts customary in agriculture, G) active compounds from the class of the hydroxyaromatics and aromatic-aliphatic carboxylic acid derivatives, for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;

H) active compounds from the class of the 1,2-dihydroquinoxalin-2-ones, for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO 2005112630, I) active compounds which, in addition to a herbicidal action against harmful plants, also have safener action on crop plants such as rice, such as, for example, "dimepiperate" or "MY-93" (see Pestic. Man.) (=S-1-methyl-1-phenylethyl piperidine-1-thiocarboxylate), which is known as safener for rice against damage by the herbicide molinate, "daimuron" or "SK 23" (see Pestic. Man.) (=1-(1-methyl-1-phenylethyl)-3-p-tolylurea), which is known as safener for rice against damage by the herbicide imazosulfuron, "cumyluron"="JC-940" (=3-(2-chlorophenylmethyl)-1-(1-methyl-1-phenyl-ethyl)urea, see JP-A-60087254), which is known as safener for rice against damage by a number of herbicides, "methoxyphenone" or "NK 049" (=3,3'-dimethyl-4-methoxybenzophenone), which is known as safener for rice against damage by a number of herbicides, "CSB" (=1-bromo-4-(chloromethylsulfonyl)benzene) (CAS Reg. No. 54091-06-4 from Kumiai), which is known as safener against damage by a number of herbicides in rice, K) compounds of the formula (S-IX),
as described in WO-A-1998/38856

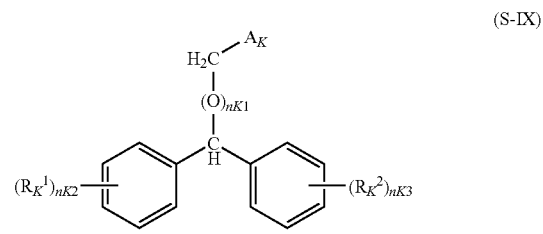

(S-IX)

in which the symbols and indices have the following meanings:

$R_K^1$, $R_K^2$ independently of one another are halogen, ($C_1$-$C_4$)-alkyl, ($C_1$-$C_4$)-alkoxy, ($C_1$-$C_4$)-haloalkyl, ($C_1$-$C_4$)-alkylamino, di-($C_1$-$C_4$)-alkylamino, nitro;

$A_K$ is COOR$_K^3$ or COOR$_K^4$ $R_K^3$, $R_K^4$ independently of one another are hydrogen, ($C_1$-$C_4$)-alkyl, ($C_2$-$C_6$)-alkenyl, ($C_2$-$C_4$)-alkynyl, cyanoalkyl, ($C_1$-$C_4$)-haloalkyl, phenyl, nitrophenyl, benzyl, halobenzyl, pyridinylalkyl or alkylammonium, $n_K^1$ is 0 or 1, $n_K^2$, $n_K^3$ independently of one another are 0, 1 or 2, preferably:

methyl(diphenylmethoxy)acetate (CAS-Reg. No.: 41858-19-9),

L) compounds of the formula (S-X),
as described in WO A-98/27049

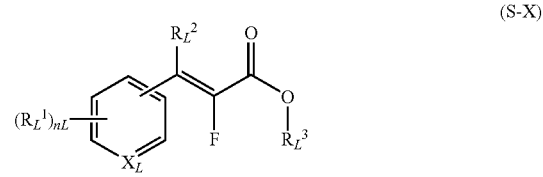

(S-X)

in which the symbols and indices have the following meanings:

$X_L$ is CH or N, $n_L$ is, in the case that X=N, an integer from 0 to 4 and in the case that X=CH, an integer from 0 to 5, $R_L^1$ is halogen, ($C_1$-$C_4$)-alkyl, ($C_1$-$C_4$)-haloalkyl, ($C_1$-$C_4$)-alkoxy, ($C_1$-$C_4$)-nitro, ($C_1$-$C_4$)-alkylthio, ($C_1$-$C_4$)-alkylsulfonyl, ($C_1$-$C_4$)-alkoxycarbonyl, optionally substituted phenyl, optionally substituted phenoxy, $R_L^2$ is hydrogen or ($C_1$-$C_4$)-alkyl, $R_L^3$ is hydrogen, $(C_1-C_8)$-alkyl, $(C_2-C_4)$-alkenyl, $(C_2-C_4)$-alkynyl or aryl, where each of the carbon-containing radicals mentioned above is unsubstituted or substituted by one or more, preferably by up to three, identical or different radicals selected from the group consisting of halogen and alkoxy; or salts thereof.

M) active compounds from the class of the 3-(5-tetrazolylcarbonyl)-2-quinolones, for example
   1,2-dihydro-4-hydroxy-1-ethyl-3-(5-tetrazolylcarbonyl)-2-quinolone (CAS Reg. No.: 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII)
   as described in WO-A-2007023719 and WO-A-2007023764

(S-XI)

(S-XII)

in which
$R_N^1$ is halogen, $(C_1-C_4)$-alkyl, methoxy, nitro, cyano, $CF_3$, $OCF_3$,
Y, Z independently of one another are O or S,
$n_N$ is an integer from 0 to 4,
$R_N^2$ is $(C_1-C_{16})$-alkyl, $(C_2-C_6)$-alkenyl, $(C_3-C_6)$-cycloalkyl, aryl, benzyl, halobenzyl,
$R_N^3$ is hydrogen, $(C_1-C_6)$alkyl;

O) one or more compounds from the group consisting of:
   1,8-naphthalic anhydride,
   O,O-diethyl S-2-ethylthioethyl phosphorodithioate (disulfoton),
   4-chlorophenyl methylcarbamate (mephenate),
   O,O-diethyl O-phenyl phosphorothioate (dietholate),
   4-carboxy-3,4-dihydro-2H-1-benzopyran-4-acetic acid (CL-304415, CAS Reg. No.: 31541-57-8),
   2-propenyl 1-oxa-4-azaspiro[4.5]decane-4-carbodithioate (MG-838, CAS Reg. No.: 133993-74-5),
   methyl[(3-oxo-1H-2-benzothiopyran-4(3H)-ylidene)methoxy]acetate (from WO-A-98/13361; CAS Reg. No.: 205121-04-6),
   cyanomethoxyimino(phenyl)acetonitrile (cyometrinil),
   1,3-dioxolan-2-ylmethoxyimino(phenyl)acetonitrile (oxabetrinil),
   4'-chloro-2,2,2-trifluoroacetophenone O-1,3-dioxolan-2-ylmethyloxime (fluxofenim),
   4,6-dichloro-2-phenylpyrimidine (fenclorim),
   benzyl 2-chloro-4-trifluoromethyl-1,3-thiazole-5-carboxylate (flurazole),
   2-dichloromethyl-2-methyl-1,3-dioxolane (MG-191),
   including the stereoisomers, and the salts customary in agriculture.

The weight ratios of herbicide (mixture) to safener generally depend on the herbicide application rate and the effectiveness of the safener in question and may vary within wide limits, for example in the range from 200:1 to 1:200, preferably from 100:1 to 1:100, in particular from 20:1 to 1:20. The safeners may be formulated analogously to the compounds (I) or their mixtures with other herbicides/pesticides and be provided and used as a finished formulation or as a tank mix with the herbicides.

For use, the herbicide or herbicide/safener formulations which are present in commercially available form are, if appropriate, diluted in the customary manner, for example using water in the case of wettable powders, emulsifiable concentrates, dispersions and water-dispersible granules. Preparations in the form of dusts, granules for soil application or broadcasting and sprayable solutions are usually not diluted further with other inert substances prior to use.

The required application rate of the compounds of the formula (I) and/or their salts varies depending, inter alia, on external conditions such as temperature, humidity and the type of herbicide used. It can vary within wide limits. For the application of herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance. This applies both to application by the pre-emergence method and the post-emergence method, the post-emergence treatment generally being preferred.

The application as culm stabilizer may take place at various stages of the growth of the plants. Preferred is, for example, an application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below.

In the examples, the amounts (including percentages) refer to the weight, unless especially stated otherwise. If, in the context of the description and the examples, the terms "R" and "S" are given for the absolute configuration on a center of chirality of the stereoisomers of the formula (I), this RS nomenclature, follows, unless defined differently, the Cahn-Ingold-Prelog rule.

(A) SYNTHESIS EXAMPLES

Example A1

Methyl 5-(4-chlorophenyl)-3-methyl-1-(pyrimidin-5-yl)-1H-pyrazol-4-yl]acetate (see Table 2, Example 2-28)

a) Preparation of Methyl[5-(4-chlorophenyl)-3-methyl-1H-pyrazol-4-yl]acetate 2.236 g (45 mmol) of hydrazine hydrate were added to a solution of 10 g (37 mmol) of methyl 3-[(4-chlorophenyl)

carbonyl]-4-oxopentanoate in ethanol (100 ml). The mixture was heated under reflux for 6 hours and then added to water and extracted with dichloromethane. The combined organic phases were dried with magnesium sulfate, filtered and concentrated. This gave 6.9 g of product (63% of theory).

NMR (CDCl$_3$, 400 MHz): 2.28 (s, 3H); 3.5 (s, 2H); 3.7 (s, 3H); 7.39 (d, 2H); 7.5 (d, 2H).

b) Preparation of Methyl-[5-(4-chlorophenyl)-3-methyl-1-(pyrimidin-5-yl)-1H-pyrazol-4-yl]acetate 0.287 g (2 mmol) of cesium fluoride, 0.103 g (1 mmol) of copper(II) acetate and 0.212 g (2 mmol) of potassium tert-butoxide were added to 0.5 g (2 mmol) of methyl[5-(4-chlorophenyl)-3-methyl-1H-pyrazol-4-yl]acetate in 10 ml of dichloromethane. 0.234 g (2 mmol) of 5-pyrimidinylboronic acid was then added, and the mixture was stirred at 20° C. for 45 h. The mixture was then added to saturated ammonium chloride solution (10 ml) and extracted with dichloromethane. The combined organic phases were dried with magnesium sulfate, filtered and concentrated. The crude product was purified by preparative HPLC. This gave 0.040 g of product (5.8% of theory).

NMR (CDCl$_3$, 400 MHz): 2.36 (s, 3H); 3.4 (s, 2H); 3.71 (s, 3H); 7.2 (d, 2H); 7.41 (d, 2H); 8.53 (s, 2H); 9.05 (s, 1H).

Example A2

Methyl-[5-(4-chlorophenyl)-1-(2-chloropyrimidin-5-yl)-3-methyl-1H-pyrazol-4-yl]acetate (see Table 2, Example 2-29)

0.515 g (3 mmol) of copper(II) acetate and 0.306 ml (4 mmol) of pyridine were added to 0.5 g (2 mmol) of methyl [5-(4-chlorophenyl)-3-methyl-1H-pyrazol-4-yl]acetate in 10 ml of dichloromethane. 0.598 g (4 mmol) of 2-chloropyrimidine-5-boronic acid was then added, and the mixture was stirred at 20° C. for 24 h. The mixture was then added to 1 M HCl and extracted with dichloromethane. The combined organic phases were dried with magnesium sulfate, filtered and concentrated. The crude product was purified by preparative HPLC. This gave 0.015 g of product (2% of theory).

NMR (CDCl$_3$, 400 MHz): 2.34 (s, 3H); 3.39 (s, 2H); 3.71 (s, 3H); 7.2 (d, 2H); 7.45 (d, 2H); 8.52 (s, 2H).

Example A3

Methyl[3-methyl-5-phenyl-1-(pyrazin-2-yl)-1H-pyrazol-4-yl]acetate (see Table 11, Example 11-2)

0.378 g (3.330 mmol) of 3-hydrazinopyrazine in 12.5 ml of ethanol was added to 0.600 g (2.561 mmol) of methyl 4-oxo-3-(phenylcarbonyl)pentanoate, and the mixture was heated at 135° C. in a sealed vessel in a microwave oven for 1.5 h. The solvent was removed under reduced pressure, and the residue was taken up in dichloromethane and washed twice with in each case 25 ml of water. The combined organic phases were dried over sodium sulfate and the solvent was removed under reduced pressure. Chromatography of the residue gave 0.115 g (13.8% of theory) of a light-yellow wax.

NMR (CDCl$_3$, 300 MHz): 2.39 (s, 3H); 3.40 (s, 2H); 3.69 (s, 3H); 7.23 (m, 2H); 7.39 (m, 3H); 8.22 (dd, 1H); 8.38 (dd, 1H); 8.66 (d, 1H).

Example A4

[3-Methyl-5-phenyl-1-(pyrazin-2-yl)-1H-pyrazol-4-yl]acetic acid (see Table 10, Example 10-2)

0.073 g (1.819 mmol) of 2-molar aqueous sodium hydroxide solution was added to 0.165 g (0.455 mmol) of methyl[3-methyl-5-phenyl-1-(pyrazin-2-yl)-1H-pyrazol-4-yl]acetate (see A3) dissolved in 5 ml of methanol, and the mixture was stirred at 20° C. for 1 h. The methanol was removed under reduced pressure and the residue was poured into a mixture of 10 ml of water and 15 ml of dichloromethane. The aqueous phase was extracted with 15 ml of dichloromethane, acidified with concentrated hydrochloric acid (pH=3) and extracted three times with in each case 15 ml of dichloromethane. Drying of the combined organic phases and removal of the solvent under reduced pressure gave 0.080 g (59.7% of theory) of a colorless foamy solid, melting point 125° C.

NMR (CDCl$_3$, 300 MHz): 2.4 (s, 3H); 3.42 (s, 2H); 7.25 (m, 2H); 7.39 (m, 3H); 8.22 (dd, 1H); 8.39 (dd, 1H); 8.70 (d, 1H); 8.97 (br s, 1H).

Example A5

Methyl[1-(6-chloropyridazin-3-yl)-3-methyl-5-phenyl-1H-pyrazol-4-yl]acetate (see Table 5, Example 5-7)

a) Preparation of Methyl[1-(6-chloropyridazin-3-yl)-5-hydroxy-3-methyl-5-phenyl-4,5-dihydro-1H-pyrazol-4-yl]acetate 0.296 g (2.049 mmol) of 3-chloro-6-hydrazinylpyridazine in 5.00 ml of ethanol was added to 0.400 g (1.708 mmol) of methyl 4-oxo-3-(phenylcarbonyl)pentanoate, and the mixture was stirred at reflux for 8 h. The solvent was removed under reduced pressure which gave, after chromatography of the residue, 0.300 g (48% of theory) of a viscous yellow oil.

NMR (CDCl$_3$, 300 MHz): 1.94 (s, 3H); 2.81 (dd, 1H); 3.12 (dd, 1H); 3.67 (s, 3H); 4.91 (dd, 1H); 7.34 (d, 1H); 7.41 (d, 1H); 7.45 (m, 2H); 7.59 (m, 1H); 8.01 (d, 1H); 8.03 (d, 1H).

b) Preparation of Methyl-[1-(6-chloropyridazin-3-yl)-3-methyl-5-phenyl-1H-pyrazol-4-yl]acetate 0.111 g (2.772 mmol) of 2-molar aqueous sodium hydroxide solution was added to 0.200 g (0.554 mmol) of methyl[1-(6-chloropyridazin-3-yl)-5-hydroxy-3-methyl-5-phenyl-4,5-dihydro-1H-pyrazol-4-yl]acetate in 8 ml of methanol, and the mixture was stirred at 20° C. for 1 h. The methanol was removed under reduced pressure and the residue was poured into a mixture of 10 ml of water and 15 ml of dichloromethane. The aqueous phase was extracted with 15 ml of dichloromethane, acidified with concentrated hydrochloric acid (pH=3) and extracted three times with in each case 15 ml of dichloromethane. Drying of the combined organic phases and removal of the solvent under reduced pressure gave 0.207 g (99% of theory) of a brown wax-like solid, melting point 55° C.

NMR (CDCl$_3$, 300 MHz): 2.39 (s, 3H); 3.42 (s, 2H); 4.3 (s, 3H); 6.9 (d, 1H); 7.28 (m, 2H); 7.37 (m, 3H); 7.63 (d, 1H).

Example A6

[1-(6-Chloropyridazin-3-yl)-3-methyl-5-phenyl-1H-pyrazol-4-yl]acetic acid (see Table 4, Example 4-7)

0.058 g (1.444 mmol) of 2-molar aqueous sodium hydroxide solution was added to 0.099 g (0.289 mmol) of methyl[1-

(6-chloropyridazin-3-yl)-3-methyl-5-phenyl-1H-pyrazol-4-yl]acetate in 5.00 ml of methanol, and the mixture was stirred at 20° C. for 1 h. The methanol was removed under reduced pressure and the residue was poured into a mixture of 10 ml of water and 15 ml of dichloromethane. The aqueous phase was extracted with 15 ml of dichloromethane, acidified with concentrated hydrochloric acid (pH=3) and extracted three times with in each case 15 ml of dichloromethane. Drying of the combined organic phases and removal of the solvent under reduced pressure gave 0.052 g (54.7% of theory) of a brown wax-like solid.

NMR (CDCl$_3$, 300 MHz): 2.36 (s, 3H); 3.40 (s, 2H); 7.28 (m, 2H); 7.37 (m, 3H); 7.51 (d, 1H); 7.87 (br d, 1H).

Example A7

Methyl 3-[(4-chlorophenyl)carbonyl]-4-oxopentanoate (see Table 13, Example 13-13)

A solution of 10 g (51 mmol) of 1-(4-chlorophenyl)butane-1,3-dione (commercially available) dissolved in dimethyl sulfoxide was slowly added dropwise to 2.237 g (56 mmol) of sodium hydride in 200 ml of dimethyl sulfoxide such that the temperature did not exceed 30° C. The mixture was stirred at 20° C. for another 30 minutes. 8.558 g (56 mmol) of methyl bromoacetate in a little dimethyl sulfoxide were then slowly added dropwise at 0° C. The mixture was stirred at 20° C. for 4 hours. The reaction mixture was poured into ice-water and extracted with dichloromethane. The organic phase was washed repeatedly with water. Drying of the combined organic phases, removal of the solvent under reduced pressure and chromatography of the residue gave 7.750 g of product (56.7% of theory).

NMR (CDCl$_3$, 400 MHz): 2.19 (s, 3H); 2.99 (d, 1H); 3.03 (d, 1H); 3.69 (s, 3H); 4.95 (dd, 1H); 7.49 (d, 2H); 7.98 (d, 2H).

Example A8

Methyl 4-oxo-3-(pyridin-2-ylcarbonyl)pentanoate (see Table 13, Example 13-68)

a) Preparation of 1-(pyridin-2-yl)butane-1,3-dione

A sodium methoxide solution (28% in methanol) was added dropwise to a mixture of 10 g (73 mmol) of methyl picolinate and 25 ml (124 mmol) of acetone in 150 ml of tetrahydrofuran. The mixture was stirred at 20° C. for 3 hours and the solvent was removed under reduced pressure. The residue was taken up in water, acidified with 2-molar aqueous hydrochloric acid and extracted with dichloromethane. Drying of the combined organic phases and removal of the solvent under reduced pressure gave 7.940 g of product (60% of theory).

NMR (CDCl$_3$, 400 MHz): 2.23 (s, 3H); 6.81 (s, 1H); 7.41 (m, 1H); 7.83 (m, 1H); 8.09 (m, 1H); 8.68 (m, 1H); 15.7 (br, 1H).

b)

A solution of 3.38 g (20.7 mmol) of 1-(pyridin-2-yl)butane-1,3-dione dissolved in dimethyl sulfoxide was slowly added dropwise to 0.911 g (22.78 mmol) of sodium hydride in 25 ml of dimethyl sulfoxide such that the temperature did not exceed 30° C. The mixture was stirred at 20° C. for another 30 minutes. 3.486 g (22.78 mmol) of methyl bromoacetate in a little dimethyl sulfoxide were then slowly added dropwise at 0° C. The mixture was stirred at 20° C. for a further 4 hours. The reaction mixture was poured into ice-water and extracted with dichloromethane. The organic phase was washed repeatedly with water. Drying of the combined organic phases, removal of the solvent under reduced pressure and chromatography of the residue gave 3.48 g of product (71.4% of theory).

NMR (CDCl$_3$, 400 MHz): 2.4 (s, 3H); 2.9 (d, 1H); 3.05 (d, 1H); 3.69 (s, 3H); 5.49 (dd, 1H); 7.50 (m, 1H); 7.86 (m, 1H); 8.07 (m, 1H); 8.7 (m, 1H).

Example A9

Methyl[3-methyl-5-(pyridin-2-yl)-1-(pyrimidin-5-yl)-1H-pyrazol-4-yl]acetate (see Table 2, Example 2-116)

a) Preparation of Methyl[3-methyl-5-(pyridin-2-yl)-1H-pyrazol-4-yl]acetate 1.170 g (23 mmol) of hydrazine hydrate were added to a solution of 5 g (21 mmol) of methyl 4-oxo-3-(pyridin-2-ylcarbonyl)pentanoate in ethanol (50 ml). The mixture was heated at reflux for 7 hours, added to water and extracted with ethyl acetate. The combined organic phases were dried with magnesium sulfate, filtered and concentrated. This gave 2.290 g of product (41.9% of theory).

NMR (CDCl$_3$, 400 MHz): 2.3 (s, 3H); 3.84 (s, 2H); 7.19 (m, 1H); 7.72 (m, 1H); 7.84 (m, 1H); 8.59 (m, 1H).

b)

1.767 g (9.73 mmol) of copper(II) acetate and 1.049 ml (12.973 mmol) of pyridine were added to 1.5 g (6.486 mmol) of methyl[3-methyl-5-(pyridin-2-yl)-1H-pyrazol-4-yl]acetate in 20 ml of dichloromethane. 1.607 g (12.973 mmol) of 5-pyrimidinylboronic acid were then added, and the mixture was stirred at 20° C. for 48 h. The mixture was poured into 1-molar aqueous HCl (10 ml) and extracted with dichloromethane. The combined organic phases were dried with magnesium sulfate, filtrered and concentrated. The crude product was purified by preparative HPLC. This gave a mixture of ester and acid which was heated at reflux in methanol with a drop of sulfuric acid for 4 h. The reaction mixture was poured into water (20 ml), neutralized and extracted with dichloromethane. The combined organic phases were dried with magnesium sulfate and concentrated. This gave 0.031 g of product (1.47% of theory).

NMR (CDCl$_3$, 400 MHz): 2.38 (s, 3H); 3.57 (s, 2H); 3.71 (s, 3H); 7.32 (m, 1H); 7.46 (m, 1H); 7.79 (m, 1H); 8.61 (m, 1H); 8.63 (s, 2H); 9.04 (s, 1H).

The compounds described in Tables 1 to 12 below are obtained according to or analogously to the examples described above.

Table 13 lists intermediates of the formula (III) which can be used according to the processes described above.

In Tables 1 to 13:

F, Cl, Br, I=fluorine, chlorine, bromine and iodine, respectively, in accordance with the customary chemical symbols for the atoms Me=methyl MeO or OMe=methoxy 3,5-Me$_2$=3,5-dimethyl (e.g. as substitution at the phenyl ring)

4,5-Cl$_2$=4,5-dichloro (e.g. as substitution at the phenyl ring)

Et=ethyl

Pr=nPr=n-propyl iPr=isopropyl iOPr=O-iPr=iPrO=isopropyloxy
cyPr=cyclopropyl
Bu=nBu=n-butyl=but-1-yl
iBu=isobutyl=2-methylprop-1-yl
sBu=sec-Bu
tBu=t-butyl=tertiary butyl=2-methylprop-2-yl
Ph=phenyl
PhO=phenoxy
Ac=COCH$_3$=acetyl
allyl=prop-2-en-1-yl
COOH=carboxy
OSO$_2$Me=—O—S(=O)$_2$—CH$_3$, methylsulfonyloxy, methanesulfonate
"(R$^6$)$_n$=H"=unsubstituted cycle (n=0)

In addition, the customary chemical symbols apply, such as, for example, CH$_2$ for methylene or CF$_3$ for trifluoromethyl or OH for hydroxyl. Correspondingly, composite meanings are defined as composed of the abbreviations mentioned.

Physical data ("Data") of the compounds in the tables are, if appropriate, given in the detailed preparation examples (see above) or at the end of the tables. Here:

"NMR"=data according to the $^1$H-NMR spectrum ($^1$H nuclear magnetic resonance data)

"m.p."=melting point

TABLE 1

Compounds of the formula (Ia")

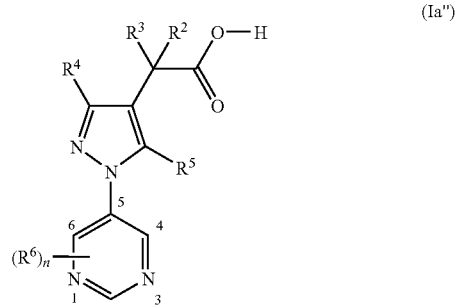

(Ia")

| No. | R$^2$ | R$^3$ | R$^4$ | R$^5$ | (R$^6$)$_n$ |
|---|---|---|---|---|---|
| 1-1 | H | H | Ph | Ph | H |
| 1-2 | H | H | Me | Ph | H |
| 1-3 | H | H | Me | 5-I-2-thienyl | H |
| 1-4 | H | H | Me | 2-furyl | H |
| 1-5 | H | H | Me | Ph | 2-OMe |
| 1-6 | Me | H | Me | Ph | 4-Me |
| 1-7 | H | H | Me | Ph | 2-Cl |
| 1-8 | H | H | Me | Ph | 4-CF$_3$ |
| 1-9 | H | H | Me | Ph | 2-CF$_3$ |
| 1-10 | H | H | Me | Ph | 4-Me |
| 1-11 | H | H | Me | Ph | 2,4-Me$_2$ |
| 1-12 | H | H | Me | Ph | 2,4-Cl$_2$ |
| 1-13 | H | H | Me | 4-MeO-Ph | 4-Me |
| 1-14 | H | H | Me | 4-MeO-Ph | H |
| 1-15 | Me | H | Me | Ph | H |
| 1-16 | H | H | Me | 4-Me-Ph | 4-Me |
| 1-17 | H | H | Me | 4-Me-Ph | 4-Cl |
| 1-18 | H | H | Me | 4-Me-Ph | H |
| 1-19 | H | H | Me | 3-Cl-Ph | H |
| 1-20 | H | H | Me | 3-CF$_3$-Ph | H |
| 1-21 | H | H | Me | 3-CF$_3$-Ph | 4-Me |
| 1-22 | H | H | Me | 3,4-Cl$_2$-Ph | 4-Me |
| 1-23 | H | H | Me | 3-Cl-Ph | 4-Me |
| 1-24 | H | H | Me | 2-Cl-Ph | 4-Me |
| 1-25 | H | H | Me | 2,4-Cl$_2$-Ph | 4-Me |
| 1-26 | H | H | Me | 4-CF$_3$-Ph | 4-Me |
| 1-27 | H | H | Me | 4-Cl-Ph | 4-Me |
| 1-28 | H | H | Me | 4-Cl-Ph | H |
| 1-29 | H | H | Me | 3,4-Cl$_2$-Ph | H |
| 1-30 | H | H | Me | 4-CF$_3$-Ph | H |
| 1-31 | H | H | Me | 4-Cl-Ph | 4-Cl |
| 1-32 | H | H | Me | Ph | 4-Cl |
| 1-33 | H | H | Me | 2-Cl-Ph | H |
| 1-34 | H | H | Me | 4-tBu-Ph | 4-Me |
| 1-35 | H | H | Me | 3,5-Me$_2$-Ph | 4-Me |
| 1-36 | H | H | Me | Ph | 4-OMe |
| 1-37 | H | H | Me | 4-Cl-Ph | 4-OMe |
| 1-38 | H | H | Me | 4-Me-Ph | 4-Me |
| 1-39 | H | H | Me | 4-F-Ph | 4-Cl |
| 1-40 | H | H | Me | 4-F-Ph | 4-Me |
| 1-41 | H | H | Me | 3-Me-Ph | 4-Me |
| 1-42 | H | H | Me | 4-(COOH)-Ph | 4-Me |
| 1-43 | H | H | Me | 3-Br-Ph | 4-Me |
| 1-44 | H | H | Me | 4-Ph-Ph | 4-Me |
| 1-45 | H | H | Me | 4-(COOH)-Ph | H |
| 1-46 | H | H | Me | 3,5-Me$_2$-Ph | H |
| 1-47 | H | H | Me | Ph | 4-SMe |
| 1-48 | H | H | Me | 4-Cl-Ph | 4-SMe |
| 1-49 | H | H | Me | 3-Cl-4-Me-Ph | H |
| 1-50 | H | H | Me | 3-CF$_3$-4-Cl-Ph | H |
| 1-51 | H | H | Me | 3-CF$_3$-4-Cl-Ph | 4-Me |
| 1-52 | H | H | Me | 3-Cl-4-Me-Ph | 4-Me |
| 1-53 | H | H | Me | 2-pyridyl | 4-Cl |
| 1-54 | H | H | Me | 4-Cl-Ph | 4-F |
| 1-55 | H | H | Me | 2-thienyl | 4-Me |
| 1-56 | H | H | Me | 3-Me-2-thienyl | 4-Me |
| 1-57 | H | H | Me | 4-Me-2-thienyl | 4-Me |
| 1-58 | H | H | Me | 5-Cl-2-thienyl | 4-Me |
| 1-59 | H | H | Me | 5-Cl-2-thienyl | 4-Cl |
| 1-60 | H | H | Me | 3-thienyl | 4-Me |
| 1-61 | H | H | Me | 2-thienyl | H |
| 1-62 | H | H | Me | 3-Me-2-thienyl | H |
| 1-63 | H | H | Me | 4-Me-2-thienyl | H |
| 1-64 | H | H | Me | 5-Cl-2-thienyl | H |
| 1-65 | H | H | Me | 5-Me-2-thienyl | H |
| 1-66 | H | H | Me | 6-MeO-pyridin-3-yl | H |
| 1-67 | H | H | Me | 5-Br-2-thienyl | H |
| 1-68 | H | H | Me | 5-Br-2-thienyl | 4-Me |
| 1-69 | H | H | Me | 3-thienyl | H |
| 1-70 | H | H | Me | 4-Cl-Ph | 4-S(O)Me |
| 1-71 | H | H | Me | 4-Br-Ph | 4-Me |
| 1-72 | H | H | Me | 1,3-benzodioxol-5-yl | 4-Me |
| 1-73 | H | H | Me | 4-I-Ph | 4-Me |
| 1-74 | H | H | Me | 3,5-Cl$_2$-Ph | 4-Me |
| 1-75 | H | H | Me | 4-PhO-Ph | 4-Me |
| 1-76 | H | H | Me | 6-OH-pyridin-3-yl | H |
| 1-77 | H | H | Me | Ph | 4-S(O)Me |
| 1-78 | H | H | H | Ph | H |
| 1-79 | H | H | H | Ph | 4-Me |
| 1-80 | H | H | Et | Ph | H |
| 1-81 | H | H | n-Pr | Ph | H |
| 1-82 | H | H | CH$_2$Cl | Ph | H |
| 1-83 | H | H | CHCl$_2$ | Ph | H |
| 1-84 | H | H | CH$_2$F | Ph | H |
| 1-85 | H | H | CHF$_2$ | Ph | H |
| 1-86 | H | H | Cl | Ph | H |
| 1-87 | H | H | Et | Ph | 4-Me |

TABLE 1-continued

Compounds of the formula (Ia'')

$$\text{(Ia'')}$$

Structure: pyrazole with R³, R², COOH group at position bearing R²/R³; R⁴ on pyrazole; R⁵ on pyrazole; N1 of pyrazole attached to pyrimidin-5-yl bearing (R⁶)ₙ.

| No. | R² | R³ | R⁴ | R⁵ | (R⁶)ₙ |
|---|---|---|---|---|---|
| 1-88 | H | H | n-Pr | Ph | 4-Me |
| 1-89 | H | H | CH₂Cl | Ph | 4-Me |
| 1-90 | H | H | CHCl₂ | Ph | 4-Me |
| 1-91 | H | H | CH₂F | Ph | 4-Me |
| 1-92 | H | H | CHF₂ | Ph | 4-Me |
| 1-93 | H | H | Cl | Ph | 4-Me |
| 1-94 | H | H | Et | 4-Cl-Ph | H |
| 1-95 | H | H | n-Pr | 4-Cl-Ph | H |
| 1-96 | H | H | CH₂Cl | 4-Cl-Ph | H |
| 1-97 | H | H | CHCl₂ | 4-Cl-Ph | H |
| 1-98 | H | H | CH₂F | 4-Cl-Ph | H |
| 1-99 | H | H | CHF₂ | 4-Cl-Ph | H |
| 1-100 | H | H | Cl | 4-Cl-Ph | H |
| 1-101 | H | H | Et | 4-Me-Ph | H |
| 1-102 | H | H | n-Pr | 4-Me-Ph | H |
| 1-103 | H | H | CH₂Cl | 4-Me-Ph | H |
| 1-104 | H | H | CHCl₂ | 4-Me-Ph | H |
| 1-105 | H | H | CH₂F | 4-Me-Ph | H |
| 1-106 | H | H | CHF₂ | 4-Me-Ph | H |
| 1-107 | H | H | Cl | 4-Me-Ph | H |
| 1-108 | H | H | Et | 2-pyridyl | H |
| 1-109 | H | H | n-Pr | 2-pyridyl | H |
| 1-110 | H | H | CH₂Cl | 2-pyridyl | H |
| 1-111 | H | H | CHCl₂ | 2-pyridyl | H |
| 1-112 | H | H | CH₂F | 2-pyridyl | H |
| 1-113 | H | H | CHF₂ | 2-pyridyl | H |
| 1-114 | H | H | Cl | 2-pyridyl | H |
| 1-115 | H | H | Me | 2-pyridyl | H |
| 1-116 | H | H | Me | 5-Cl-pyridin-2-yl | H |
| 1-117 | H | H | Me | 5-Cl-pyridin-2-yl | 4-Cl |
| 1-118 | H | H | Me- | 5-Cl-pyridin-2-yl | 4-Me |
| 1-119 | H | H | Me | 5-Br-pyridin-2-yl | H |
| 1-120 | H | H | Me | 5-Br-pyridin-2-yl | 4-Cl |
| 1-121 | H | H | Me | 5-Br-pyridin-2-yl | 4-Me |
| 1-122 | H | H | Me | 5-F-pyridin-2-yl | H |
| 1-123 | H | H | Me | 5-Me-pyridin-2-yl | H |
| 1-124 | H | H | Me | 5-Me-pyridin-2-yl | 4-Me |
| 1-125 | H | H | Me | 2,4-Cl₂-Ph | H |
| 1-126 | H | H | Me | 4-CH₂COOH-Ph | 4-Me |
| 1-127 | H | H | Me | 3,4-Me₂-Ph | 4-Me |
| 1-128 | H | H | Me | 4-Br-Ph | H |
| 1-129 | H | H | Me | 3,4-Me₂-Ph | H |
| 1-130 | H | H | Me | 3-Me-Ph | H |
| 1-131 | H | H | Me | 4-F-Ph | H |
| 1-132 | H | H | Me | 4-(Me-CO)-Ph | H |
| 1-133 | H | H | Me | 4-tBu-Ph | H |
| 1-134 | H | H | Me | 4-Cl-3-Me-Ph | H |
| 1-135 | H | H | n-Pr | 4-Cl-Ph | 4-Me |
| 1-136 | H | H | Me | 3-pyridyl | H |
| 1-137 | H | H | Me | 4-pyridyl | H |
| 1-138 | H | H | C(O)OMe | Ph | H |
| 1-139 | H | H | Me | 6-Me-pyridin-3-yl | H |
| 1-140 | H | H | Me | 4-Cl-Ph | 4-SO₂Me |
| 1-141 | H | H | Me | 3-pyridyl | 4-Me |
| 1-142 | H | H | Me | 2,3-Cl₂-Ph | 4-Me |
| 1-143 | H | H | Me | 2-pyridyl | 4-Me |
| 1-144 | H | H | H | 4-Cl-Ph | 4-Me |
| 1-145 | H | H | Me | 6-Cl-pyridin-3-yl | H |
| 1-146 | H | H | Me | Ph | 2-Me |
| 1-147 | H | H | Me | 4-Me-pyridin-2-yl | H |
| 1-148 | H | H | Me | 4-Me-pyridin-2-yl | 4-Me |
| 1-149 | H | H | Me | 4-Me-pyridin-2-yl | 4-Cl |
| 1-150 | H | H | Me | 4-Me-pyridin-2-yl | 4-F |
| 1-151 | H | H | Me | 4-F-pyridin-2-yl | H |
| 1-152 | H | H | Me | 4-Cl-pyridin-2-yl | H |
| 1-153 | H | H | Me | 4-Br-pyridin-2-yl | H |
| 1-154 | H | H | Me | 4-OMe-pyridin-2-yl | H |
| 1-155 | H | H | Me | 5-CF₃-pyridin-2-yl | H |
| 1-156 | H | H | Me | 6-OMe-pyridin-2-yl | H |
| 1-157 | H | H | cyPr | 4-Cl-Ph | H |
| 1-158 | H | H | CN | 4-Cl-Ph | H |
| 1-159 | H | H | CN | 4-Cl-Ph | 4-Me |
| 1-160 | H | H | CN | 4-Me-Ph | H |
| 1-161 | H | H | CN | 4-Me-Ph | 4-Me |
| 1-162 | H | H | CN | Ph | H |
| 1-163 | H | H | CN | Ph | 4-Me |
| 1-164 | H | H | CN | 2-pyridyl | H |
| 1-165 | H | H | CN | 3-pyridyl | H |
| 1-166 | H | H | CN | 5-Cl-pyridin-2-yl | H |
| 1-167 | H | H | CN | 5-Br-pyridin-2-yl | H |
| 1-168 | H | H | CN | 5-F-pyridin-2-yl | H |
| 1-169 | H | H | CN | 5-Me-pyridin-2-yl | H |
| 1-170 | H | H | CN | 6-Me-pyridin-3-yl | H |
| 1-171 | H | H | CN | 4-Me-pyridin-2-yl | H |
| 1-172 | H | H | CN | 4-F-pyridin-2-yl | H |
| 1-173 | H | H | CN | 4-Cl-pyridin-2-yl | H |
| 1-174 | H | H | CN | 4-Br-pyridin-2-yl | H |
| 1-175 | H | H | CN | 4-OMe-pyridin-2-yl | H |
| 1-176 | H | H | formyl | 4-Cl-Ph | H |
| 1-177 | H | H | formyl | 4-Cl-Ph | 4-Me |
| 1-178 | H | H | formyl | 4-Me-Ph | H |
| 1-179 | H | H | formyl | 4-Me-Ph | 4-Me |
| 1-180 | H | H | formyl | Ph | H |
| 1-181 | H | H | formyl | Ph | 4-Me |
| 1-182 | H | H | formyl | 2-pyridyl | H |
| 1-183 | H | H | formyl | 3-pyridyl | H |
| 1-184 | H | H | formyl | 5-Cl-pyridin-2-yl | H |
| 1-185 | H | H | formyl | 5-Br-pyridin-2-yl | H |
| 1-186 | H | H | formyl | 5-F-pyridin-2-yl | H |
| 1-187 | H | H | formyl | 5-Me-pyridin-2-yl | H |
| 1-188 | H | H | formyl | 6-Me-pyridin-3-yl | H |
| 1-189 | H | H | formyl | 4-Me-pyridin-2-yl | H |
| 1-190 | H | H | formyl | 4-F-pyridin-2-yl | H |
| 1-191 | H | H | formyl | 4-Cl-pyridin-2-yl | H |
| 1-192 | H | H | formyl | 4-Br-pyridin-2-yl | H |
| 1-193 | H | H | formyl | 4-OMe-pyridin-2-yl | H |
| 1-194 | H | H | CH₂OH | 5-Me-pyridin-2-yl | H |
| 1-195 | H | H | CH₂OH | 4-Cl-Ph | H |
| 1-196 | H | H | CH₂OH | 4-Me-pyridin-2-yl | H |
| 1-197 | H | H | CH₂OH | 4-Me-Ph | H |
| 1-198 | H | H | CH₂OH | Ph | H |
| 1-199 | H | H | CH₂OH | 2-pyridyl | H |
| 1-200 | H | H | Me | 2-thiazolyl | H |
| 1-201 | H | H | Me | 2-thiazolyl | 4-Cl |
| 1-202 | H | H | Me | 2-thiazolyl | 4-Me |
| 1-203 | H | H | Me | 4-Me-thiazol-2-yl | H |
| 1-204 | H | H | Me | 4-Me-thiazol-2-yl | 4-Cl |
| 1-205 | H | H | Me | 4-Me-thiazol-2-yl | 4-Me |

TABLE 1-continued

Compounds of the formula (Ia")

| No. | R² | R³ | R⁴ | R⁵ | (R⁶)ₙ |
|---|---|---|---|---|---|
| 1-206 | H | H | Me | 5-Me-thiazol-2-yl | H |
| 1-207 | H | H | Me | 5-Br-thiazol-2-yl | H |
| 1-208 | H | H | Me | 5-Br-thiazol-2-yl | 4-Me |
| 1-209 | H | H | Me | 5-Cl-thiazol-2-yl | H |
| 1-210 | H | H | Me | 4,6-Me₂-pyridin-2-yl | H |
| 1-211 | H | H | Me | 4,6-Me₂-pyridin-2-yl | 4-Me |
| 1-212 | H | H | Me | 2-pyridyl | 4-F |
| 1-213 | H | H | Me | 2-pyrazinyl | H |
| 1-214 | H | H | Me | 5-Me-pyrazin-2-yl | H |
| 1-215 | H | H | Me | 2-pyrazinyl | 4-Me |
| 1-216 | H | H | Me | 1,3-benzothiazol-2-yl | H |
| 1-217 | H | H | Me | 1,3-benzothiazol-2-yl | 4-Me |
| 1-218 | H | H | Me | 7-Cl-1,3-benzothiazol-2-yl | H |
| 1-219 | H | H | Me | 1,5-Me₂-pyrazol-3-yl | H |
| 1-220 | H | H | Me | 1,5-Me₂-pyrazol-3-yl | 4-Me |
| 1-221 | H | H | Me | 4,5-Me₂-thiazol-2-yl | H |
| 1-222 | H | H | Me | 4,5-Cl₂-thiazol-2-yl | H |
| 1-223 | H | H | Me | 2-pyrimidinyl | H |
| 1-224 | H | H | Me | 2-pyrimidinyl | 4-Me |
| 1-225 | H | H | Me | 5-F-pyrimidin-2-yl | H |
| 1-226 | H | H | Me | 5-Cl-pyrimidin-2-yl | H |
| 1-227 | H | H | Me | 5-Br-pyrimidin-2-yl | H |
| 1-228 | H | H | Me | 5-Me-pyrimidin-2-yl | H |
| 1-229 | H | H | Me | 5-Me-pyrimidin-2-yl | 4-Me |
| 1-230 | H | H | Me | 4,6-Me₂-pyrimidin-2-yl | H |
| 1-231 | H | H | Me | 4,6-Me₂-pyrimidin-2-yl | 4-Me |
| 1-232 | H | H | Me | 3-pyridazinyl | H |
| 1-233 | H | H | Me | 6-Me-pyridazin-3-yl | H |
| 1-234 | H | H | Me | 1,2,4-triazin-3-yl | H |
| 1-235 | H | H | Me | 6-Me-1,2,4-triazin-3-yl | H |
| 1-236 | H | H | Me | isoquinolin-3-yl | H |
| 1-237 | H | H | Me | quinolin-2-yl | H |
| 1-238 | H | H | Me | 3,5-Cl₂-Ph | H |
| 1-239 | H | H | Me | 2-Me-pyridin-4-yl | H |
| 1-240 | H | H | Me | 4-Cl-6-Me-pyridin-2-yl | H |
| 1-241 | H | H | Me | 4-Br-3-Me-Ph | H |
| 1-242 | H | H | Me | 5-Cl-pyridin-3-yl | H |
| 1-243 | H | H | Me | 5-allylpyridin-2-yl | H |
| 1-244 | H | H | Me | 5-cyclopropylpyridin-2-yl | H |
| 1-245 | H | H | Me | 5-ethynylpyridin-2-yl | H |
| 1-246 | H | H | Me | 5-Ph-pyridin-2-yl | H |
| 1-247 | H | H | Me | 5-I-pyridin-2-yl | H |
| 1-248 | H | H | Me | 5-I-pyrimidin-2-yl | H |
| 1-249 | H | H | Cl | 4-F-Ph | H |
| 1-250 | H | H | Cl | 3-pyridyl | H |
| 1-251 | H | H | Cl | 5-Cl-pyridin-2-yl | H |
| 1-252 | H | H | Cl | 5-Br-pyridin-2-yl | H |
| 1-253 | H | H | Cl | 5-F-pyridin-2-yl | H |
| 1-254 | H | H | Cl | 5-I-pyridin-2-yl | H |
| 1-255 | H | H | Cl | 5-Me-pyridin-2-yl | H |
| 1-256 | H | H | Cl | 6-Me-pyridin-3-yl | H |
| 1-257 | H | H | Cl | 4-Me-pyridin-2-yl | H |
| 1-258 | H | H | Cl | 4-F-pyridin-2-yl | H |
| 1-259 | H | H | Cl | 4-Cl-pyridin-2-yl | H |
| 1-260 | H | H | Cl | 4-Br-pyridin-2-yl | H |
| 1-261 | H | H | Cl | 4-OMe-pyridin-2-yl | H |
| 1-262 | H | H | Cl | 2-pyrimidinyl | H |
| 1-263 | H | H | Cl | 5-F-pyrimidin-2-yl | H |
| 1-264 | H | H | Cl | 5-Cl-pyrimidin-2-yl | H |
| 1-265 | H | H | Cl | 5-Br-pyrimidin-2-yl | H |
| 1-266 | H | H | Cl | 5-I-pyrimidin-2-yl | H |
| 1-267 | H | H | Cl | 5-Me-pyrimidin-2-yl | H |
| 1-268 | H | H | Cl | 5-Me-pyrazin-2-yl | H |
| 1-269 | H | H | Cl | 2-pyrazinyl | H |
| 1-270 | H | H | Cl | isoquinolin-3-yl | H |
| 1-271 | H | H | Cl | quinolin-2-yl | H |
| 1-272 | H | H | Cl | 1,3-benzothiazol-2-yl | H |
| 1-273 | H | H | Cl | 7-Cl-1,3-benzothiazol-2-yl | H |
| 1-274 | H | H | Cl | 2-thiazolyl | H |
| 1-275 | H | H | Cl | 5-Br-thiazol-2-yl | H |
| 1-276 | H | H | Cl | 5-Me-thiazol-2-yl | H |
| 1-277 | H | H | Cl | 5-Cl-thiazol-2-yl | H |
| 1-278 | H | H | Cl | 2-thienyl | H |
| 1-279 | H | H | Cl | 3-Me-2-thienyl | H |
| 1-280 | H | H | Cl | 4-Me-2-thienyl | H |
| 1-281 | H | H | Cl | 5-Br-2-thienyl | H |
| 1-282 | H | H | Cl | 5-Cl-2-thienyl | H |
| 1-283 | H | H | Me | 4-thiazolyl | H |
| 1-284 | H | H | Me | 3-Br-Me | H |
| 1-285 | H | H | Me | 2-Cl-thiazol-4-yl | H |
| 1-286 | H | H | Me | 2-Br-thiazol-4-yl | H |
| 1-287 | H | H | Me | 5-OSO₂Me-pyridin-2-yl | H |
| 1-288 | H | H | Me | 6-Cl-1,3-benzothiazol-2-yl | H |
| 1-289 | H | H | Me | 6-Br-1,3-benzothiazol-2-yl | H |
| 1-290 | H | H | Me | 1,3-benzoxazol-2-yl | H |
| 1-291 | H | H | Me | 6-Cl-1,3-benzoxazol-2-yl | H |
| 1-292 | H | H | Me | 6-Br-1,3-benzoxazol-2-yl | H |
| 1-293 | H | H | Me | 7-Cl-1,3-benzoxazol-2-yl | H |
| 1-294 | H | H | Me | 5-NH₂-pyridin-2-yl | H |
| 1-295 | H | H | Me | 5-OH-pyridin-2-yl | H |
| 1-296 | H | H | Me | 5-OCHF₂-pyridin-2-yl | H |
| 1-297 | H | H | Me | 5-MeO-pyridin-2-yl | H |
| 1-298 | H | H | Me | 5-MeS-pyridin-2-yl | H |
| 1-299 | H | H | Me | 5-NHMe-pyridin-2-yl | H |
| 1-300 | H | H | Me | 5-NMe₂-pyridin-2-yl | H |

In addition, NMR data of compounds of the general formula (I) according to the invention were generated. The NMR of the exemplary compounds were in each case recorded as ¹H-NMR spectrum at 400 MHz (CDCl₃ or DMSO-D₆) (¹H nuclear magnetic resonance data). Characteristic chemical shifts δ (ppm) for some exemplary compounds are listed below:

NMR compound 1-116 (DMSO-D₆, 400 MHz, δ in ppm):

2.28 (s, 3H); 3.54 (s, 2H); 7.61 (d, 1H); 8.11 (dd, 1H); 8.61 (d, 1H); 8.66 (s, 2H); 9.10 (s, 1H). m.p.: 234.3° C.

NMR compound 1-214 (CDCl₃, 400 MHz, δ in ppm):

2.43 (s, 3H); 2.68 (s, 3H); 3.54 (s, 2H); 8.43 (s, 1H); 8.55 (s, 1H); 8.70 (s, 2H); 9.15 (s, 1H). m.p.: 195.6° C.

NMR compound 1-236 (CDCl₃, 400 MHz, δ in ppm):

2.47 (s, 3H); 3.56 (s, 2H); 7.39 (m, 1H); 7.69 (m, 1H); 7.78-7.86 (m, 2H); 8.13 (m, 1H); 8.73 (s, 2H); 9.14 (s, 1H)); 9.40 (s, 1H). m.p.: 103.9° C.

NMR compound 1-154 (CDCl$_3$, 400 MHz, δ in ppm):
2.43 (s, 3H); 3.52 (s, 2H); 3.73 (s, 3H); 6.42 (m, 1H); 6.98 (m, 1H); 8.57 (m, 1H); 8.72 (s, 2H); 9.18 (s, 1H). 15.3 (brs, 1H). m.p.: 173° C.

NMR compound 1-119 (CDCl$_3$, 400 MHz, δ in ppm):
2.42 (s, 3H); 3.55 (s, 2H); 6.98 (m, 1H); 7.92 (m, 1H); 8.70 (s, 2H); 8.83 (m, 1H); 9.19 (s, 1H).

NMR compound 1-210 (CDCl$_3$, 400 MHz, δ in ppm):
2.22 (s, 3H); 2.43 (s, 3H); 2.66 (s, 3H); 3.50 (s, 2H); 6.61 (s, 1H); 7.13 (s, 1H); 8.72 (s, 2H); 9.17 (s, 1H).

NMR compound 1-28 (CDCl$_3$, 400 MHz, δ in ppm):
2.38 (s, 3H); 3.44 (s, 2H); 7.20 (d, 2H); 7.41 (d, 2H); 8.62 (s, 2H); 9.04 (s, 1H).

TABLE 2

Compounds of the formula (Ia''')

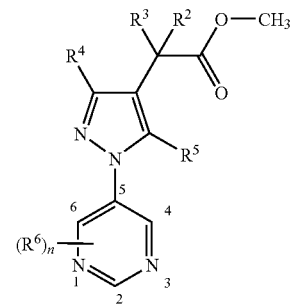

| No. | R$^2$ | R$^3$ | R$^4$ | R$^5$ | (R$^6$)$_n$ |
|---|---|---|---|---|---|
| 2-1 | H | H | Ph | Ph | H |
| 2-2 | H | H | Me | Ph | H |
| 2-3 | H | H | Me | 5-I-2-thienyl | H |
| 2-4 | H | H | Me | 2-furyl | H |
| 2-5 | H | H | Me | Ph | 2-OMe |
| 2-6 | Me | H | Me | Ph | 4-Me |
| 2-7 | H | H | Me | Ph | 2-Cl |
| 2-8 | H | H | Me | Ph | 4-CF$_3$ |
| 2-9 | H | H | Me | Ph | 2-CF$_3$ |
| 2-10 | H | H | Me | Ph | 4-Me |
| 2-11 | H | H | Me | Ph | 2,4-Me$_2$ |
| 2-12 | H | H | Me | Ph | 2,4-Cl$_2$ |
| 2-13 | H | H | Me | 4-MeO-Ph | 4-Me |
| 2-14 | H | H | Me | 4-MeO-Ph | H |
| 2-15 | Me | H | Me | Ph | H |
| 2-16 | H | H | Me | 4-Me-Ph | H |
| 2-17 | H | H | Me | 4-Me-Ph | 4-Me |
| 2-18 | H | H | Me | 4-Me-Ph | 4-Cl |
| 2-19 | H | H | Me | 3-Cl-Ph | H |
| 2-20 | H | H | Me | 3-CF$_3$-Ph | H |
| 2-21 | H | H | Me | 3-CF$_3$-Ph | 4-Me |
| 2-22 | H | H | Me | 3,4-Cl$_2$-Ph | 4-Me |
| 2-23 | H | H | Me | 3-Cl-Ph | 4-Me |
| 2-24 | H | H | Me | 2-Cl-Ph | 4-Me |
| 2-25 | H | H | Me | 2,4-Cl$_2$-Ph | 4-Me |
| 2-26 | H | H | Me | 4-CF$_3$-Ph | 4-Me |
| 2-27 | H | H | Me | 4-Cl-Ph | 4-Me |
| 2-28 | H | H | Me | 4-Cl-Ph | H |
| 2-29 | H | H | Me | 4-Cl-Ph | 2-Cl |
| 2-30 | H | H | Me | 3,4-Cl$_2$-Ph | H |
| 2-31 | H | H | Me | 4-CF$_3$-Ph | H |
| 2-32 | H | H | Me | 4-Cl-Ph | 4-Cl |
| 2-33 | H | H | Me | Ph | 4-Cl |
| 2-34 | H | H | Me | 2-Cl-Ph | H |
| 2-35 | H | H | Me | 4-tBu-Ph | 4-Me |
| 2-36 | H | H | Me | 3,5-Me$_2$-Ph | 4-Me |
| 2-37 | H | H | Me | Ph | 4-OMe |
| 2-38 | H | H | Me | 4-Cl-Ph | 4-OMe |
| 2-39 | H | H | Me | 4-Me-Ph | 4-Me |
| 2-40 | H | H | Me | 4-F-Ph | 4-Me |
| 2-41 | H | H | Me | 4-F-Ph | 4-Cl |
| 2-42 | H | H | Me | 3-Me-Ph | 4-Me |
| 2-43 | H | H | Me | 4-COOH-Ph | 4-Me |

TABLE 2-continued

Compounds of the formula (Ia''')

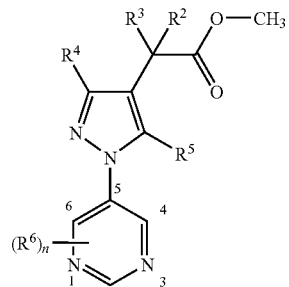

| No. | R$^2$ | R$^3$ | R$^4$ | R$^5$ | (R$^6$)$_n$ |
|---|---|---|---|---|---|
| 2-44 | H | H | Me | 3-Br-Ph | 4-Me |
| 2-45 | H | H | Me | 4-Ph-Ph | 4-Me |
| 2-46 | H | H | Me | 4-COOH-Ph | H |
| 2-47 | H | H | Me | 3,5-Me$_2$-Ph | H |
| 2-48 | H | H | Me | Ph | 4-SMe |
| 2-49 | H | H | Me | 4-Cl-Ph | 4-SMe |
| 2-50 | H | H | Me | 3-Cl-4-Me-Ph | H |
| 2-51 | H | H | Me | 3-CF$_3$-4-Cl-Ph | H |
| 2-52 | H | H | Me | 3-CF$_3$-4-Cl-Ph | 4-Me |
| 2-53 | H | H | Me | 3-Cl-4-Me-Ph | 4-Me |
| 2-54 | H | H | Me | 2-pyridyl | 4-Cl |
| 2-55 | H | H | Me | 4-Cl-Ph | 4-F |
| 2-56 | H | H | Me | 2-thienyl | 4-Me |
| 2-57 | H | H | Me | 3-Me-2-thienyl | 4-Me |
| 2-58 | H | H | Me | 4-Me-2-thienyl | 4-Me |
| 2-59 | H | H | Me | 5-Cl-2-thienyl | 4-Me |
| 2-60 | H | H | Me | 5-Cl-2-thienyl | 4-Cl |
| 2-61 | H | H | Me | 3-thienyl | 4-Me |
| 2-62 | H | H | Me | 2-thienyl | H |
| 2-63 | H | H | Me | 3-Me-2-thienyl | H |
| 2-64 | H | H | Me | 4-Me-2-thienyl | H |
| 2-65 | H | H | Me | 5-Cl-2-thienyl | H |
| 2-66 | H | H | Me | 5-Me-2-thienyl | H |
| 2-67 | H | H | Me | 6-MeO-pyridin-3-yl | H |
| 2-68 | H | H | Me | 5-Br-2-thienyl | H |
| 2-69 | H | H | Me | 5-Br-2-thienyl | 4-Me |
| 2-70 | H | H | Me | 3-thienyl | H |
| 2-71 | H | H | Me | 4-Cl-Ph | 4-S(O)Me |
| 2-72 | H | H | Me | 4-Br-Ph | 4-Me |
| 2-73 | H | H | Me | 1,3-benzodioxol-5-yl | 4-Me |
| 2-74 | H | H | Me | 4-I-Ph | 4-Me |
| 2-75 | H | H | Me | 3,5-Cl$_2$-Ph | 4-Me |
| 2-76 | H | H | Me | 4-PhO-Ph | 4-Me |
| 2-77 | H | H | Me | 6-OH-pyridin-3-yl | H |
| 2-78 | H | H | Me | Ph | 4-S(O)Me |
| 2-79 | H | H | H | Ph | H |
| 2-80 | H | H | H | Ph | 4-Me |
| 2-81 | H | H | Et | Ph | H |
| 2-82 | H | H | n-Pr | Ph | H |
| 2-83 | H | H | CH$_2$Cl | Ph | H |
| 2-84 | H | H | CHCl$_2$ | Ph | H |
| 2-85 | H | H | CH$_2$F | Ph | H |
| 2-86 | H | H | CHF$_2$ | Ph | H |
| 2-87 | H | H | Cl | Ph | H |
| 2-88 | H | H | Et | Ph | 4-Me |
| 2-89 | H | H | n-Pr | Ph | 4-Me |
| 2-90 | H | H | CH$_2$Cl | Ph | 4-Me |
| 2-91 | H | H | CHCl$_2$ | Ph | 4-Me |
| 2-92 | H | H | CH$_2$F | Ph | 4-Me |
| 2-93 | H | H | CHF$_2$ | Ph | 4-Me |
| 2-94 | H | H | Cl | Ph | 4-Me |
| 2-95 | H | H | Et | 4-Cl-Ph | H |
| 2-96 | H | H | n-Pr | 4-Cl-Ph | H |
| 2-97 | H | H | CH$_2$Cl | 4-Cl-Ph | H |
| 2-98 | H | H | CHCl$_2$ | 4-Cl-Ph | H |
| 2-99 | H | H | CH$_2$F | 4-Cl-Ph | H |
| 2-100 | H | H | CHF$_2$ | 4-Cl-Ph | H |
| 2-101 | H | H | Cl | 4-Cl-Ph | H |
| 2-102 | H | H | Et | 4-Me-Ph | H |

TABLE 2-continued

Compounds of the formula (Ia''')

| No. | R² | R³ | R⁴ | R⁵ | (R⁶)ₙ |
|---|---|---|---|---|---|
| 2-103 | H | H | n-Pr | 4-Me-Ph | H |
| 2-104 | H | H | CH₂Cl | 4-Me-Ph | H |
| 2-105 | H | H | CHCl₂ | 4-Me-Ph | H |
| 2-106 | H | H | CH₂F | 4-Me-Ph | H |
| 2-107 | H | H | CHF₂ | 4-Me-Ph | H |
| 2-108 | H | H | Cl | 4-Me-Ph | H |
| 2-109 | H | H | Et | 2-pyridyl | H |
| 2-110 | H | H | n-Pr | 2-pyridyl | H |
| 2-111 | H | H | CH₂Cl | 2-pyridyl | H |
| 2-112 | H | H | CHCl₂ | 2-pyridyl | H |
| 2-113 | H | H | CH₂F | 2-pyridyl | H |
| 2-114 | H | H | CHF₂ | 2-pyridyl | H |
| 2-115 | H | H | Cl | 2-pyridyl | H |
| 2-116 | H | H | Me | 2-pyridyl | H |
| 2-117 | H | H | Me | 5-Cl-pyridin-2-yl | H |
| 2-118 | H | H | Me | 5-Cl-pyridin-2-yl | 4-Cl |
| 2-119 | H | H | Me | 5-Cl-pyridin-2-yl | 4-Me |
| 2-120 | H | H | Me | 5-Br-pyridin-2-yl | H |
| 2-121 | H | H | Me | 5-Br-pyridin-2-yl | 4-Cl |
| 2-122 | H | H | Me | 5-Br-pyridin-2-yl | 4-Me |
| 2-123 | H | H | Me | 5-F-pyridin-2-yl | H |
| 2-124 | H | H | Me | 5-Me-pyridin-2-yl | H |
| 2-125 | H | H | Me | 5-Me-pyridin-2-yl | 4-Me |
| 2-126 | H | H | Me | 2,4-Cl₂-Ph | H |
| 2-127 | H | H | Me | 4-(CH₂COOH)-Ph | 4-Me |
| 2-128 | H | H | Me | 3,4-Me₂-Ph | 4-Me |
| 2-129 | H | H | Me | 4-Br-Ph | 4-Me |
| 2-130 | H | H | Me | 3,4-Me₂-Ph | H |
| 2-131 | H | H | Me | 3-Me-Ph | H |
| 2-132 | H | H | Me | 4-F-Ph | H |
| 2-133 | H | H | Me | 4-(Me-CO)-Ph | H |
| 2-134 | H | H | Me | 4-tBu-Ph | H |
| 2-135 | H | H | Me | 4-Cl-3-Me-Ph | H |
| 2-136 | H | H | n-Pr | 4-Cl-Ph | 4-Me |
| 2-137 | H | H | Me | 3-pyridyl | H |
| 2-138 | H | H | Me | 4-pyridyl | H |
| 2-139 | H | H | C(O)OMe | Ph | H |
| 2-140 | H | H | Me | 6-Me-pyridin-3-yl | H |
| 2-141 | H | H | Me | 4-Cl-Ph | 4-SO₂Me |
| 2-142 | H | H | Me | 3-pyridyl | 4-Me |
| 2-143 | H | H | Me | 2,3-Cl₂-Ph | 4-Me |
| 2-144 | H | H | Me | 2-pyridyl | 4-Me |
| 2-145 | H | H | H | 4-Cl-Ph | 4-Me |
| 2-146 | H | H | Me | 6-Cl-pyridin-3-yl | H |
| 2-147 | H | H | Me | Ph | 2-Me |
| 2-148 | H | H | Me | 4-Me-pyridin-2-yl | H |
| 2-149 | H | H | Me | 4-Me-pyridin-2-yl | 4-Me |
| 2-150 | H | H | Me | 4-Me-pyridin-2-yl | 4-Cl |
| 2-151 | H | H | Me | 4-Me-pyridin-2-yl | 4-F |
| 2-152 | H | H | Me | 4-F-pyridin-2-yl | H |
| 2-153 | H | H | Me | 4-Cl-pyridin-2-yl | H |
| 2-154 | H | H | Me | 4-Br-pyridin-2-yl | H |
| 2-155 | H | H | Me | 4-OMe-pyridin-2-yl | H |
| 2-156 | H | H | Me | 5-CF₃-pyridin-2-yl | H |
| 2-157 | H | H | Me | 6-OMe-pyridin-2-yl | H |
| 2-158 | H | H | cyPr | 4-Cl-Ph | H |
| 2-159 | H | H | CN | 4-Cl-Ph | H |
| 2-160 | H | H | CN | 4-Cl-Ph | 4-Me |
| 2-161 | H | H | CN | 4-Me-Ph | H |
| 2-162 | H | H | CN | 4-Me-Ph | 4-Me |
| 2-163 | H | H | CN | Ph | H |
| 2-164 | H | H | CN | Ph | 4-Me |
| 2-165 | H | H | CN | 2-pyridyl | H |
| 2-166 | H | H | CN | 3-pyridyl | H |
| 2-167 | H | H | CN | 5-Cl-pyridin-2-yl | H |
| 2-168 | H | H | CN | 5-Br-pyridin-2-yl | H |
| 2-169 | H | H | CN | 5-F-pyridin-2-yl | H |
| 2-170 | H | H | CN | 5-Me-pyridin-2-yl | H |
| 2-171 | H | H | CN | 6-Me-pyridin-3-yl | H |
| 2-172 | H | H | CN | 4-Me-pyridin-2-yl | H |
| 2-173 | H | H | CN | 4-F-pyridin-2-yl | H |
| 2-174 | H | H | CN | 4-Cl-pyridin-2-yl | H |
| 2-175 | H | H | CN | 4-Br-pyridin-2-yl | H |
| 2-176 | H | H | CN | 4-OMe-pyridin-2-yl | H |
| 2-177 | H | H | formyl | 4-Cl-Ph | H |
| 2-178 | H | H | formyl | 4-Cl-Ph | 4-Me |
| 2-179 | H | H | formyl | 4-Me-Ph | H |
| 2-180 | H | H | formyl | 4-Me-Ph | 4-Me |
| 2-181 | H | H | formyl | Ph | H |
| 2-182 | H | H | formyl | Ph | 4-Me |
| 2-183 | H | H | formyl | 2-pyridyl | H |
| 2-184 | H | H | formyl | 3-pyridyl | H |
| 2-185 | H | H | formyl | 5-Cl-pyridin-2-yl | H |
| 2-186 | H | H | formyl | 5-Br-pyridin-2-yl | H |
| 2-187 | H | H | formyl | 5-F-pyridin-2-yl | H |
| 2-188 | H | H | formyl | 5-Me-pyridin-2-yl | H |
| 2-189 | H | H | formyl | 6-Me-pyridin-3-yl | H |
| 2-190 | H | H | formyl | 4-Me-pyridin-2-yl | H |
| 2-191 | H | H | formyl | 4-F-pyridin-2-yl | H |
| 2-192 | H | H | formyl | 4-Cl-pyridin-2-yl | H |
| 2-193 | H | H | formyl | 4-Br-pyridin-2-yl | H |
| 2-194 | H | H | formyl | 4-OMe-pyridin-2-yl | H |
| 2-195 | H | H | CH₂OH | 5-Me-pyridin-2-yl | H |
| 2-196 | H | H | CH₂OH | 4-Cl-Ph | H |
| 2-197 | H | H | CH₂OH | 4-Me-pyridin-2-yl | H |
| 2-198 | H | H | CH₂OH | 4-Me-Ph | H |
| 2-199 | H | H | CH₂OH | Ph | H |
| 2-200 | H | H | CH₂OH | 2-pyridyl | H |
| 2-201 | H | H | Me | 2-thiazolyl | H |
| 2-202 | H | H | Me | 2-thiazolyl | 4-Cl |
| 2-203 | H | H | Me | 2-thiazolyl | 4-Me |
| 2-204 | H | H | Me | 4-Me-thiazol-2-yl | H |
| 2-205 | H | H | Me | 4-Me-thiazol-2-yl | 4-Cl |
| 2-206 | H | H | Me | 4-Me-thiazol-2-yl | 4-Me |
| 2-207 | H | H | Me | 5-Me-thiazol-2-yl | H |
| 2-208 | H | H | Me | 5-Br-thiazol-2-yl | H |
| 2-209 | H | H | Me | 5-Br-thiazol-2-yl | 4-Me |
| 2-210 | H | H | Me | 5-Cl-thiazol-2-yl | H |
| 2-211 | H | H | Me | 4,6-Me₂-pyridin-2-yl | H |
| 2-212 | H | H | Me | 4,6-Me₂-pyridin-2-yl | 4-Me |
| 2-213 | H | H | Me | 2-pyridyl | 4-F |
| 2-214 | H | H | Me | 2-pyrazinyl | H |
| 2-215 | H | H | Me | 5-Me-pyrazin-2-yl | H |
| 2-216 | H | H | Me | 2-pyrazinyl | 4-Me |
| 2-217 | H | H | Me | 1,3-benzothiazol-2-yl | H |
| 2-218 | H | H | Me | 1,3-benzothiazol-2-yl | 4-Me |
| 2-219 | H | H | Me | 7-Cl-1,3-benzothiazol-2-yl | H |
| 2-220 | H | H | Me | 1,5-Me₂-pyrazol-3-yl | H |

TABLE 2-continued

Compounds of the formula (Ia''')

| No. | R² | R³ | R⁴ | R⁵ | (R⁶)ₙ |
|---|---|---|---|---|---|
| 2-221 | H | H | Me | 1,5-Me₂-pyrazol-3-yl | 4-Me |
| 2-222 | H | H | Me | 4,5-Me₂-thiazol-2-yl | H |
| 2-223 | H | H | Me | 4,5-Cl₂-thiazol-2-yl | H |
| 2-224 | H | H | Me | 2-pyrimidinyl | H |
| 2-225 | H | H | Me | 2-pyrimidinyl | 4-Me |
| 2-226 | H | H | Me | 5-F-pyrimidin-2-yl | H |
| 2-227 | H | H | Me | 5-Cl-pyrimidin-2-yl | H |
| 2-228 | H | H | Me | 5-Br-pyrimidin-2-yl | H |
| 2-229 | H | H | Me | 5-Me-pyrimidin-2-yl | H |
| 2-230 | H | H | Me | 5-Me-pyrimidin-2-yl | 4-Me |
| 2-231 | H | H | Me | 4,6-Me₂-pyrimidin-2-yl | H |
| 2-232 | H | H | Me | 4,6-Me₂-pyrimidin-2-yl | 4-Me |
| 2-233 | H | H | Me | 3-pyridazinyl | H |
| 2-234 | H | H | Me | 6-Me-pyridazin-3-yl | H |
| 2-235 | H | H | Me | 1,2,4-triazin-3-yl | H |
| 2-236 | H | H | Me | 6-Me-1,2,4-triazin-3-yl | H |
| 2-237 | H | H | Me | 4-Cl-Ph | 2-OMe |
| 2-238 | H | H | Me | 2-pyridyl | 2-SO₂Me |
| 2-239 | H | H | Me | 4-Me-pyridin-2-yl | H |
| 2-240 | H | H | Me | 4-Br-Ph | H |
| 2-241 | H | H | Me | isoquinolin-3-yl | H |
| 2-242 | H | H | Me | quinolin-2-yl | H |
| 2-243 | H | H | Me | 4-NO₂-Ph | H |
| 2-244 | H | H | Me | 3,5-Cl₂-Ph | H |
| 2-245 | H | H | Me | 2-Me-pyridin-4-yl | H |
| 2-246 | H | H | Me | 4-Cl-6-Me-pyridin-2-yl | H |
| 2-247 | H | H | Me | 4-Br-3-Me-Ph | H |
| 2-248 | H | H | Me | 5-Cl-pyridin-3-yl | H |
| 2-249 | H | H | Me | 5-allylpyridin-2-yl | H |
| 2-250 | H | H | Me | 5-cyclopropylpyridin-2-yl | H |
| 2-251 | H | H | Me | 5-ethynylpyridin-2-yl | H |
| 2-252 | H | H | Me | 5-Ph-pyridin-2-yl | H |
| 2-253 | H | H | Me | 5-I-pyridin-2-yl | H |
| 2-254 | H | H | Me | 5-I-pyrimidin-2-yl | H |
| 2-255 | H | H | Cl | 4-F-Ph | H |
| 2-256 | H | H | Cl | 3-pyridyl | H |
| 2-257 | H | H | Cl | 5-Cl-pyridin-2-yl | H |
| 2-258 | H | H | Cl | 5-Br-pyridin-2-yl | H |
| 2-259 | H | H | Cl | 5-F-pyridin-2-yl | H |
| 2-260 | H | H | Cl | 5-I-pyridin-2-yl | H |
| 2-261 | H | H | Cl | 5-Me-pyridin-2-yl | H |
| 2-262 | H | H | Cl | 6-Me-pyridin-3-yl | H |
| 2-263 | H | H | Cl | 4-Me-pyridin-2-yl | H |
| 2-264 | H | H | Cl | 4-F-pyridin-2-yl | H |
| 2-265 | H | H | Cl | 4-Cl-pyridin-2-yl | H |
| 2-266 | H | H | Cl | 4-Br-pyridin-2-yl | H |
| 2-267 | H | H | Cl | 4-OMe-pyridin-2-yl | H |
| 2-268 | H | H | Cl | 2-pyrimidinyl | H |
| 2-269 | H | H | Cl | 5-F-pyrimidin-2-yl | H |
| 2-270 | H | H | Cl | 5-Cl-pyrimidin-2-yl | H |
| 2-271 | H | H | Cl | 5-Br-pyrimidin-2-yl | H |
| 2-272 | H | H | Cl | 5-I-pyrimidin-2-yl | H |
| 2-273 | H | H | Cl | 5-Me-pyrimidin-2-yl | H |
| 2-274 | H | H | Cl | 5-Me-pyrazin-2-yl | H |
| 2-275 | H | H | Cl | 2-pyrazinyl | H |
| 2-276 | H | H | Cl | isoquinolin-3-yl | H |
| 2-277 | H | H | Cl | quinolin-2-yl | H |
| 2-278 | H | H | Cl | 1,3-benzothiazol-2-yl | H |
| 2-279 | H | H | Cl | 7-Cl-1,3-benzothiazol-2-yl | H |
| 2-280 | H | H | Cl | 2-thiazolyl | H |
| 2-281 | H | H | Cl | 5-Br-thiazol-2-yl | H |
| 2-282 | H | H | Cl | 5-Me-thiazol-2-yl | H |
| 2-283 | H | H | Cl | 5-Cl-thiazol-2-yl | H |
| 2-284 | H | H | Cl | 2-thienyl | H |
| 2-285 | H | H | Cl | 3-Me-2-thienyl | H |
| 2-286 | H | H | Cl | 4-Me-2-thienyl | H |
| 2-287 | H | H | Cl | 5-Br-2-thienyl | H |
| 2-288 | H | H | Cl | 5-Cl-2-thienyl | H |
| 2-289 | H | H | Me | 3-Br-Ph | H |
| 2-290 | H | H | Me | 4-thiazolyl | H |
| 2-291 | H | H | Me | 2-Cl-thiazol-4-yl | H |
| 2-292 | H | H | Me | 2-Br-thiazol-4-yl | H |
| 2-293 | H | H | Me | 5-OSO₂Me-pyridin-2-yl | H |
| 2-294 | H | H | Me | 6-Cl-1,3-benzothiazol-2-yl | H |
| 2-295 | H | H | Me | 6-Br-1,3-benzothiazol-2-yl | H |
| 2-296 | H | H | Me | 1,3-benzoxazol-2-yl | H |
| 2-297 | H | H | Me | 6-Cl-1,3-benzoxazol-2-yl | H |
| 2-298 | H | H | Me | 6-Br-1,3-benzoxazol-2-yl | H |
| 2-299 | H | H | Me | 7-Cl-1,3-benzoxazol-2-yl | H |
| 2-300 | H | H | Me | 5-NH₂-pyridin-2-yl | H |
| 2-301 | H | H | Me | 5-OH-pyridin-2-yl | H |
| 2-302 | H | H | Me | 5-OCHF₂-pyridin-2-yl | H |
| 2-303 | H | H | Me | 5-MeO-pyridin-2-yl | H |
| 2-304 | H | H | Me | 5-MeS-pyridin-2-yl | H |
| 2-305 | H | H | Me | 5-NHMe-pyridin-2-yl | H |
| 2-306 | H | H | Me | 5-NMe₂-pyridin-2-yl | H |

In addition, NMR data of compounds of the general formula (I) according to the invention were generated. The NMR of the exemplary compounds were in each case recorded as ¹H-NMR spectrum at 400 MHz (CDCl₃) (¹H nuclear magnetic resonance data). Characteristic chemical shifts δ (ppm) for some exemplary compounds are listed below:

NMR compound 2-237 (CDCl₃, 400 MHz, δ in ppm):
2.32 (s, 3H); 3.39 (s, 2H); 3.70 (s, 3H); 4.00 (s, 3H); 7.18 (d, 2H); 7.39 (d, 2H); 8.38 (s, 2H).

NMR compound 2-117 (CDCl₃, 400 MHz, δ in ppm):
2.35 (s, 3H); 3.52 (s, 2H); 3.71 (s, 3H); 7.45 (d, 1H); 7.77 (dd, 1H); 8.53 (d, 1H); 8.65 (s, 2H); 9.08 (s, 1H).

NMR compound 2-120 (CDCl₃, 400 MHz, δ in ppm):
2.38 (s, 3H); 3.54 (s, 2H); 3.72 (s, 3H); 7.39 (d, 1H); 7.92 (dd, 1H); 8.64 (d, 1H); 8.67 (s, 2H); 9.09 (s, 1H).

NMR compound 2-28 (CDCl₃, 400 MHz, δ in ppm):
2.36 (s, 3H); 3.40 (s, 2H); 3.71 (s, 3H); 7.20 (d, 2H); 7.41 (d, 2H); 8.63 (s, 2H); 9.03 (s, 1H).

NMR compound 2-29 (CDCl₃, 400 MHz, δ in ppm):
2.34 (s, 3H); 3.38 (s, 2H); 3.72 (s, 3H); 7.20 (d, 2H); 7.44 (d, 2H); 8.50 (s, 2H).

NMR compound 2-116 (CDCl₃, 400 MHz, δ in ppm):
2.38 (s, 3H); 3.57 (s, 2H); 3.71 (s, 3H); 7.32 (m, 1H); 7.46 (m, 1H); 7.69 (m, 1H); 8.61 (m, 1H); 8.63 (s, 2H); 9.04 (s, 1H).

NMR compound 2-238 (CDCl$_3$, 400 MHz, δ in ppm):
2.38 (s, 3H); 3.33 (s, 3H); 3.52 (s, 2H); 3.72 (s, 3H); 7.32 (m, 1H); 7.58 (m, 1H); 7.85 (m, 1H); 8.62 (m, 1H); 8.75 (s, 2H).

NMR compound 2-239 (CDCl$_3$, 400 MHz, δ in ppm):
2.38 (s, 3H); 2.39 (s, 3H); 3.57 (s, 2H); 3.73 (s, 3H); 7.14 (d, 1H); 7.26 (s, 1H); 8.46 (d, 1H); 8.67 (s, 2H); 9.05 (s, 1H).

NMR compound 2-215 (CDCl$_3$, 400 MHz, δ in ppm):
2.38 (s, 3H); 2.61 (s, 3H); 3.56 (s, 2H); 3.72 (s, 3H); 8.43 (s, 1H); 8.60 (s, 1H); 8.68 (s, 2H); 9.09 (s, 1H). m.p.: 193° C.

NMR compound 2-135 (CDCl$_3$, 400 MHz, δ in ppm):
2.35 (s, 3H); 2.36 (s, 3H); 3.40 (s, 2H); 3.72 (s, 3H); 7.00 (m, 1H); 7.11 (m, 1H); 7.39 (m, 1H); 8.62 (s, 2H); 9.02 (s, 1H).

NMR compound 2-16 (CDCl$_3$, 400 MHz, δ in ppm):
2.34 (s, 3H); 2.39 (s, 3H); 3.41 (s, 2H); 3.71 (s, 3H); 7.11 (d, 2H); 7.22 (d, 2H); 8.63 (s, 2H); 9.01 (s, 1H).

NMR compound 2-132 (CDCl$_3$, 400 MHz, δ in ppm):
2.36 (s, 3H); 3.39 (s, 2H); 3.71 (s, 3H); 7.12 (m, 2H); 7.25 (m, 2H); 8.65 (brs, 2H); 9.05 (brs, 1H).

NMR compound 2-148 (CDCl$_3$, 400 MHz, δ in ppm):
2.39 (s, 3H); 2.40 (s, 3H); 3.57 (s, 2H); 3.74 (s, 3H); 7.14 (dd, 2H); 7.26 (d, 2H); 8.47 (d, 1H); 8.66 (s, 2H); 9.05 (s, 1H).

NMR compound 2-240 (CDCl$_3$, 400 MHz, δ in ppm):
2.37 (s, 3H); 3.39 (s, 2H); 3.72 (s, 3H); 7.13 (d, 2H); 7.58 (d, 2H); 8.63 (s, 2H); 9.04 (s, 1H).

NMR compound 2-65 (CDCl$_3$, 400 MHz, δ in ppm):
2.33 (s, 3H); 3.48 (s, 2H); 3.72 (s, 3H); 6.87 (d, 2H); 6.93 (d, 2H); 8.75 (brs, 2H); 9.11 (brs, 1H).

NMR compound 2-64 (CDCl$_3$, 400 MHz, δ in ppm):
2.25 (s, 3H); 2.33 (s, 3H); 3.48 (s, 2H); 3.72 (s, 3H); 6.85 (d, 2H); 7.05 (d, 2H); 8.73 (brs, 2H); 9.09 (brs, 1H).

NMR compound 2-47 (CDCl$_3$, 400 MHz, δ in ppm):
2.28 (s, 6H); 2.35 (s, 3H); 3.41 (s, 2H); 3.70 (s, 3H); 6.82 (s, 2H); 7.05 (s, 1H); 8.63 (s, 2H); 9.01 (s, 1H).

NMR compound 2-241 (CDCl$_3$, 400 MHz, δ in ppm):
2.40 (s, 3H); 3.59 (s, 2H); 3.73 (s, 3H); 7.72 (m, 1H); 7.78 (m, 1H); 7.87 (m, 1H); 7.92 (s, 1H); 8.01 (m, 1H); 8.67 (s, 2H); 9.02 (s, 1H); 9.18 (s, 1H). m.p.: 100.7° C.

NMR compound 2-217 (CDCl$_3$, 400 MHz, δ in ppm):
2.48 (s, 3H); 3.71 (s, 3H); 3.81 (s, 2H); 7.43 (t, 1H); 7.51 (t, 1H); 7.89 (d, 1H); 8.00 (d, 1H); 8.82 (s, 2H); 9.17 (s, 1H).

NMR compound 2-243 (CDCl$_3$, 400 MHz, δ in ppm):
2.38 (s, 3H); 3.42 (s, 2H); 3.73 (s, 3H); 7.48 (d, 2H); 8.30 (d, 2H); 8.61 (s, 2H); 9.08 (s, 1H).

NMR compound 2-68 (CDCl$_3$, 400 MHz, δ in ppm):
2.33 (s, 3H); 3.48 (s, 2H); 3.72 (s, 3H); 6.83 (d, 2H); 7.08 (d, 2H); 8.73 (s, 2H); 9.11 (s, 1H).

NMR compound 2-224 (CDCl$_3$, 400 MHz, δ in ppm):
2.37 (s, 3H); 3.68 (s, 3H); 3.96 (s, 2H); 7.17 (t, 1H); 8.64 (d, 2H); 8.74 (s, 2H); 9.14 (s, 1H).

NMR compound 2-2 (CDCl$_3$, 400 MHz, δ in ppm):
2.36 (s, 3H); 3.41 (s, 2H); 3.70 (s, 3H); 7.24 (m, 2H); 7.43 (m, 2H); 8.61 (s, 2H); 9.01 (s, 1H).

NMR compound 2-289 (CDCl$_3$, 400 MHz, δ in ppm):
2.36 (s, 3H); 3.41 (s, 2H); 3.72 (s, 3H); 7.14 (m, 1H); 7.29 (m, 1H); 7.44 (m, 1H); 7.58 (m, 1H); 8.63 (s, 2H); 9.03 (s, 1H).

NMR compound 2-247 (CDCl$_3$, 400 MHz, δ in ppm):
2.34 (s, 3H); 2.37 (s, 3H); 3.39 (s, 2H); 3.71 (s, 3H); 6.92 (m, 1H); 7.13 (m, 1H); 7.58 (m, 1H); 8.64 (s, 2H); 9.04 (s, 1H).

NMR compound 2-124 (CDCl$_3$, 400 MHz, δ in ppm):
2.38 (s, 3H); 2.39 (s, 3H); 3.54 (s, 2H); 3.70 (s, 3H); 7.33 (m, 1H); 7.59 (m, 1H); 8.42 (s, 1H); 8.63 (s, 2H); 9.03 (s, 1H).

NMR compound 2-155 (CDCl$_3$, 400 MHz, δ in ppm):
2.38 (s, 3H); 3.55 (s, 2H); 3.72 (s, 3H); 3.86 (s, 3H); 6.82 (m, 1H); 7.10 (m, 1H); 8.39 (m, 1H); 8.64 (s, 2H); 9.04 (s, 1H). m.p.: 161.7° C.

NMR compound 2-249 (CDCl$_3$, 400 MHz, δ in ppm):
2.37 (s, 3H); 3.56 (s, 2H); 3.71 (s, 3H); 5.48 (m, 1H); 5.88 (m, 1H); 6.71 (m, 1H); 7.41 (m, 1H); 7.80 (m, 1H); 8.58 (m, 1H); 8.65 (s, 2H); 9.05 (s, 1H).

NMR compound 2-242 (CDCl$_3$, 400 MHz, δ in ppm):
2.40 (s, 3H); 3.68 (s, 2H); 3.69 (s, 3H); 7.43 (m, 1H); 7.61 (m, 1H); 7.72 (m, 1H); 7.84 (m, 1H); 7.95 (m, 1H); 8.21 (m, 1H); 8.69 (s, 2H); 9.04 (s, 1H).

NMR compound 2-290 (CDCl$_3$, 400 MHz, δ in ppm):
2.39 (s, 3H); 3.53 (s, 2H); 3.75 (s, 3H); 7.75 (s, 1H); 8.68 (s, 2H); 8.83 (s, 1H); 9.09 (s, 1H).

NMR compound 2-211 (CDCl$_3$, 400 MHz, δ in ppm):
2.32 (s, 3H); 2.35 (s, 3H); 2.40 (s, 3H); 3.54 (s, 2H); 3.71 (s, 3H); 7.00 (s, 1H); 7.06 (s, 1H); 8.65 (s, 2H); 9.03 (s, 1H).

NMR compound 2-66 (CDCl$_3$, 400 MHz, δ in ppm):
2.32 (s, 3H); 2.48 (s, 3H); 3.48 (s, 2H); 3.72 (s, 3H); 6.72 (d, 1H); 6.82 (d, 1H); 8.72 (s, 2H); 9.08 (s, 1H).

NMR compound 2-219 (CDCl$_3$, 400 MHz, δ in ppm):
2.39 (s, 3H); 3.73 (s, 3H); 3.82 (s, 2H); 7.43 (m, 1H); 7.47 (m, 1H); 7.89 (m, 1H); 8.83 (s, 2H); 9.19 (s, 1H).

NMR compound 2-244 (CDCl$_3$, 400 MHz, δ in ppm):
2.35 (s, 3H); 3.40 (s, 2H); 3.72 (s, 3H); 7.17 (d, 2H); 7.43 (t, 1H); 8.64 (s, 2H); 9.09 (s, 1H).

TABLE 3

Compounds of the formula (Ia'''')

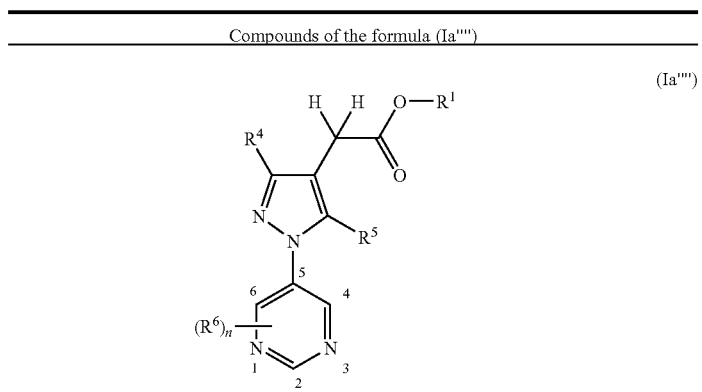

| No. | R$^1$ | R$^4$ | R$^5$ | (R$^6$)$_n$ |
|---|---|---|---|---|
| 3-1 | Et | Me | Ph | H |
| 3-2 | Et | Me | Ph | 4-Me |
| 3-3 | Et | Me | 3-Cl-Ph | H |
| 3-4 | Et | Me | 4-Cl-Ph | H |

TABLE 3-continued

Compounds of the formula (Ia'''')

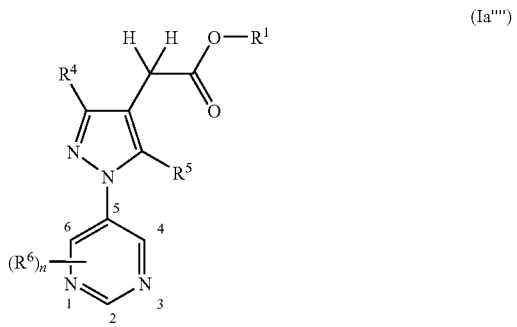

| No. | R[1] | R[4] | R[5] | (R[6])n |
|---|---|---|---|---|
| 3-5 | Et | Me | 4-Cl-Ph | 4-Me |
| 3-6 | Et | Me | 2-thienyl | H |
| 3-7 | Et | Me | 3-thienyl | H |
| 3-8 | Et | Me | 3-Me-2-thienyl | H |
| 3-9 | Et | Me | 4-Me-2-thienyl | H |
| 3-10 | Et | Me | 5-Br-2-thienyl | H |
| 3-11 | Et | Me | 5-Br-2-thienyl | 4-Me |
| 3-12 | Et | Me | 5-Cl-2-thienyl | H |
| 3-13 | Et | Me | 5-Cl-2-thienyl | 4-Me |
| 3-14 | Et | Me | 5-I-2-thienyl | H |
| 3-15 | Et | Me | 5-Me-2-thienyl | H |
| 3-16 | Et | Me | 3-pyridyl | H |
| 3-17 | Et | Me | 6-MeO-pyridin-3-yl | H |
| 3-18 | Et | Me | 6-OH-pyridin-3-yl | H |
| 3-19 | Et | Me | 6-Me-pyridin-3-yl | H |
| 3-20 | Et | Me | 4-Me-Ph | H |
| 3-21 | Et | Me | 4-Me-Ph | 4-Me |
| 3-22 | Et | Me | 4-Br-Ph | H |
| 3-23 | Et | Me | 4-F-Ph | H |
| 3-24 | Et | Me | 4-F-Ph | 4-Me |
| 3-25 | Et | Me | 5-Cl-pyridin-2-yl | H |
| 3-26 | Et | Me | 5-Br-pyridin-2-yl | H |
| 3-27 | Et | Me | 5-F-pyridin-2-yl | H |
| 3-28 | Et | Me | 5-F-pyridin-2-yl | 4-Me |
| 3-29 | Et | Me | 5-Cl-pyridin-2-yl | 4-Me |
| 3-30 | Et | Me | 5-Br-pyridin-2-yl | 4-Me |
| 3-31 | Et | Me | 5-Me-pyridin-2-yl | H |
| 3-32 | Et | Me | 5-Me-pyridin-2-yl | 4-Me |
| 3-33 | Et | Me | 2-pyridyl | 4-Me |
| 3-34 | Et | Me | 2-pyridyl | H |
| 3-35 | Et | Me | 4-pyridyl | H |
| 3-36 | Et | Me | 4-Me-pyridin-2-yl | H |
| 3-37 | Et | Me | 4-Me-pyridin-2-yl | 4-Me |
| 3-38 | Et | Me | 2-thiazolyl | H |
| 3-39 | Et | Me | 4-Me-thiazol-2-yl | H |
| 3-40 | Et | Me | 5-Br-thiazol-2-yl | H |
| 3-41 | Et | Me | 5-Cl-thiazol-2-yl | H |
| 3-42 | Et | Me | 5-Me-thiazoi-2-yl | H |
| 3-43 | Et | Me | 4,5-Me$_2$-thiazol-2-yl | H |
| 3-44 | Et | Me | 4,5-Cl$_2$-thiazol-2-yl | H |
| 3-45 | Et | Me | 4,6-Me$_2$-pyridin-2-yl | H |
| 3-46 | Et | Me | 2-pyrazinyl | H |
| 3-47 | Et | Me | 2-pyrimidinyl | H |
| 3-48 | Et | Me | 2-pyrimidinyl | 4-Me |
| 3-49 | Et | Me | 5-Cl-pyrimidin-2-yl | H |
| 3-50 | Et | Me | 5-Br-pyrimidin-2-yl | H |
| 3-51 | Et | Me | 5-Me-pyrimidin-2-yl | H |
| 3-52 | Et | Me | 5-Me-pyrimidin-2-yl | 4-Me |
| 3-53 | Et | Me | 4,6-Me$_2$-pyrimidin-2-yl | H |
| 3-54 | Et | Me | 4,6-Me$_2$-pyrimidin-2-yl | 4-Me |
| 3-55 | Et | Me | 1,3-benzothiazol-2-yl | H |
| 3-56 | Et | Me | 7-Cl-1,3-benzothiazol-2-yl | H |
| 3-57 | Et | Me | 1,5-Me$_2$-pyrazol-3-yl | H |
| 3-58 | Et | Me | 5-Me-pyrazin-2-yl | H |
| 3-59 | Et | Me | 5-F-pyrimidin-2-yl | H |
| 3-60 | Et | Me | 4,6-Me$_2$-pyrimidin-2-yl | H |
| 3-61 | Et | Me | 3-pyridazinyl | H |
| 3-62 | Et | Me | 6-Me-pyridazin-3-yl | H |
| 3-63 | Et | Me | 3-(1,2,4)-triazinyl | H |

TABLE 3-continued

Compounds of the formula (Ia'''')

$$\text{(Ia'''')}$$

| No. | R¹ | R⁴ | R⁵ | (R⁶)ₙ |
|---|---|---|---|---|
| 3-64 | Et | Me | 6-Me-(1,2,4)-triazin-3-yl | H |
| 3-65 | Pr | Me | Ph | H |
| 3-66 | Pr | Me | 4-Cl-Ph | H |
| 3-67 | Pr | Me | 2-thienyl | H |
| 3-68 | Pr | Me | 3-pyridyl | H |
| 3-69 | Pr | Me | 6-Me-pyridin-3-yl | H |
| 3-70 | Pr | Me | 4-Me-Ph | H |
| 3-71 | Pr | Me | 4-Br-Ph | H |
| 3-72 | Pr | Me | 4-F-Ph | H |
| 3-73 | Pr | Me | 5-Cl-pyridin-2-yl | H |
| 3-74 | Pr | Me | 5-Br-pyridin-2-yl | H |
| 3-75 | Pr | Me | 5-F-pyridin-2-yl | H |
| 3-76 | Pr | Me | 5-Me-pyridin-2-yl | H |
| 3-77 | Pr | Me | 2-pyridyl | H |
| 3-78 | Pr | Me | 4-pyridyl | H |
| 3-79 | i-Pr | Me | Ph | H |
| 3-80 | i-Pr | Me | 4-Cl-Ph | H |
| 3-81 | i-Pr | Me | 2-thienyl | H |
| 3-82 | i-Pr | Me | 3-pyridyl | H |
| 3-83 | i-Pr | Me | 6-Me-pyridin-3-yl | H |
| 3-84 | i-Pr | Me | 4-Me-Ph | H |
| 3-85 | i-Pr | Me | 4-Br-Ph | H |
| 3-86 | i-Pr | Me | 4-F-Ph | H |
| 3-87 | i-Pr | Me | 5-Cl-pyridin-2-yl | H |
| 3-88 | i-Pr | Me | 5-Br-pyridin-2-yl | H |
| 3-89 | i-Pr | Me | 5-F-pyridin-2-yl | H |
| 3-90 | i-Pr | Me | 5-Me-pyridin-2-yl | H |
| 3-91 | i-Pr | Me | 2-pyridyl | H |
| 3-92 | i-Pr | Me | 4-pyridyl | H |
| 3-93 | CH₂Ph | Me | Ph | H |
| 3-94 | CH₂Ph | Me | 4-Cl-Ph | H |
| 3-95 | CH₂Ph | Me | 2-thienyl | H |
| 3-96 | CH₂Ph | Me | 2-pyridyl | H |
| 3-97 | prop-2-yn-1-yl | Me | Ph | H |
| 3-98 | prop-2-yn-1-yl | Me | 4-Cl-Ph | H |
| 3-99 | prop-2-yn-1-yl | Me | 2-thienyl | H |
| 3-100 | prop-2-yn-1-yl | Me | 3-thienyl | H |
| 3-101 | prop-2-yn-1-yl | Me | 3-Me-2-thienyl | H |
| 3-102 | prop-2-yn-1-yl | Me | 4-Me-2-thienyl | H |
| 3-103 | prop-2-yn-1-yl | Me | 5-Cl-2-thienyl | H |
| 3-104 | prop-2-yn-1-yl | Me | 5-Me-2-thienyl | H |
| 3-105 | prop-2-yn-1-yl | Me | 3-pyridyl | H |
| 3-106 | prop-2-yn-1-yl | Me | 6-MeO-pyridin-3-yl | H |
| 3-107 | prop-2-yn-1-yl | H | Ph | H |
| 3-108 | prop-2-yn-1-yl | Me | 6-Me-pyridin-3-yl | H |
| 3-109 | prop-2-yn-1-yl | Me | 4-Me-Ph | H |
| 3-110 | prop-2-yn-1-yl | Me | 4-Br-Ph | H |
| 3-111 | prop-2-yn-1-yl | Me | 4-F-Ph | H |
| 3-112 | prop-2-yn-1-yl | Me | 5-Cl-pyridin-2-yl | H |
| 3-113 | prop-2-yn-1-yl | Me | 5-Br-pyridin-2-yl | H |
| 3-114 | prop-2-yn-1-yl | Me | 5-F-pyridin-2-yl | H |
| 3-115 | prop-2-yn-1-yl | Me | 5-Me-pyridin-2-yl | H |
| 3-116 | prop-2-yn-1-yl | Me | 2-pyridyl | H |
| 3-117 | prop-2-yn-1-yl | Me | 4-pyridyl | H |
| 3-118 | prop-2-yn-1-yl | Me | 4-Cl-Ph | 4-Me |
| 3-119 | prop-2-yn-1-yl | Me | Ph | 4-Me |
| 3-120 | cyclopropylmethyl | Me | Ph | H |
| 3-121 | cyclopropylmethyl | Me | 4-Cl-Ph | H |
| 3-122 | cyclopropylmethyl | Me | 2-thienyl | H |

TABLE 3-continued

Compounds of the formula (Ia'''')

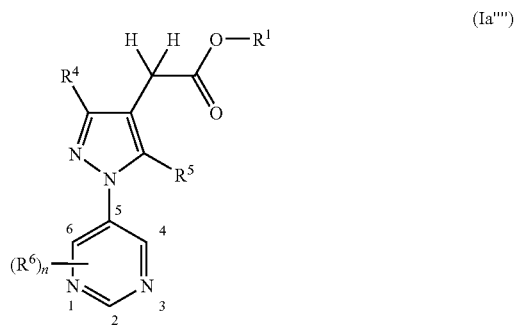

| No. | R$^1$ | R$^4$ | R$^5$ | (R$^6$)$_n$ |
|---|---|---|---|---|
| 3-123 | cyclopropylmethyl | Me | 3-thienyl | H |
| 3-124 | cyclopropylmethyl | Me | 3-Me-2-thienyl | H |
| 3-125 | cyclopropylmethyl | Me | 3-pyridyl | H |
| 3-126 | cyclopropylmethyl | Me | 5-Cl-2-thienyl | H |
| 3-127 | cyclopropylmethyl | Me | 5-Me-2-thienyl | H |
| 3-128 | cyclopropylmethyl | Me | 4-Me-2-thienyl | H |
| 3-129 | cyclopropylmethyl | Me | 6-MeO-pyridin-3-yl | H |
| 3-130 | cyclopropylmethyl | Me | 6-OH-pyridin-3-yl | H |
| 3-131 | cyclopropylmethyl | Me | 6-Me-pyridin-3-yl | H |
| 3-132 | cyclopropylmethyl | Me | 4-Me-Ph | H |
| 3-133 | cyclopropylmethyl | Me | 4-Br-Ph | H |
| 3-134 | cyclopropylmethyl | Me | 4-F-Ph | H |
| 3-135 | cyclopropylmethyl | Me | 5-Cl-pyridin-2-yl | H |
| 3-136 | cyclopropylmethyl | Me | 5-Br-pyridin-2-yl | H |
| 3-137 | cyclopropylmethyl | Me | 5-F-pyridin-2-yl | H |
| 3-138 | cyclopropylmethyl | Me | 5-Me-pyridin-2-yl | H |
| 3-139 | cyclopropylmethyl | Me | 2-pyridyl | H |
| 3-140 | cyclopropylmethyl | Me | 4-pyridyl | H |
| 3-141 | cyclopropylmethyl | Me | 4-Cl-Ph | 4-Me |
| 3-142 | cyclopropylmethyl | Me | Ph | 4-Me |
| 3-143 | cyclopropylmethyl | H | Ph | H |
| 3-144 | 3,3-dichloro-2-fluoroprop-2-en-1-yl | Me | Ph | H |
| 3-145 | 3,3-dichloro-2-fluoroprop-2-en-1-yl | Me | 4-Cl-Ph | H |
| 3-146 | 3,3-dichloro-2-fluoroprop-2-en-1-yl | Me | 2-thienyl | H |
| 3-147 | 3,3-dichloro-2-fluoroprop-2-en-1-yl | Me | 2-pyridyl | H |
| 3-148 | (1-methylcyclopropyl)methyl | Me | Ph | H |
| 3-149 | (1-methylcyclopropyl)methyl | Me | 4-Cl-Ph | H |
| 3-150 | (1-methylcyclopropyl)methyl | Me | 2-thienyl | H |
| 3-151 | (1-methylcyclopropyl)methyl | Me | 2-pyridyl | H |
| 3-152 | 4-chlorobut-2-yn-1-yl | Me | Ph | H |
| 3-153 | 4-chlorobut-2-yn-1-yl | Me | 4-Cl-Ph | H |
| 3-154 | 4-chlorobut-2-yn-1-yl | Me | 2-thienyl | H |
| 3-155 | 4-chlorobut-2-yn-1-yl | Me | 2-pyridyl | H |
| 3-156 | (2,2-dichlorocyclopropyl)methyl | Me | Ph | H |
| 3-157 | (2,2-dichlorocyclopropyl)methyl | Me | 4-Cl-Ph | H |
| 3-158 | (2,2-dichlorocyclopropyl)methyl | Me | 2-thienyl | H |
| 3-159 | (2,2-dichlorocyclopropyl)methyl | Me | 2-pyridyl | H |
| 3-160 | but-2-yn-1-yl | Me | Ph | H |
| 3-161 | but-2-yn-1-yl | Me | 4-Cl-Ph | H |
| 3-162 | but-2-yn-1-yl | Me | 2-thienyl | H |
| 3-163 | but-2-yn-1-yl | Me | 3-thienyl | H |
| 3-164 | but-2-yn-1-yl | Me | 3-Me-2-thienyl | H |
| 3-165 | but-2-yn-1-yl | Me | 4-Me-2-thienyl | H |
| 3-166 | but-2-yn-1-yl | Me | 5-Cl-2-thienyl | H |
| 3-167 | but-2-yn-1-yl | Me | 5-Me-2-thienyl | H |
| 3-168 | but-2-yn-1-yl | Me | 3-pyridyl | H |
| 3-169 | but-2-yn-1-yl | Me | 6-MeO-pyridin-3-yl | H |
| 3-170 | but-2-yn-1-yl | H | Ph | H |
| 3-171 | but-2-yn-1-yl | Me | 6-Me-pyridin-3-yl | H |
| 3-172 | but-2-yn-1-yl | Me | 4-Me-Ph | H |
| 3-173 | but-2-yn-1-yl | Me | 4-Br-Ph | H |
| 3-174 | but-2-yn-1-yl | Me | 4-F-Ph | H |
| 3-175 | but-2-yn-1-yl | Me | 5-Cl-pyridin-2-yl | H |
| 3-176 | but-2-yn-1-yl | Me | 5-Br-pyridin-2-yl | H |
| 3-177 | but-2-yn-1-yl | Me | 5-F-pyridin-2-yl | H |
| 3-178 | but-2-yn-1-yl | Me | 5-Me-pyridin-2-yl | H |
| 3-179 | but-2-yn-1-yl | Me | 2-pyridyl | H |
| 3-180 | but-2-yn-1-yl | Me | 4-pyridyl | H |
| 3-181 | but-2-yn-1-yl | Me | 4-Cl-Ph | 4-Me |

TABLE 3-continued

Compounds of the formula (Ia'''')

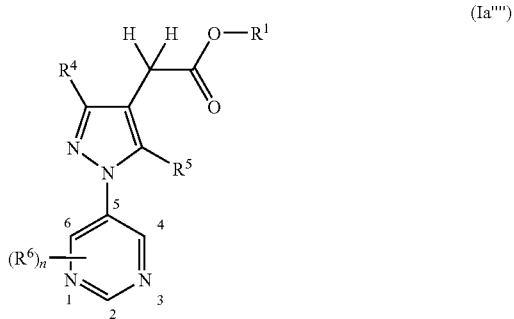

| No. | R¹ | R⁴ | R⁵ | (R⁶)ₙ |
|---|---|---|---|---|
| 3-182 | but-2-yn-1-yl | Me | Ph | 4-Me |
| 3-183 | 1-methylprop-2-yn-1-yl | Me | Ph | H |
| 3-184 | 1-methylprop-2-yn-1-yl | Me | 4-Cl-Ph | H |
| 3-185 | 1-methylprop-2-yn-1-yl | Me | 2-thienyl | H |
| 3-186 | 1-methylprop-2-yn-1-yl | Me | 2-pyridyl | H |
| 3-187 | 1-cyclopropylethyl | Me | Ph | H |
| 3-188 | 1-cyclopropylethyl | Me | 4-Cl-Ph | H |
| 3-189 | 1-cyclopropylethyl | Me | 2-thienyl | H |
| 3-190 | 1-cyclopropylethyl | Me | 2-pyridyl | H |
| 3-191 | allyl | Me | Ph | H |
| 3-192 | allyl | Me | 4-Cl-Ph | H |
| 3-193 | allyl | Me | 2-thienyl | H |
| 3-194 | allyl | Me | 2-pyridyl | H |
| 3-195 | 3-methylbut-2-en-1-yl | Me | Ph | H |
| 3-196 | 3-methylbut-2-en-1-yl | Me | 4-Cl-Ph | H |
| 3-197 | 3-methylbut-2-en-1-yl | Me | 2-thienyl | H |
| 3-198 | 3-methylbut-2-en-1-yl | Me | 2-pyridyl | H |
| 3-199 | 2-methylprop-2-en-1-yl | Me | Ph | H |
| 3-200 | 2-methylprop-2-en-1-yl | Me | 4-Cl-Ph | H |
| 3-201 | 2-methylprop-2-en-1-yl | Me | 2-thienyl | H |
| 3-202 | 2-methylprop-2-en-1-yl | Me | 2-pyridyl | H |
| 3-203 | (2E)-1-methylbut-2-en-1-yl | Me | Ph | H |
| 3-204 | (2E)-1-methylbut-2-en-1-yl | Me | 4-Cl-Ph | H |
| 3-205 | (2E)-1-methylbut-2-en-1-yl | Me | 2-thienyl | H |
| 3-206 | (2E)-1-methylbut-2-en-1-yl | Me | 2-pyridyl | H |
| 3-207 | 3-phenylprop-2-yn-1-yl | Me | Ph | H |
| 3-208 | 3-phenylprop-2-yn-1-yl | Me | 4-Cl-Ph | H |
| 3-209 | 3-phenylprop-2-yn-1-yl | Me | 2-thienyl | H |
| 3-210 | 3-phenylprop-2-yn-1-yl | Me | 2-pyridyl | H |
| 3-211 | cyclobutylmethyl | Me | Ph | H |
| 3-212 | cyclobutylmethyl | Me | 4-Cl-Ph | H |
| 3-213 | cyclobutylmethyl | Me | 2-thienyl | H |
| 3-214 | cyclobutylmethyl | Me | 2-pyridyl | H |
| 3-215 | cyclopentylmethyl | Me | Ph | H |
| 3-216 | cyclopentylmethyl | Me | 4-Cl-Ph | H |
| 3-217 | cyclopentylmethyl | Me | 2-thienyl | H |
| 3-218 | cyctopentylmethyl | Me | 2-pyridyl | H |
| 3-219 | cyclohexylmethyl | Me | Ph | H |
| 3-220 | cyclohexylmethyl | Me | 4-Cl-Ph | H |
| 3-221 | cyclohexylmethyl | Me | 2-thienyl | H |
| 3-222 | cyclohexylmethyl | Me | 2-pyridyl | H |
| 3-223 | but-3-en-1-yl | Me | Ph | H |
| 3-224 | but-3-en-1-yl | Me | 4-Cl-Ph | H |
| 3-225 | but-3-en-1-yl | Me | 2-thienyl | H |
| 3-226 | but-3-en-1-yl | Me | 2-pyridyl | H |
| 3-227 | 2-chloroprop-2-en-1-yl | Me | Ph | H |
| 3-228 | 2-chloroprop-2-en-1-yl | Me | 4-Cl-Ph | H |
| 3-229 | 2-chloroprop-2-en-1-yl | Me | 2-thienyl | H |
| 3-230 | 2-chloroprop-2-en-1-yl | Me | 3-thienyl | H |
| 3-231 | 2-chloroprop-2-en-1-yl | Me | 3-Me-2-thienyl | H |
| 3-232 | 2-chloroprop-2-en-1-yl | Me | 4-Me-2-thienyl | H |
| 3-233 | 2-chloroprop-2-en-1-yl | Me | 5-Cl-2-thienyl | H |
| 3-234 | 2-chloroprop-2-en-1-yl | Me | 5-Me-2-thienyl | H |
| 3-235 | 2-chloroprop-2-en-1-yl | Me | 3-pyridyl | H |
| 3-236 | 2-chloroprop-2-en-1-yl | Me | 6-MeO-pyridin-3-yl | H |
| 3-237 | 2-chloroprop-2-en-1-yl | Me | 6-OH-pyridin-3-yl | H |
| 3-238 | 2-chloroprop-2-en-1-yl | Me | 6-Me-pyridin-3-yl | H |
| 3-239 | 2-chloroprop-2-en-1-yl | Me | 4-Me-Ph | H |
| 3-240 | 2-chloroprop-2-en-1-yl | Me | 4-Br-Ph | H |

TABLE 3-continued

Compounds of the formula (Ia'''')

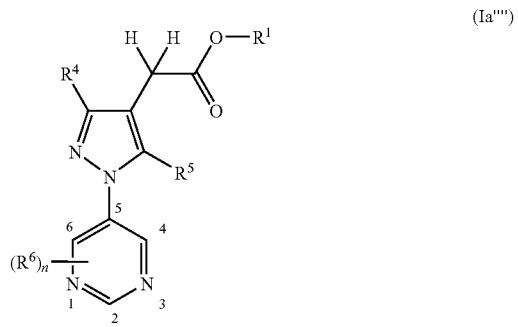

| No. | R¹ | R⁴ | R⁵ | (R⁶)ₙ |
|---|---|---|---|---|
| 3-241 | 2-chloroprop-2-en-1-yl | Me | 4-F-Ph | H |
| 3-242 | 2-chloroprop-2-en-1-yl | Me | 5-Cl-pyridin-2-yl | H |
| 3-243 | 2-chloroprop-2-en-1-yl | Me | 5-Br-pyridin-2-yl | H |
| 3-244 | 2-chloroprop-2-en-1-yl | Me | 5-F-pyridin-2-yl | H |
| 3-245 | 2-chloroprop-2-en-1-yl | Me | 5-Me-pyridin-2-yl | H |
| 3-246 | 2-chloroprop-2-en-1-yl | Me | 2-pyridyl | H |
| 3-247 | 2-chloroprop-2-en-1-yl | Me | 4-pyridyl | H |
| 3-248 | 2-chloroprop-2-en-1-yl | Me | 4-Cl-Ph | 4-Me |
| 3-249 | 2-chloroprop-2-en-1-yl | Me | Ph | 4-Me |
| 3-250 | 2-chloroprop-2-en-1-yl | H | Ph | H |
| 3-251 | 2-methoxyethyl | Me | Ph | H |
| 3-252 | 2-methoxyethyl | Me | 4-Cl-Ph | H |
| 3-253 | 2-methoxyethyl | Me | 2-thienyl | H |
| 3-254 | 2-methoxyethyl | Me | 2-pyridyl | H |
| 3-255 | tetrahydrofuran-2-ylmethyl | Me | Ph | H |
| 3-256 | tetrahydrofuran-2-ylmethyl | Me | 4-Cl-Ph | H |
| 3-257 | tetrahydrofuran-2-ylmethyl | Me | 2-thienyl | H |
| 3-258 | tetrahydrofuran-2-ylmethyl | Me | 2-pyridyl | H |
| 3-259 | 2-(dimethylamino)ethyl | Me | Ph | H |
| 3-260 | 2-(dimethylamino)ethyl | Me | 4-Cl-Ph | H |
| 3-261 | 2-(dimethylamino)ethyl | Me | 2-thienyl | H |
| 3-262 | 2-(dimethylamino)ethyl | Me | 2-pyridyl | H |
| 3-263 | oxetan-3-yl | Me | Ph | H |
| 3-264 | oxetan-3-yl | Me | 4-Cl-Ph | H |
| 3-265 | oxetan-3-yl | Me | 2-thienyl | H |
| 3-266 | oxetan-3-yl | Me | 2-pyridyl | H |
| 3-267 | (3-methyloxetan-3-yl)methyl | Me | Ph | H |
| 3-268 | (3-methyloxetan-3-yl)methyl | Me | 4-Cl-Ph | H |
| 3-269 | (3-methyloxetan-3-yl)methyl | Me | 2-thienyl | H |
| 3-270 | (3-methyloxetan-3-yl)methyl | Me | 2-pyridyl | H |
| 3-271 | 2,2,2-trifluoroethyl | Me | Ph | H |
| 3-272 | 2,2,2-trifluoroethyl | Me | 4-Cl-Ph | H |
| 3-273 | 2,2,2-trifluoroethyl | Me | 2-thienyl | H |
| 3-274 | 2,2,2-trifluoroethyl | Me | 3-pyridyl | H |
| 3-275 | 2,2,2-trifluoroethyl | Me | 6-Me-pyridin-3-yl | H |
| 3-276 | 2,2,2-trifluoroethyl | Me | 4-Me-Ph | H |
| 3-277 | 2,2,2-trifluoroethyl | Me | 4-Br-Ph | H |
| 3-278 | 2,2,2-trifluoroethyl | Me | 4-F-Ph | H |
| 3-279 | 2,2,2-trifluoroethyl | Me | 5-Cl-pyridin-2-yl | H |
| 3-280 | 2,2,2-trifluoroethyl | Me | 5-Br-pyridin-2-yl | H |
| 3-281 | 2,2,2-trifluoroethyl | Me | 5-F-pyridin-2-yl | H |
| 3-282 | 2,2,2-trifluoroethyl | Me | 5-Me-pyridin-2-yl | H |
| 3-283 | 2,2,2-trifluoroethyl | Me | 2-pyridyl | H |
| 3-284 | 2,2,2-trifluoroethyl | Me | 4-pyridyl | H |
| 3-285 | CH₂(4-Cl-Ph) | Me | Ph | H |
| 3-286 | CH₂(4-Cl-Ph) | Me | 4-Cl-Ph | H |
| 3-287 | CH₂(4-Cl-Ph) | Me | 2-thienyl | H |
| 3-288 | CH₂(4-Cl-Ph) | Me | 3-pyridyl | H |
| 3-289 | CH₂(4-Cl-Ph) | Me | 6-Me-pyridin-3-yl | H |
| 3-290 | CH₂(4-Cl-Ph) | Me | 4-Me-Ph | H |
| 3-291 | CH₂(4-Cl-Ph) | Me | 4-Br-Ph | H |
| 3-292 | CH₂(4-Cl-Ph) | Me | 4-F-Ph | H |
| 3-293 | CH₂(4-Cl-Ph) | Me | 5-Cl-pyridin-2-yl | H |
| 3-294 | CH₂(4-Cl-Ph) | Me | 5-Br-pyridin-2-yl | H |
| 3-295 | CH₂(4-Cl-Ph) | Me | 5-F-pyridin-2-yl | H |
| 3-296 | CH₂(4-Cl-Ph) | Me | 5-Me-pyridin-2-yl | H |
| 3-297 | CH₂(4-Cl-Ph) | Me | 2-pyridyl | H |
| 3-298 | CH₂(4-Cl-Ph) | Me | 4-pyridyl | H |
| 3-299 | CH₂(4-F-Ph) | Me | Ph | H |

TABLE 3-continued

Compounds of the formula (Ia'''')

(Ia'''')

| No. | R¹ | R⁴ | R⁵ | (R⁶)ₙ |
|---|---|---|---|---|
| 3-300 | CH₂(4-F-Ph) | Me | 4-Cl-Ph | H |
| 3-301 | CH₂(4-F-Ph) | Me | 2-thienyl | H |
| 3-302 | CH₂(4-F-Ph) | Me | 3-pyridyl | H |
| 3-303 | CH₂(4-F-Ph) | Me | 6-Me-pyridin-3-yl | H |
| 3-304 | CH₂(4-F-Ph) | Me | 4-Me-Ph | H |
| 3-305 | CH₂(4-F-Ph) | Me | 4-Br-Ph | H |
| 3-306 | CH₂(4-F-Ph) | Me | 4-F-Ph | H |
| 3-307 | CH₂(4-F-Ph) | Me | 5-Cl-pyridin-2-yl | H |
| 3-308 | CH₂(4-F-Ph) | Me | 5-Br-pyridin-2-yl | H |
| 3-309 | CH₂(4-F-Ph) | Me | 5-F-pyridin-2-yl | H |
| 3-310 | CH₂(4-F-Ph) | Me | 5-Me-pyridin-2-yl | H |
| 3-311 | CH₂(4-F-Ph) | Me | 2-pyridyl | H |
| 3-312 | CH₂(4-F-Ph) | Me | 4-pyridyl | H |
| 3-313 | CH₂(4-OMe-Ph) | Me | Ph | H |
| 3-314 | CH₂(4-OMe-Ph) | Me | 4-Cl-Ph | H |
| 3-315 | CH₂(4-OMe-Ph) | Me | 2-thienyl | H |
| 3-316 | CH₂(4-OMe-Ph) | Me | 3-pyridyl | H |
| 3-317 | CH₂(4-OMe-Ph) | Me | 6-Me-pyridin-3-yl | H |
| 3-318 | CH₂(4-OMe-Ph) | Me | 4-Me-Ph | H |
| 3-319 | CH₂(4-OMe-Ph) | Me | 4-Br-Ph | H |
| 3-320 | CH₂(4-OMe-Ph) | Me | 4-F-Ph | H |
| 3-321 | CH₂(4-OMe-Ph) | Me | 5-Cl-pyridin-2-yl | H |
| 3-322 | CH₂(4-OMe-Ph) | Me | 5-Br-pyridin-2-yl | H |
| 3-323 | CH₂(4-OMe-Ph) | Me | 5-F-pyridin-2-yl | H |
| 3-324 | CH₂(4-OMe-Ph) | Me | 5-Me-pyridin-2-yl | H |
| 3-325 | CH₂(4-OMe-Ph) | Me | 2-pyridyl | H |
| 3-326 | CH₂(4-OMe-Ph) | Me | 4-pyridyl | H |
| 3-327 | 2,2-difluoroethyl | Me | Ph | H |
| 3-328 | 2,2-difluoroethyl | Me | 4-Cl-Ph | H |
| 3-329 | 2,2-difluoroethyl | Me | 2-thienyl | H |
| 3-330 | 2,2-difluoroethyl | Me | 2-pyridyl | H |
| 3-331 | Ph | Me | Ph | H |
| 3-332 | Ph | Me | 4-Cl-Ph | H |
| 3-333 | Ph | Me | 2-thienyl | H |
| 3-334 | Ph | Me | 2-pyridyl | H |
| 3-335 | 2-fluoroethyl | Me | Ph | H |
| 3-336 | 2-fluoroethyl | Me | 4-Cl-Ph | H |
| 3-337 | 2-fluoroethyl | Me | 2-thienyl | H |
| 3-338 | 2-fluoroethyl | Me | 2-pyridyl | H |
| 3-339 | 2,2,3,3,3-pentafluoropropyl | Me | Ph | H |
| 3-340 | 2,2,3,3,3-pentafluoropropyl | Me | 4-Cl-Ph | H |
| 3-341 | 2,2,3,3,3-pentafluoropropyl | Me | 2-thienyl | H |
| 3-342 | 2,2,3,3,3-pentafluoropropyl | Me | 2-pyridyl | H |
| 3-343 | 1-ethyl-5-methyl-1H-pyrazol-4-methyl | Me | Ph | H |
| 3-344 | 1-ethyl-5-methyl-1H-pyrazol-4-ylmethyl | Me | 4-Cl-Ph | H |
| 3-345 | 1-ethyl-5-methyl-1H-pyrazol-4-ylmethyl | Me | 2-thienyl | H |
| 3-346 | 1-ethyl-5-methyl-1H-pyrazol-4-ylmethyl | Me | 2-pyridyl | H |
| 3-347 | Et | Me | isoquinolin-3-yl | H |
| 3-348 | Et | Me | quinolin-2-yl | H |
| 3-349 | prop-2-yn-1-yl | Me | isoquinolin-3-yl | H |
| 3-350 | prop-2-yn-1-yl | Me | quinolin-2-yl | H |
| 3-351 | but-2-yn-1-yl | Me | isoquinolin-3-yl | H |
| 3-352 | but-2-yn-1-yl | Me | quinolin-2-yl | H |
| 3-353 | 2,2-difluoroethyl | Me | 5-Cl-pyridin-2-yl | H |
| 3-354 | but-3-yn-2-yl | Me | 5-Cl-pyridin-2-yl | H |

TABLE 3-continued

Compounds of the formula (Ia'''')

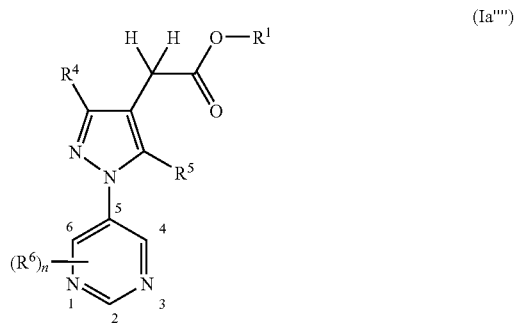

| No. | $R^1$ | $R^4$ | $R^5$ | $(R^6)_n$ |
|---|---|---|---|---|
| 3-355 | but-3-yn-2-yl | Me | isoquinolin-3-yl | H |
| 3-356 | but-3-yn-2-yl | Me | quinolin-2-yl | H |
| 3-357 | but-3-yn-2-yl | Me | Ph | H |
| 3-358 | but-3-yn-2-yl | Me | 4-Cl-Ph | H |
| 3-359 | but-3-yn-2-yl | Me | 2-thienyl | H |
| 3-360 | but-3-yn-2-yl | Me | 3-pyridyl | H |
| 3-361 | but-3-yn-2-yl | Me | 6-Me-pyridin-3-yl | H |
| 3-362 | but-3-yn-2-yl | Me | 4-Me-Ph | H |
| 3-363 | but-3-yn-2-yl | Me | 4-Br-Ph | H |
| 3-364 | but-3-yn-2-yl | Me | 4-F-Ph | H |
| 3-365 | but-3-yn-2-yl | Me | 5-Br-pyridin-2-yl | H |
| 3-366 | but-3-yn-2-yl | Me | 5-F-pyridin-2-yl | H |
| 3-367 | but-3-yn-2-yl | Me | 5-Me-pyridin-2-yl | H |
| 3-368 | but-3-yn-2-yl | Me | 2-pyridyl | H |
| 3-369 | but-3-yn-2-yl | Me | 4-pyridyl | H |
| 3-370 | Pr | Me | isoquinolin-3-yl | H |
| 3-371 | Pr | Me | quinolin-2-yl | H |
| 3-372 | iPr | Me | isoquinolin-3-yl | H |
| 3-373 | iPr | Me | quinolin-2-yl | H |
| 3-374 | $CH_2Ph$ | Me | isoquinolin-3-yl | H |
| 3-375 | $CH_2Ph$ | Me | quinolin-2-yl | H |
| 3-376 | cyclopropylmethyl | Me | isoquinolin-3-yl | H |
| 3-377 | cyclopropylmethyl | Me | quinolin-2-yl | H |
| 3-378 | 3,3-dichloro-2-fluoroprop-2-en-1-yl | Me | isoquinolin-3-yl | H |
| 3-379 | 3,3-dichloro-2-fluoroprop-2-en-1-yl | Me | quinolin-2-yl | H |
| 3-380 | (1-methylcyclopropyl)methyl | Me | isoquinolin-3-yl | H |
| 3-381 | (1-methylcyclopropyl)methyl | Me | quinolin-2-yl | H |
| 3-382 | 4-chlorobut-2-yn-1-yl | Me | isoquinolin-3-yl | H |
| 3-383 | 4-chlorobut-2-yn-1-yl | Me | quinolin-2-yl | H |
| 3-384 | (2,2-dichlorocyclopropyl)methyl | Me | isoquinolin-3-yl | H |
| 3-385 | (2,2-dichlorocyclopropyl)methyl | Me | quinolin-2-yl | H |
| 3-386 | 1-methylprop-2-yn-1-yl | Me | isoquinolin-3-yl | H |
| 3-387 | 1-methylprop-2-yn-1-yl | Me | quinolin-2-yl | H |
| 3-388 | 1-cyclopropylethyl | Me | isoquinolin-3-yl | H |
| 3-389 | 1-cyclopropylethyl | Me | quinolin-2-yl | H |
| 3-390 | allyl | Me | isoquinolin-3-yl | H |
| 3-391 | allyl | Me | quinolin-2-yl | H |
| 3-392 | 3-methylbut-2-en-1-yl | Me | isoquinolin-3-yl | H |
| 3-393 | 3-methylbut-2-en-1-yl | Me | quinolin-2-yl | H |
| 3-394 | cyclobutylmethyl | Me | isoquinolin-3-yl | H |
| 3-395 | cyclobutylmethyl | Me | quinolin-2-yl | H |
| 3-396 | cyclopentylmethyl | Me | isoquinolin-3-yl | H |
| 3-397 | cyclopentylmethyl | Me | quioiin-2-yl | H |
| 3-398 | 2-chloroprop-2-en-1-yl | Me | isoquinolin-3-yl | H |
| 3-399 | 2-chloroprop-2-en-1-yl | Me | quinolin-2-yl | H |
| 3-400 | tetrahydrofuran-2-ylmethyl | Me | isoquinolin-3-yl | H |
| 3-401 | tetrahydrofuran-2-ylmethyl | Me | quinolin-2-yl | H |
| 3-402 | tetrahydrofuran-2-ylmethyl | Me | 5-Cl-pyridin-2-yl | H |
| 3-403 | tetrahydrofuran-2-ylmethyl | Me | 5-Br-pyridin-2-yl | H |
| 3-404 | oxetan-3-yl | Me | isoquinolin-3-yl | H |
| 3-405 | oxetan-3-yl | Me | quinolin-2-yl | H |
| 3-406 | oxetan-3-yl | Me | 5-Cl-pyridin-2-yl | H |
| 3-407 | oxetan-3-yl | Me | 5-Br-pyridin-2-yl | H |
| 3-408 | oxetan-3-yl | Me | 5-Me-pyridin-2-yl | H |
| 3-409 | (3-methyloxetan-3-yl)methyl | Me | isoquinolin-3-yl | H |
| 3-410 | (3-methyloxetan-3-yl)methyl | Me | quinolin-2-yl | H |
| 3-411 | (3-methyloxetan-3-yl)methyl | Me | 5-Cl-pyridin-2-yl | H |
| 3-412 | (3-methyloxetan-3-yl)methyl | Me | 5-Br-pyridin-2-yl | H |
| 3-413 | 2,2,2-trifluoroethyl | Me | isoquinolin-3-yl | H |

TABLE 3-continued

Compounds of the formula (Ia'''')

$$\text{(Ia'''')}$$

| No. | R$^1$ | R$^4$ | R$^5$ | (R$^6$)$_n$ |
|---|---|---|---|---|
| 3-414 | 2,2,2-trifluoroethyl | Me | quinolin-2-yl | H |
| 3-415 | 2,2,2-trifluoroethyl | Me | 5-Cl-pyridin-2-yl | H |
| 3-416 | 2,2,2-trifluoroethyl | Me | 5-Br-pyridin-2-yl | H |
| 3-417 | 2,2-difluoroethyl | Me | isoquinolin-3-yl | H |
| 3-418 | 2,2-difluoroethyl | Me | quinolin-2-yl | H |
| 3-419 | 2,2-difluoroethyl | Me | 5-Cl-pyridin-2-yl | H |
| 3-420 | 2,2-difluoroethyl | Me | 5-Br-pyridin-2-yl | H |
| 3-421 | Et | Me | 5-I-pyridin-2-yl | H |
| 3-422 | Et | Me | 5-I-pyrimidin-2-yl | H |
| 3-423 | Et | Cl | 4-F-Ph | H |
| 3-424 | Et | Cl | 3-pyridyl | H |
| 3-425 | Et | Cl | 5-Cl-pyridin-2-yl | H |
| 3-426 | Et | Cl | 5-Br-pyridin-2-yl | H |
| 3-427 | Et | Cl | 5-F-pyridin-2-yl | H |
| 3-428 | Et | Cl | 5-I-pyridin-2-yl | H |
| 3-429 | Et | Cl | 5-Me-pyridin-2-yl | H |
| 3-430 | Et | Cl | 6-Me-pyridin-3-yl | H |
| 3-431 | Et | Cl | 4-Me-pyridin-2-yl | H |
| 3-432 | Et | Cl | 4-F-pyridin-2-yl | H |
| 3-433 | Et | Cl | 4-Cl-pyridin-2-yl | H |
| 3-434 | Et | Cl | 4-Br-pyridin-2-yl | H |
| 3-435 | Et | Cl | 4-OMe-pyridin-2-yl | H |
| 3-436 | Et | Cl | 2-pyrimidinyl | H |
| 3-437 | Et | Cl | 5-F-pyrimidin-2-yl | H |
| 3-438 | Et | Cl | 5-Cl-pyrimidin-2-yl | H |
| 3-439 | Et | Cl | 5-Br-pyrimidin-2-yl | H |
| 3-440 | Et | Cl | 5-I-pyrimidin-2-yl | H |
| 3-441 | Et | Cl | 5-Me-pyrimidin-2-yl | H |
| 3-442 | Et | Cl | 5-Me-pyrazin-2-yl | H |
| 3-443 | Et | Cl | 2-pyrazinyl | H |
| 3-444 | Et | Cl | isoquinolin-3-yl | H |
| 3-445 | Et | Cl | quinolin-2-yl | H |
| 3-446 | Et | Cl | 1,3-benzothiazol-2-yl | H |
| 3-447 | Et | Cl | 7-Cl-1,3-benzothiazol-2-yl | H |
| 3-448 | Et | Cl | 2-thiazolyl | H |
| 3-449 | Et | Cl | 5-Br-thiazol-2-yl | H |
| 3-450 | Et | Cl | 5-Me-thiazol-2-yl | H |
| 3-451 | Et | Cl | 5-Cl-thiazol-2-yl | H |
| 3-452 | Et | Cl | 2-thienyl | H |
| 3-453 | Et | Cl | 3-Me-2-thienyl | H |
| 3-454 | Et | Cl | 4-Me-2-thienyl | H |
| 3-455 | Et | Cl | 5-Br-2-thienyl | H |
| 3-456 | Et | Cl | 5-Cl-2-thienyl | H |
| 3-457 | Et | Me | 3-Br-Ph | H |
| 3-458 | Et | Me | 4-thiazolyl | H |
| 3-459 | cyclopropylmethyl | Me | 4-thiazolyl | H |
| 3-460 | prop-2-yn-1-yl | Me | 4-thiazolyl | H |
| 3-461 | but-2-yn-1-yl | Me | 4-thiazolyl | H |
| 3-462 | but-3-yn-2-yl | Me | 4-thiazolyl | H |
| 3-463 | Pr | Me | 4-thiazolyl | H |
| 3-464 | iPr | Me | 4-thiazolyl | H |
| 3-465 | CH$_2$Ph | Me | 4-thiazolyl | H |
| 3-466 | 3,3-dichloro-2-fluoroprop-2-en-1-yl | Me | 4-thiazoiyl | H |
| 3-467 | (1-methylcyclopropyl)methyl | Me | 4-thiazolyl | H |
| 3-468 | 4-chlorobut-2-yn-1-yl | Me | 4-thiazolyl | H |
| 3-469 | (2,2-dichlorocyclopropyl)methyl | Me | 4-thiazolyl | H |
| 3-470 | 1-methylprop-2-yn-1-yl | Me | 4-thiazoiyl | H |
| 3-471 | 1-cyclopropylethyl | Me | 4-thiazolyl | H |
| 3-472 | allyl | Me | 4-thiazolyl | H |

TABLE 3-continued

Compounds of the formula (Ia'''')

| No. | R¹ | R⁴ | R⁵ | (R⁶)ₙ |
|---|---|---|---|---|
| 3-473 | 3-methylbut-2-en-1-yl | Me | 4-thiazolyl | H |
| 3-474 | cyclobutylmethyl | Me | 4-thiazolyl | H |
| 3-475 | cyclopentylmethyl | Me | 4-thiazolyl | H |
| 3-476 | 2-chloroprop-2-en-1-yl | Me | 4-thiazolyl | H |
| 3-477 | tetrahydrofuran-2-ylmethyl | Me | 4-thiazolyl | H |
| 3-478 | (3-methyloxetan-3-yl)methyl | Me | 4-thiazolyl | H |
| 3-479 | 2,2,2-trifluoroethyl | Me | 4-thiazolyl | H |
| 3-480 | 2,2-difluoroethyl | Me | 4-thiazolyl | H |
| 3-481 | oxetan-3-yl | Me | 4-thiazolyl | H |
| 3-482 | cyclopropylmethyl | Me | 3-Br-Ph | H |
| 3-483 | prop-2-yn-1-yl | Me | 3-Br-Ph | H |
| 3-484 | but-2-yn-1-yl | Me | 3-Br-Ph | H |
| 3-485 | but-3-yn-2-yl | Me | 3-Br-Ph | H |
| 3-486 | Pr | Me | 3-Br-Ph | H |
| 3-487 | iPr | Me | 3-Br-Ph | H |
| 3-488 | CH₂Ph | Me | 3-Br-Ph | H |
| 3-489 | 3,3-dichloro-2-fluoroprop-2-en-1-yl | Me | 3-Br-Ph | H |
| 3-490 | (1-methylcyclopropyl)methyl | Me | 3-Br-Ph | H |
| 3-491 | 4-chlorobut-2-yn-1-yl | Me | 3-Br-Ph | H |
| 3-492 | (2,2-dichlorocyclopropyl)methyl | Me | 3-Br-Ph | H |
| 3-493 | 1-methylprop-2-yn-1-yl | Me | 3-Br-Ph | H |
| 3-494 | 1-cyclopropylethyl | Me | 3-Br-Ph | H |
| 3-495 | allyl | Me | 3-Br-Ph | H |
| 3-496 | 3-methylbut-2-en-1-yl | Me | 3-Br-Ph | H |
| 3-497 | cyclobutylmethyl | Me | 3-Br-Ph | H |
| 3-498 | cyclopentylmethyl | Me | 3-Br-Ph | H |
| 3-499 | 2-chloroprop-2-en-1-yl | Me | 3-Br-Ph | H |
| 3-500 | tetrahydrofuran-2-ylmethyl | Me | 3-Br-Ph | H |
| 3-501 | (3-methyloxetan-3-yl)methyl | Me | 3-Br-Ph | H |
| 3-502 | 2,2,2-trifluoroethyl | Me | 3-Br-Ph | H |
| 3-503 | 2,2-difluoroethyl | Me | 3-Br-Ph | H |
| 3-504 | oxetan-3-yl | Me | 3-Br-Ph | H |
| 3-505 | Et | Me | 2-Cl-thiazol-4-yl | H |
| 3-506 | cyclopropylmethyl | Me | 2-Cl-thiazol-4-yl | H |
| 3-507 | prop-2-yn-1-yl | Me | 2-Cl-thiazol-4-yl | H |
| 3-508 | but-2-yn-1-yl | Me | 2-Cl-thiazol-4-yl | H |
| 3-509 | but-3-yn-2-yl | Me | 2-Cl-thiazol-4-yl | H |
| 3-510 | Pr | Me | 2-Cl-thiazol-4-yl | H |
| 3-511 | iPr | Me | 2-Cl-thiazol-4-yl | H |
| 3-512 | CH₂Ph | Me | 2-Cl-thiazol-4-yl | H |
| 3-513 | 3,3-dichloro-2-fluoroprop-2-en-1-yl | Me | 2-Cl-thiazol-4-yl | H |
| 3-514 | (1-methylcyclopropyl)methyl | Me | 2-Cl-thiazol-4-yl | H |
| 3-515 | 4-chlorobut-2-yn-1-yl | Me | 2-Cl-thiazol-4-yl | H |
| 3-516 | (2,2-dichlorocyclopropyl)methyl | Me | 2-Cl-thiazol-4-yl | H |
| 3-517 | 1-methylprop-2-yn-1-yl | Me | 2-Cl-thiazol-4-yl | H |
| 3-518 | 1-cyclopropylethyl | Me | 2-Cl-thiazol-4-yl | H |
| 3-519 | allyl | Me | 2-Cl-thiazol-4-yl | H |
| 3-520 | 3-methylbut-2-en-1-yl | Me | 2-Cl-thiazol-4-yl | H |
| 3-521 | cyclobutylmethyl | Me | 2-Cl-thiazol-4-yl | H |
| 3-522 | cyclopentylmethyl | Me | 2-Cl-thiazol-4-yl | H |
| 3-523 | 2-chloroprop-2-en-1-yl | Me | 2-Cl-thiazol-4-yl | H |
| 3-524 | tetrahydrofuran-2-ylmethyl | Me | 2-Cl-thiazol-4-yl | H |
| 3-525 | (3-methyloxetan-3-yl)methyl | Me | 2-Cl-thiazol-4-yl | H |
| 3-526 | 2,2,2-trifluoroethyl | Me | 2-Cl-thiazol-4-yl | H |
| 3-527 | 2,2-difluoroethyl | Me | 2-Cl-thiazol-4-yl | H |
| 3-528 | oxetan-3-yl | Me | 2-Cl-thiazol-4-yl | H |
| 3-529 | Et | Me | 2-Br-thiazol-4-yl | H |
| 3-530 | cyclopropylmethyl | Me | 2-Br-thiazol-4-yl | H |
| 3-531 | prop-2-yn-1-yl | Me | 2-Br-thiazol-4-yl | H |

TABLE 3-continued

Compounds of the formula (Ia'''')

(Ia'''')

| No. | R¹ | R⁴ | R⁵ | (R⁶)ₙ |
|---|---|---|---|---|
| 3-532 | but-2-yn-1-yl | Me | 2-Br-thiazol-4-yl | H |
| 3-533 | but-3-yn-2-yl | Me | 2-Br-thiazol-4-yl | H |
| 3-534 | Pr | Me | 2-Br-thiazol-4-yl | H |
| 3-535 | iPr | Me | 2-Br-thiazol-4-yl | H |
| 3-536 | CH₂Ph | Me | 2-Br-thiazol-4-yl | H |
| 3-537 | 3,3-dichloro-2-fluoroprop-2-en-1-yl | Me | 2-Br-thiazol-4-yl | H |
| 3-538 | (1-methylcyclopropyl)methyl | Me | 2-Br-thiazol-4-yl | H |
| 3-539 | 4-chlorobut-2-yn-1-yl | Me | 2-Br-thiazol-4-yl | H |
| 3-540 | (2,2-dichlorocyclopropyl)methyl | Me | 2-Br-thiazol-4-yl | H |
| 3-541 | 1-methylprop-2-yn-1-yl | Me | 2-Br-thiazol-4-yl | H |
| 3-542 | 1-cyclopropylethyl | Me | 2-Br-thiazol-4-yl | H |
| 3-543 | allyl | Me | 2-Br-thiazol-4-yl | H |
| 3-544 | 3-methylbut-2-en-1-yl | Me | 2-Br-thiazol-4-yl | H |
| 3-545 | cyclobutylmethyl | Me | 2-Br-thiazol-4-yl | H |
| 3-546 | cyclopentylmethyl | Me | 2-Br-thiazol-4-yl | H |
| 3-547 | 2-chloroprop-2-en-1-yl | Me | 2-Br-thiazol-4-yl | H |
| 3-548 | tetrahydrofuran-2-ylmethyl | Me | 2-Br-thiazol-4-yl | H |
| 3-549 | (3-methyloxetan-3-yl)methyl | Me | 2-Br-thiazol-4-yl | H |
| 3-550 | 2,2,2-trifluoroethyl | Me | 2-Br-thiazol-4-yl | H |
| 3-551 | 2,2-difluoroethyl | Me | 2-Br-thiazol-4-yl | H |
| 3-552 | oxetan-3-yl | Me | 2-Br-thiazol-4-yl | H |
| 3-553 | cyclopropylmethyl | Me | 5-Br-thiazol-2-yl | H |
| 3-554 | prop-2-yn-1-yl | Me | 5-Br-thiazol-2-yl | H |
| 3-555 | but-2-yn-1-yl | Me | 5-Br-thiazol-2-yl | H |
| 3-556 | but-3-yn-2-yl | Me | 5-Br-thiazol-2-yl | H |
| 3-557 | Pr | Me | 5-Br-thiazol-2-yl | H |
| 3-558 | iPr | Me | 5-Br-thiazol-2-yl | H |
| 3-559 | CH₂Ph | Me | 5-Br-thiazol-2-yl | H |
| 3-560 | 3,3-dichloro-2-fluoroprop-2-en-1-yl | Me | 5-Br-thiazol-2-yl | H |
| 3-561 | (1-methylcyclopropyl)methyl | Me | 5-Br-thiazol-2-yl | H |
| 3-562 | 4-chlorobut-2-yn-1-yl | Me | 5-Br-thiazol-2-yl | H |
| 3-563 | (2,2-dichlorocyclopropyl)methyl | Me | 5-Br-thiazol-2-yl | H |
| 3-564 | 1-methylprop-2-yn-1-yl | Me | 5-Br-thiazol-2-yl | H |
| 3-565 | 1-cyclopropylethyl | Me | 5-Br-thiazol-2-yl | H |
| 3-566 | allyl | Me | 5-Br-thiazol-2-yl | H |
| 3-567 | 3-methylbut-2-en-1-yl | Me | 5-Br-thiazol-2-yl | H |
| 3-568 | cyclobutylmethyl | Me | 5-Br-thiazol-2-yl | H |
| 3-569 | cyclopentylmethyl | Me | 5-Br-thiazol-2-yl | H |
| 3-570 | 2-chloroprop-2-en-1-yl | Me | 5-Br-thiazol-2-yl | H |
| 3-571 | tetrahydrofuran-2-ylmethyl | Me | 5-Br-thiazol-2-yl | H |
| 3-572 | (3-methyloxetan-3-yl)methyl | Me | 5-Br-thiazol-2-yl | H |
| 3-573 | 2,2,2-trifluoroethyl | Me | 5-Br-thiazol-2-yl | H |
| 3-574 | 2,2-difluoroethyl | Me | 5-Br-thiazol-2-yl | H |
| 3-575 | oxetan-3-yl | Me | 5-Br-thiazol-2-yl | H |
| 3-576 | cyclopropylmethyl | Me | 5-Cl-thiazol-2-yl | H |
| 3-577 | prop-2-yn-1-yl | Me | 5-Cl-thiazol-2-yl | H |
| 3-578 | but-2-yn-1-yl | Me | 5-Cl-thiazol-2-yl | H |
| 3-579 | but-3-yn-2-yl | Me | 5-Cl-thiazol-2-yl | H |
| 3-580 | Pr | Me | 5-Cl-thiazol-2-yl | H |
| 3-581 | iPr | Me | 5-Cl-thiazol-2-yl | H |
| 3-582 | CH₂Ph | Me | 5-Cl-thiazol-2-yl | H |
| 3-583 | 3,3-dichloro-2-fluoroprop-2-en-1-yl | Me | 5-Cl-thiazol-2-yl | H |
| 3-584 | (1-methylcyclopropyl)methyl | Me | 5-Cl-thiazol-2-yl | H |
| 3-585 | 4-chlorobut-2-yn-1-yl | Me | 5-Cl-thiazol-2-yl | H |
| 3-586 | (2,2-dichlorocyclopropyl)methyl | Me | 5-Cl-thiazol-2-yl | H |
| 3-587 | 1-methylprop-2-yn-1-yl | Me | 5-Cl-thiazol-2-yl | H |
| 3-588 | 1-cyclopropylethyl | Me | 5-Cl-thiazol-2-yl | H |
| 3-589 | allyl | Me | 5-Cl-thiazol-2-yl | H |
| 3-590 | 3-methylbut-2-en-1-yl | Me | 5-Cl-thiazol-2-yl | H |

TABLE 3-continued

Compounds of the formula (Ia'''')

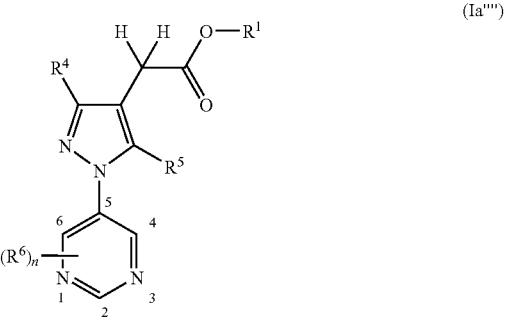

| No. | R$^1$ | R$^4$ | R$^5$ | (R$^6$)$_n$ |
|---|---|---|---|---|
| 3-591 | cyclobutylmethyl | Me | 5-Cl-thiazol-2-yl | H |
| 3-592 | cyclopentylmethyl | Me | 5-Cl-thiazol-2-yl | H |
| 3-593 | 2-chloroprop-2-en-1-yl | Me | 5-Cl-thiazol-2-yl | H |
| 3-594 | tetrahydrofuran-2-ylmethyl | Me | 5-Cl-thiazol-2-yl | H |
| 3-595 | (3-methyloxetan-3-yl)methyl | Me | 5-Cl-thiazol-2-yl | H |
| 3-596 | 2,2,2-trifluoroethyl | Me | 5-Cl-thiazol-2-yl | H |
| 3-597 | 2,2-difluoroethyl | Me | 5-Cl-thiazol-2-yl | H |
| 3-598 | oxetan-3-yl | Me | 5-Cl-thiazol-2-yl | H |
| 3-599 | Et | Me | 5-OSO$_2$Me-pyridin-2-yl | H |
| 3-600 | cyclopropylmethyl | Me | 5-OSO$_2$Me-pyridin-2-yl | H |
| 3-601 | prop-2-yn-1-yl | Me | 5-OSO2Me-pyridin-2-yl | H |
| 3-602 | but-3-yn-2-yl | Me | 5-OSO$_2$Me-pyridin-2-yl | H |
| 3-603 | iPr | Me | 5-OSO$_2$Me-pyridin-2-yl | H |
| 3-604 | CH$_2$Ph | Me | 5-OSO$_2$Me-pyridin-2-yl | H |
| 3-605 | (2,2-dichlorocyclopropyl)methyl | Me | 5-OSO$_2$Me-pyridin-2-yl | H |
| 3-606 | allyl | Me | 5-OSO$_2$Me-pyridin-2-yl | H |
| 3-607 | 2,2,2-trifluoroethyl | Me | 5-OSO$_2$Me-pyridin-2-yl | H |
| 3-608 | 2,2-difluoroethyl | Me | 5-OSO$_2$Me-pyridin-2-yl | H |
| 3-609 | oxetan-3-yl | Me | 5-OSO$_2$Me-pyridin-2-yl | H |
| 3-610 | Et | Me | 6-Cl-1,3-benzothiazol-2-yl | H |
| 3-611 | cyclopropylmethyl | Me | 6-Cl-1,3-benzothiazol-2-yl | H |
| 3-612 | prop-2-yn-1-yl | Me | 6-Cl-1,3-benzothiazol-2-yl | H |
| 3-613 | but-3-yn-2-yl | Me | 6-Cl-1,3-benzothiazol-2-yl | H |
| 3-614 | iPr | Me | 6-Cl-1,3-benzothiazol-2-yl | H |
| 3-615 | CH$_2$Ph | Me | 6-Cl-1,3-benzothiazol-2-yl | H |
| 3-616 | (2,2-dichlorocyclopropyl)methyl | Me | 6-Cl-1, 3-benzothiazol-2-yl | H |
| 3-617 | allyl | Me | 6-Cl-1,3-benzothiazol-2-yl | H |
| 3-618 | 2,2,2-trifluoroethyl | Me | 6-Cl-1,3-benzothiazol-2-yl | H |
| 3-619 | 2,2-difluoroethyl | Me | 6-Cl-1,3-benzothiazol-2-yl | H |
| 3-620 | oxetan-3-yl | Me | 6-Cl-1,3-benzothiazol-2-yl | H |
| 3-621 | Et | Me | 6-Br-1,3-benzothiazol-2-yl | H |
| 3-622 | cyclopropylmethyl | Me | 6-Br-1,3-benzothiazol-2-yl | H |
| 3-623 | prop-2-yn-1-yl | Me | 6-Br-1,3-benzothiazol-2-yl | H |
| 3-624 | but-3-yn-2-yl | Me | 6-Br-1,3-benzothiazol-2-yl | H |
| 3-625 | iPr | Me | 6-Br-1,3-benzothiazol-2-yl | H |
| 3-626 | CH$_2$Ph | Me | 6-Br-1,3-benzothiazol-2-yl | H |
| 3-627 | (2,2-dichlorocyclopropyl)methyl | Me | 6-Br-1,3-benzothiazol-2-yl | H |
| 3-628 | allyl | Me | 6-Br-1,3-benzothiazol-2-yl | H |
| 3-629 | 2,2,2-trifluoroethyl | Me | 6-Br-1,3-benzothiazol-2-yl | H |
| 3-630 | 2,2-difluoroethyl | Me | 6-Br-1,3-benzothiazol-2-yl | H |
| 3-631 | oxetan-3-yl | Me | 6-Br-1,3-benzothiazol-2-yl | H |
| 3-632 | Et | Me | 1,3-benzoxazol-2-yl | H |
| 3-633 | cyclopropylmethyl | Me | 1,3-benzoxazol-2-yl | H |
| 3-634 | prop-2-yn-1-yl | Me | 1,3-benzoxazol-2-yl | H |
| 3-635 | but-3-yn-2-yl | Me | 1,3-benzoxazol-2-yl | H |
| 3-636 | iPr | Me | 1,3-benzoxazol-2-yl | H |
| 3-637 | CH$_2$Ph | Me | 1,3-benzoxazol-2-yl | H |
| 3-638 | (2,2-dichlorocyclopropyl) methyl | Me | 1,3-benzoxazol-2-yl | H |
| 3-639 | allyl | Me | 1,3-benzoxazol-2-yl | H |
| 3-640 | 2,2,2-trifluoroethyl | Me | 1,3-benzoxazol-2-yl | H |
| 3-641 | 2,2-difluoroethyl | Me | 1,3-benzoxazol-2-yl | H |
| 3-642 | oxetan-3-yl | Me | 1,3-benzoxazol-2-yl | H |
| 3-643 | Et | Me | 6-Cl-1,3-benzoxazol-2-yl | H |
| 3-644 | cyclopropylmethyl | Me | 6-Cl-1,3-benzoxazol-2-yl | H |
| 3-645 | prop-2-yn-1-yl | Me | 6-Cl-1,3-benzoxazol-2-yl | H |
| 3-646 | but-3-yn-2-yl | Me | 6-Cl-1,3-benzoxazol-2-yl | H |
| 3-647 | iPr | Me | 6-Cl-1,3-benzoxazol-2-yl | H |
| 3-648 | CH$_2$Ph | Me | 6-Cl-1,3-benzoxazol-2-yl | H |
| 3-649 | (2,2-dichlorocyclopropyl)methyl | Me | 6-Cl-1,3-benzoxazol-2-yl | H |

TABLE 3-continued

Compounds of the formula (Ia'''')

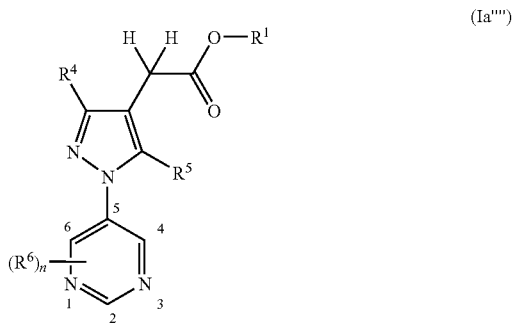

(Ia'''')

| No. | $R^1$ | $R^4$ | $R^5$ | $(R^6)_n$ |
|---|---|---|---|---|
| 3-650 | allyl | Me | 6-Cl-1,3-benzoxazol-2-yl | H |
| 3-651 | 2,2,2-trifluoroethyl | Me | 6-Cl-1,3-benzoxazol-2-yl | H |
| 3-652 | 2,2-difluoroethyl | Me | 6-Cl-1,3-benzoxazol-2-yl | H |
| 3-653 | oxetan-3-yl | Me | 6-Cl-1,3-benzoxazol-2-yl | H |
| 3-654 | Et | Me | 6-Br-1,3-benzoxazol-2-yl | H |
| 3-655 | cyclopropylmethyl | Me | 6-Br-1,3-benzoxazol-2-yl | H |
| 3-656 | prop-2-yn-1-yl | Me | 6-Br-1,3-benzoxazol-2-yl | H |
| 3-657 | but-3-yn-2-yl | Me | 6-Br-1,3-benzoxazol-2-yl | H |
| 3-658 | iPr | Me | 6-Br-1,3-benzoxazol-2-yl | H |
| 3-659 | $CH_2Ph$ | Me | 6-Br-1,3-benzoxazol-2-yl | H |
| 3-660 | (2,2-dichlorocyclopropyl)methyl | Me | 6-Br-1,3-benzoxazol-2-yl | H |
| 3-661 | allyl | Me | 6-Br-1,3-benzoxazol-2-yl | H |
| 3-662 | 2,2,2-trifluoroethyl | Me | 6-Br-1,3-benzoxazol-2-yl | H |
| 3-663 | 2,2-difluoroethyl | Me | 6-Br-1,3-benzoxazol-2-yl | H |
| 3-664 | oxetan-3-yl | Me | 6-Br-1,3-benzoxazol-2-yl | H |
| 3-665 | Et | Me | 7-Cl-1,3-benzoxazol-2-yl | H |
| 3-666 | cyclopropylmethyl | Me | 7-Cl-1,3-benzoxazol-2-yl | H |
| 3-667 | prop-2-yn-1-yl | Me | 7-Cl-1,3-benzoxazol-2-yl | H |
| 3-668 | but-3-yn-2-yl | Me | 7-Cl-1,3-benzoxazol-2-yl | H |
| 3-669 | iPr | Me | 7-Cl-1,3-benzoxazol-2-yl | H |
| 3-670 | $CH_2Ph$ | Me | 7-Cl-1,3-benzoxazol-2-yl | H |
| 3-671 | (2,2-dichlorocyclopropyl)methyl | Me | 7-Cl-1,3-benzoxazol-2-yl | H |
| 3-672 | allyl | Me | 7-Cl-1,3-benzoxazol-2-yl | H |
| 3-673 | 2,2,2-trifluoroethyl | Me | 7-Cl-1,3-benzoxazol-2-yl | H |
| 3-674 | 2,2-difluoroethyl | Me | 7-Cl-1,3-benzoxazol-2-yl | H |
| 3-675 | oxetan-3-yl | Me | 7-Cl-1,3-benzoxazol-2-yl | H |
| 3-676 | cyclopropylmethyl | Me | 5-I-pyridin-2-yl | H |
| 3-677 | prop-2-yn-1-yl | Me | 5-I-pyridin-2-yl | H |
| 3-678 | but-3-yn-2-yl | Me | 5-I-pyridin-2-yl | H |
| 3-679 | iPr | Me | 5-I-pyridin-2-yl | H |
| 3-680 | $CH_2Ph$ | Me | 5-I-pyridin-2-yl | H |
| 3-681 | (2,2-dichlorocyclopropyl)methyl | Me | 5-I-pyrid in-2-yl | H |
| 3-682 | allyl | Me | 5-I-pyridin-2-yl | H |
| 3-683 | 2,2,2-trifluoroethyl | Me | 5-I-pyridin-2-yl | H |
| 3-684 | 2,2-difluoroethyl | Me | 5-I-pyridin-2-yl | H |
| 3-685 | oxetan-3-yl | Me | 5-I-pyridin-2-yl | H |
| 3-686 | Et | Me | 5-$NH_2$-pyridin-2-yl | H |
| 3-687 | cyclopropylmethyl | Me | 5-$NH_2$-pyridin-2-yl | H |
| 3-688 | prop-2-yn-1-yl | Me | 5-$NH_2$-pyridin-2-yl | H |
| 3-689 | $CH_2Ph$ | Me | 5-$NH_2$-pyridin-2-yl | H |
| 3-690 | (2,2-dichlorocyclopropyl)methyl | Me | 5-$NH_2$-pyridin-2-yl | H |
| 3-691 | 2,2,2-trifluoroethyl | Me | 5-$NH_2$-pyridin-2-yl | H |
| 3-692 | 2,2-difluoroethyl | Me | 5-$NH_2$-pyridin-2-yl | H |
| 3-693 | oxetan-3-yl | Me | 5-$NH_2$-pyridin-2-yl | H |
| 3-694 | Et | Me | 5-OH-pyridin-2-yl | H |
| 3-695 | cyclopropylmethyl | Me | 5-OH-pyridin-2-yl | H |
| 3-696 | prop-2-yn-1-yl | Me | 5-OH-pyridin-2-yl | H |
| 3-697 | $CH_2Ph$ | Me | 5-OH-pyridin-2-yl | H |
| 3-698 | (2,2-dichlorocyclopropyl)methyl | Me | 5-OH-pyridin-2-yl | H |
| 3-699 | 2,2,2-trifluoroethyl | Me | 5-OH-pyridin-2-yl | H |
| 3-700 | 2,2-difluoroethyl | Me | 5-OH-pyridin-2-yl | H |
| 3-701 | oxetan-3-yl | Me | 5-OH-pyridin-2-yl | H |
| 3-702 | Et | Me | 5-$OCHF_2$-pyridin-2-yl | H |
| 3-703 | cyclopropylmethyl | Me | 5-$OCHF_2$-pyridin-2-yl | H |
| 3-704 | prop-2-yn-1-yl | Me | 5-$OCHF_2$-pyridin-2-yl | H |
| 3-705 | $CH_2Ph$ | Me | 5-$OCHF_2$-pyridin-2-yl | H |
| 3-706 | (2,2-dichlorocyclopropyl)methyl | Me | 5-$OCHF_2$-pyridin-2-yl | H |
| 3-707 | 2,2,2-trifluoroethyl | Me | 5-$OCHF_2$-pyridin-2-yl | H |
| 3-708 | 2,2-difluoroethyl | Me | 5-$OCHF_2$-pyridin-2-yl | H |

TABLE 3-continued

Compounds of the formula (Ia'''')

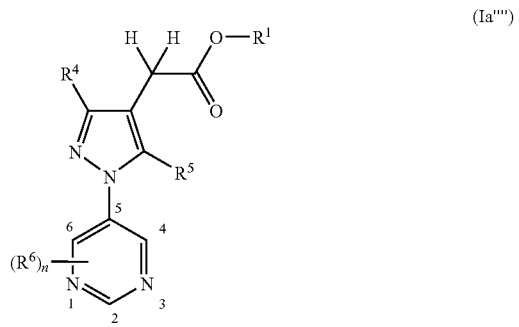

| No. | R$^1$ | R$^4$ | R$^5$ | (R$^6$)$_n$ |
|---|---|---|---|---|
| 3-709 | oxetan-3-yl | Me | 5-OCHF$_2$-pyridin-2-yl | H |
| 3-710 | Et | Me | 5-MeO-pyridin-2-yl | H |
| 3-711 | cyclopropylmethyl | Me | 5-MeO-pyridin-2-yl | H |
| 3-712 | prop-2-yn-1-yl | Me | 5-MeO-pyridin-2-yl | H |
| 3-713 | CH$_2$Ph | Me | 5-MeO-pyridin-2-yl | H |
| 3-714 | (2,2-dichlorocyclopropyl)methyl | Me | 5-MeO-pyridin-2-yl | H |
| 3-715 | 2,2,2-trifluoroethyl | Me | 5-MeO-pyridin-2-yl | H |
| 3-716 | 2,2-difluoroethyl | Me | 5-MeO-pyridin-2-yl | H |
| 3-717 | oxetan-3-yl | Me | 5-MeO-pyridin-2-yl | H |
| 3-718 | Et | Me | 5-MeS-pyridin-2-yl | H |
| 3-719 | cyclopropylmethyl | Me | 5-MeS-pyridin-2-yl | H |
| 3-720 | prop-2-yn-1-yl | Me | 5-MeS-pyridin-2-yl | H |
| 3-721 | CH$_2$Ph | Me | 5-MeS-pyridin-2-yl | H |
| 3-722 | (2,2-dichlorocyclopropyl)methyl | Me | 5-MeS-pyridin-2-yl | H |
| 3-723 | 2 2,2-trifluoroethyl | Me | 5-MeS-pyrid in-2-yl | H |
| 3-724 | 2,2-difluoroethyl | Me | 5-MeS-pyridin-2-yl | H |
| 3-725 | oxetan-3-yl | Me | 5-MeS-pyridin-2-yl | H |
| 3-726 | Et | Me | 5-NHMe-pyridin-2-yl | H |
| 3-727 | cyclopropylmethyl | Me | 5-NHMe-pyridin-2-yl | H |
| 3-728 | prop-2-yn-1-yl | Me | 5-NHMe-pyridin-2-yl | H |
| 3-729 | CH$_2$Ph | Me | 5-NHMe-pyridin-2-yl | H |
| 3-730 | (2,2-dichlorocyclopropyl)methyl | Me | 5-NHMe-pyridin-2-yl | H |
| 3-731 | 2,2,2-trifluoroethyl | Me | 5-NHMe-pyridin-2-yl | H |
| 3-732 | 2,2-difluoroethyl | Me | 5-NHMe-pyridin-2-yl | H |
| 3-733 | oxetan-3-yl | Me | 5-NHMe-pyridin-2-yl | H |
| 3-734 | Et | Me | 5-NMe$_2$-pyridin-2-yl | H |
| 3-735 | cyclopropylmethyl | Me | 5-NMe$_2$-pyridin-2-yl | H |
| 3-736 | prop-2-yn-1-yl | Me | 5-NMe$_2$-pyridin-2-yl | H |
| 3-737 | CH$_2$Ph | Me | 5-NMe$_2$-pyridin-2-yl | H |
| 3-738 | (2,2-dichlorocyclopropyl)methyl | Me | 5-NMe$_2$-pyridin-2-yl | H |
| 3-739 | 2,2,2-trifluoroethyl | Me | 5-NMe$_2$-pyridin-2-yl | H |
| 3-740 | 2,2-difluoroethyl | Me | 5-NMe$_2$-pyridin-2-yl | H |
| 3-741 | oxetan-3-yl | Me | 5-NMe$_2$-pyridin-2-yl | H |
| 3-742 | 3-hydroxybut-2-yl | Me | 4-Cl-Ph | H |
| 3-743 | 3-hydroxybut-2-yl | Me | 4-Br-Ph | H |
| 3-744 | 3-hydroxybut-2-yl | Me | 5-Cl-pyridin-2-yl | H |
| 3-745 | 3-hydroxybut-2-yl | Me | 5-Br-pyridin-2-yl | H |
| 3-746 | 3-hydroxybut-2-yl | Me | 5-Cl-2-thienyl | H |
| 3-747 | 3-hydroxybut-2-yl | Me | 5-Br-2-thienyl | H |
| 3-748 | 3-ethylpent-1-yn-3-yl | Me | 4-Cl-Ph | H |
| 3-749 | 3-ethylpent-1-yn-3-yl | Me | 4-Br-Ph | H |
| 3-750 | 3-ethylpent-1-yn-3-yl | Me | 5-Cl-pyridin-2-yl | H |
| 3-751 | 3-ethylpent-1-yn-3-yl | Me | 5-Br-pyridin-2-yl | H |
| 3-752 | 3-ethylpent-1-yn-3-yl | Me | 5-Cl-2-thienyl | H |
| 3-753 | 3-ethylpent-1-yn-3-yl | Me | 5-Br-2-thienyl | H |
| 3-754 | difluoromethyl | Me | 4-Cl-Ph | H |
| 3-755 | difluoromethyl | Me | 4-Br-Ph | H |
| 3-756 | difluoromethyl | Me | 5-Cl-pyridin-2-yl | H |
| 3-757 | difluoromethyl | Me | 5-Br-pyridin-2-yl | H |
| 3-758 | difluoromethyl | Me | 5-Cl-2-thienyl | H |
| 3-759 | difluoromethyl | Me | 5-Br-2-thienyl | H |
| 3-760 | 2,2,3,3-tetrafluoropropyl | Me | 4-Cl-Ph | H |
| 3-761 | 2,2,3,3-tetrafluoropropyl | Me | 4-Br-Ph | H |
| 3-762 | 2,2,3,3-tetrafluoropropyl | Me | 5-Cl-pyridin-2-yl | H |
| 3-763 | 2,2,3,3-tetrafluoropropyl | Me | 5-Br-pyridin-2-yl | H |
| 3-764 | 2,2,3,3-tetrafluoropropyl | Me | 5-Cl-2-thienyl | H |
| 3-765 | 2,2,3,3-tetrafluoropropyl | Me | 5-Br-2-thienyl | H |
| 3-766 | 4,4,4-trifluorobutyl | Me | 4-Cl-Ph | H |
| 3-767 | 4,4,4-trifluorobutyl | Me | 4-Br-Ph | H |

TABLE 3-continued

Compounds of the formula (Ia'''')

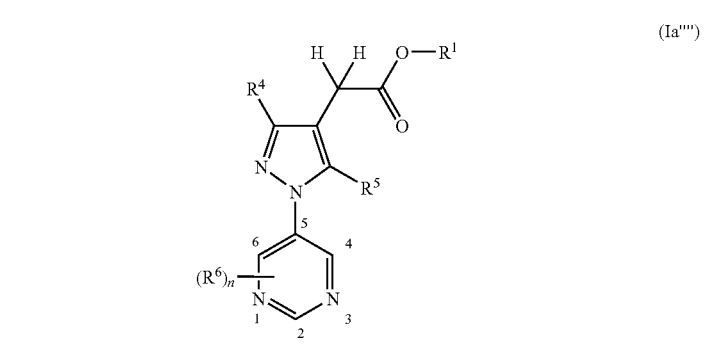

| No. | R¹ | R⁴ | R⁵ | (R⁶)ₙ |
|---|---|---|---|---|
| 3-768 | 4,4,4-trifluorobutyl | Me | 5-Cl-pyridin-2-yl | H |
| 3-769 | 4,4,4-trifluorobutyl | Me | 5-Br-pyridin-2-yl | H |
| 3-770 | 4,4,4-trifluorobutyl | Me | 5-Cl-2-thienyl | H |
| 3-771 | 4,4,4-trifluorobutyl | Me | 5-Br-2-thienyl | H |
| 3-772 | acetoxymethyl | Me | 4-Cl-Ph | H |
| 3-773 | acetoxymethyl | Me | 4-Br-Ph | H |
| 3-774 | acetoxymethyl | Me | 5-Cl-pyridin-2-yl | H |
| 3-775 | acetoxymethyl | Me | 5-Br-pyridin-2-yl | H |
| 3-776 | acetoxymethyl | Me | 5-Cl-2-thienyl | H |
| 3-777 | acetoxymethyl | Me | 5-Br-2-thienyl | H |
| 3-778 | 2-chloroethyl | Me | 4-Cl-Ph | H |
| 3-779 | 2-chloroethyl | Me | 4-Br-Ph | H |
| 3-780 | 2-chloroethyl | Me | 5-Cl-pyridin-2-yl | H |
| 3-781 | 2-chloroethyl | Me | 5-Br-pyridin-2-yl | H |
| 3-782 | 2-chloroethyl | Me | 5-Cl-2-thienyl | H |
| 3-783 | 2-chloroethyl | Me | 5-Br-2-thienyl | H |
| 3-784 | 3-fluoropropyl | Me | 4-Cl-Ph | H |
| 3-785 | 3-fluoropropyl | Me | 4-Br-Ph | H |
| 3-786 | 3-fluoropropyl | Me | 5-Cl-pyridin-2-yl | H |
| 3-787 | 3-fluoropropyl | Me | 5-Br-pyridin-2-yl | H |
| 3-788 | 3-fluoropropyl | Me | 5-Cl-2-thienyl | H |
| 3-789 | 3-fluoropropyl | Me | 5-Br-2-thienyl | H |
| 3-790 | 2-ethoxyethyl | Me | 4-Cl-Ph | H |
| 3-791 | 2-ethoxyethyl | Me | 4-Br-Ph | H |
| 3-792 | 2-ethoxyethyl | Me | 5-Cl-pyridin-2-yl | H |
| 3-793 | 2-ethoxyethyl | Me | 5-Br-pyridin-2-yl | H |
| 3-794 | 2-ethoxyethyl | Me | 5-Cl-2-thienyl | H |
| 3-795 | 2-ethoxyethyl | Me | 5-Br-2-thienyl | H |
| 3-796 | 2-propan-1-ol | Me | 4-Cl-Ph | H |
| 3-797 | 2-propan-1-ol | Me | 4-Br-Ph | H |
| 3-798 | 1-hydroxyprop-2-yl | Me | 5-Cl-pyridin-2-yl | H |
| 3-799 | 1-hydroxyprop-2-yl | Me | 5-Br-pyridin-2-yl | H |
| 3-800 | 1-hydroxyprop-2-yl | Me | 5-Cl-2-thienyl | H |
| 3-801 | 1-hydroxyprop-2-yl | Me | 5-Br-2-thienyl | H |
| 3-802 | 2-methoxybut-1-yl | Me | 4-Cl-Ph | H |
| 3-803 | 2-methoxybut-1-yl | Me | 4-Br-Ph | H |
| 3-804 | 2-methoxybut-1-yl | Me | 5-Cl-pyridin-2-yl | H |
| 3-805 | 2-methoxybut-1-yl | Me | 5-Br-pyridin-2-yl | H |
| 3-806 | 2-methoxybut-1-yl | Me | 5-Cl-2-thienyl | H |
| 3-807 | 2-methoxybut-1-yl | Me | 5-Br-2-thienyl | H |
| 3-808 | 1,3-difluoropropan-2-yl | Me | 4-Cl-Ph | H |
| 3-809 | 1,3-difluoropropan-2-yl | Me | 4-Br-Ph | H |
| 3-810 | 1,3-difluoropropan-2-yl | Me | 5-Cl-pyridin-2-yl | H |
| 3-811 | 1,3-difluoropropan-2-yl | Me | 5-Br-pyridin-2-yl | H |
| 3-812 | 1,3-difluoropropan-2-yl | Me | 5-Cl-2-thienyl | H |
| 3-813 | 1,3-difluoropropan-2-yl | Me | 5-Br-2-thienyl | H |
| 3-814 | 2,3-dimethoxypropyl | Me | 4-Cl-Ph | H |
| 3-815 | 2,3-dimethoxypropyl | Me | 4-Br-Ph | H |
| 3-816 | 2,3-dimethoxypropyl | Me | 5-Cl-pyridin-2-yl | H |
| 3-817 | 2,3-dimethoxypropyl | Me | 5-Br-pyridin-2-yl | H |
| 3-818 | 2,3-dimethoxypropyl | Me | 5-Cl-2-thienyl | H |
| 3-819 | 2,3-dimethoxypropyl | Me | 5-Br-2-thienyl | H |
| 3-820 | 1,3-dioxolan-4-ylmethyl | Me | 4-Cl-Ph | H |
| 3-821 | 1,3-dioxolan-4-ylmethyl | Me | 4-Br-Ph | H |
| 3-822 | 1,3-dioxolan-4-ylmethyl | Me | 5-Cl-pyridin-2-yl | H |
| 3-823 | 1,3-dioxolan-4-ylmethyl | Me | 5-Br-pyridin-2-yl | H |
| 3-824 | 1,3-dioxolan-4-ylmethyl | Me | 5-Cl-2-thienyl | H |
| 3-825 | 1,3-dioxolan-4-ylmethyl | Me | 5-Br-2-thienyl | H |
| 3-826 | 1,1,1,4,4,4-hexafluorobutan-2-yl | Me | 4-Cl-Ph | H |

TABLE 3-continued

Compounds of the formula (Ia'''')

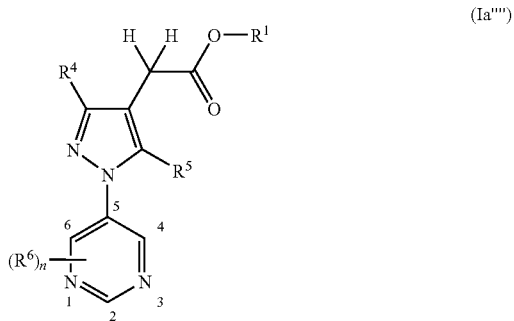

| No. | $R^1$ | $R^4$ | $R^5$ | $(R^6)_n$ |
|---|---|---|---|---|
| 3-827 | 1,1,1,4,4,4-hexafluorobutan-2-yl | Me | 4-Br-Ph | H |
| 3-828 | 1,1,1,4,4,4-hexafluorobutan-2-yl | Me | 5-Cl-pyridin-2-yl | H |
| 3-829 | 1,1,1,4,4,4-hexafluorobutan-2-yl | Me | 5-Br-pyridin-2-yl | H |
| 3-830 | 1,1,1,4,4,4-hexafluorobutan-2-yl | Me | 5-Cl-2-thienyl | H |
| 3-831 | 1,1,1,4,4,4-hexafluorobutan-2-yl | Me | 5-Br-2-thienyl | H |
| 3-832 | 1,1-difluoropropan-2-yl | Me | 4-Cl-Ph | H |
| 3-833 | 1,1-difluoropropan-2-yl | Me | 4-Br-Ph | H |
| 3-834 | 1,1-difluoropropan-2-yl | Me | 5-Cl-pyridin-2-yl | H |
| 3-835 | 1,1-difluoropropan-2-yl | Me | 5-Br-pyridin-2-yl | H |
| 3-836 | 1,1-difluoropropan-2-yl | Me | 5-Cl-2-thienyl | H |
| 3-837 | 1,1-difluoropropan-2-yl | Me | 5-Br-2-thienyl | H |
| 3-838 | 1-fluoropropan-2-yl | Me | 4-Cl-Ph | H |
| 3-839 | 1-fluoropropan-2-yl | Me | 4-Br-Ph | H |
| 3-840 | 1-fluoropropan-2-yl | Me | 5-Cl-pyridin-2-yl | H |
| 3-841 | 1-fluoropropan-2-yl | Me | 5-Br-pyridin-2-yl | H |
| 3-842 | 1-fluoropropan-2-yl | Me | 5-Cl-2-thienyl | H |
| 3-843 | 1-fluoropropan-2-yl | Me | 5-Br-2-thienyl | H |
| 3-844 | 1-bromopropan-2-yl | Me | 4-Cl-Ph | H |
| 3-845 | 1-bromopropan-2-yl | Me | 4-Br-Ph | H |
| 3-846 | 1-bromopropan-2-yl | Me | 5-Cl-pyridin-2-yl | H |
| 3-847 | 1-bromopropan-2-yl | Me | 5-Br-pyridin-2-yl | H |
| 3-848 | 1-bromopropan-2-yl | Me | 5-Cl-2-thienyl | H |
| 3-849 | 1-bromopropan-2-yl | Me | 5-Br-2-thienyl | H |
| 3-850 | 1-chloropropan-2-yl | Me | 4-Cl-Ph | H |
| 3-851 | 1-chloropropan-2-yl | Me | 4-Br-Ph | H |
| 3-852 | 1-chloropropan-2-yl | Me | 5-Cl-pyridin-2-yl | H |
| 3-853 | 1-chloropropan-2-yl | Me | 5-Br-pyridin-2-yl | H |
| 3-854 | 1-chloropropan-2-yl | Me | 5-Cl-2-thienyl | H |
| 3-855 | 1-chloropropan-2-yl | Me | 5-Br-2-thienyl | H |
| 3-856 | 2-isopropoxyethyl | Me | 4-Cl-Ph | H |
| 3-857 | 2-isopropoxyethyl | Me | 4-Br-Ph | H |
| 3-858 | 2-isopropoxyethyl | Me | 5-Cl-pyridin-2-yl | H |
| 3-859 | 2-isopropoxyethyl | Me | 5-Br-pyridin-2-yl | H |
| 3-860 | 2-isopropoxyethyl | Me | 5-Cl-2-thienyl | H |
| 3-861 | 2-isopropoxyethyl | Me | 5-Br-2-thienyl | H |
| 3-862 | tetrahydrofuran-3-yl | Me | 4-Cl-Ph | H |
| 3-863 | tetrahydrofuran-3-yl | Me | 4-Br-Ph | H |
| 3-864 | tetrahydrofuran-3-yl | Me | 5-Cl-pyridin-2-yl | H |
| 3-865 | tetrahydrofuran-3-yl | Me | 5-Br-pyridin-2-yl | H |
| 3-866 | tetrahydrofuran-3-yl | Me | 5-Cl-2-thienyl | H |
| 3-867 | tetrahydrofuran-3-yl | Me | 5-Br-2-thienyl | H |
| 3-868 | 2-(2,2,2-trifluoroethoxy)ethyl | Me | 4-Cl-Ph | H |
| 3-869 | 2-(2,2,2-trifluoroethoxy)ethyl | Me | 4-Br-Ph | H |
| 3-870 | 2-(2,2,2-trifluoroethoxy)ethyl | Me | 5-Cl-pyridin-2-yl | H |
| 3-871 | 2-(2,2,2-trifluoroethoxy)ethyl | Me | 5-Br-pyridin-2-yl | H |
| 3-872 | 2-(2,2,2-trifluoroethoxy)ethyl | Me | 5-Cl-2-thienyl | H |
| 3-873 | 2-(2,2,2-trifluoroethoxy)ethyl | Me | 5-Br-2-thienyl | H |
| 3-874 | (3,3,4,4,4-pentafluorobutan-2-yl | Me | 4-Cl-Ph | H |
| 3-875 | (3,3,4,4,4-pentafluorobutan-2-yl | Me | 4-Br-Ph | H |
| 3-876 | (3,3,4,4,4-pentafluorobutan-2-yl | Me | 5-Cl-pyridin-2-yl | H |
| 3-877 | (3,3,4,4,4-pentafluorobutan-2-yl | Me | 5-Br-pyridin-2-yl | H |
| 3-878 | (3,3,4,4,4-pentafluorobutan-2-yl | Me | 5-Cl-2-thienyl | H |
| 3-879 | (3,3,4,4,4-pentafluorobutan-2-yl | Me | 5-Br-2-thienyl | H |
| 3-880 | 1-(N,N-dimethylaminocarbonyl)eth-1-yl | Me | 4-Cl-Ph | H |
| 3-881 | 1-(N,N-dimethylaminocarbonyl)eth-1-yl | Me | 4-Br-Ph | H |
| 3-882 | 1-(N,N-dimethylaminocarbonyl)eth-1-yl | Me | 5-Cl-pyridin-2-yl | H |

TABLE 3-continued

Compounds of the formula (Ia'''')

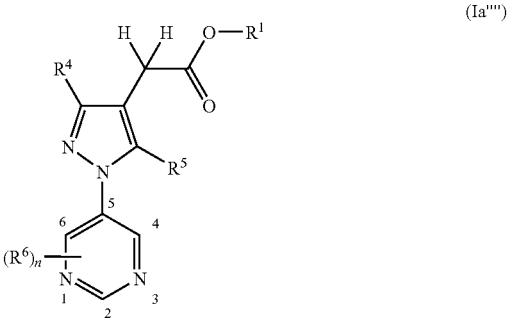

(Ia'''')

| No. | R$^1$ | R$^4$ | R$^5$ | (R$^6$)$_n$ |
|---|---|---|---|---|
| 3-883 | 1-(N,N-dimethylaminocarbonyl)eth-1-yl | Me | 5-Br-pyridin-2-yl | H |
| 3-884 | 1-(N,N-dimethylaminocarbonyl)eth-1-yl | Me | 5-Cl-2-thienyl | H |
| 3-885 | 1-(N,N-dimethylaminocarbonyl)eth-1-yl | Me | 5-Br-2-thienyl | H |
| 3-886 | (1,3-dioxan-2-yl)methyl | Me | 4-Cl-Ph | H |
| 3-887 | (1,3-dioxan-2-yl)methyl | Me | 4-Br-Ph | H |
| 3-888 | (1,3-dioxan-2-yl)methyl | Me | 5-Cl-pyridin-2-yl | H |
| 3-889 | (1,3-dioxan-2-yl)methyl | Me | 5-Br-pyridin-2-yl | H |
| 3-890 | (1,3-dioxan-2-yl)methyl | Me | 5-Cl-2-thienyl | H |
| 3-891 | (1,3-dioxan-2-yl)methyl | Me | 5-Br-2-thienyl | H |
| 3-892 | 1,1,1-trifluorobutan-2-yl | Me | 4-Cl-Ph | H |
| 3-893 | 1,1,1-trifluorobutan-2-yl | Me | 4-Br-Ph | H |
| 3-894 | 1,1,1-trifluorobutan-2-yl | Me | 5-Cl-pyridin-2-yl | H |
| 3-895 | 1,1,1-trifluorobutan-2-yl | Me | 5-Br-pyridin-2-yl | H |
| 3-896 | 1,1,1-trifluorobutan-2-yl | Me | 5-Cl-2-thienyl | H |
| 3-897 | 1,1,1-trifluorobutan-2-yl | Me | 5-Br-2-thienyl | H |
| 3-898 | 2-(but-2-ylideneaminooxy)eth-1-yl | Me | 4-Cl-Ph | H |
| 3-899 | 2-(but-2-ylideneaminooxy)eth-1-yl | Me | 4-Br-Ph | H |
| 3-900 | 2-(but-2-ylideneaminooxy)eth-1-yl | Me | 5-Cl-pyridin-2-yl | H |
| 3-901 | 2-(but-2-ylideneaminooxy)eth-1-yl | Me | 5-Br-pyridin-2-yl | H |
| 3-902 | 2-(but-2-ylideneaminooxy)eth-1-yl | Me | 5-Cl-2-thienyl | H |
| 3-903 | 2-(but-2-ylideneaminooxy)eth-1-yl | Me | 5-Br-2-thienyl | H |
| 3-904 | oxetan-2-ylmethyl | Me | 4-Cl-Ph | H |
| 3-905 | oxetan-2-ylmethyl | Me | 4-Br-Ph | H |
| 3-906 | oxetan-2-ylmethyl | Me | 5-Cl-pyridin-2-yl | H |
| 3-907 | oxetan-2-ylmethyl | Me | 5-Br-pyridin-2-yl | H |
| 3-908 | oxetan-2-ylmethyl | Me | 5-Cl-2-thienyl | H |
| 3-909 | oxetan-2-ylmethyl | Me | 5-Br-2-thienyl | H |
| 3-910 | 2,2-dimethoxyethyl | Me | 4-Cl-Ph | H |
| 3-911 | 2,2-dimethoxyethyl | Me | 4-Br-Ph | H |
| 3-912 | 2,2-dimethoxyethyl | Me | 5-Cl-pyridin-2-yl | H |
| 3-913 | 2,2-dimethoxyethyl | Me | 5-Br-pyridin-2-yl | H |
| 3-914 | 2,2-dimethoxyethyl | Me | 5-Cl-2-thienyl | H |
| 3-915 | 2,2-dimethoxyethyl | Me | 5-Br-2-thienyl | H |
| 3-916 | 1-chloropropyl | Me | 4-Cl-Ph | H |
| 3-917 | 1-chloropropyl | Me | 4-Br-Ph | H |
| 3-918 | 1-chloropropyl | Me | 5-Cl-pyridin-2-yl | H |
| 3-919 | 1-chloropropyl | Me | 5-Br-pyridin-2-yl | H |
| 3-920 | 1-chloropropyl | Me | 5-Cl-2-thienyl | H |
| 3-921 | 1-chloropropyl | Me | 5-Br-2-thienyl | H |
| 3-922 | 4-chlorobutan-2-yl | Me | 4-Cl-Ph | H |
| 3-923 | 4-chlorobutan-2-yl | Me | 4-Br-Ph | H |
| 3-924 | 4-chlorobutan-2-yl | Me | 5-Cl-pyridin-2-yl | H |
| 3-925 | 4-chlorobutan-2-yl | Me | 5-Br-pyridin-2-yl | H |
| 3-926 | 4-chlorobutan-2-yl | Me | 5-Cl-2-thienyl | H |
| 3-927 | 4-chlorobutan-2-yl | Me | 5-Br-2-thienyl | H |
| 3-928 | 3-chloropropan-2-yl | Me | 4-Cl-Ph | H |
| 3-929 | 3-chloropropan-2-yl | Me | 4-Br-Ph | H |
| 3-930 | 3-chloropropan-2-yl | Me | 5-Cl-pyridin-2-yl | H |
| 3-931 | 3-chloropropan-2-yl | Me | 5-Br-pyridin-2-yl | H |
| 3-932 | 3-chloropropan-2-yl | Me | 5-Cl-2-thienyl | H |
| 3-933 | 3-chloropropan-2-yl | Me | 5-Br-2-thienyl | H |
| 3-934 | 2-(2-chloroethoxy)ethyl | Me | 4-Cl-Ph | H |
| 3-935 | 2-(2-chloroethoxy)ethyl | Me | 4-Br-Ph | H |
| 3-936 | 2-(2-chloroethoxy)ethyl | Me | 5-Cl-pyridin-2-yl | H |
| 3-937 | 2-(2-chloroethoxy)ethyl | Me | 5-Br-pyridin-2-yl | H |
| 3-938 | 2-(2-chloroethoxy)ethyl | Me | 5-Cl-2-thienyl | H |

TABLE 3-continued

Compounds of the formula (Ia'''')

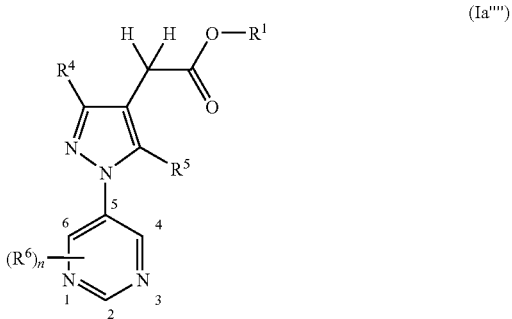

(Ia'''')

| No. | R¹ | R⁴ | R⁵ | (R⁶)ₙ |
|---|---|---|---|---|
| 3-939 | 2-(2-chloroethoxy)ethyl | Me | 5-Br-2-thienyl | H |
| 3-940 | 2,2-dichloroethyl | Me | 4-Cl-Ph | H |
| 3-941 | 2,2-dichloroethyl | Me | 4-Br-Ph | H |
| 3-942 | 2,2-dichloroethyl | Me | 5-Cl-pyridin-2-yl | H |
| 3-943 | 2,2-dichloroethyl | Me | 5-Br-pyridin-2-yl | H |
| 3-944 | 2,2-dichloroethyl | Me | 5-Cl-2-thienyl | H |
| 3-945 | 2,2-dichloroethyl | Me | 5-Br-2-thienyl | H |
| 3-946 | 2,3-dichloropropyl | Me | 4-Cl-Ph | H |
| 3-947 | 2,3-dichloropropyl | Me | 4-Br-Ph | H |
| 3-948 | 2,3-dichloropropyl | Me | 5-Cl-pyridin-2-yl | H |
| 3-949 | 2,3-dichloropropyl | Me | 5-Br-pyridin-2-yl | H |
| 3-950 | 2,3-dichloropropyl | Me | 5-Cl-2-thienyl | H |
| 3-951 | 2,3-dichloropropyl | Me | 5-Br-2-thienyl | H |
| 3-952 | 1,3-dichloroprop-2-yl | Me | 4-Cl-Ph | H |
| 3-953 | 1,3-dichloroprop-2-yl | Me | 4-Br-Ph | H |
| 3-954 | 1,3-dichloroprop-2-yl | Me | 5-Cl-pyridin-2-yl | H |
| 3-955 | 1,3-dichloroprop-2-yl | Me | 5-Br-pyridin-2-yl | H |
| 3-956 | 1,3-dichloroprop-2-yl | Me | 5-Cl-2-thienyl | H |
| 3-957 | 1,3-dichloroprop-2-yl | Me | 5-Br-2-thienyl | H |
| 3-958 | 2-chloro-2,2-difluoroethyl | Me | 4-Cl-Ph | H |
| 3-959 | 2-chloro-2,2-difluoroethyl | Me | 4-Br-Ph | H |
| 3-960 | 2-chloro-2,2-difluoroethyl | Me | 5-Cl-pyridin-2-yl | H |
| 3-961 | 2-chloro-2,2-difluoroethyl | Me | 5-Br-pyridin-2-yl | H |
| 3-962 | 2-chloro-2,2-difluoroethyl | Me | 5-Cl-2-thienyl | H |
| 3-963 | 2-chloro-2,2-difluoroethyl | Me | 5-Br-2-thienyl | H |
| 3-964 | 1-chloro-2-methylpropan-2-yl | Me | 4-Cl-Ph | H |
| 3-965 | 1-chloro-2-methylpropan-2-yl | Me | 4-Br-Ph | H |
| 3-966 | 1-chloro-2-methylpropan-2-yl | Me | 5-Cl-pyridin-2-yl | H |
| 3-967 | 1-chloro-2-methylpropan-2-yl | Me | 5-Br-pyridin-2-yl | H |
| 3-968 | 1-chloro-2-methylpropan-2-yl | Me | 5-Cl-2-thienyl | H |
| 3-969 | 1-chloro-2-methylpropan-2-yl | Me | 5-Br-2-thienyl | H |
| 3-970 | 1-fluoro-3-methoxypropan-2-yl | Me | 4-Cl-Ph | H |
| 3-971 | 1-fluoro-3-methoxypropan-2-yl | Me | 4-Br-Ph | H |
| 3-972 | 1-fluoro-3-methoxypropan-2-yl | Me | 5-Cl-pyridin-2-yl | H |
| 3-973 | 1-fluoro-3-methoxypropan-2-yl | Me | 5-Br-pyridin-2-yl | H |
| 3-974 | 1-fluoro-3-methoxypropan-2-yl | Me | 5-Cl-2-thienyl | H |
| 3-975 | 1-fluoro-3-methoxypropan-2-yl | Me | 5-Br-2-thienyl | H |
| 3-976 | 3,3,3-trifluoropropyl | Me | 4-Cl-Ph | H |
| 3-977 | 3,3,3-trifluoropropyl | Me | 4-Br-Ph | H |
| 3-978 | 3,3,3-trifluoropropyl | Me | 5-Cl-pyridin-2-yl | H |
| 3-979 | 3,3,3-trifluoropropyl | Me | 5-Br-pyridin-2-yl | H |
| 3-980 | 3,3,3-trifluoropropyl | Me | 5-Cl-2-thienyl | H |
| 3-981 | 3,3,3-trifluoropropyl | Me | 5-Br-2-thienyl | H |
| 3-982 | 2-chlorophenyl | Me | 4-Cl-Ph | H |
| 3-983 | 2-chlorophenyl | Me | 4-Br-Ph | H |
| 3-984 | 2-chlorophenyl | Me | 5-Cl-pyridin-2-yl | H |
| 3-985 | 2-ohlorophenyl | Me | 5-Br-pyridin-2-yl | H |
| 3-986 | 2-chlorophenyl | Me | 5-Cl-2-thienyl | H |
| 3-987 | 2-chlorophenyl | Me | 5-Br-2-thienyl | H |
| 3-988 | 2-chloropyridin-3-yl | Me | 4-Cl-Ph | H |
| 3-989 | 2-chloropyridin-3-yl | Me | 4-Br-Ph | H |
| 3-990 | 2-chloropyridin-3-yl | Me | 5-Cl-pyridin-2-yl | H |
| 3-991 | 2-chloropyridin-3-yl | Me | 5-Br-pyridin-2-yl | H |
| 3-992 | 2-chloropyridin-3-yl | Me | 5-Cl-2-thienyl | H |
| 3-993 | 2-chloropyridin-3-yl | Me | 5-Br-2-thienyl | H |
| 3-994 | 3-chloropyridin-2-yl | Me | 4-Cl-Ph | H |
| 3-995 | 3-chloropyridin-2-yl | Me | 4-Br-Ph | H |
| 3-996 | 3-chloropyridin-2-yl | Me | 5-Cl-pyridin-2-yl | H |
| 3-997 | 3-chloropyridin-2-yl | Me | 5-Br-pyridin-2-yl | H |

TABLE 3-continued

Compounds of the formula (Ia'''')

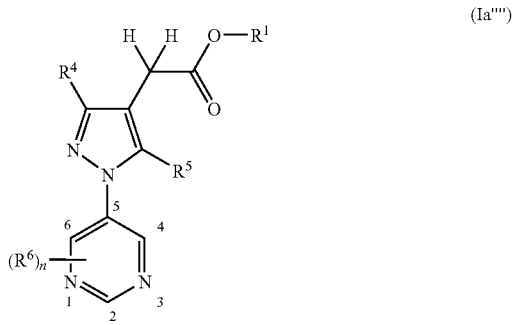

| No. | R¹ | R⁴ | R⁵ | (R⁶)ₙ |
|---|---|---|---|---|
| 3-998 | 3-chloropyridin-2-yl | Me | 5-Cl-2-thienyl | H |
| 3-999 | 3-chloropyridin-2-yl | Me | 5-Br-2-thienyl | H |
| 3-1000 | pentafluoroethyl | Me | 4-Cl-Ph | H |
| 3-1001 | pentafluoroethyl | Me | 4-Br-Ph | H |
| 3-1002 | pentafluoroethyl | Me | 5-Cl-pyridin-2-yl | H |
| 3-1003 | pentafluoroethyl | Me | 5-Br-pyridin-2-yl | H |
| 3-1004 | pentafluoroethyl | Me | 5-Cl-2-thienyl | H |
| 3-1005 | pentafluoroethyl | Me | 5-Br-2-thienyl | H |
| 3-1006 | 1,2,2,2-tetrafluoroethyl | Me | 4-Cl-Ph | H |
| 3-1007 | 1,2,2,2-tetrafluoroethyl | Me | 4-Br-Ph | H |
| 3-1008 | 1,2,2,2-tetrafluoroethyl | Me | 5-Cl-pyridin-2-yl | H |
| 3-1009 | 1,2,2,2-tetrafluoroethyl | Me | 5-Br-pyridin-2-yl | H |
| 3-1010 | 1,2,2,2-tetrafluoroethyl | Me | 5-Cl-2-thienyl | H |
| 3-1011 | 1,2,2,2-tetrafluoroethyl | Me | 5-Br-2-thienyl | H |
| 3-1012 | 1,1,2,2-tetrafluoroethyl | Me | 4-Cl-Ph | H |
| 3-1013 | 1,1,2,2-tetrafluoroethyl | Me | 4-Br-Ph | H |
| 3-1014 | 1,1,2,2-tetrafluoroethyl | Me | 5-Cl-pyridin-2-yl | H |
| 3-1015 | 1,1,2,2-tetrafluoroethyl | Me | 5-Br-pyridin-2-yl | H |
| 3-1016 | 1,1 2,2-tetrafluoroethyl | Me | 5-Cl-2-thienyl | H |
| 3-1017 | 1,1,2,2-tetrafluoroethyl | Me | 5-Br-2-thienyl | H |
| 3-1018 | 1,1,2-trifluoroethyl | Me | 4-Cl-Ph | H |
| 3-1019 | 1,1,2-trifluoroethyl | Me | 4-Br-Ph | H |
| 3-1020 | 1,1,2-trifluoroethyl | Me | 5-Cl-pyridin-2-yl | H |
| 3-1021 | 1,1,2-trifluoroethyl | Me | 5-Br-pyridin-2-yl | H |
| 3-1022 | 1,1,2-trifluoroethyl | Me | 5-Cl-2-thienyl | H |
| 3-1023 | 1,1,2-trifluoroethyl | Me | 5-Br-2-thienyl | H |
| 3-1024 | 2-methylbut-3-yn-2-yl | Me | 4-Cl-Ph | H |
| 3-1025 | 2-methylbut-3-yn-2-yl | Me | 4-Br-Ph | H |
| 3-1026 | 2-methylbut-3-yn-2-yl | Me | 5-Cl-pyridin-2-yl | H |
| 3-1027 | 2-methylbut-3-yn-2-yl | Me | 5-Br-pyridin-2-yl | H |
| 3-1028 | 2-methylbut-3-yn-2-yl | Me | 5-Cl-2-thienyl | H |
| 3-1029 | 2-methylbut-3-yn-2-yl | Me | 5-Br-2-thienyl | H |
| 3-1030 | 1-(ethoxycarbonyl)eth-1-yl | Me | 4-Cl-Ph | H |
| 3-1031 | 1-(ethoxycarbonyl)eth-1-yl | Me | 4-Br-Ph | H |
| 3-1032 | 1-(ethoxycarbonyl)eth-1-yl | Me | 5-Cl-pyridin-2-yl | H |
| 3-1033 | 1-(ethoxycarbonyl)eth-1-yl | Me | 5-Br-pyridin-2-yl | H |
| 3-1034 | 1-(ethoxycarbonyl)eth-1-yl | Me | 5-Cl-2-thienyl | H |
| 3-1035 | 1-(ethoxycarbonyl)eth-1-yl | Me | 5-Br-2-thienyl | H |
| 3-1036 | 1,1,2,3,3,3-hexafluoropropyl | Me | 4-Cl-Ph | H |
| 3-1037 | 1,1,2,3,3,3-hexafluoropropyl | Me | 4-Br-Ph | H |
| 3-1038 | 1,1,2,3,3,3-hexafluoropropyl | Me | 5-Cl-pyridin-2-yl | H |
| 3-1039 | 1,1,2,3,3,3-hexafluoropropyl | Me | 5-Br-pyridin-2-yl | H |
| 3-1040 | 1,1,2,3,3,3-hexafluoropropyl | Me | 5-Cl-2-thienyl | H |
| 3-1041 | 1,1,2,3,3,3-hexafluoropropyl | Me | 5-Br-2-thienyl | H |
| 3-1042 | isobutyl | Me | 4-Cl-Ph | H |
| 3-1043 | isobutyl | Me | 4-Br-Ph | H |
| 3-1044 | isobutyl | Me | 5-Cl-pyridin-2-yl | H |
| 3-1045 | isobutyl | Me | 5-Br-pyridin-2-yl | H |
| 3-1046 | isobutyl | Me | 5-Cl-2-thienyl | H |
| 3-1047 | isobutyl | Me | 5-Br-2-thienyl | H |
| 3-1048 | n-pentyl | Me | 4-Cl-Ph | H |
| 3-1049 | n-pentyl | Me | 4-Br-Ph | H |
| 3-1050 | n-pentyl | Me | 5-Cl-pyridin-2-yl | H |
| 3-1051 | n-pentyl | Me | 5-Br-pyridin-2-yl | H |
| 3-1052 | n-pentyl | Me | 5-Cl-2-thienyl | H |
| 3-1053 | n-pentyl | Me | 5-Br-2-thienyl | H |
| 3-1054 | n-heptyl | Me | 4-Cl-Ph | H |
| 3-1055 | n-heptyl | Me | 4-Br-Ph | H |
| 3-1056 | n-heptyl | Me | 5-Cl-pyridin-2-yl | H |

TABLE 3-continued

Compounds of the formula (Ia'''')

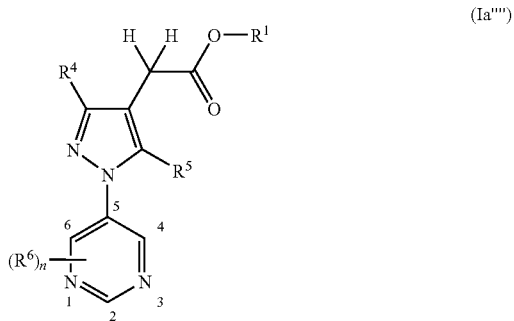

| No. | R¹ | R⁴ | R⁵ | (R⁶)$_n$ |
|---|---|---|---|---|
| 3-1057 | n-heptyl | Me | 5-Br-pyridin-2-yl | H |
| 3-1058 | n-heptyl | Me | 5-Cl-2-thienyl | H |
| 3-1059 | n-heptyl | Me | 5-Br-2-thienyl | H |
| 3-1060 | n-nonyl | Me | 4-Cl-Ph | H |
| 3-1061 | n-nonyl | Me | 4-Br-Ph | H |
| 3-1062 | n-nonyl | Me | 5-Cl-pyridin-2-yl | H |
| 3-1063 | n-nonyl | Me | 5-Br-pyridin-2-yl | H |
| 3-1064 | n-nonyl | Me | 5-Cl-2-thienyl | H |
| 3-1065 | n-nonyl | Me | 5-Br-2-thienyl | H |
| 3-1066 | cyclopentyl | Me | 4-Cl-Ph | H |
| 3-1067 | cyclopentyl | Me | 4-Br-Ph | H |
| 3-1068 | cyclopentyl | Me | 5-Cl-pyridin-2-yl | H |
| 3-1069 | cyclopentyl | Me | 5-Br-pyridin-2-yl | H |
| 3-1070 | cyclopentyl | Me | 5-Cl-2-thienyl | H |
| 3-1071 | cyclopentyl | Me | 5-Br-2-thienyl | H |
| 3-1072 | cyclohexyl | Me | 4-Cl-Ph | H |
| 3-1073 | cyclohexyl | Me | 4-Br-Ph | H |
| 3-1074 | cyclohexyl | Me | 5-Cl-pyridin-2-yl | H |
| 3-1075 | cyclohexyl | Me | 5-Br-pyridin-2-yl | H |
| 3-1076 | cyclohexyl | Me | 5-Cl-2-thienyl | H |
| 3-1077 | cyclohexyl | Me | 5-Br-2-thienyl | H |
| 3-1078 | sBu | Me | 4-Cl-Ph | H |
| 3-1079 | sBu | Me | 4-Br-Ph | H |
| 3-1080 | sBu | Me | 5-Cl-pyridin-2-yl | H |
| 3-1081 | sBu | Me | 5-Br-pyridin-2-yl | H |
| 3-1082 | sBu | Me | 5-Cl-2-thienyl | H |
| 3-1083 | sBu | Me | 5-Br-2-thienyl | H |
| 3-1084 | pentan-3-yl | Me | 4-Cl-Ph | H |
| 3-1085 | pentan-3-yl | Me | 4-Br-Ph | H |
| 3-1086 | pentan-3-yl | Me | 5-Cl-pyridin-2-yl | H |
| 3-1087 | pentan-3-yl | Me | 5-Br-pyridin-2-yl | H |
| 3-1088 | pentan-3-yl | Me | 5-Cl-2-thienyl | H |
| 3-1089 | pentan-3-yl | Me | 5-Br-2-thienyl | H |
| 3-1090 | 1-(methoxycarbonyl)eth-1-yl | Me | 4-Cl-Ph | H |
| 3-1091 | 1-(methoxycarbonyl)eth-1-yl | Me | 4-Br-Ph | H |
| 3-1092 | 1-(methoxycarbonyl)eth-1-yl | Me | 5-Cl-pyridin-2-yl | H |
| 3-1093 | 1-(methoxycarbonyl)eth-1-yl | Me | 5-Br-pyridin-2-yl | H |
| 3-1094 | 1-(methoxycarbonyl)eth-1-yl | Me | 5-Cl-2-thienyl | H |
| 3-1095 | 1-(methoxycarbonyl)eth-1-yl | Me | 5-Br-2-thienyl | H |
| 3-1096 | 2,2,2-trichloroethyl | Me | 4-Cl-Ph | H |
| 3-1097 | 2,2,2-trichloroethyl | Me | 4-Br-Ph | H |
| 3-1098 | 2,2,2-trichloroethyl | Me | 5-Cl-pyridin-2-yl | H |
| 3-1099 | 2,2,2-trichloroethyl | Me | 5-Br-pyridin-2-yl | H |
| 3-1100 | 2,2,2-trichloroethyl | Me | 5-Cl-2-thienyl | H |
| 3-1101 | 2,2,2-trichloroethyl | Me | 5-Br-2-thienyl | H |
| 3-1102 | 3-chloropropyl | Me | 4-Cl-Ph | H |
| 3-1103 | 3-chloropropyl | Me | 4-Br-Ph | H |
| 3-1104 | 3-chloropropyl | Me | 5-Cl-pyridin-2-yl | H |
| 3-1105 | 3-chloropropyl | Me | 5-Br-pyridin-2-yl | H |
| 3-1106 | 3-chloropropyl | Me | 5-Cl-2-thienyl | H |
| 3-1107 | 3-chloropropyl | Me | 5-Br-2-thienyl | H |
| 3-1108 | 2-(2-methoxyethoxy)ethyl | Me | 4-Cl-Ph | H |
| 3-1109 | 2-(2-methoxyethoxy)ethyl | Me | 4-Br-Ph | H |
| 3-1110 | 2-(2-methoxyethoxy)ethyl | Me | 5-Cl-pyridin-2-yl | H |
| 3-1111 | 2-(2-methoxyethoxy)ethyl | Me | 5-Br-pyridin-2-yl | H |
| 3-1112 | 2-(2-methoxyethoxy)ethyl | Me | 5-Cl-2-thienyl | H |
| 3-1113 | 2-(2-methoxyethoxy)ethyl | Me | 5-Br-2-thienyl | H |
| 3-1114 | butyl-2-ylmethyl | Me | 4-Cl-Ph | H |
| 3-1115 | butyl-2-ylmethyl | Me | 4-Br-Ph | H |

TABLE 3-continued

Compounds of the formula (Ia'''')

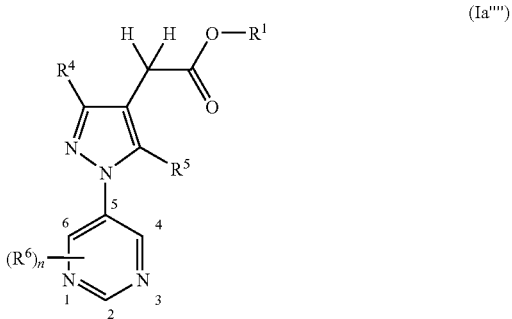

| No. | R¹ | R⁴ | R⁵ | (R⁶)ₙ |
|---|---|---|---|---|
| 3-1116 | butyl-2-ylmethyl | Me | 5-Cl-pyridin-2-yl | H |
| 3-1117 | butyl-2-ylmethyl | Me | 5-Br-pyridin-2-yl | H |
| 3-1118 | butyl-2-ylmethyl | Me | 5-Cl-2-thienyl | H |
| 3-1119 | butyl-2-ylmethyl | Me | 5-Br-2-thienyl | H |
| 3-1120 | but-3-yn-1-yl | Me | 4-Cl-Ph | H |
| 3-1121 | but-3-yn-1-yl | Me | 4-Br-Ph | H |
| 3-1122 | but-3-yn-1-yl | Me | 5-Cl-pyridin-2-yl | H |
| 3-1123 | but-3-yn-1-yl | Me | 5-Br-pyridin-2-yl | H |
| 3-1124 | but-3-yn-1-yl | Me | 5-Cl-2-thienyl | H |
| 3-1125 | but-3-yn-1-yl | Me | 5-Br-2-thienyl | H |
| 3-1126 | (2,2-dichlorocyclopropyl)methyl | Me | 4-Cl-Ph | H |
| 3-1127 | (2,2-dichlorocyclopropyl)methyl | Me | 4-Br-Ph | H |
| 3-1128 | (2,2-dichlorocyclopropyl)methyl | Me | 5-Cl-pyridin-2-yl | H |
| 3-1129 | (2,2-dichlorocyclopropyl)methyl | Me | 5-Br-pyridin-2-yl | H |
| 3-1130 | (2,2-dichlorocyclopropyl)methyl | Me | 5-Cl-2-thienyl | H |
| 3-1131 | (2,2-dichlorocyclopropyl)methyl | Me | 5-Br-2-thienyl | H |
| 3-1132 | 2-(N,N-diethylamino)eth-1-yl | Me | 4-Cl-Ph | H |
| 3-1133 | 2-(N,N-diethylamino)eth-1-yl | Me | 4-Br-Ph | H |
| 3-1134 | 2-(N,N-diethylamino)eth-1-yl | Me | 5-Cl-pyridin-2-yl | H |
| 3-1135 | 2-(N,N-diethylamino)eth-1-yl | Me | 5-Br-pyridin-2-yl | H |
| 3-1136 | 2-(N N-diethylamino)eth-1-yl | Me | 5-Cl-2-thienyl | H |
| 3-1137 | 2-(N,N-diethylamino)eth-1-yl | Me | 5-Br-2-thienyl | H |
| 3-1138 | 2-carboxyphenyl | Me | 4-Cl-Ph | H |
| 3-1139 | 2-carboxyphenyl | Me | 4-Br-Ph | H |
| 3-1140 | 2-carboxyphenyl | Me | 5-Cl-pyridin-2-yl | H |
| 3-1141 | 2-carboxyphenyl | Me | 5-Br-pyridin-2-yl | H |
| 3-1142 | 2-carboxyphenyl | Me | 5-Cl-2-thienyl | H |
| 3-1143 | 2-carboxyphenyl | Me | 5-Br-2-thienyl | H |
| 3-1144 | tbutyl | Me | 4-Cl-Ph | H |
| 3-1145 | tBu | Me | 4-Br-Ph | H |
| 3-1146 | tBu | Me | 5-Cl-pyridin-2-yl | H |
| 3-1147 | tBu | Me | 5-Br-pyridin-2-yl | H |
| 3-1148 | tBu | Me | 5-Cl-2-thienyl | H |
| 3-1149 | tBu | Me | 5-Br-2-thienyl | H |
| 3-1150 | 1-methylcyclopropyl | Me | 4-Cl-Ph | H |
| 3-1151 | 1-methylcyclopropyl | Me | 4-Br-Ph | H |
| 3-1152 | 1-methylcyclopropyl | Me | 5-Cl-pyridin-2-yl | H |
| 3-1153 | 1-methylcyclopropyl | Me | 5-Br-pyridin-2-yl | H |
| 3-1154 | 1-methylcyclopropyl | Me | 5-Cl-2-thienyl | H |
| 3-1155 | 1-methylcyclopropyl | Me | 5-Br-2-thienyl | H |
| 3-1156 | trimethylsilylmethyl | Me | 4-Cl-Ph | H |
| 3-1157 | trimethylsilylmethyl | Me | 4-Br-Ph | H |
| 3-1158 | trimethylsilylmethyl | Me | 5-Cl-pyridin-2-yl | H |
| 3-1159 | trimethylsilylmethyl | Me | 5-Br-pyridin-2-yl | H |
| 3-1160 | trimethylsilylmethyl | Me | 5-Cl-2-thienyl | H |
| 3-1161 | trimethylsilylmethyl | Me | 5-Br-2-thienyl | H |
| 3-1162 | 2,3-dihydro-1H-inden-5-yl | Me | 4-Cl-Ph | H |
| 3-1163 | 2,3-dihydro-1H-inden-5-yl | Me | 4-Br-Ph | H |
| 3-1164 | 2,3-dihydro-1H-inden-5-yl | Me | 5-Cl-pyridin-2-yl | H |
| 3-1165 | 2,3-dihydro-1H-inden-5-yl | Me | 5-Br-pyridin-2-yl | H |
| 3-1166 | 2,3-dihydro-1H-inden-5-yl | Me | 5-Cl-2-thienyl | H |
| 3-1167 | 2,3-dihydro-1H-inden-5-yl | Me | 5-Br-2-thienyl | H |
| 3-1168 | 1-methylcyclobutyl | Me | 4-Cl-Ph | H |
| 3-1169 | 1-methylcyclobutyl | Me | 4-Br-Ph | H |
| 3-1170 | 1-methylcyclobutyl | Me | 5-Cl-pyridin-2-yl | H |
| 3-1171 | 1-methylcyclobutyl | Me | 5-Br-pyridin-2-yl | H |
| 3-1172 | 1-methylcyclobutyl | Me | 5-Cl-2-thienyl | H |
| 3-1173 | 1-methylcyclobutyl | Me | 5-Br-2-thienyl | H |
| 3-1174 | 2-(oxetan-3-yl)eth-1-yl | Me | 4-Cl-Ph | H |

TABLE 3-continued

Compounds of the formula (Ia'''')

| No. | R¹ | R⁴ | R⁵ | (R⁶)$_n$ |
|---|---|---|---|---|
| 3-1175 | 2-(oxetan-3-yl)eth-1-yl | Me | 4-Br-Ph | H |
| 3-1176 | 2-(oxetan-3-yl)eth-1-yl | Me | 5-Cl-pyridin-2-yl | H |
| 3-1177 | 2-(oxetan-3-yl)eth-1-yl | Me | 5-Br-pyridin-2-yl | H |
| 3-1178 | 2-(oxetan-3-yl)eth-1-yl | Me | 5-Cl-2-thienyl | H |
| 3-1179 | 2-(oxetan-3-yl)eth-1-yl | Me | 5-Br-2-thienyl | H |
| 3-1180 | Bu | Me | 4-Cl-Ph | H |
| 3-1181 | Bu | Me | 4-Br-Ph | H |
| 3-1182 | Bu | Me | 5-Cl-pyridin-2-yl | H |
| 3-1183 | Bu | Me | 5-Br-pyridin-2-yl | H |
| 3-1184 | Bu | Me | 5-Cl-2-thienyl | H |
| 3-1185 | Bu | Me | 5-Br-2-thienyl | H |
| 3-1186 | 2-(N,N-diethylamino)eth-1-yl | Me | 4-Cl-Ph | H |
| 3-1187 | 2-(N,N-diethylamino)eth-1-yl | Me | 4-Br-Ph | H |
| 3-1188 | 2-(N,N-diethylamino)eth-1-yl | Me | 5-Cl-pyridin-2-yl | H |
| 3-1189 | 2-(N,N-diethylamino)eth-1-yl | Me | 5-Br-pyridin-2-yl | H |
| 3-1190 | 2-(N,N-diethylamino)eth-1-yl | Me | 5-Cl-2-thienyl | H |
| 3-1191 | 2-(N,N-diethylamino)eth-1-yl | Me | 5-Br-2-thienyl | H |
| 3-1192 | 2-(morpholin-4-yl)eth-1-yl | Me | 4-Cl-Ph | H |
| 3-1193 | 2-(morpholin-4-yl)eth-1-yl | Me | 4-Br-Ph | H |
| 3-1194 | 2-(morpholin-4-yl)eth-1-yl | Me | 5-Cl-pyridin-2-yl | H |
| 3-1195 | 2-(morpholin-4-yl)eth-1-yl | Me | 5-Br-pyridin-2-yl | H |
| 3-1196 | 2-(morpholin-4-yl)eth-1-yl | Me | 5-Cl-2-thienyl | H |
| 3-1197 | 2-(morpholin-4-yl)eth-1-yl | Me | 5-Br-2-thienyl | H |
| 3-1198 | 2-chlorothiophen-3-yl | Me | 4-Cl-Ph | H |
| 3-1199 | 2-chlorothiophen-3-yl | Me | 4-Br-Ph | H |
| 3-1200 | 2-chlorothiophen-3-yl | Me | 5-Cl-pyridin-2-yl | H |
| 3-1201 | 2-chlorothiophen-3-yl | Me | 5-Br-pyridin-2-yl | H |
| 3-1202 | 2-chlorothiophen-3-yl | Me | 5-Cl-2-thienyl | H |
| 3-1203 | 2-chlorothiophen-3-yl | Me | 5-Br-2-thienyl | H |
| 3-1204 | (N,N-dimethylaminocarbonyl)methyl | Me | 4-Cl-Ph | H |
| 3-1205 | (N,N-dimethylaminocarbonyl)methyl | Me | 4-Br-Ph | H |
| 3-1206 | (N,N-dimethylaminocarbonyl)methyl | Me | 5-Cl-pyridin-2-yl | H |
| 3-1207 | (N,N-dimethylaminocarbonyl)methyl | Me | 5-Br-pyridin-2-yl | H |
| 3-1208 | (N,N-dimethylaminocarbonyl)methyl | Me | 5-Cl-2-thienyl | H |
| 3-1209 | (N,N-dimethylaminocarbonyl)methyl | Me | 5-Br-2-thienyl | H |
| 3-1210 | 1-(t-butylcarbonyloxy)-2-methylprop-1-yl | Me | 4-Cl-Ph | H |
| 3-1211 | 1-(t-butylcarbonyloxy)-2-methylprop-1-yl | Me | 4-Br-Ph | H |
| 3-1212 | 1-(t-butylcarbonyloxy)-2-methylprop-1-yl | Me | 5-Cl-pyridin-2-yl | H |
| 3-1213 | 1-(t-butylcarbonyloxy)-2-methylprop-1-yl | Me | 5-Br-pyridin-2-yl | H |
| 3-1214 | 1-(t-butylcarbonyloxy)-2-methylprop-1-yl | Me | 5-Cl-2-thienyl | H |
| 3-1215 | 1-(t-butylcarbonyloxy)-2-methylprop-1-yl | Me | 5-Br-2-thienyl | H |
| 3-1216 | (5-methyl-2-oxo-1,3-dioxol-4-yl)methyl | Me | 4-Cl-Ph | H |
| 3-1217 | (5-methyl-2-oxo-1,3-dioxol-4-yl)methyl | Me | 4-Br-Ph | H |
| 3-1218 | (5-methyl-2-oxo-1,3-dioxol-4-yl)methyl | Me | 5-Cl-pyridin-2-yl | H |
| 3-1219 | (5-methyl-2-oxo-1,3-dioxol-4-yl)methyl | Me | 5-Br-pyridin-2-yl | H |
| 3-1220 | (5-methyl-2-oxo-1,3-dioxol-4-yl) methyl | Me | 5-Cl-2-thienyl | H |
| 3-1221 | (5-methyl-2-oxo-1,3-dioxol-4-yl)methyl | Me | 5-Br-2-thienyl | H |

TABLE 3-continued

Compounds of the formula (Ia'''')

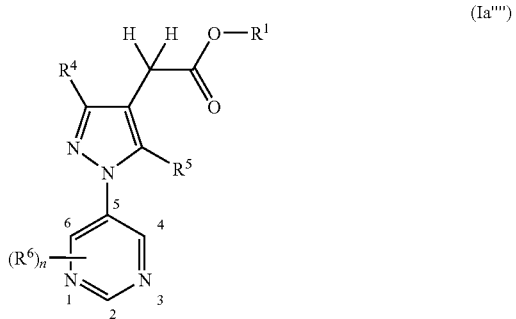

| No. | $R^1$ | $R^4$ | $R^5$ | $(R^6)_n$ |
|---|---|---|---|---|
| 3-1222 | [(t-butoxycarbonyl)oxy]methyl | Me | 4-Cl-Ph | H |
| 3-1223 | [(t-butoxycarbonyl)oxy]methyl | Me | 4-Br-Ph | H |
| 3-1224 | [(t-butoxycarbonyl)oxy]methyl | Me | 5-Cl-pyridin-2-yl | H |
| 3-1225 | [(t-butoxycarbonyl)oxy]methyl | Me | 5-Br-pyridin-2-yl | H |
| 3-1226 | [(t-butoxycarbonyl)oxy]methyl | Me | 5-Cl-2-thienyl | H |
| 3-1227 | [(t-butoxycarbonyl)oxy]methyl | Me | 5-Br-2-thienyl | H |
| 3-1228 | [(isopropoxycarbonyl)oxy]methyl | Me | 4-Cl-Ph | H |
| 3-1229 | [(isopropoxycarbonyl)oxy]methyl | Me | 4-Br-Ph | H |
| 3-1230 | [(isopropoxycarbonyl)oxy]methyl | Me | 5-Cl-pyridin-2-yl | H |
| 3-1231 | [(isopropoxycarbonyl)oxy]methyl | Me | 5-Br-pyridin-2-yl | H |
| 3-1232 | [(isopropoxycarbonyl)oxy]methyl | Me | 5-Cl-2-thienyl | H |
| 3-1233 | [(isopropoxycarbonyl)oxy]methyl | Me | 5-Br-2-thienyl | H |
| 3-1234 | [(methoxycarbonyl)oxy]methyl | Me | 4-Cl-Ph | H |
| 3-1235 | [(methoxycarbonyl)oxy]methyl | Me | 4-Br-Ph | H |
| 3-1236 | [(methoxycarbonyl)oxy]methyl | Me | 5-Cl-pyrid in-2-yl | H |
| 3-1237 | [(methoxycarbonyl)oxy]methyl | Me | 5-Br-pyridin-2-yl | H |
| 3-1238 | [(methoxycarbonyl)oxy]methyl | Me | 5-Cl-2-thienyl | H |
| 3-1239 | [(methoxycarbonyl)oxy]methyl | Me | 5-Br-2-thienyl | H |
| 3-1240 | 1-[(ethoxycarbonyl)oxy]ethyl | Me | 4-Cl-Ph | H |
| 3-1241 | 1-[(ethoxycarbonyl)oxy]ethyl | Me | 4-Br-Ph | H |
| 3-1242 | 1-[(ethoxycarbonyl)oxy]ethyl | Me | 5-Cl-pyridin-2-yl | H |
| 3-1243 | 1-[(ethoxycarbonyl)oxy]ethyl | Me | 5-Br-pyridin-2-yl | H |
| 3-1244 | 1-[(ethoxycarbonyl)oxy]ethyl | Me | 5-Cl-2-thienyl | H |
| 3-1245 | 1-[(ethoxycarbonyl)oxy]ethyl | Me | 5-Br-2-thienyl | H |
| 3-1246 | 1-acetoxyeth-1-yl | Me | 4-Cl-Ph | H |
| 3-1247 | 1-acetoxyeth-1-yl | Me | 4-Br-Ph | H |
| 3-1248 | 1-acetoxyeth-1-yl | Me | 5-Cl-pyridin-2-yl | H |
| 3-1249 | 1-acetoxyeth-1-yl | Me | 5-Br-pyridin-2-yl | H |
| 3-1250 | 1-acetoxyeth-1-yl | Me | 5-Cl-2-thienyl | H |
| 3-1251 | 1-acetoxyeth-1-yl | Me | 5-Br-2-thienyl | H |
| 3-1252 | 1-(2-methylpropanoyloxy)eth-1-yl | Me | 4-Cl-Ph | H |
| 3-1253 | 1-(2-methylpropanoyloxy)eth-1-yl | Me | 4-Br-Ph | H |
| 3-1254 | 1-(2-methylpropanoyloxy)eth-1-yl | Me | 5-Cl-pyrid in-2-yl | H |
| 3-1255 | 1-(2-methylpropanoyloxy)eth-1-yl | Me | 5-Br-pyridin-2-yl | H |
| 3-1256 | 1-(2-methylpropanoyloxy)eth-1-yl | Me | 5-Cl-2-thienyl | H |
| 3-1257 | 1-(2-methylpropanoyloxy)eth-1-yl | Me | 5-Br-2-thienyl | H |
| 3-1258 | 1-propanoyl-2-methylprop-1-yl | Me | 4-Cl-Ph | H |
| 3-1259 | 1-propanoyl-2-methylprop-1-yl | Me | 4-Br-Ph | H |
| 3-1260 | 1-propanoyl-2-methylprop-1-yl | Me | 5-Cl-pyridin-2-yl | H |
| 3-1261 | 1-propanoyl-2-methylprop-1-yl | Me | 5-Br-pyridin-2-yl | H |
| 3-1262 | 1-propanoyl-2-methylprop-1-yl | Me | 5-Cl-2-thienyl | H |
| 3-1263 | 1-propanoyl-2-methylprop-1-yl | Me | 5-Br-2-thienyl | H |
| 3-1264 | 1-(cyclohexoxycarbonyloxy)eth-1-yl | Me | 4-Cl-Ph | H |
| 3-1265 | 1-(cyclohexoxycarbonyloxy)eth-1-yl | Me | 4-Br-Ph | H |
| 3-1266 | 1-(cyclohexoxycarbonyloxy)eth-1-yl | Me | 5-Cl-pyridin-2-yl | H |
| 3-1267 | 1-(cyclohexoxycarbonyloxy)eth-1-yl | Me | 5-Br-pyridin-2-yl | H |
| 3-1268 | 1-(cyclohexoxycarbonyloxy)eth-1-yl | Me | 5-Cl-2-thienyl | H |
| 3-1269 | 1-(cyclohexoxycarbonyloxy)eth-1-yl | Me | 5-Br-2-thienyl | H |
| 3-1270 | cyclobutyl | Me | 4-Cl-Ph | H |
| 3-1271 | cyclobutyl | Me | 4-Br-Ph | H |
| 3-1272 | cyclobutyl | Me | 5-Cl-pyridin-2-yl | H |
| 3-1273 | cyclobutyl | Me | 5-Br-pyridin-2-yl | H |
| 3-1274 | cyclobutyl | Me | 5-Cl-2-thienyl | H |
| 3-1275 | cyclobutyl | Me | 5-Br-2-thienyl | H |
| 3-1276 | $CH_2$(4-Me-Ph) | Me | 4-Cl-Ph | H |
| 3-1277 | $CH_2$(4-Me-Ph) | Me | 4-Br-Ph | H |
| 3-1278 | $CH_2$(4-Me-Ph) | Me | 5-Cl-pyridin-2-yl | H |
| 3-1279 | $CH_2$(4-Me-Ph) | Me | 5-Br-pyridin-2-yl | H |
| 3-1280 | $CH_2$(4-Me-Ph) | Me | 5-Cl-2-thienyl | H |

TABLE 3-continued

Compounds of the formula (Ia'''')

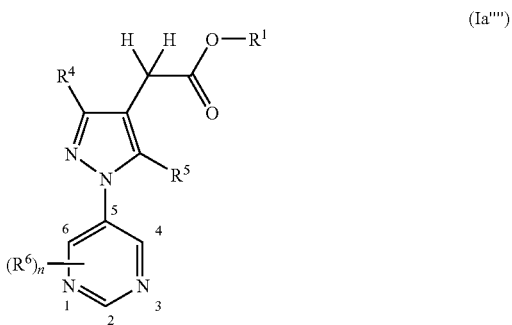

| No. | R$^1$ | R$^4$ | R$^5$ | (R$^6$)$_n$ |
|---|---|---|---|---|
| 3-1281 | CH$_2$(4-Me-Ph) | Me | 5-Br-2-thienyl | H |
| 3-1282 | CHMe(4-Cl-Ph) | Me | 4-Cl-Ph | H |
| 3-1283 | CHMe(4-Cl-Ph) | Me | 4-Br-Ph | H |
| 3-1284 | CHMe(4-Cl-Ph) | Me | 5-Cl-pyridin-2-yl | H |
| 3-1285 | CHMe(4-Cl-Ph) | Me | 5-Br-pyridin-2-yl | H |
| 3-1286 | CHMe(4-Cl-Ph) | Me | 5-Cl-2-thienyl | H |
| 3-1287 | CHMe(4-Cl-Ph) | Me | 5-Br-2-thienyl | H |
| 3-1288 | CHMePh | Me | 4-Cl-Ph | H |
| 3-1289 | CHMePh | Me | 4-Br-Ph | H |
| 3-1290 | CHMePh | Me | 5-Cl-pyridin-2-yl | H |
| 3-1291 | CHMePh | Me | 5-Br-pyridin-2-yl | H |
| 3-1292 | CHMePh | Me | 5-Cl-2-thienyl | H |
| 3-1293 | CHMePh | Me | 5-Br-2-thienyl | H |
| 3-1294 | 1,1,1-trifluoropropan-2-yl | Me | 4-Cl-Ph | H |
| 3-1295 | 1,1,1-trifluoropropan-2-yl | Me | 4-Br-Ph | H |
| 3-1296 | 1,1,1-trifluoropropan-2-yl | Me | 5-Cl-pyridin-2-yl | H |
| 3-1297 | 1,1,1-trifluoropropan-2-yl | Me | 5-Br-pyridin-2-yl | H |
| 3-1298 | 1,1,1-trifluoropropan-2-yl | Me | 5-Cl-2-thienyl | H |
| 3-1299 | 1,1,1-trifluoropropan-2-yl | Me | 5-Br-2-thienyl | H |
| 3-1300 | (1-ethyl-3-methyl-1H-pyrazol-4-yl)methyl | Me | 4-Cl-Ph | H |
| 3-1301 | (1-ethyl-3-methyl-1H-pyrazol-4-yl)methyl | Me | 4-Br-Ph | H |
| 3-1302 | (1-ethyl-3-methyl-1H-pyrazol-4-yl)methyl | Me | 5-Cl-pyridin-2-yl | H |
| 3-1303 | (1-ethyl-3-methyl-1H-pyrazol-4-yl)methyl | Me | 5-Br-pyridin-2-yl | H |
| 3-1304 | (1-ethyl-3-methyl-1H-pyrazol-4-yl)methyl | Me | 5-Cl-2-thienyl | H |
| 3-1305 | (1-ethyl-3-methyl-1H-pyrazol-4-yl)methyl | Me | 5-Br-2-thienyl | H |
| 3-1306 | Pr | Me | 4-Cl-Ph | H |
| 3-1307 | Pr | Me | 4-Br-Ph | H |
| 3-1308 | Pr | Me | 5-Cl-pyridin-2-yl | H |
| 3-1309 | Pr | Me | 5-Br-pyridin-2-yl | H |
| 3-1310 | Pr | Me | 5-Cl-2-thienyl | H |
| 3-1311 | Pr | Me | 5-Br-2-thienyl | H |
| 3-1312 | n-octadecyl | Me | 4-Cl-Ph | H |
| 3-1313 | n-octadecyl | Me | 4-Br-Ph | H |
| 3-1314 | n-octadecyl | Me | 5-Cl-pyridin-2-yl | H |
| 3-1315 | n-octadecyl | Me | 5-Br-pyridin-2-yl | H |
| 3-1316 | n-octadecyl | Me | 5-Cl-2-thienyl | H |
| 3-1317 | n-octadecyl | Me | 5-Br-2-thienyl | H |
| 3-1318 | n-hexadecyl | Me | 4-Cl-Ph | H |
| 3-1319 | n-hexadeoyl | Me | 4-Br-Ph | H |
| 3-1320 | n-hexadecyl | Me | 5-Cl-pyridin-2-yl | H |
| 3-1321 | n-hexadecyl | Me | 5-Br-pyridin-2-yl | H |
| 3-1322 | n-hexadecyl | Me | 5-Cl-2-thienyl | H |
| 3-1323 | n-hexadecyl | Me | 5-Br-2-thienyl | H |
| 3-1324 | oxetan-3-ylmethyl | Me | 4-Cl-Ph | H |
| 3-1325 | oxetan-3-ylmethyl | Me | 4-Br-Ph | H |
| 3-1326 | oxetan-3-ylmethyl | Me | 5-Cl-pyridin-2-yl | H |
| 3-1327 | oxetan-3-ylmethyl | Me | 5-Br-pyridin-2-yl | H |
| 3-1328 | oxetan-3-ylmethyl | Me | 5-Cl-2-thienyl | H |
| 3-1329 | oxetan-3-ylmethyl | Me | 5-Br-2-thienyl | H |
| 3-1330 | 3-methyloxetan-3-yl | Me | 4-Cl-Ph | H |
| 3-1331 | 3-methyloxetan-3-yl | Me | 4-Br-Ph | H |
| 3-1332 | 3-methyloxetan-3-yl | Me | 5-Cl-pyridin-2-yl | H |
| 3-1333 | 3-methyloxetan-3-yl | Me | 5-Br-pyridin-2-yl | H |

TABLE 3-continued

Compounds of the formula (Ia'''')

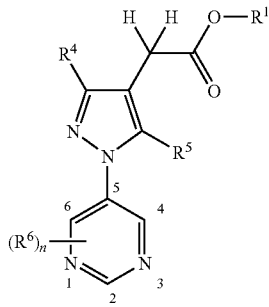

(Ia'''')

| No. | R¹ | R⁴ | R⁵ | $(R^6)_n$ |
|---|---|---|---|---|
| 3-1334 | 3-methyloxetan-3-yl | Me | 5-Cl-2-thienyl | H |
| 3-1335 | 3-methyloxetan-3-yl | Me | 5-Br-2-thienyl | H |
| 3-1336 | 2-chloroprop-2-en-1-yl | Me | 4-Cl-Ph | H |
| 3-1337 | 2-chloroprop-2-en-1-yl | Me | 4-Br-Ph | H |
| 3-1338 | 2-chloroprop-2-en-1-yl | Me | 5-Cl-pyridin-2-yl | H |
| 3-1339 | 2-chloroprop-2-en-1-yl | Me | 5-Br-pyridin-2-yl | H |
| 3-1340 | 2-chloroprop-2-en-1-yl | Me | 5-Cl-2-thienyl | H |
| 3-1341 | 2-chloroprop-2-en-1-yl | Me | 5-Br-2-thienyl | H |
| 3-1342 | (3E)-pent-3-en-2-yl | Me | 4-Cl-Ph | H |
| 3-1343 | (3E)-pent-3-en-2-yl | Me | 4-Br-Ph | H |
| 3-1344 | (3E)-pent-3-en-2-yl | Me | 5-Cl-pyridin-2-yl | H |
| 3-1345 | (3E)-pent-3-en-2-yl | Me | 5-Br-pyridin-2-yl | H |
| 3-1346 | (3E)-pent-3-en-2-yl | Me | 5-Cl-2-thienyl | H |
| 3-1347 | (3E)-pent-3-en-2-yl | Me | 5-Br-2-thienyl | H |
| 3-1348 | (2,2-dimethylpropanoyloxy)methyl | Me | 4-Cl-Ph | H |
| 3-1349 | (2,2-dimethylpropanoyloxy)methyl | Me | 4-Br-Ph | H |
| 3-1350 | (2,2-dimethylpropanoyloxy)methyl | Me | 5-Cl-pyridin-2-yl | H |
| 3-1351 | (2,2-dimethylpropanoyloxy)methyl | Me | 5-Br-pyridin-2-yl | H |
| 3-1352 | (2,2-dimethylpropanoyloxy)methyl | Me | 5-Cl-2-thienyl | H |
| 3-1353 | (2,2-dimethylpropanoyloxy)methyl | Me | 5-Br-2-thienyl | H |
| 3-1354 | 2-(isopropoxycarbonyloxy)eth-1-yl | Me | 4-Cl-Ph | H |
| 3-1355 | 2-(isopropoxycarbonyloxy)eth-1-yl | Me | 4-Br-Ph | H |
| 3-1356 | 2-(isopropoxycarbonyloxy)eth-1-yl | Me | 5-Cl-pyridin-2-yl | H |
| 3-1357 | 2-(isopropoxycarbonyloxy)eth-1-yl | Me | 5-Br-pyridin-2-yl | H |
| 3-1358 | 2-(isopropoxycarbonyloxy)eth-1-yl | Me | 5-Cl-2-thienyl | H |
| 3-1359 | 2-(isopropoxycarbonyloxy)eth-1-yl | Me | 5-Br-2-thienyl | H |

In addition, NMR data of compounds of the general formula (I) according to the invention were generated. The NMR of the exemplary compounds were in each case recorded as ¹H-NMR spectum at 400 MHz (CDCl₃) (¹H nuclear magnetic resonance data). Characteristic chemical shifts δ (ppm) for some exemplary compounds are listed below:

NMR compound 3-135 (CDCl₃, 400 MHz, δ in ppm):
0.28 (m, 2H); 0.58 (m, 2H); 1.12 (m, 1H); 2.40 (s, 3H); 3.54 (s, 2H); 3.95 (d, 2H); 7.52 (d, 1H); 7.78 (dd, 1H); 8.52 (d, 1H); 8.65 (s, 2H); 9.09 (s, 1H).

NMR compound 3-353 (CDCl₃, 400 MHz, δ in ppm):
2.38 (s, 3H); 3.62 (s, 2H); 4.32 (txd, 2H); 5.95 (txt, 1H); 7.33 (d, 1H); 7.75 (dd, 1H); 8.58 (d, 1H); 8.67 (s, 2H); 9.10 (s, 1H).

NMR compound 3-112 (CDCl₃, 400 MHz, δ in ppm):
2.38 (s, 3H); 2.49 (t, 1H); 3.60 (s, 2H); 4.70 (d, 2H); 7.41 (d, 1H); 7.74 (dd, 1H); 8.54 (d, 1H); 8.65 (s, 2H); 9.08 (s, 1H).

NMR compound 3-25 (CDCl₃, 400 MHz, δ in ppm):
1.26 (t, 3H); 2.38 (s, 3H); 3.52 (s, 2H); 4.16 (q, 2H); 7.49 (d, 1H); 7.77 (dd, 1H); 8.53 (d, 1H); 8.65 (s, 2H); 9.08 (s, 1H).

NMR compound 3-26 (CDCl₃, 400 MHz, δ in ppm):
1.28 (t, 3H); 2.38 (s, 3H); 3.51 (s, 2H); 4.17 (q, 2H); 7.41 (d, 1H); 7.91 (dd, 1H); 8.63 (d, 1H); 8.64 (s, 2H); 9.09 (s, 1H).

NMR compound 3-136 (CDCl₃, 400 MHz, δ in ppm):
0.28 (m, 2H); 0.58 (m, 2H); 1.12 (m, 1H); 2.40 (s, 3H); 3.52 (s, 2H); 3.97 (d, 2H); 7.43 (d, 1H); 7.91 (dd, 1H); 8.63 (d, 1H); 8.65 (s, 2H); 9.08 (s, 1H).

NMR compound 3-176 (CDCl₃, 400 MHz, δ in ppm):
1.82 (s, 3H); 2.38 (s, 3H); 3.59 (s, 2H); 4.22 (s, 2H); 7.48 (d, 1H); 7.90 (dd, 1H); 8.64 (d, 1H); 8.65 (s, 2H); 9.09 (s, 1H).

NMR compound 3-161 (CDCl₃, 400 MHz, δ in ppm):
1.85 (s, 3H); 2.38 (s, 3H); 3.42 (s, 2H); 4.22 (s, 2H); 7.21 (d, 2H); 7.40 (d, 2H); 8.62 (s, 2H); 9.04 (s, 1H).

NMR compound 3-121 (CDCl₃, 400 MHz, δ in ppm):
0.29 (m, 2H); 0.59 (m, 2H); 1.12 (m, 1H); 2.39 (s, 3H); 3.40 (s, 2H); 3.92 (d, 2H); 7.21 (d, 2H); 7.40 (d, 2H); 8.62 (s, 2H); 9.03 (s, 1H).

NMR compound 3-4 (CDCl₃, 400 MHz, δ in ppm):
1.27 (t, 3H); 2.38 (s, 3H); 3.38 (s, 2H); 4.17 (q, 2H); 7.20 (d, 2H); 7.40 (d, 2H); 8.62 (s, 2H); 9.03 (s, 1H).

TABLE 4

Compounds of the formula (Ib'')

| No. | R² | R³ | R⁴ | R⁵ | (R⁶)ₙ |
|---|---|---|---|---|---|
| 4-1 | H | H | Ph | Ph | H |
| 4-2 | H | H | Me | Ph | H |
| 4-3 | H | H | Me | 5-I-2-thienyl | H |
| 4-4 | H | H | Me | 2-furyl | H |
| 4-5 | H | H | Me | Ph | 6-OMe |
| 4-6 | Me | H | Me | Ph | 4-Me |
| 4-7 | H | H | Me | Ph | 6-Cl |
| 4-8 | H | H | Me | Ph | 4-CF₃ |
| 4-9 | H | H | Me | Ph | 6-CF₃ |
| 4-10 | H | H | Me | Ph | 4-Me |
| 4-11 | H | H | Me | Ph | 4,6-Me₂ |
| 4-12 | H | H | Me | Ph | 4,6-Cl₂ |
| 4-13 | H | H | Me | 4-MeO-Ph | 4-Me |
| 4-14 | H | H | Me | 4-MeO-Ph | H |
| 4-15 | Me | H | Me | Ph | H |
| 4-16 | H | H | Me | 4-Me-Ph | 4-Me |
| 4-17 | H | H | Me | 4-Me-Ph | 4-Cl |
| 4-18 | H | H | Me | 4-Me-Ph | H |
| 4-19 | H | H | Me | 3-Cl-Ph | H |
| 4-20 | H | H | Me | 3-CF₃-Ph | H |
| 4-21 | H | H | Me | 3-CF₃-Ph | 4-Me |
| 4-22 | H | H | Me | 3,4-Cl₂-Ph | 4-Me |
| 4-23 | H | H | Me | 3-Cl-Ph | 4-Me |
| 4-24 | H | H | Me | 2-Cl-Ph | 4-Me |
| 4-25 | H | H | Me | 2,4-Cl₂-Ph | 4-Me |
| 4-26 | H | H | Me | 4-CF₃-Ph | 4-Me |
| 4-27 | H | H | Me | 4-Cl-Ph | 4-Me |
| 4-28 | H | H | Me | 4-Cl-Ph | H |
| 4-29 | H | H | Me | 3,4-Cl₂-Ph | H |
| 4-30 | H | H | Me | 4-CF₃-Ph | H |
| 4-31 | H | H | Me | 4-Cl-Ph | 4-Cl |
| 4-32 | H | H | Me | Ph | 4-Cl |
| 4-33 | H | H | Me | 2-Cl-Ph | H |
| 4-34 | H | H | Me | 4-tBu-Ph | 4-Me |
| 4-35 | H | H | Me | 3,5-Me₂-Ph | 4-Me |
| 4-36 | H | H | Me | Ph | 4-OMe |
| 4-37 | H | H | Me | 4-Cl-Ph | 4-OMe |
| 4-38 | H | H | Me | 4-Me-Ph | 4-Me |
| 4-39 | H | H | Me | 4-F-Ph | 4-Cl |
| 4-40 | H | H | Me | 4-F-Ph | 4-Me |
| 4-41 | H | H | Me | 3-Me-Ph | 4-Me |
| 4-42 | H | H | Me | 4-(COOH)-Ph | 4-Me |
| 4-43 | H | H | Me | 3-Br-Ph | 4-Me |
| 4-44 | H | H | Me | 4-Ph-Ph | 4-Me |
| 4-45 | H | H | Me | 4-(COOH)-Ph | H |
| 4-46 | H | H | Me | 3,5-Me₂-Ph | H |
| 4-47 | H | H | Me | Ph | 4-SMe |
| 4-48 | H | H | Me | 4-Cl-Ph | 4-SMe |
| 4-49 | H | H | Me | 3-Cl-4-Me-Ph | H |
| 4-50 | H | H | Me | 3-CF₃-4-Cl-Ph | H |
| 4-51 | H | H | Me | 3-CF₃-4-Cl-Ph | 4-Me |
| 4-52 | H | H | Me | 3-Cl-4-Me-Ph | 4-Me |
| 4-53 | H | H | Me | 2-pyridyl | 4-Cl |
| 4-54 | H | H | Me | 4-Cl-Ph | 4-F |
| 4-55 | H | H | Me | 2-thienyl | 4-Me |
| 4-56 | H | H | Me | 3-Me-2-thienyl | 4-Me |
| 4-57 | H | H | Me | 4-Me-2-thienyl | 4-Me |
| 4-58 | H | H | Me | 5-Cl-2-thienyl | 4-Me |
| 4-59 | H | H | Me | 5-Cl-2-thienyl | 4-Cl |
| 4-60 | H | H | Me | 3-thienyl | 4-Me |
| 4-61 | H | H | Me | 2-thienyl | H |
| 4-62 | H | H | Me | 3-Me-2-thienyl | H |
| 4-63 | H | H | Me | 4-Me-2-thienyl | H |
| 4-64 | H | H | Me | 5-Cl-2-thienyl | H |
| 4-65 | H | H | Me | 5-Me-2-thienyl | H |
| 4-66 | H | H | Me | 6-MeO-pyridin-3-yl | H |
| 4-67 | H | H | Me | 5-Br-2-thienyl | H |
| 4-68 | H | H | Me | 5-Br-2-thienyl | 4-Me |
| 4-69 | H | H | Me | 3-thienyl | H |
| 4-70 | H | H | Me | 4-Cl-Ph | 4-S(O)Me |
| 4-71 | H | H | Me | 4-Br-Ph | 4-Me |
| 4-72 | H | H | Me | 1,3-benzodioxol-5-yl | 4-Me |
| 4-73 | H | H | Me | 4-I-Ph | 4-Me |
| 4-74 | H | H | Me | 3,5-Cl₂-Ph | 4-Me |
| 4-75 | H | H | Me | 4-PhO-Ph | 4-Me |
| 4-76 | H | H | Me | 6-OH-pyridin-3-yl | H |
| 4-77 | H | H | Me | Ph | 4-S(O)Me |
| 4-78 | H | H | H | Ph | H |
| 4-79 | H | H | H | Ph | 4-Me |
| 4-80 | H | H | Et | Ph | H |
| 4-81 | H | H | n-Pr | Ph | H |
| 4-82 | H | H | CH₂Cl | Ph | H |
| 4-83 | H | H | CHCl₂ | Ph | H |
| 4-84 | H | H | CH₂F | Ph | H |
| 4-85 | H | H | CHF₂ | Ph | H |
| 4-86 | H | H | Cl | Ph | H |
| 4-87 | H | H | Et | Ph | 4-Me |
| 4-88 | H | H | n-Pr | Ph | 4-Me |
| 4-89 | H | H | CH₂Cl | Ph | 4-Me |
| 4-90 | H | H | CHCl₂ | Ph | 4-Me |
| 4-91 | H | H | CH₂F | Ph | 4-Me |
| 4-92 | H | H | CHF₂ | Ph | 4-Me |
| 4-93 | H | H | Cl | Ph | 4-Me |
| 4-94 | H | H | Et | 4-Cl-Ph | H |
| 4-95 | H | H | n-Pr | 4-Cl-Ph | H |
| 4-96 | H | H | CH₂Cl | 4-Cl-Ph | H |
| 4-97 | H | H | CHCl₂ | 4-Cl-Ph | H |
| 4-98 | H | H | CH₂F | 4-Cl-Ph | H |
| 4-99 | H | H | CHF₂ | 4-Cl-Ph | H |
| 4-100 | H | H | Cl | 4-Cl-Ph | H |
| 4-101 | H | H | Et | 4-Me-Ph | H |
| 4-102 | H | H | n-Pr | 4-Me-Ph | H |
| 4-103 | H | H | CH₂Cl | 4-Me-Ph | H |
| 4-104 | H | H | CHCl₂ | 4-Me-Ph | H |
| 4-105 | H | H | CH₂F | 4-Me-Ph | H |
| 4-106 | H | H | CHF₂ | 4-Me-Ph | H |
| 4-107 | H | H | Cl | 4-Me-Ph | H |
| 4-108 | H | H | Et | 2-pyridyl | H |
| 4-109 | H | H | n-Pr | 2-pyridyl | H |
| 4-110 | H | H | CH₂Cl | 2-pyridyl | H |
| 4-111 | H | H | CHCl₂ | 2-pyridyl | H |
| 4-112 | H | H | CH₂F | 2-pyridyl | H |
| 4-113 | H | H | CHF₂ | 2-pyridyl | H |
| 4-114 | H | H | Cl | 2-pyridyl | H |
| 4-115 | H | H | Me | 2-pyridyl | H |
| 4-116 | H | H | Me | 5-Cl-pyridin-2-yl | H |
| 4-117 | H | H | Me | 5-Cl-pyridin-2-yl | 4-Cl |
| 4-118 | H | H | Me | 5-Cl-pyridin-2-yl | 4-Me |

TABLE 4-continued

Compounds of the formula (Ib")

| No. | R² | R³ | R⁴ | R⁵ | (R⁶)ₙ |
|---|---|---|---|---|---|
| 4-119 | H | H | Me | 5-Br-pyridin-2-yl | H |
| 4-120 | H | H | Me | 5-Br-pyridin-2-yl | 4-Cl |
| 4-121 | H | H | Me | 5-Br-pyridin-2-yl | 4-Me |
| 4-122 | H | H | Me | 5-F-pyridin-2-yl | H |
| 4-123 | H | H | Me | 5-Me-pyridin-2-yl | H |
| 4-124 | H | H | Me | 5-Me-pyridin-2-yl | 4-Me |
| 4-125 | H | H | Me | 2,4-Cl₂-Ph | H |
| 4-126 | H | H | Me | 4-CH₂COOH-Ph | 4-Me |
| 4-127 | H | H | Me | 3,4-Me₂-Ph | 4-Me |
| 4-128 | H | H | Me | 4-Br-Ph | H |
| 4-129 | H | H | Me | 3,4-Me₂-Ph | H |
| 4-130 | H | H | Me | 3-Me-Ph | H |
| 4-131 | H | H | Me | 4-F-Ph | H |
| 4-132 | H | H | Me | 4-(Me-CO)-Ph | H |
| 4-133 | H | H | Me | 4-tBu-Ph | H |
| 4-134 | H | H | Me | 4-Cl-3-Me-Ph | H |
| 4-135 | H | H | n-Pr | 4-Cl-Ph | 4-Me |
| 4-136 | H | H | Me | 3-pyridyl | H |
| 4-137 | H | H | Me | 4-pyridyl | H |
| 4-138 | H | H | C(O)Me | Ph | H |
| 4-139 | H | H | Me | 6-Me-pyridin-3-yl | H |
| 4-140 | H | H | Me | 4-Cl-Ph | 4-SO₂Me |
| 4-141 | H | H | Me | 3-pyridyl | 4-Me |
| 4-142 | H | H | Me | 2,3-Cl₂-Ph | 4-Me |
| 4-143 | H | H | Me | 2-pyridyl | 4-Me |
| 4-144 | H | H | H | 4-Cl-Ph | 4-Me |
| 4-145 | H | H | Me | 6-Cl-pyridin-3-yl | H |
| 4-146 | H | H | Me | Ph | 4-Me |
| 4-147 | H | H | Me | 4-Me-pyridin-2-yl | H |
| 4-148 | H | H | Me | 4-Me-pyridin-2-yl | 4-Me |
| 4-149 | H | H | Me | 4-Me-pyridin-2-yl | 4-Cl |
| 4-150 | H | H | Me | 4-Me-pyridin-2-yl | 4-F |
| 4-151 | H | H | Me | 4-F-pyridin-2-yl | H |
| 4-152 | H | H | Me | 4-Cl-pyridin-2-yl | H |
| 4-153 | H | H | Me | 4-Br-pyridin-2-yl | H |
| 4-154 | H | H | Me | 4-OMe-pyridin-2-yl | H |
| 4-155 | H | H | Me | 5-CF₃-pyridin-2-yl | H |
| 4-156 | H | H | Me | 6-OMe-pyridin-2-yl | H |
| 4-157 | H | H | cyPr | 4-Cl-Ph | H |
| 4-158 | H | H | CN | 4-Cl-Ph | H |
| 4-159 | H | H | CN | 4-Cl-Ph | 4-Me |
| 4-160 | H | H | CN | 4-Me-Ph | H |
| 4-161 | H | H | CN | 4-Me-Ph | 4-Me |
| 4-162 | H | H | CN | Ph | H |
| 4-163 | H | H | CN | Ph | 4-Me |
| 4-164 | H | H | CN | 2-pyridyl | H |
| 4-165 | H | H | CN | 3-pyridyl | H |
| 4-166 | H | H | CN | 5-Cl-pyridin-2-yl | H |
| 4-167 | H | H | CN | 5-Br-pyridin-2-yl | H |
| 4-168 | H | H | CN | 5-F-pyridin-2-yl | H |
| 4-169 | H | H | CN | 5-Me-pyridin-2-yl | H |
| 4-170 | H | H | CN | 6-Me-pyridin-3-yl | H |
| 4-171 | H | H | CN | 4-Me-pyridin-2-yl | H |
| 4-172 | H | H | CN | 4-F-pyridin-2-yl | H |
| 4-173 | H | H | CN | 4-Cl-pyridin-2-yl | H |
| 4-174 | H | H | CN | 4-Br-pyridin-2-yl | H |
| 4-175 | H | H | CN | 4-OMe-pyridin-2-yl | H |
| 4-176 | H | H | formyl | 4-Cl-Ph | H |
| 4-177 | H | H | formyl | 4-Cl-Ph | 4-Me |
| 4-178 | H | H | formyl | 4-Me-Ph | H |
| 4-179 | H | H | formyl | 4-Me-Ph | 4-Me |
| 4-180 | H | H | formyl | Ph | H |
| 4-181 | H | H | formyl | Ph | 4-Me |
| 4-182 | H | H | formyl | 2-pyridyl | H |
| 4-183 | H | H | formyl | 3-pyridyl | H |
| 4-184 | H | H | formyl | 5-Cl-pyridin-2-yl | H |
| 4-185 | H | H | formyl | 5-Br-pyridin-2-yl | H |
| 4-186 | H | H | formyl | 5-F-pyridin-2-yl | H |
| 4-187 | H | H | formyl | 5-Me-pyridin-2-yl | H |
| 4-188 | H | H | formyl | 6-Me-pyridin-3-yl | H |
| 4-189 | H | H | formyl | 4-Me-pyridin-2-yl | H |
| 4-190 | H | H | formyl | 4-F-pyridin-2-yl | H |
| 4-191 | H | H | formyl | 4-Cl-pyridin-2-yl | H |
| 4-192 | H | H | formyl | 4-Br-pyridin-2-yl | H |
| 4-193 | H | H | formyl | 4-OMe-pyridin-2-yl | H |
| 4-194 | H | H | CH₂OH | 5-Me-pyridin-2-yl | H |
| 4-195 | H | H | CH₂OH | 4-Cl-Ph | H |
| 4-196 | H | H | CH₂OH | 4-Me-pyridin-2-yl | H |
| 4-197 | H | H | CH₂OH | 4-Me-Ph | H |
| 4-198 | H | H | CH₂OH | Ph | H |
| 4-199 | H | H | CH₂OH | 2-pyridyl | H |
| 4-200 | H | H | Me | 2-thiazolyl | H |
| 4-201 | H | H | Me | 2-thiazolyl | 4-Cl |
| 4-202 | H | H | Me | 2-thiazolyl | 4-Me |
| 4-203 | H | H | Me | 4-Me-thiazol-2-yl | H |
| 4-204 | H | H | Me | 4-Me-thiazol-2-yl | 4-Cl |
| 4-205 | H | H | Me | 4-Me-thiazol-2-yl | 4-Me |
| 4-206 | H | H | Me | 5-Me-thiazol-2-yl | H |
| 4-207 | H | H | Me | 5-Br-thiazol-2-yl | H |
| 4-208 | H | H | Me | 5-Br-thiazol-2-yl | 4-Me |
| 4-209 | H | H | Me | 5-Cl-thiazol-2-yl | H |
| 4-210 | H | H | Me | 4,6-Me₂-pyridin-2-yl | H |
| 4-211 | H | H | Me | 4,6-Me₂-pyridin-2-yl | 4-Me |
| 4-212 | H | H | Me | 2-pyridyl | 4-F |
| 4-213 | H | H | Me | 2-pyrazinyl | H |
| 4-214 | H | H | Me | 5-Me-pyrazin-2-yl | H |
| 4-215 | H | H | Me | 2-pyrazinyl | 4-Me |
| 4-216 | H | H | Me | 1,3-benzothiazol-2-yl | H |
| 4-217 | H | H | Me | 1,3-benzothiazol-2-yl | 4-Me |
| 4-218 | H | H | Me | 7-Cl-1,3-benzothiazol-2-yl | H |
| 4-219 | H | H | Me | 1,5-Me₂-pyrazol-3-yl | H |
| 4-220 | H | H | Me | 1,5-Me₂-pyrazol-3-yl | 4-Me |
| 4-221 | H | H | Me | 4,5-Me₂-thiazol-2-yl | H |
| 4-222 | H | H | Me | 4,5-Cl₂-thiazol-2-yl | H |
| 4-223 | H | H | Me | 2-pyrimidinyl | H |
| 4-224 | H | H | Me | 2-pyrimidinyl | 4-Me |
| 4-225 | H | H | Me | 5-F-pyrimidin-2-yl | H |
| 4-226 | H | H | Me | 5-Cl-pyrimidin-2-yl | H |
| 4-227 | H | H | Me | 5-Br-pyrimidin-2-yl | H |
| 4-228 | H | H | Me | 5-Me-pyrimidin-2-yl | H |
| 4-229 | H | H | Me | 5-Me-pyrimidin-2-yl | 4-Me |
| 4-230 | H | H | Me | 4,6-Me₂-pyrimidin-2-yl | H |

TABLE 4-continued

Compounds of the formula (Ib'')

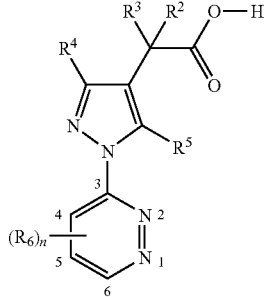

(Ib'')

| No. | R² | R³ | R⁴ | R⁵ | (R⁶)ₙ |
|---|---|---|---|---|---|
| 4-231 | H | H | Me | 4,6-Me₂-pyrimidin-2-yl | 4-Me |
| 4-232 | H | H | Me | 3-pyridazinyl | H |
| 4-233 | H | H | Me | 6-Me-pyridazin-3-yl | H |
| 4-234 | H | H | Me | 1,2,4-triazin-3-yl | H |
| 4-235 | H | H | Me | 6-Me-1,2,4-triazin-3-yl | H |
| 4-236 | H | H | Me | 2-pyridyl | 6-OMe |
| 4-237 | H | H | Me | 2-pyridyl | 6-Cl |
| 4-238 | H | H | Me | 3,5-Cl₂-Ph | H |
| 4-239 | H | H | Me | isoquinolin-3-yl | H |
| 4-240 | H | H | Me | quinolin-2-yl | H |

In addition, NMR data of compounds of the general formula (I) according to the invention were generated. The NMR of the exemplary compounds were in each case recorded as $^1$H-NMR spectum at 400 MHz (CDCl₃) ($^1$H nuclear magnetic resonance data). Characteristic chemical shifts δ (ppm) for some exemplary compounds are listed below:

NMR compound 4-236 (CDCl₃, 400 MHz, δ in ppm):

2.42 (s, 3H); 3.50 (s, 2H); 4.06 (s, 3H); 7.18 (d, 1H); 7.58 (m, 1H); 7.60 (m, 1H); 7.88 (brs, 1H); 8.01 (m, 1H); 8.03 (d, 1H); 8.70 (m, 1H).

NMR compound 4-237 (CDCl₃, 400 MHz, δ in ppm):

2.43 (s, 3H); 3.47 (s, 2H); 7.44 (m, 1H); 7.48 (m, 1H); 7.64 (d, 1H); 7.86 (m, 1H); 8.17 (d, 1H); 8.67 (m, 1H).

TABLE 5

Compounds of the formula (Ib''')

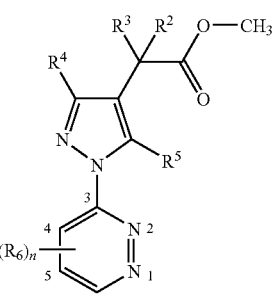

(Ib''')

| No. | R² | R³ | R⁴ | R⁵ | (R⁶)ₙ |
|---|---|---|---|---|---|
| 5-1 | H | H | Ph | Ph | H |
| 5-2 | H | H | Me | Ph | H |

TABLE 5-continued

Compounds of the formula (Ib''')

| No. | R² | R³ | R⁴ | R⁵ | (R⁶)ₙ |
|---|---|---|---|---|---|
| 5-3 | H | H | Me | 5-I-2-thienyl | H |
| 5-4 | H | H | Me | 2-furyl | H |
| 5-5 | H | H | Me | Ph | 6-OMe |
| 5-6 | Me | H | Me | Ph | 4-Me |
| 5-7 | H | H | Me | Ph | 6-Cl |
| 5-8 | H | H | Me | Ph | 4-CF₃ |
| 5-9 | H | H | Me | Ph | 6-CF₃ |
| 5-10 | H | H | Me | Ph | 4-Me |
| 5-11 | H | H | Me | Ph | 4,6-Me₂ |
| 5-12 | H | H | Me | Ph | 4,6-Cl₂ |
| 5-13 | H | H | Me | 4-MeO-Ph | 4-Me |
| 5-14 | H | H | Me | 4-MeO-Ph | H |
| 5-15 | Me | H | Me | Ph | H |
| 5-16 | H | H | Me | 4-Me-Ph | H |
| 5-17 | H | H | Me | 4-Me-Ph | 4-Me |
| 5-18 | H | H | Me | 4-Me-Ph | 4-Cl |
| 5-19 | H | H | Me | 3-Cl-Ph | H |
| 5-20 | H | H | Me | 3-CF₃-Ph | H |
| 5-21 | H | H | Me | 3-CF₃-Ph | 4-Me |
| 5-22 | H | H | Me | 3,4-Cl₂-Ph | 4-Me |
| 5-23 | H | H | Me | 3-Cl-Ph | 4-Me |
| 5-24 | H | H | Me | 2-Cl-Ph | 4-Me |
| 5-25 | H | H | Me | 2,4-Cl₂-Ph | 4-Me |
| 5-26 | H | H | Me | 4-CF₃-Ph | 4-Me |
| 5-27 | H | H | Me | 4-Cl-Ph | 4-Me |
| 5-28 | H | H | Me | 4-Cl-Ph | H |
| 5-29 | H | H | Me | 3,4-Cl₂-Ph | H |
| 5-30 | H | H | Me | 4-CF₃-Ph | H |
| 5-31 | H | H | Me | 4-Cl-Ph | 4-Cl |
| 5-32 | H | H | Me | Ph | 4-Cl |
| 5-33 | H | H | Me | 2-Cl-Ph | H |
| 5-34 | H | H | Me | 4-tBu-Ph | 4-Me |
| 5-35 | H | H | Me | 3,5-Me₂-Ph | 4-Me |
| 5-36 | H | H | Me | Ph | 4-OMe |
| 5-37 | H | H | Me | 4-Cl-Ph | 4-OMe |
| 5-38 | H | H | Me | 4-Me-Ph | 4-Me |
| 5-39 | H | H | Me | 4-F-Ph | 4-Me |
| 5-40 | H | H | Me | 4-F-Ph | 4-Cl |
| 5-41 | H | H | Me | 3-Me-Ph | 4-Me |
| 5-42 | H | H | Me | 4-COOH-Ph | 4-Me |
| 5-43 | H | H | Me | 3-Br-Ph | 4-Me |
| 5-44 | H | H | Me | 4-Ph-Ph | 4-Me |
| 5-45 | H | H | Me | 4-COOH-Ph | H |
| 5-46 | H | H | Me | 3,5-Me₂-Ph | H |
| 5-47 | H | H | Me | Ph | 4-SMe |
| 5-48 | H | H | Me | 4-Cl-Ph | 4-SMe |
| 5-49 | H | H | Me | 3-Cl-4-Me-Ph | H |
| 5-50 | H | H | Me | 3-CF₃-4-Cl-Ph | H |
| 5-51 | H | H | Me | 3-CF₃-4-Cl-Ph | 4-Me |
| 5-52 | H | H | Me | 3-Cl-4-Me-Ph | 4-Me |
| 5-53 | H | H | Me | 2-pyridyl | 4-Cl |
| 5-54 | H | H | Me | 4-Cl-Ph | 4-F |
| 5-55 | H | H | Me | 2-thienyl | 4-Me |
| 5-56 | H | H | Me | 3-Me-2-thienyl | 4-Me |
| 5-57 | H | H | Me | 4-Me-2-thienyl | 4-Me |

TABLE 5-continued

Compounds of the formula (Ib''')

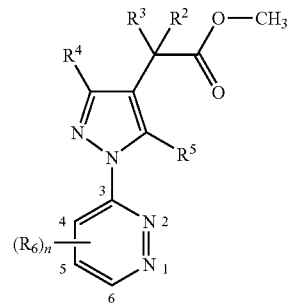

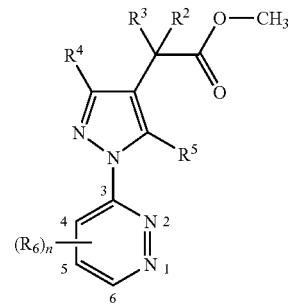

| No. | R² | R³ | R⁴ | R⁵ | (R⁶)ₙ |
|---|---|---|---|---|---|
| 5-58 | H | H | Me | 5-Cl-2-thienyl | 4-Me |
| 5-59 | H | H | Me | 5-Cl-2-thienyl | 4-Cl |
| 5-60 | H | H | Me | 3-thienyl | 4-Me |
| 5-61 | H | H | Me | 2-thienyl | H |
| 5-62 | H | H | Me | 3-Me-2-thienyl | H |
| 5-63 | H | H | Me | 4-Me-2-thienyl | H |
| 5-64 | H | H | Me | 5-Cl-2-thienyl | H |
| 5-65 | H | H | Me | 5-Me-2-thienyl | H |
| 5-66 | H | H | Me | 6-MeO-pyridin-3-yl | H |
| 5-67 | H | H | Me | 5-Br-2-thienyl | H |
| 5-68 | H | H | Me | 5-Br-2-thienyl | 4-Me |
| 5-69 | H | H | Me | 3-thienyl | H |
| 5-70 | H | H | Me | 4-Cl-Ph | 4-S(O)Me |
| 5-71 | H | H | Me | 4-Br-Ph | 4-Me |
| 5-72 | H | H | Me | 1,3-benzodioxol-5-yl | 4-Me |
| 5-73 | H | H | Me | 4-I-Ph | 4-Me |
| 5-74 | H | H | Me | 3,5-Cl₂-Ph | 4-Me |
| 5-75 | H | H | Me | 4-PhO-Ph | 4-Me |
| 5-76 | H | H | Me | 6-OH-pyridin-3-yl | H |
| 5-77 | H | H | Me | Ph | 4-S(O)Me |
| 5-78 | H | H | H | Ph | H |
| 5-79 | H | H | H | Ph | 4-Me |
| 5-80 | H | H | Et | Ph | H |
| 5-81 | H | H | n-Pr | Ph | H |
| 5-82 | H | H | CH₂Cl | Ph | H |
| 5-83 | H | H | CHCl₂ | Ph | H |
| 5-84 | H | H | CH₂F | Ph | H |
| 5-85 | H | H | CHF₂ | Ph | H |
| 5-86 | H | H | Cl | Ph | H |
| 5-87 | H | H | Et | Ph | 4-Me |
| 5-88 | H | H | n-Pr | Ph | 4-Me |
| 5-89 | H | H | CH₂Cl | Ph | 4-Me |
| 5-90 | H | H | CHCl₂ | Ph | 4-Me |
| 5-91 | H | H | CH₂F | Ph | 4-Me |
| 5-92 | H | H | CHF₂ | Ph | 4-Me |
| 5-93 | H | H | Cl | Ph | 4-Me |
| 5-94 | H | H | Et | 4-Cl-Ph | H |
| 5-95 | H | H | n-Pr | 4-Cl-Ph | H |
| 5-96 | H | H | CH₂Cl | 4-Cl-Ph | H |
| 5-97 | H | H | CHCl₂ | 4-Cl-Ph | H |
| 5-98 | H | H | CH₂F | 4-Cl-Ph | H |
| 5-99 | H | H | CHF₂ | 4-Cl-Ph | H |
| 5-100 | H | H | Cl | 4-Cl-Ph | H |
| 5-101 | H | H | Et | 4-Me-Ph | H |
| 5-102 | H | H | n-Pr | 4-Me-Ph | H |
| 5-103 | H | H | CH₂Cl | 4-Me-Ph | H |
| 5-104 | H | H | CHCl₂ | 4-Me-Ph | H |
| 5-105 | H | H | CH₂F | 4-Me-Ph | H |
| 5-106 | H | H | CHF₂ | 4-Me-Ph | H |
| 5-107 | H | H | Cl | 4-Me-Ph | H |
| 5-108 | H | H | Et | 2-pyridyl | H |
| 5-109 | H | H | n-Pr | 2-pyridyl | H |
| 5-110 | H | H | CH₂Cl | 2-pyridyl | H |
| 5-111 | H | H | CHCl₂ | 2-pyridyl | H |
| 5-112 | H | H | CH₂F | 2-pyridyl | H |
| 5-113 | H | H | CHF₂ | 2-pyridyl | H |
| 5-114 | H | H | Cl | 2-pyridyl | H |
| 5-115 | H | H | Me | 2-pyridyl | H |
| 5-116 | H | H | Me | 5-Cl-pyridin-2-yl | H |
| 5-117 | H | H | Me | 5-Cl-pyridin-2-yl | 4-Cl |
| 5-118 | H | H | Me | 5-Cl-pyridin-2-yl | 4-Me |
| 5-119 | H | H | Me | 5-Br-pyridin-2-yl | H |
| 5-120 | H | H | Me | 5-Br-pyridin-2-yl | 4-Cl |
| 5-121 | H | H | Me | 5-Br-pyridin-2-yl | 4-Me |
| 5-122 | H | H | Me | 5-F-pyridin-2-yl | H |
| 5-123 | H | H | Me | 5-Me-pyridin-2-yl | H |
| 5-124 | H | H | Me | 5-Me-pyridin-2-yl | 4-Me |
| 5-125 | H | H | Me | 2,4-Cl₂-Ph | H |
| 5-126 | H | H | Me | 4-(CH₂COOH)-Ph | 4-Me |
| 5-127 | H | H | Me | 3,4-Me₂-Ph | 4-Me |
| 5-128 | H | H | Me | 4-Br-Ph | 4-Me |
| 5-129 | H | H | Me | 3,4-Me₂-Ph | H |
| 5-130 | H | H | Me | 3-Me-Ph | H |
| 5-131 | H | H | Me | 4-F-Ph | H |
| 5-132 | H | H | Me | 4-(Me-CO)-Ph | H |
| 5-133 | H | H | Me | 4-tBu-Ph | H |
| 5-134 | H | H | Me | 4-Cl-3-Me-Ph | H |
| 5-135 | H | H | n-Pr | 4-Cl-Ph | 4-Me |
| 5-136 | H | H | Me | 3-pyridyl | H |
| 5-137 | H | H | Me | 4-pyridyl | H |
| 5-138 | H | H | C(O)OMe | Ph | H |
| 5-139 | H | H | Me | 6-Me-pyridin-3-yl | H |
| 5-140 | H | H | Me | 4-Cl-Ph | 4-SO₂Me |
| 5-141 | H | H | Me | 3-pyridyl | 4-Me |
| 5-142 | H | H | Me | 2,3-Cl₂-Ph | 4-Me |
| 5-143 | H | H | Me | 2-pyridyl | 4-Me |
| 5-144 | H | H | H | 4-Cl-Ph | 4-Me |
| 5-145 | H | H | Me | 6-Cl-pyridin-3-yl | H |
| 5-146 | H | H | Me | Ph | 4-Me |
| 5-147 | H | H | Me | 4-Me-pyridin-2-yl | H |
| 5-148 | H | H | Me | 4-Me-pyridin-2-yl | 4-Me |
| 5-149 | H | H | Me | 4-Me-pyridin-2-yl | 4-Cl |
| 5-150 | H | H | Me | 4-Me-pyridin-2-yl | 4-F |
| 5-151 | H | H | Me | 4-F-pyridin-2-yl | H |
| 5-152 | H | H | Me | 4-Cl-pyridin-2-yl | H |
| 5-153 | H | H | Me | 4-Br-pyridin-2-yl | H |
| 5-154 | H | H | Me | 4-OMe-pyridin-2-yl | H |
| 5-155 | H | H | Me | 5-CF₃-pyridin-2-yl | H |
| 5-156 | H | H | Me | 6-OMe-pyridin-2-yl | H |
| 5-157 | H | H | cyPr | 4-Cl-Ph | H |
| 5-158 | H | H | CN | 4-Cl-Ph | H |
| 5-159 | H | H | CN | 4-Cl-Ph | 4-Me |
| 5-160 | H | H | CN | 4-Me-Ph | H |
| 5-161 | H | H | CN | 4-Me-Ph | 4-Me |
| 5-162 | H | H | CN | Ph | H |
| 5-163 | H | H | CN | Ph | 4-Me |
| 5-164 | H | H | CN | 2-pyridyl | H |
| 5-165 | H | H | CN | 3-pyridyl | H |
| 5-166 | H | H | CN | 5-Cl-pyridin-2-yl | H |
| 5-167 | H | H | CN | 5-Br-pyridin-2-yl | H |

TABLE 5-continued

Compounds of the formula (Ib''')

| No. | R² | R³ | R⁴ | R⁵ | (R⁶)ₙ |
|---|---|---|---|---|---|
| 5-168 | H | H | CN | 5-F-pyridin-2-yl | H |
| 5-169 | H | H | CN | 5-Me-pyridin-2-yl | H |
| 5-170 | H | H | CN | 6-Me-pyridin-3-yl | H |
| 5-171 | H | H | CN | 4-Me-pyridin-2-yl | H |
| 5-172 | H | H | CN | 4-F-pyridin-2-yl | H |
| 5-173 | H | H | CN | 4-Cl-pyridin-2-yl | H |
| 5-174 | H | H | CN | 4-Br-pyridin-2-yl | H |
| 5-175 | H | H | CN | 4-OMe-pyridin-2-yl | H |
| 5-176 | H | H | formyl | 4-Cl-Ph | H |
| 5-177 | H | H | formyl | 4-Cl-Ph | 4-Me |
| 5-178 | H | H | formyl | 4-Me-Ph | H |
| 5-179 | H | H | formyl | 4-Me-Ph | 4-Me |
| 5-180 | H | H | formyl | Ph | H |
| 5-181 | H | H | formyl | Ph | 4-Me |
| 5-182 | H | H | formyl | 2-pyridyl | H |
| 5-183 | H | H | formyl | 3-pyridyl | H |
| 5-184 | H | H | formyl | 5-Cl-pyridin-2-yl | H |
| 5-185 | H | H | formyl | 5-Br-pyridin-2-yl | H |
| 5-186 | H | H | formyl | 5-F-pyridin-2-yl | H |
| 5-187 | H | H | formyl | 5-Me-pyridin-2-yl | H |
| 5-188 | H | H | formyl | 6-Me-pyridin-3-yl | H |
| 5-189 | H | H | formyl | 4-Me-pyridin-2-yl | H |
| 5-190 | H | H | formyl | 4-F-pyridin-2-yl | H |
| 5-191 | H | H | formyl | 4-Cl-pyridin-2-yl | H |
| 5-192 | H | H | formyl | 4-Br-pyridin-2-yl | H |
| 5-193 | H | H | formyl | 4-OMe-pyridin-2-yl | H |
| 5-194 | H | H | CH₂OH | 5-Me-pyridin-2-yl | H |
| 5-195 | H | H | CH₂OH | 4-Cl-Ph | H |
| 5-196 | H | H | CH₂OH | 4-Me-pyridin-2-yl | H |
| 5-197 | H | H | CH₂OH | 4-Me-Ph | H |
| 5-198 | H | H | CH₂OH | Ph | H |
| 5-199 | H | H | CH₂OH | 2-pyridyl | H |
| 5-200 | H | H | Me | 2-thiazolyl | H |
| 5-201 | H | H | Me | 2-thiazolyl | 4-Cl |
| 5-202 | H | H | Me | 2-thiazolyl | 4-Me |
| 5-203 | H | H | Me | 4-Me-thiazol-2-yl | H |
| 5-204 | H | H | Me | 4-Me-thiazol-2-yl | 4-Cl |
| 5-205 | H | H | Me | 4-Me-thiazol-2-yl | 4-Me |
| 5-206 | H | H | Me | 5-Me-thiazol-2-yl | H |
| 5-207 | H | H | Me | 5-Br-thiazol-2-yl | H |
| 5-208 | H | H | Me | 5-Br-thiazol-2-yl | 4-Me |
| 5-209 | H | H | Me | 5-Cl-thiazol-2-yl | H |
| 5-210 | H | H | Me | 4,6-Me₂-pyridin-2-yl | H |
| 5-211 | H | H | Me | 4,6-Me₂-pyridin-2-yl | 4-Me |
| 5-212 | H | H | Me | 2-pyridyl | 4-F |
| 5-213 | H | H | Me | 2-pyrazinyl | H |
| 5-214 | H | H | Me | 5-Me-pyrazin-2-yl | H |
| 5-215 | H | H | Me | 2-pyrazinyl | 4-Me |
| 5-216 | H | H | Me | 1,3-benzothiazol-2-yl | H |
| 5-217 | H | H | Me | 1,3-benzothiazol-2-yl | 4-Me |
| 5-218 | H | H | Me | 7-Cl-1,3-benzothiazol-2-yl | H |
| 5-219 | H | H | Me | 1,5-Me₂-pyrazol-3-yl | H |
| 5-220 | H | H | Me | 1,5-Me₂-pyrazol-3-yl | 4-Me |
| 5-221 | H | H | Me | 4,5-Me₂-thiazol-2-yl | H |
| 5-222 | H | H | Me | 4,5-Cl₂-thiazol-2-yl | H |
| 5-223 | H | H | Me | 2-pyrimidinyl | H |
| 5-224 | H | H | Me | 2-pyrimidinyl | 4-Me |
| 5-225 | H | H | Me | 5-F-pyrimidin-2-yl | H |
| 5-226 | H | H | Me | 5-Cl-pyrimidin-2-yl | H |
| 5-227 | H | H | Me | 5-Br-pyrimidin-2-yl | H |
| 5-228 | H | H | Me | 5-Me-pyrimidin-2-yl | H |
| 5-229 | H | H | Me | 5-Me-pyrimidin-2-yl | 4-Me |
| 5-230 | H | H | Me | 4,6-Me₂-pyrimidin-2-yl | H |
| 5-231 | H | H | Me | 4,6-Me₂-pyrimidin-2-yl | 4-Me |
| 5-232 | H | H | Me | 3-pyridazinyl | H |
| 5-233 | H | H | Me | 6-Me-pyridazin-3-yl | H |
| 5-234 | H | H | Me | 1,2,4-triazin-3-yl | H |
| 5-235 | H | H | Me | 6-Me-1,2,4-triazin-3-yl | H |
| 5-236 | H | H | Me | 4-Cl-Ph | 5-Me-6-Cl |
| 5-237 | H | H | Me | 4-Cl-Ph | 6-Cl |
| 5-238 | H | H | Me | 2-pyridyl | 6-Cl |
| 5-239 | H | H | Me | 3,5-Cl₂-Ph | H |
| 5-240 | H | H | Me | isoquinolin-3-yl | H |
| 5-241 | H | H | Me | quinolin-2-yl | H |

In addition, NMR data of compounds of the general formula (I) according to the invention were generated. The NMR of the exemplary compounds were in each case recorded as $^1$H-NMR spectrum at 400 MHz (CDCl$_3$) ($^1$H nuclear magnetic resonance data). Characteristic chemical shifts δ (ppm) for some exemplary compounds are listed below:

NMR compound 5-236 (CDCl$_3$, 400 MHz, δ in ppm):

2.37 (s, 3H); 2.43 (s, 3H); 3.35 (s, 2H); 3.69 (s, 3H); 7.22 (d, 2H); 7.35 (d, 2H); 7.90 (s, 1H).

NMR compound 5-237 (CDCl$_3$, 400 MHz, δ in ppm):

2.35 (s, 3H); 3.36 (s, 2H); 3.69 (s, 3H); 7.24 (d, 2H); 7.37 (d, 2H); 7.52 (d, 1H); 8.01 (d, 1H).

NMR compound 5-238 (CDCl$_3$, 400 MHz, δ in ppm):

2.37 (s, 3H); 3.49 (s, 2H); 3.68 (s, 3H); 7.30 (m, 1H); 7.54 (m, 1H); 7.56 (d, 1H); 7.80 (m, 1H); 8.05 (d, 1H); 8.55 (m, 1H).

NMR compound 5-2 (CDCl$_3$, 400 MHz, δ in ppm):

2.38 (s, 3H); 3.41 (s, 2H); 3.69 (s, 3H); 7.28 (m, 2H); 7.39 (m, 3H); 7.55 (dd, 1H); 7.88 (dd, 1H); 9.02 (dd, 1H).

NMR compound 5-28 (CDCl$_3$, 400 MHz, δ in ppm):

2.37 (s, 3H); 3.38 (s, 2H); 3.69 (s, 3H); 7.23 (d, 2H); 7.38 (d, 2H); 7.57 (dd, 1H); 7.98 (dd, 1H); 9.01 (dd, 1H).

TABLE 6

Compounds of the formula (Ib'''')

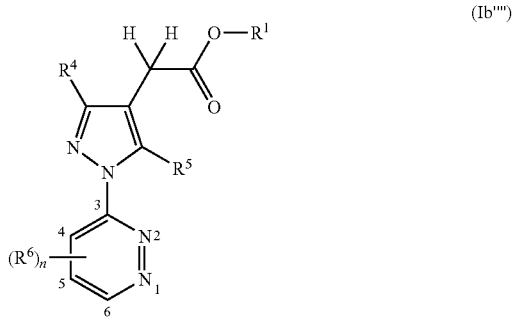

| No. | $R^1$ | $R^4$ | $R^5$ | $(R^6)_n$ |
|---|---|---|---|---|
| 6-1 | Et | Me | Ph | H |
| 6-2 | Et | Me | Ph | 4-Me |
| 6-3 | Et | Me | 3-Cl-Ph | H |
| 6-4 | Et | Me | 4-Cl-Ph | H |
| 6-5 | Et | Me | 4-Cl-Ph | 4-Me |
| 6-6 | Et | Me | 2-thienyl | H |
| 6-7 | Et | Me | 3-thienyl | H |
| 6-8 | Et | Me | 3-Me-2-thienyl | H |
| 6-9 | Et | Me | 4-Me-2-thienyl | H |
| 6-10 | Et | Me | 5-Br-2-thienyl | H |
| 6-11 | Et | Me | 5-Br-2-thienyl | 4-Me |
| 6-12 | Et | Me | 5-Cl-2-thienyl | H |
| 6-13 | Et | Me | 5-Cl-2-thienyl | 4-Me |
| 6-14 | Et | Me | 5-I-2-thienyl | H |
| 6-15 | Et | Me | 5-Me-2-thienyl | H |
| 6-16 | Et | Me | 3-pyridyl | H |
| 6-17 | Et | Me | 6-MeO-pyridin-3-yl | H |
| 6-18 | Et | Me | 6-OH-pyridin-3-yl | H |
| 6-19 | Et | Me | 6-Me-pyridin-3-yl | H |
| 6-20 | Et | Me | 4-Me-Ph | H |
| 6-21 | Et | Me | 4-Me-Ph | 4-Me |
| 6-22 | Et | Me | 4-Br-Ph | H |
| 6-23 | Et | Me | 4-F-Ph | H |
| 6-24 | Et | Me | 4-F-Ph | 4-Me |
| 6-25 | Et | Me | 5-Cl-pyridin-2-yl | H |
| 6-26 | Et | Me | 5-Br-pyridin-2-yl | H |
| 6-27 | Et | Me | 5-F-pyridin-2-yl | H |
| 6-28 | Et | Me | 5-F-pyridin-2-yl | 4-Me |
| 6-29 | Et | Me | 5-Cl-pyridin-2-yl | 4-Me |
| 6-30 | Et | Me | 5-Br-pyridin-2-yl | 4-Me |
| 6-31 | Et | Me | 5-Me-pyridin-2-yl | H |
| 6-32 | Et | Me | 5-Me-pyridin-2-yl | 4-Me |
| 6-33 | Et | Me | 2-pyridyl | 4-Me |
| 6-34 | Et | Me | 2-pyridyl | H |
| 6-35 | Et | Me | 4-pyridyl | H |
| 6-36 | Et | Me | 4-Me-pyridin-2-yl | H |
| 6-37 | Et | Me | 4-Me-pyridin-2-yl | 4-Me |
| 6-38 | Et | Me | 2-thiazolyl | H |
| 6-39 | Et | Me | 4-Me-thiazol-2-yl | H |
| 6-40 | Et | Me | 5-Br-thiazol-2-yl | H |
| 6-41 | Et | Me | 5-Cl-thiazol-2-yl | H |
| 6-42 | Et | Me | 5-Me-thiazol-2-yl | H |
| 6-43 | Et | Me | 4,5-Me$_2$-thiazol-2-yl | H |
| 6-44 | Et | Me | 4,5-Cl$_2$-thiazol-2-yl | H |
| 6-45 | Et | Me | 4,6-Me$_2$-pyridin-2-yl | H |
| 6-46 | Et | Me | 2-pyrazinyl | H |
| 6-47 | Et | Me | 2-pyrimidinyl | H |
| 6-48 | Et | Me | 2-pyrimidinyl | 4-Me |
| 6-49 | Et | Me | 5-Cl-pyrimidin-2-yl | H |
| 6-50 | Et | Me | 5-Br-pyrimidin-2-yl | H |
| 6-51 | Et | Me | 5-Me-pyrimidin-2-yl | H |
| 6-52 | Et | Me | 5-Me-pyrimidin-2-yl | 4-Me |
| 6-53 | Et | Me | 4,6-Me$_2$-pyrimidin-2-yl | H |
| 6-54 | Et | Me | 4,6-Me$_2$-pyrimidin-2-yl | 4-Me |
| 6-55 | Et | Me | 1,3-benzothiazol-2-yl | H |
| 6-56 | Et | Me | 7-Cl-1,3-benzothiazol-2-yl | H |
| 6-57 | Et | Me | 1,5-Me$_2$-pyrazol-3-yl | H |
| 6-58 | Et | Me | 5-Me-pyrazin-2-yl | H |
| 6-59 | Et | Me | 5-F-pyrimidin-2-yl | H |

TABLE 6-continued

Compounds of the formula (Ib'''')

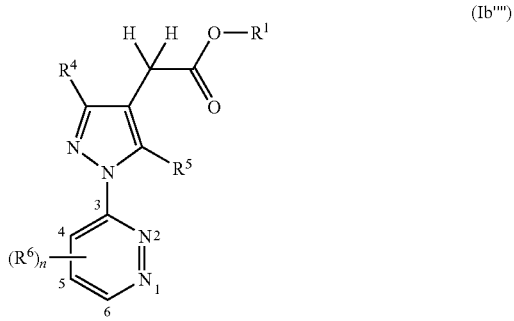

| No. | $R^1$ | $R^4$ | $R^5$ | $(R^6)_n$ |
|---|---|---|---|---|
| 6-60 | Et | Me | 4,6-Me$_2$-pyrimidin-2-yl | H |
| 6-61 | Et | Me | 3-pyridazinyl | H |
| 6-62 | Et | Me | 6-Me-pyridazin-3-yl | H |
| 6-63 | Et | Me | 1,2,4)-triazin-3-yl | H |
| 6-64 | Et | Me | 6-Me-1,2,4-triazin-3-yl | H |
| 6-65 | Pr | Me | Ph | H |
| 6-66 | Pr | Me | 4-Cl-Ph | H |
| 6-67 | Pr | Me | 2-thienyl | H |
| 6-68 | Pr | Me | 3-pyridyl | H |
| 6-69 | Pr | Me | 6-Me-pyridin-3-yl | H |
| 6-70 | Pr | Me | 4-Me-Ph | H |
| 6-71 | Pr | Me | 4-Br-Ph | H |
| 6-72 | Pr | Me | 4-F-Ph | H |
| 6-73 | Pr | Me | 5-Cl-pyridin-2-yl | H |
| 6-74 | Pr | Me | 5-Br-pyridin-2-yl | H |
| 6-75 | Pr | Me | 5-F-pyridin-2-yl | H |
| 6-76 | Pr | Me | 5-Me-pyridin-2-yl | H |
| 6-77 | Pr | Me | 2-pyridyl | H |
| 6-78 | Pr | Me | 4-pyridyl | H |
| 6-79 | i-Pr | Me | Ph | H |
| 6-80 | i-Pr | Me | 4-Cl-Ph | H |
| 6-81 | i-Pr | Me | 2-thienyl | H |
| 6-82 | i-Pr | Me | 3-pyridyl | H |
| 6-83 | i-Pr | Me | 6-Me-pyridin-3-yl | H |
| 6-84 | i-Pr | Me | 4-Me-Ph | H |
| 6-85 | i-Pr | Me | 4-Br-Ph | H |
| 6-86 | i-Pr | Me | 4-F-Ph | H |
| 6-87 | i-Pr | Me | 5-Cl-pyridin-2-yl | H |
| 6-88 | i-Pr | Me | 5-Br-pyridin-2-yl | H |
| 6-89 | i-Pr | Me | 5-F-pyridin-2-yl | H |
| 6-90 | i-Pr | Me | 5-Me-pyridin-2-yl | H |
| 6-91 | i-Pr | Me | 2-pyridyl | H |
| 6-92 | i-Pr | Me | 4-pyridyl | H |
| 6-93 | CH$_2$Ph | Me | Ph | H |
| 6-94 | CH$_2$Ph | Me | 4-Cl-Ph | H |
| 6-95 | CH$_2$Ph | Me | 2-thienyl | H |
| 6-96 | CH$_2$Ph | Me | 2-pyridyl | H |
| 6-97 | prop-2-yn-1-yl | Me | Ph | H |
| 6-98 | prop-2-yn-1-yl | Me | 4-Cl-Ph | H |
| 6-99 | prop-2-yn-1-yl | Me | 2-thienyl | H |
| 6-100 | prop-2-yn-1-yl | Me | 3-thienyl | H |
| 6-101 | prop-2-yn-1-yl | Me | 3-Me-2-thienyl | H |
| 6-102 | prop-2-yn-1-yl | Me | 4-Me-2-thienyl | H |
| 6-103 | prop-2-yn-1-yl | Me | 5-Cl-2-thienyl | H |
| 6-104 | prop-2-yn-1-yl | Me | 5-Me-2-thienyl | H |
| 6-105 | prop-2-yn-1-yl | Me | 3-pyridyl | H |
| 6-106 | prop-2-yn-1-yl | Me | 6-MeO-pyridin-3-yl | H |
| 6-107 | prop-2-yn-1-yl | H | Ph | H |
| 6-108 | prop-2-yn-1-yl | Me | 6-Me-pyridin-3-yl | H |
| 6-109 | prop-2-yn-1-yl | Me | 4-Me-Ph | H |
| 6-110 | prop-2-yn-1-yl | Me | 4-Br-Ph | H |
| 6-111 | prop-2-yn-1-yl | Me | 4-F-Ph | H |
| 6-112 | prop-2-yn-1-yl | Me | 5-Cl-pyridin-2-yl | H |
| 6-113 | prop-2-yn-1-yl | Me | 5-Br-pyridin-2-yl | H |
| 6-114 | prop-2-yn-1-yl | Me | 5-F-pyridin-2-yl | H |
| 6-115 | prop-2-yn-1-yl | Me | 5-Me-pyridin-2-yl | H |
| 6-116 | prop-2-yn-1-yl | Me | 2-pyridyl | H |
| 6-117 | prop-2-yn-1-yl | Me | 4-pyridyl | H |
| 6-118 | prop-2-yn-1-yl | Me | 4-Cl-Ph | 4-Me |

TABLE 6-continued

Compounds of the formula (Ib'''')

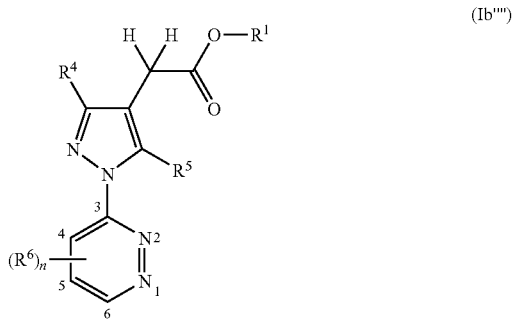

| No. | R¹ | R⁴ | R⁵ | $(R^6)_n$ |
|---|---|---|---|---|
| 6-119 | prop-2-yn-1-yl | Me | Ph | 4-Me |
| 6-120 | cyclopropylmethyl | Me | Ph | H |
| 6-121 | cyclopropylmethyl | Me | 4-Cl-Ph | H |
| 6-122 | cyclopropylmethyl | Me | 2-thienyl | H |
| 6-123 | cyclopropylmethyl | Me | 3-thienyl | H |
| 6-124 | cyclopropylmethyl | Me | 3-Me-2-thienyl | H |
| 6-125 | cyclopropylmethyl | Me | 3-pyridyl | H |
| 6-126 | cyclopropylmethyl | Me | 5-Cl-2-thienyl | H |
| 6-127 | cyclopropylmethyl | Me | 5-Me-2-thienyl | H |
| 6-128 | cyclopropylmethyl | Me | 4-Me-2-thienyl | H |
| 6-129 | cyclopropylmethyl | Me | 6-MeO-pyridin-3-yl | H |
| 6-130 | cyclopropylmethyl | Me | 6-OH-pyridin-3-yl | H |
| 6-131 | cyclopropylmethyl | Me | 6-Me-pyridin-3-yl | H |
| 6-132 | cyclopropylmethyl | Me | 4-Me-Ph | H |
| 6-133 | cyclopropylmethyl | Me | 4-Br-Ph | H |
| 6-134 | cyclopropylmethyl | Me | 4-F-Ph | H |
| 6-135 | cyclopropylmethyl | Me | 5-Cl-pyridin-2-yl | H |
| 6-136 | cyclopropylmethyl | Me | 5-Br-pyridin-2-yl | H |
| 6-137 | cyclopropylmethyl | Me | 5-F-pyridin-2-yl | H |
| 6-138 | cyclopropylmethyl | Me | 5-Me-pyridin-2-yl | H |
| 6-139 | cyclopropylmethyl | Me | 2-pyridyl | H |
| 6-140 | cyclopropylmethyl | Me | 4-pyridyl | H |
| 6-141 | cyclopropylmethyl | Me | 4-Cl-Ph | 4-Me |
| 6-142 | cyclopropylmethyl | Me | Ph | 4-Me |
| 6-143 | cyclopropylmethyl | H | Ph | H |
| 6-144 | 3,3-dichloro-2-fluoroprop-2-en-1-yl | Me | Ph | H |
| 6-145 | 3,3-dichloro-2-fluoroprop-2-en-1-yl | Me | 4-Cl-Ph | H |
| 6-146 | 3,3-dichloro-2-fluoroprop-2-en-1-yl | Me | 2-thienyl | H |
| 6-147 | 3,3-dichloro-2-fluoroprop-2-en-1-yl | Me | 2-pyridyl | H |
| 6-148 | (1-methylcyclopropyl)methyl | Me | Ph | H |
| 6-149 | (1-methylcyclopropyl)methyl | Me | 4-Cl-Ph | H |
| 6-150 | (1-methylcyclopropyl)methyl | Me | 2-thienyl | H |
| 6-151 | (1-methylcyclopropyl)methyl | Me | 2-pyridyl | H |
| 6-152 | 4-chlorobut-2-yn-1-yl | Me | Ph | H |
| 6-153 | 4-chlorobut-2-yn-1-yl | Me | 4-Cl-Ph | H |
| 6-154 | 4-chlorobut-2-yn-1-yl | Me | 2-thienyl | H |
| 6-155 | 4-chlorobut-2-yn-1-yl | Me | 2-pyridyl | H |
| 6-156 | (2,2-dichlorocyclopropyl)methyl | Me | Ph | H |
| 6-157 | (2,2-dichlorocyclopropyl)methyl | Me | 4-Cl-Ph | H |
| 6-158 | (2,2-dichlorocyclopropyl)methyl | Me | 2-thienyl | H |
| 6-159 | (2,2-dichlorocyclopropyl)methyl | Me | 2-pyridyl | H |
| 6-160 | but-2-yn-1-yl | Me | Ph | H |
| 6-161 | but-2-yn-1-yl | Me | 4-Cl-Ph | H |
| 6-162 | but-2-yn-1-yl | Me | 2-thienyl | H |
| 6-163 | but-2-yn-1-yl | Me | 3-thienyl | H |
| 6-164 | but-2-yn-1-yl | Me | 3-Me-2-thienyl | H |
| 6-165 | but-2-yn-1-yl | Me | 4-Me-2-thienyl | H |
| 6-166 | but-2-yn-1-yl | Me | 5-Cl-2-thienyl | H |
| 6-167 | but-2-yn-1-yl | Me | 5-Me-2-thienyl | H |
| 6-168 | but-2-yn-1-yl | Me | 3-pyridyl | H |
| 6-169 | but-2-yn-1-yl | Me | 6-MeO-pyridin-3-yl | H |
| 6-170 | but-2-yn-1-yl | H | Ph | H |
| 6-171 | but-2-yn-1-yl | Me | 6-Me-pyridin-3-yl | H |
| 6-172 | but-2-yn-1-yl | Me | 4-Me-Ph | H |
| 6-173 | but-2-yn-1-yl | Me | 4-Br-Ph | H |
| 6-174 | but-2-yn-1-yl | Me | 4-F-Ph | H |
| 6-175 | but-2-yn-1-yl | Me | 5-Cl-pyridin-2-yl | H |
| 6-176 | but-2-yn-1-yl | Me | 5-Br-pyridin-2-yl | H |
| 6-177 | but-2-yn-1-yl | Me | 5-F-pyridin-2-yl | H |

TABLE 6-continued

Compounds of the formula (Ib'''')

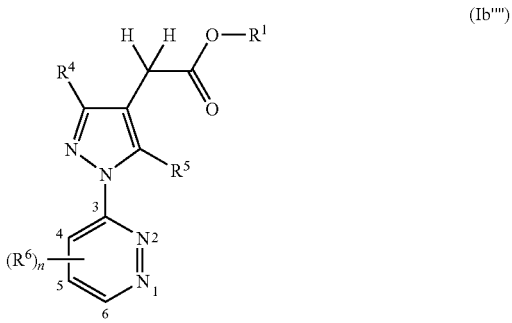

| No. | $R^1$ | $R^4$ | $R^5$ | $(R^6)_n$ |
|---|---|---|---|---|
| 6-178 | but-2-yn-1-yl | Me | 5-Me-pyridin-2-yl | H |
| 6-179 | but-2-yn-1-yl | Me | 2-pyridyl | H |
| 6-180 | but-2-yn-1-yl | Me | 4-pyridyl | H |
| 6-181 | but-2-yn-1-yl | Me | 4-Cl-Ph | 4-Me |
| 6-182 | but-2-yn-1-yl | Me | Ph | 4-Me |
| 6-183 | 1-methylprop-2-yn-1-yl | Me | Ph | H |
| 6-184 | 1-methylprop-2-yn-1-yl | Me | 4-Cl-Ph | H |
| 6-185 | 1-methylprop-2-yn-1-yl | Me | 2-thienyl | H |
| 6-186 | 1-methylprop-2-yn-1-yl | Me | 2-pyridyl | H |
| 6-187 | 1-cyclopropylethyl | Me | Ph | H |
| 6-188 | 1-cyclopropylethyl | Me | 4-Cl-Ph | H |
| 6-189 | 1-cyclopropylethyl | Me | 2-thienyl | H |
| 6-190 | 1-cyclopropylethyl | Me | 2-pyridyl | H |
| 6-191 | allyl | Me | Ph | H |
| 6-192 | allyl | Me | 4-Cl-Ph | H |
| 6-193 | allyl | Me | 2-thienyl | H |
| 6-194 | allyl | Me | 2-pyridyl | H |
| 6-195 | 3-methylbut-2-en-1-yl | Me | Ph | H |
| 6-196 | 3-methylbut-2-en-1-yl | Me | 4-Cl-Ph | H |
| 6-197 | 3-methylbut-2-en-1-yl | Me | 2-thienyl | H |
| 6-198 | 3-methylbut-2-en-1-yl | Me | 2-pyridyl | H |
| 6-199 | 2-methylprop-2-en-1-yl | Me | Ph | H |
| 6-200 | 2-methylprop-2-en-1-yl | Me | 4-Cl-Ph | H |
| 6-201 | 2-methylprop-2-en-1-yl | Me | 2-thienyl | H |
| 6-202 | 2-methylprop-2-en-1-yl | Me | 2-pyridyl | H |
| 6-203 | (2E)-1-methylbut-2-en-1-yl | Me | Ph | H |
| 6-204 | (2E)-1-methylbut-2-en-1-yl | Me | 4-Cl-Ph | H |
| 6-205 | (2E)-1-methylbut-2-en-1-yl | Me | 2-thienyl | H |
| 6-206 | (2E)-1-methylbut-2-en-1-yl | Me | 2-pyridyl | H |
| 6-207 | 3-phenylprop-2-yn-1-yl | Me | Ph | H |
| 6-208 | 3-phenylprop-2-yn-1-yl | Me | 4-Cl-Ph | H |
| 6-209 | 3-phenylprop-2-yn-1-yl | Me | 2-thienyl | H |
| 6-210 | 3-phenylprop-2-yn-1-yl | Me | 2-pyridyl | H |
| 6-211 | cyclobutylmethyl | Me | Ph | H |
| 6-212 | cyclobutylmethyl | Me | 4-Cl-Ph | H |
| 6-213 | cyclobutylmethyl | Me | 2-thienyl | H |
| 6-214 | cyclobutylmethyl | Me | 2-pyridyl | H |
| 6-215 | cyclopentylmethyl | Me | Ph | H |
| 6-216 | cyclopentylmethyl | Me | 4-Cl-Ph | H |
| 6-217 | cyclopentylmethyl | Me | 2-thienyl | H |
| 6-218 | cyclopentylmethyl | Me | 2-pyridyl | H |
| 6-219 | cyclohexylmethyl | Me | Ph | H |
| 6-220 | cyclohexylmethyl | Me | 4-Cl-Ph | H |
| 6-221 | cyclohexylmethyl | Me | 2-thienyl | H |
| 6-222 | cyclohexylmethyl | Me | 2-pyridyl | H |
| 6-223 | but-3-en-1-yl | Me | Ph | H |
| 6-224 | but-3-en-1-yl | Me | 4-Cl-Ph | H |
| 6-225 | but-3-en-1-yl | Me | 2-thienyl | H |
| 6-226 | but-3-en-1-yl | Me | 2-pyridyl | H |
| 6-227 | 2-chloroprop-2-en-1-yl | Me | Ph | H |
| 6-228 | 2-chloroprop-2-en-1-yl | Me | 4-Cl-Ph | H |
| 6-229 | 2-chloroprop-2-en-1-yl | Me | 2-thienyl | H |
| 6-230 | 2-chloroprop-2-en-1-yl | Me | 3-thienyl | H |
| 6-231 | 2-chloroprop-2-en-1-yl | Me | 3-Me-2-thienyl | H |
| 6-232 | 2-chloroprop-2-en-1-yl | Me | 4-Me-2-thienyl | H |
| 6-233 | 2-chloroprop-2-en-1-yl | Me | 5-Cl-2-thienyl | H |
| 6-234 | 2-chloroprop-2-en-1-yl | Me | 5-Me-2-thienyl | H |
| 6-235 | 2-chloroprop-2-en-1-yl | Me | 3-pyridyl | H |
| 6-236 | 2-chloroprop-2-en-1-yl | Me | 6-MeO-pyridin-3-yl | H |

TABLE 6-continued

Compounds of the formula (Ib'''')

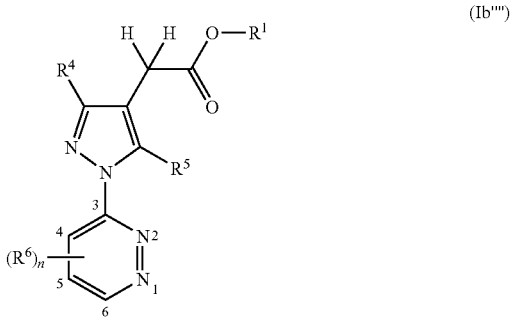

| No. | $R^1$ | $R^4$ | $R^5$ | $(R^6)_n$ |
|---|---|---|---|---|
| 6-237 | 2-chloroprop-2-en-1-yl | Me | 6-OH-pyridin-3-yl | H |
| 6-238 | 2-chloroprop-2-en-1-yl | Me | 6-Me-pyridin-3-yl | H |
| 6-239 | 2-chloroprop-2-en-1-yl | Me | 4-Me-Ph | H |
| 6-240 | 2-chloroprop-2-en-1-yl | Me | 4-Br-Ph | H |
| 6-241 | 2-chloroprop-2-en-1-yl | Me | 4-F-Ph | H |
| 6-242 | 2-chloroprop-2-en-1-yl | Me | 5-Cl-pyridin-2-yl | H |
| 6-243 | 2-chloroprop-2-en-1-yl | Me | 5-Br-pyridin-2-yl | H |
| 6-244 | 2-chloroprop-2-en-1-yl | Me | 5-F-pyridin-2-yl | H |
| 6-245 | 2-chloroprop-2-en-1-yl | Me | 5-Me-pyridin-2-yl | H |
| 6-246 | 2-chloroprop-2-en-1-yl | Me | 2-pyridyl | H |
| 6-247 | 2-chloroprop-2-en-1-yl | Me | 4-pyridyl | H |
| 6-248 | 2-chloroprop-2-en-1-yl | Me | 4-Cl-Ph | 4-Me |
| 6-249 | 2-chloroprop-2-en-1-yl | Me | Ph | 4-Me |
| 6-250 | 2-chloroprop-2-en-1-yl | H | Ph | H |
| 6-251 | 2-methoxyethyl | Me | Ph | H |
| 6-252 | 2-methoxyethyl | Me | 4-Cl-Ph | H |
| 6-253 | 2-methoxyethyl | Me | 2-thienyl | H |
| 6-254 | 2-methoxyethyl | Me | 2-pyridyl | H |
| 6-255 | tetrahydrofuran-2-ylmethyl | Me | Ph | H |
| 6-256 | tetrahydrofuran-2-ylmethyl | Me | 4-Cl-Ph | H |
| 6-257 | tetrahydrofuran-2-ylmethyl | Me | 2-thienyl | H |
| 6-258 | tetrahydrofuran-2-ylmethyl | Me | 2-pyridyl | H |
| 6-259 | 2-(dimethylamino)ethyl | Me | Ph | H |
| 6-260 | 2-(dimethylamino)ethyl | Me | 4-Cl-Ph | H |
| 6-261 | 2-(dimethylamino)ethyl | Me | 2-thienyl | H |
| 6-262 | 2-(dimethylamino)ethyl | Me | 2-pyridyl | H |
| 6-263 | oxetan-3-yl | Me | Ph | H |
| 6-264 | oxetan-3-yl | Me | 4-Cl-Ph | H |
| 6-265 | oxetan-3-yl | Me | 2-thienyl | H |
| 6-266 | oxetan-3-yl | Me | 2-pyridyl | H |
| 6-267 | (3-methyloxetan-3-yl)methyl | Me | Ph | H |
| 6-268 | (3-methyloxetan-3-yl)methyl | Me | 4-Cl-Ph | H |
| 6-269 | (3-methyloxetan-3-yl)methyl | Me | 2-thienyl | H |
| 6-270 | (3-methyloxetan-3-yl)methyl | Me | 2-pyridyl | H |
| 6-271 | 2,2,2-trifluoroethyl | Me | Ph | H |
| 6-272 | 2,2,2-trifluoroethyl | Me | 4-Cl-Ph | H |
| 6-273 | 2,2,2-trifluoroethyl | Me | 2-thienyl | H |
| 6-274 | 2,2,2-trifluoroethyl | Me | 3-pyridyl | H |
| 6-275 | 2,2,2-trifluoroethyl | Me | 6-Me-pyridin-3-yl | H |
| 6-276 | 2,2,2-trifluoroethyl | Me | 4-Me-Ph | H |
| 6-277 | 2,2,2-trifluoroethyl | Me | 4-Br-Ph | H |
| 6-278 | 2,2,2-trifluoroethyl | Me | 4-F-Ph | H |
| 6-279 | 2,2,2-trifluoroethyl | Me | 5-Cl-pyridin-2-yl | H |
| 6-280 | 2,2,2-trifluoroethyl | Me | 5-Br-pyridin-2-yl | H |
| 6-281 | 2,2,2-trifluoroethyl | Me | 5-F-pyridin-2-yl | H |
| 6-282 | 2,2,2-trifluoroethyl | Me | 5-Me-pyridin-2-yl | H |
| 6-283 | 2,2,2-trifluoroethyl | Me | 2-pyridyl | H |
| 6-284 | 2,2,2-trifluoroethyl | Me | 4-pyridyl | H |
| 6-285 | $CH_2$(4-Cl-Ph) | Me | Ph | H |
| 6-286 | $CH_2$(4-Cl-Ph) | Me | 4-Cl-Ph | H |
| 6-287 | $CH_2$(4-Cl-Ph) | Me | 2-thienyl | H |
| 6-288 | $CH_2$(4-Cl-Ph) | Me | 3-pyridyl | H |
| 6-289 | $CH_2$(4-Cl-Ph) | Me | 6-Me-pyridin-3-yl | H |
| 6-290 | $CH_2$(4-Cl-Ph) | Me | 4-Me-Ph | H |
| 6-291 | $CH_2$(4-Cl-Ph) | Me | 4-Br-Ph | H |
| 6-292 | $CH_2$(4-Cl-Ph) | Me | 4-F-Ph | H |
| 6-293 | $CH_2$(4-Cl-Ph) | Me | 5-Cl-pyridin-2-yl | H |
| 6-294 | $CH_2$(4-Cl-Ph) | Me | 5-Br-pyridin-2-yl | H |
| 6-295 | $CH_2$(4-Cl-Ph) | Me | 5-F-pyridin-2-yl | H |

TABLE 6-continued

Compounds of the formula (Ib'''')

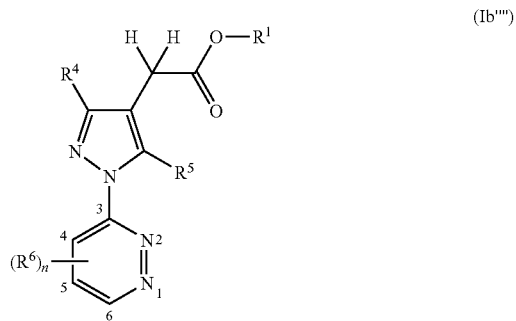

| No. | $R^1$ | $R^4$ | $R^5$ | $(R^6)_n$ |
|---|---|---|---|---|
| 6-296 | CH$_2$(4-Cl-Ph) | Me | 5-Me-pyridin-2-yl | H |
| 6-297 | CH$_2$(4-Cl-Ph) | Me | 2-pyridyl | H |
| 6-298 | CH$_2$(4-Cl-Ph) | Me | 4-pyridyl | H |
| 6-299 | CH$_2$(4-F-Ph) | Me | Ph | H |
| 6-300 | CH$_2$(4-F-Ph) | Me | 4-Cl-Ph | H |
| 6-301 | CH$_2$(4-F-Ph) | Me | 2-thienyl | H |
| 6-302 | CH$_2$(4-F-Ph) | Me | 3-pyridyl | H |
| 6-303 | CH$_2$(4-F-Ph) | Me | 6-Me-pyridin-3-yl | H |
| 6-304 | CH$_2$(4-F-Ph) | Me | 4-Me-Ph | H |
| 6-305 | CH$_2$(4-F-Ph) | Me | 4-Br-Ph | H |
| 6-306 | CH$_2$(4-F-Ph) | Me | 4-F-Ph | H |
| 6-307 | CH$_2$(4-F-Ph) | Me | 5-Cl-pyridin-2-yl | H |
| 6-308 | CH$_2$(4-F-Ph) | Me | 5-Br-pyridin-2-yl | H |
| 6-309 | CH$_2$(4-F-Ph) | Me | 5-F-pyridin-2-yl | H |
| 6-310 | CH$_2$(4-F-Ph) | Me | 5-Me-pyridin-2-yl | H |
| 6-311 | CH$_2$(4-F-Ph) | Me | 2-pyridyl | H |
| 6-312 | CH$_2$(4-F-Ph) | Me | 4-pyridyl | H |
| 6-313 | CH$_2$(4-OMe-Ph) | Me | Ph | H |
| 6-314 | CH$_2$(4-OMe-Ph) | Me | 4-Cl-Ph | H |
| 6-315 | CH$_2$(4-OMe-Ph) | Me | 2-thienyl | H |
| 6-316 | CH$_2$(4-OMe-Ph) | Me | 3-pyridyl | H |
| 6-317 | CH$_2$(4-OMe-Ph) | Me | 6-Me-pyridin-3-yl | H |
| 6-318 | CH$_2$(4-OMe-Ph) | Me | 4-Me-Ph | H |
| 6-319 | CH$_2$(4-OMe-Ph) | Me | 4-Br-Ph | H |
| 6-320 | CH$_2$(4-OMe-Ph) | Me | 4-F-Ph | H |
| 6-321 | CH$_2$(4-OMe-Ph) | Me | 5-Cl-pyridin-2-yl | H |
| 6-322 | CH$_2$(4-OMe-Ph) | Me | 5-Br-pyridin-2-yl | H |
| 6-323 | CH$_2$(4-OMe-Ph) | Me | 5-F-pyridin-2-yl | H |
| 6-324 | CH$_2$(4-OMe-Ph) | Me | 5-Me-pyridin-2-yl | H |
| 6-325 | CH$_2$(4-OMe-Ph) | Me | 2-pyridyl | H |
| 6-326 | CH$_2$(4-OMe-Ph) | Me | 4-pyridyl | H |
| 6-327 | 2,2-difluoroethyl | Me | Ph | H |
| 6-328 | 2,2-difluoroethyl | Me | 4-Cl-Ph | H |
| 6-329 | 2,2-difluoroethyl | Me | 2-thienyl | H |
| 6-330 | 2,2-difluoroethyl | Me | 2-pyridyl | H |
| 6-331 | Ph | Me | Ph | H |
| 6-332 | Ph | Me | 4-Cl-Ph | H |
| 6-333 | Ph | Me | 2-thienyl | H |
| 6-334 | Ph | Me | 2-pyridyl | H |
| 6-335 | 2-fluoroethyl | Me | Ph | H |
| 6-336 | 2-fluoroethyl | Me | 4-Cl-Ph | H |
| 6-337 | 2-fluoroethyl | Me | 2-thienyl | H |
| 6-338 | 2-fluoroethyl | Me | 2-pyridyl | H |
| 6-339 | 2,2,3,3,3-pentafluoropropyl | Me | Ph | H |
| 6-340 | 2,2,3,3,3-pentafluoropropyl | Me | 4-Cl-Ph | H |
| 6-341 | 2,2,3,3,3-pentafluoropropyl | Me | 2-thienyl | H |
| 6-342 | 2,2,3,3,3-pentafluoropropyl | Me | 2-pyridyl | H |
| 6-343 | 1-ethyl-5-methyl-1H-pyrazol-4-methyl | Me | Ph | H |
| 6-344 | 1-ethyl-5-methyl-1H-pyrazol-4-methyl | Me | 4-Cl-Ph | H |
| 6-345 | 1-ethyl-5-methyl-1H-pyrazol-4-methyl | Me | 2-thienyl | H |
| 6-346 | 1-ethyl-5-methyl-1H-pyrazol-4-methyl | Me | 2-pyridyl | H |
| 6-347 | Et | Me | 2-pyridyl | 6-Cl |
| 6-348 | but-3-yn-2-yl | Me | 5-Cl-pyridin-2-yl | H |
| 6-349 | but-3-yn-2-yl | Me | isoquinolin-3-yl | H |
| 6-350 | but-3-yn-2-yl | Me | quinolin-2-yl | H |
| 6-351 | but-3-yn-2-yl | Me | Ph | H |
| 6-352 | but-3-yn-2-yl | Me | 4-Cl-Ph | H |
| 6-353 | but-3-yn-2-yl | Me | 2-thienyl | H |
| 6-354 | but-3-yn-2-yl | Me | 3-pyridyl | H |

TABLE 6-continued

Compounds of the formula (Ib'''')

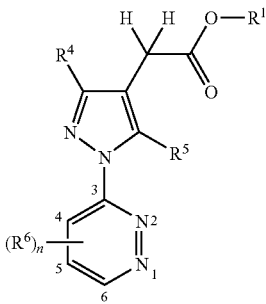

(Ib'''')

| No. | R¹ | R⁴ | R⁵ | $(R^6)_n$ |
|---|---|---|---|---|
| 6-355 | but-3-yn-2-yl | Me | 6-Me-pyridin-3-yl | H |
| 6-356 | but-3-yn-2-yl | Me | 4-Me-Ph | H |
| 6-357 | but-3-yn-2-yl | Me | 4-Br-Ph | H |
| 6-358 | but-3-yn-2-yl | Me | 4-F-Ph | H |
| 6-359 | but-3-yn-2-yl | Me | 5-Br-pyridin-2-yl | H |
| 6-360 | but-3-yn-2-yl | Me | 5-F-pyridin-2-yl | H |
| 6-361 | but-3-yn-2-yl | Me | 5-Me-pyridin-2-yl | H |
| 6-362 | but-3-yn-2-yl | Me | 2-pyridyl | H |
| 6-363 | but-3-yn-2-yl | Me | 4-pyridyl | H |
| 6-364 | Et | Me | isoquinolin-3-yl | H |
| 6-365 | Et | Me | quinolin-2-yl | H |

In addition, NMR data of compounds of the general formula (I) according to the invention were generated. The NMR of the exemplary compounds were in each case recorded as ¹H-NMR spectum at 400 MHz (CDCl₃) (¹H nuclear magnetic resonance data). Characteristic chemical shifts δ (ppm) for some exemplary compounds are listed below:

NMR compound 6-347 (CDCl₃, 400 MHz, δ in ppm):
1.23 (t, 3H); 2.38 (s, 3H); 3.48 (s, 2H); 4.12 (q, 2H); 7.41 (m, 1H); 7.57 (d, 1H); 7.68 (m, 1H); 7.93 (m, 1H); 8.09 (d, 1H); 8.62 (m, 1H).

TABLE 7

Compounds of the formula (Ic'')

(Ic'')

| No. | R² | R³ | R⁴ | R⁵ | $(R^6)_n$ |
|---|---|---|---|---|---|
| 7-1 | H | H | Ph | Ph | H |
| 7-2 | H | H | Me | Ph | H |
| 7-3 | H | H | Me | 5-I-2-thienyl | H |
| 7-4 | H | H | Me | 2-furyl | H |
| 7-5 | Me | H | Me | Ph | 5-Me |
| 7-6 | H | H | Me | Ph | 5-CF₃ |
| 7-7 | H | H | Me | Ph | 5-Me |
| 7-8 | H | H | Me | 4-MeO-Ph | 5-Me |
| 7-9 | H | H | Me | 4-MeO-Ph | H |

TABLE 7-continued

Compounds of the formula (Ic'')

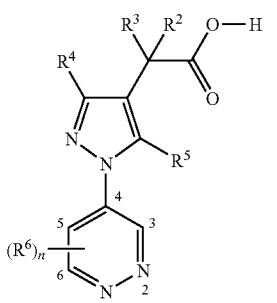

(Ic'')

| No. | R² | R³ | R⁴ | R⁵ | $(R^6)_n$ |
|---|---|---|---|---|---|
| 7-10 | Me | H | Me | Ph | H |
| 7-11 | H | H | Me | 4-Me-Ph | 5-Me |
| 7-12 | H | H | Me | 4-Me-Ph | 5-Cl |
| 7-13 | H | H | Me | 4-Me-Ph | H |
| 7-14 | H | H | Me | 3-Cl-Ph | H |
| 7-15 | H | H | Me | 3-CF₃-Ph | H |
| 7-16 | H | H | Me | 3-CF₃-Ph | 5-Me |
| 7-17 | H | H | Me | 3,4-Cl₂-Ph | 5-Me |
| 7-18 | H | H | Me | 3-Cl-Ph | 5-Me |
| 7-19 | H | H | Me | 2-Cl-Ph | 5-Me |
| 7-20 | H | H | Me | 2,4-Cl₂-Ph | 5-Me |
| 7-21 | H | H | Me | 4-CF₃-Ph | 5-Me |
| 7-22 | H | H | Me | 4-Cl-Ph | 5-Me |
| 7-23 | H | H | Me | 4-Cl-Ph | H |
| 7-24 | H | H | Me | 3,4-Cl₂-Ph | H |
| 7-25 | H | H | Me | 4-CF₃-Ph | H |
| 7-26 | H | H | Me | 4-Cl-Ph | 5-Cl |
| 7-27 | H | H | Me | Ph | 5-Cl |
| 7-28 | H | H | Me | 2-Cl-Ph | H |
| 7-29 | H | H | Me | 4-tBu-Ph | 5-Me |
| 7-30 | H | H | Me | 3,5-Me₂-Ph | 5-Me |
| 7-31 | H | H | Me | Ph | 5-OMe |

TABLE 7-continued

Compounds of the formula (Ic'')

| No. | R² | R³ | R⁴ | R⁵ | (R⁶)ₙ |
|---|---|---|---|---|---|
| 7-32 | H | H | Me | 4-Cl-Ph | 5-OMe |
| 7-33 | H | H | Me | 4-Me-Ph | 5-Me |
| 7-34 | H | H | Me | 4-F-Ph | 5-Cl |
| 7-35 | H | H | Me | 4-F-Ph | 5-Me |
| 7-36 | H | H | Me | 3-Me-Ph | 5-Me |
| 7-37 | H | H | Me | 4-(COOH)-Ph | 5-Me |
| 7-38 | H | H | Me | 3-Br-Ph | 5-Me |
| 7-39 | H | H | Me | 4-Ph-Ph | 5-Me |
| 7-40 | H | H | Me | 4-(COOH)-Ph | H |
| 7-41 | H | H | Me | 3,5-Me₂-Ph | H |
| 7-42 | H | H | Me | Ph | 5-SMe |
| 7-43 | H | H | Me | 4-Cl-Ph | 5-SMe |
| 7-44 | H | H | Me | 3-Cl-4-Me-Ph | H |
| 7-45 | H | H | Me | 3-CF₃-4-Cl-Ph | H |
| 7-46 | H | H | Me | 3-CF₃-4-Cl-Ph | 5-Me |
| 7-47 | H | H | Me | 3-Cl-4-Me-Ph | 5-Me |
| 7-48 | H | H | Me | 2-pyridyl | 5-Cl |
| 7-49 | H | H | Me | 4-Cl-Ph | 5-F |
| 7-50 | H | H | Me | 2-thienyl | 5-Me |
| 7-51 | H | H | Me | 3-Me-2-thienyl | 5-Me |
| 7-52 | H | H | Me | 4-Me-2-thienyl | 5-Me |
| 7-53 | H | H | Me | 5-Cl-2-thienyl | 5-Me |
| 7-54 | H | H | Me | 5-Cl-2-thienyl | 5-Cl |
| 7-55 | H | H | Me | 3-thienyl | 5-Me |
| 7-56 | H | H | Me | 2-thienyl | H |
| 7-57 | H | H | Me | 3-Me-2-thienyl | H |
| 7-58 | H | H | Me | 4-Me-2-thienyl | H |
| 7-59 | H | H | Me | 5-Cl-2-thienyl | H |
| 7-60 | H | H | Me | 5-Me-2-thienyl | H |
| 7-61 | H | H | Me | 6-MeO-pyridin-3-yl | H |
| 7-62 | H | H | Me | 5-Br-2-thienyl | H |
| 7-63 | H | H | Me | 5-Br-2-thienyl | 5-Me |
| 7-64 | H | H | Me | 3-thienyl | H |
| 7-65 | H | H | Me | 4-Cl-Ph | 5-S(O)Me |
| 7-66 | H | H | Me | 4-Br-Ph | 5-Me |
| 7-67 | H | H | Me | 1,3-benzodioxol-5-yl | 5-Me |
| 7-68 | H | H | Me | 4-I-Ph | 5-Me |
| 7-69 | H | H | Me | 3,5-Cl₂-Ph | 5-Me |
| 7-70 | H | H | Me | 4-PhO-Ph | 5-Me |
| 7-71 | H | H | Me | 6-OH-pyridin-3-yl | H |
| 7-72 | H | H | Me | Ph | 5-S(O)Me |
| 7-73 | H | H | H | Ph | H |
| 7-74 | H | H | H | Ph | 5-Me |
| 7-75 | H | H | Et | Ph | H |
| 7-76 | H | H | n-Pr | Ph | H |
| 7-77 | H | H | CH₂Cl | Ph | H |
| 7-78 | H | H | CHCl₂ | Ph | H |
| 7-79 | H | H | CH₂F | Ph | H |
| 7-80 | H | H | CHF₂ | Ph | H |
| 7-81 | H | H | Cl | Ph | H |
| 7-82 | H | H | Et | Ph | 5-Me |
| 7-83 | H | H | n-Pr | Ph | 5-Me |
| 7-84 | H | H | CH₂Cl | Ph | 5-Me |
| 7-85 | H | H | CHCl₂ | Ph | 5-Me |
| 7-86 | H | H | CH₂F | Ph | 5-Me |
| 7-87 | H | H | CHF₂ | Ph | 5-Me |
| 7-88 | H | H | Cl | Ph | 5-Me |
| 7-89 | H | H | Et | 4-Cl-Ph | H |
| 7-90 | H | H | n-Pr | 4-Cl-Ph | H |
| 7-91 | H | H | CH₂Cl | 4-Cl-Ph | H |
| 7-92 | H | H | CHCl₂ | 4-Cl-Ph | H |
| 7-93 | H | H | CH₂F | 4-Cl-Ph | H |
| 7-94 | H | H | CHF₂ | 4-Cl-Ph | H |
| 7-95 | H | H | Cl | 4-Cl-Ph | H |
| 7-96 | H | H | Et | 4-Me-Ph | H |
| 7-97 | H | H | n-Pr | 4-Me-Ph | H |
| 7-98 | H | H | CH₂Cl | 4-Me-Ph | H |
| 7-99 | H | H | CHCl₂ | 4-Me-Ph | H |
| 7-100 | H | H | CH₂F | 4-Me-Ph | H |
| 7-101 | H | H | CHF₂ | 4-Me-Ph | H |
| 7-102 | H | H | Cl | 4-Me-Ph | H |
| 7-103 | H | H | Et | 2-pyridyl | H |
| 7-104 | H | H | n-Pr | 2-pyridyl | H |
| 7-105 | H | H | CH₂Cl | 2-pyridyl | H |
| 7-106 | H | H | CHCl₂ | 2-pyridyl | H |
| 7-107 | H | H | CH₂F | 2-pyridyl | H |
| 7-108 | H | H | CHF₂ | 2-pyridyl | H |
| 7-109 | H | H | Cl | 2-pyridyl | H |
| 7-110 | H | H | Me | 2-pyridyl | H |
| 7-111 | H | H | Me | 5-Cl-pyridin-2-yl | H |
| 7-112 | H | H | Me | 5-Cl-pyridin-2-yl | 5-Cl |
| 7-113 | H | H | Me | 5-Cl-pyridin-2-yl | 5-Me |
| 7-114 | H | H | Me | 5-Br-pyridin-2-yl | H |
| 7-115 | H | H | Me | 5-Br-pyridin-2-yl | 5-Cl |
| 7-116 | H | H | Me | 5-Br-pyridin-2-yl | 5-Me |
| 7-117 | H | H | Me | 5-F-pyridin-2-yl | H |
| 7-118 | H | H | Me | 5-Me-pyridin-2-yl | H |
| 7-119 | H | H | Me | 5-Me-pyridin-2-yl | 5-Me |
| 7-120 | H | H | Me | 2,4-Cl₂-Ph | H |
| 7-121 | H | H | Me | 4-CH₂COOH-Ph | 5-Me |
| 7-122 | H | H | Me | 3,4-Me₂-Ph | 5-Me |
| 7-123 | H | H | Me | 4-Br-Ph | H |
| 7-124 | H | H | Me | 3,4-Me₂-Ph | H |
| 7-125 | H | H | Me | 3-Me-Ph | H |
| 7-126 | H | H | Me | 4-F-Ph | H |
| 7-127 | H | H | Me | 4-(Me-CO)-Ph | H |
| 7-128 | H | H | Me | 4-tBu-Ph | H |
| 7-129 | H | H | Me | 4-Cl-3-Me-Ph | H |
| 7-130 | H | H | n-Pr | 4-Cl-Ph | 5-Me |
| 7-131 | H | H | Me | 3-pyridyl | H |
| 7-132 | H | H | Me | 4-pyridyl | H |
| 7-133 | H | H | C(O)OMe | Ph | H |
| 7-134 | H | H | Me | 6-Me-pyridin-3-yl | H |
| 7-135 | H | H | Me | 4-Cl-Ph | 5-SO₂Me |
| 7-136 | H | H | Me | 3-pyridyl | 5-Me |
| 7-137 | H | H | Me | 2,3-Cl₂-Ph | 5-Me |
| 7-138 | H | H | Me | 2-pyridyl | 5-Me |
| 7-139 | H | H | H | 4-Cl-Ph | 5-Me |
| 7-140 | H | H | Me | 6-Cl-pyridin-3-yl | H |
| 7-141 | H | H | Me | Ph | 5-Me |
| 7-142 | H | H | Me | 4-Me-pyridin-2-yl | H |
| 7-143 | H | H | Me | 4-Me-pyridin-2-yl | 5-Me |
| 7-144 | H | H | Me | 4-Me-pyridin-2-yl | 5-Cl |
| 7-145 | H | H | Me | 4-Me-pyridin-2-yl | 5-F |
| 7-146 | H | H | Me | 4-F-pyridin-2-yl | H |
| 7-147 | H | H | Me | 4-Cl-pyridin-2-yl | H |
| 7-148 | H | H | Me | 4-Br-pyridin-2-yl | H |
| 7-149 | H | H | Me | 4-OMe-pyridin-2-yl | H |

TABLE 7-continued

Compounds of the formula (Ic'')

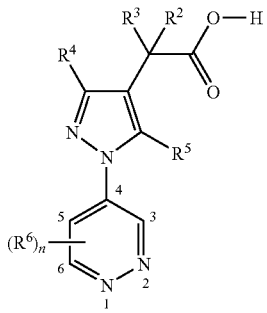

(Ic'')

| No. | R² | R³ | R⁴ | R⁵ | (R⁶)ₙ |
|---|---|---|---|---|---|
| 7-150 | H | H | Me | 5-CF₃-pyridin-2-yl | H |
| 7-151 | H | H | Me | 6-OMe-pyridin-2-yl | H |
| 7-152 | H | H | cyPr | 4-Cl-Ph | H |
| 7-153 | H | H | CN | 4-Cl-Ph | H |
| 7-154 | H | H | CN | 4-Cl-Ph | 5-Me |
| 7-155 | H | H | CN | 4-Me-Ph | H |
| 7-156 | H | H | CN | 4-Me-Ph | 5-Me |
| 7-157 | H | H | CN | Ph | H |
| 7-158 | H | H | CN | Ph | 5-Me |
| 7-159 | H | H | CN | 2-pyridyl | H |
| 7-160 | H | H | CN | 3-pyridyl | H |
| 7-161 | H | H | CN | 5-Cl-pyridin-2-yl | H |
| 7-162 | H | H | CN | 5-Br-pyridin-2-yl | H |
| 7-163 | H | H | CN | 5-F-pyridin-2-yl | H |
| 7-164 | H | H | CN | 5-Me-pyridin-2-yl | H |
| 7-165 | H | H | CN | 6-Me-pyridin-3-yl | H |
| 7-166 | H | H | CN | 4-Me-pyridin-2-yl | H |
| 7-167 | H | H | CN | 4-F-pyridin-2-yl | H |
| 7-168 | H | H | CN | 4-Cl-pyridin-2-yl | H |
| 7-169 | H | H | CN | 4-Br-pyridin-2-yl | H |
| 7-170 | H | H | CN | 4-OMe-pyridin-2-yl | H |
| 7-171 | H | H | formyl | 4-Cl-Ph | H |
| 7-172 | H | H | formyl | 4-Cl-Ph | 5-Me |
| 7-173 | H | H | formyl | 4-Me-Ph | H |
| 7-174 | H | H | formyl | 4-Me-Ph | 5-Me |
| 7-175 | H | H | formyl | Ph | H |
| 7-176 | H | H | formyl | Ph | 5-Me |
| 7-177 | H | H | formyl | 2-pyridyl | H |
| 7-178 | H | H | formyl | 3-pyridyl | H |
| 7-179 | H | H | formyl | 5-Cl-pyridin-2-yl | H |
| 7-180 | H | H | formyl | 5-Br-pyridin-2-yl | H |
| 7-181 | H | H | formyl | 5-F-pyridin-2-yl | H |
| 7-182 | H | H | formyl | 5-Me-pyridin-2-yl | H |
| 7-183 | H | H | formyl | 6-Me-pyridin-3-yl | H |
| 7-184 | H | H | formyl | 4-Me-pyridin-2-yl | H |
| 7-185 | H | H | formyl | 4-F-pyridin-2-yl | H |
| 7-186 | H | H | formyl | 4-Cl-pyridin-2-yl | H |
| 7-187 | H | H | formyl | 4-Br-pyridin-2-yl | H |
| 7-188 | H | H | formyl | 4-OMe-pyridin-2-yl | H |
| 7-189 | H | H | CH₂OH | 5-Me-pyridin-2-yl | H |
| 7-190 | H | H | CH₂OH | 4-Cl-Ph | H |
| 7-191 | H | H | CH₂OH | 4-Me-pyridin-2-yl | H |
| 7-192 | H | H | CH₂OH | 4-Me-Ph | H |
| 7-193 | H | H | CH₂OH | Ph | H |
| 7-194 | H | H | CH₂OH | 2-pyridyl | H |
| 7-195 | H | H | Me | 2-thiazolyl | H |
| 7-196 | H | H | Me | 2-thiazolyl | 5-Cl |
| 7-197 | H | H | Me | 2-thiazolyl | 5-Me |
| 7-198 | H | H | Me | 4-Me-thiazol-2-yl | H |
| 7-199 | H | H | Me | 4-Me-thiazol-2-yl | 5-Cl |
| 7-200 | H | H | Me | 4-Me-thiazol-2-yl | 5-Me |
| 7-201 | H | H | Me | 5-Me-thiazol-2-yl | H |
| 7-202 | H | H | Me | 5-Br-thiazol-2-yl | H |
| 7-203 | H | H | Me | 5-Br-thiazol-2-yl | 5-Me |
| 7-204 | H | H | Me | 5-Cl-thiazol-2-yl | H |
| 7-205 | H | H | Me | 4,6-Me₂-pyridin-2-yl | H |
| 7-206 | H | H | Me | 4,6-Me₂-pyridin-2-yl | 5-Me |
| 7-207 | H | H | Me | 2-pyridyl | 5-F |
| 7-208 | H | H | Me | 2-pyrazinyl | H |

TABLE 7-continued

Compounds of the formula (Ic'')

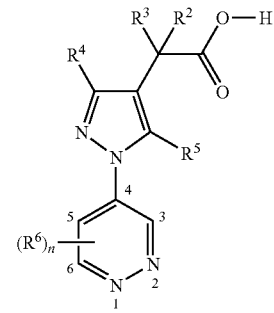

(Ic'')

| No. | R² | R³ | R⁴ | R⁵ | (R⁶)ₙ |
|---|---|---|---|---|---|
| 7-209 | H | H | Me | 5-Me-pyrazin-2-yl | H |
| 7-210 | H | H | Me | 2-pyrazinyl | 5-Me |
| 7-211 | H | H | Me | 1,3-benzothiazol-2-yl | H |
| 7-212 | H | H | Me | 1,3-benzothiazol-2-yl | 5-Me |
| 7-213 | H | H | Me | 7-Cl-1,3-benzothiazol-2-yl | H |
| 7-214 | H | H | Me | 1,5-Me₂-pyrazol-3-yl | H |
| 7-215 | H | H | Me | 1,5-Me₂-pyrazol-3-yl | 5-Me |
| 7-216 | H | H | Me | 4,5-Me₂-thiazol-2-yl | H |
| 7-217 | H | H | Me | 4,5-Cl₂-thiazol-2-yl | H |
| 7-218 | H | H | Me | 2-pyrimidinyl | H |
| 7-219 | H | H | Me | 2-pyrimidinyl | 5-Me |
| 7-220 | H | H | Me | 5-F-pyrimidin-2-yl | H |
| 7-221 | H | H | Me | 5-Cl-pyrimidin-2-yl | H |
| 7-222 | H | H | Me | 5-Br-pyrimidin-2-yl | H |
| 7-223 | H | H | Me | 5-Me-pyrimidin-2-yl | H |
| 7-224 | H | H | Me | 5-Me-pyrimidin-2-yl | 5-Me |
| 7-225 | H | H | Me | 4,6-Me₂-pyrimidin-2-yl | H |
| 7-226 | H | H | Me | 4,6-Me₂-pyrimidin-2-yl | 5-Me |
| 7-227 | H | H | Me | 3-pyridazinyl | H |
| 7-228 | H | H | Me | 6-Me-pyridazin-3-yl | H |
| 7-229 | H | H | Me | 1,2,4-triazin-3-yl | H |
| 7-230 | H | H | Me | 6-Me-1,2,4-triazin-3-yl | H |
| 7-231 | H | H | Me | 3,5-Cl₂-Ph | H |
| 7-232 | H | H | Me | isoquinolin-3-yl | H |
| 7-233 | H | H | Me | quinolin-2-yl | H |

TABLE 8

Compounds of the formula (Ic''')

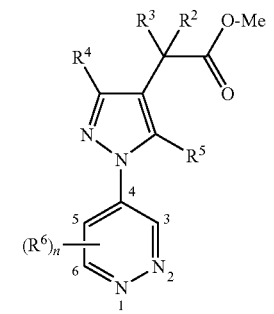

(Ic''')

| No. | R² | R³ | R⁴ | R⁵ | (R⁶)ₙ |
|---|---|---|---|---|---|
| 8-1 | H | H | Ph | Ph | H |
| 8-2 | H | H | Me | Ph | H |
| 8-3 | H | H | Me | 5-I-2-thienyl | H |
| 8-4 | H | H | Me | 2-furyl | H |
| 8-5 | Me | H | Me | Ph | 5-Me |
| 8-6 | H | H | Me | Ph | 5-CF₃ |
| 8-7 | H | H | Me | Ph | 5-Me |
| 8-8 | H | H | Me | 4-MeO-Ph | 5-Me |

TABLE 8-continued

Compounds of the formula (Ic''')

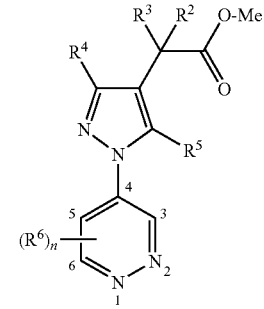

| No. | R² | R³ | R⁴ | R⁵ | (R⁶)ₙ |
|---|---|---|---|---|---|
| 8-9 | H | H | Me | 4-MeO-Ph | H |
| 8-10 | Me | H | Me | Ph | H |
| 8-11 | H | H | Me | 4-Me-Ph | H |
| 8-12 | H | H | Me | 4-Me-Ph | 5-Me |
| 8-13 | H | H | Me | 4-Me-Ph | 5-Cl |
| 8-14 | H | H | Me | 3-Cl-Ph | H |
| 8-15 | H | H | Me | 3-CF₃-Ph | H |
| 8-16 | H | H | Me | 3-CF₃-Ph | 5-Me |
| 8-17 | H | H | Me | 3,4-Cl₂-Ph | 5-Me |
| 8-18 | H | H | Me | 3-Cl-Ph | 5-Me |
| 8-19 | H | H | Me | 2-Cl-Ph | 5-Me |
| 8-20 | H | H | Me | 2,4-Cl₂-Ph | 5-Me |
| 8-21 | H | H | Me | 4-CF₃-Ph | 5-Me |
| 8-22 | H | H | Me | 4-Cl-Ph | 5-Me |
| 8-23 | H | H | Me | 4-Cl-Ph | H |
| 8-24 | H | H | Me | 3,4-Cl₂-Ph | H |
| 8-25 | H | H | Me | 4-CF₃-Ph | H |
| 8-26 | H | H | Me | 4-Cl-Ph | 5-Cl |
| 8-27 | H | H | Me | Ph | 5-Cl |
| 8-28 | H | H | Me | 2-Cl-Ph | H |
| 8-29 | H | H | Me | 4-tBu-Ph | 5-Me |
| 8-30 | H | H | Me | 3,5-Me₂-Ph | 5-Me |
| 8-31 | H | H | Me | Ph | 5-OMe |
| 8-32 | H | H | Me | 4-Cl-Ph | 5-OMe |
| 8-33 | H | H | Me | 4-Me-Ph | 5-Me |
| 8-34 | H | H | Me | 4-F-Ph | 5-Me |
| 8-35 | H | H | Me | 4-F-Ph | 5-Cl |
| 8-36 | H | H | Me | 3-Me-Ph | 5-Me |
| 8-37 | H | H | Me | 4-COOH-Ph | 5-Me |
| 8-38 | H | H | Me | 3-Br-Ph | 5-Me |
| 8-39 | H | H | Me | 4-Ph-Ph | 5-Me |
| 8-40 | H | H | Me | 4-COOH-Ph | H |
| 8-41 | H | H | Me | 3,5-Me₂-Ph | H |
| 8-42 | H | H | Me | Ph | 5-SMe |
| 8-43 | H | H | Me | 4-Cl-Ph | 5-SMe |
| 8-44 | H | H | Me | 3-Cl-4-Me-Ph | H |
| 8-45 | H | H | Me | 3-CF₃-4-Cl-Ph | H |
| 8-46 | H | H | Me | 3-CF₃-4-Cl-Ph | 5-Me |
| 8-47 | H | H | Me | 3-Cl-4-Me-Ph | 5-Me |
| 8-48 | H | H | Me | 2-pyridyl | 5-Cl |
| 8-49 | H | H | Me | 4-Cl-Ph | 5-F |
| 8-50 | H | H | Me | 2-thienyl | 5-Me |
| 8-51 | H | H | Me | 3-Me-2-thienyl | 5-Me |
| 8-52 | H | H | Me | 4-Me-2-thienyl | 5-Me |
| 8-53 | H | H | Me | 5-Cl-2-thienyl | 5-Me |
| 8-54 | H | H | Me | 5-Cl-2-thienyl | 5-Cl |
| 8-55 | H | H | Me | 3-thienyl | 5-Me |
| 8-56 | H | H | Me | 2-thienyl | H |
| 8-57 | H | H | Me | 3-Me-2-thienyl | H |
| 8-58 | H | H | Me | 4-Me-2-thienyl | H |
| 8-59 | H | H | Me | 5-Cl-2-thienyl | H |
| 8-60 | H | H | Me | 5-Me-2-thienyl | H |
| 8-61 | H | H | Me | 6-MeO-pyridin-3-yl | H |
| 8-62 | H | H | Me | 5-Br-2-thienyl | H |
| 8-63 | H | H | Me | 5-Br-2-thienyl | 5-Me |
| 8-64 | H | H | Me | 3-thienyl | H |
| 8-65 | H | H | Me | 4-Cl-Ph | 5-S(O)Me |
| 8-66 | H | H | Me | 4-Br-Ph | 5-Me |
| 8-67 | H | H | Me | 1,3-benzodioxol-5-yl | 5-Me |
| 8-68 | H | H | Me | 4-I-Ph | 5-Me |
| 8-69 | H | H | Me | 3,5-Cl₂-Ph | 5-Me |
| 8-70 | H | H | Me | 4-PhO-Ph | 5-Me |
| 8-71 | H | H | Me | 6-OH-pyridin-3-yl | H |
| 8-72 | H | H | Me | Ph | 5-S(O)Me |
| 8-73 | H | H | H | Ph | H |
| 8-74 | H | H | H | Ph | 5-Me |
| 8-75 | H | H | Et | Ph | H |
| 8-76 | H | H | n-Pr | Ph | H |
| 8-77 | H | H | CH₂Cl | Ph | H |
| 8-78 | H | H | CHCl₂ | Ph | H |
| 8-79 | H | H | CH₂F | Ph | H |
| 8-80 | H | H | CHF₂ | Ph | H |
| 8-81 | H | H | Cl | Ph | H |
| 8-82 | H | H | Et | Ph | 5-Me |
| 8-83 | H | H | n-Pr | Ph | 5-Me |
| 8-84 | H | H | CH₂Cl | Ph | 5-Me |
| 8-85 | H | H | CHCl₂ | Ph | 5-Me |
| 8-86 | H | H | CH₂F | Ph | 5-Me |
| 8-87 | H | H | CHF₂ | Ph | 5-Me |
| 8-88 | H | H | Cl | Ph | 5-Me |
| 8-89 | H | H | Et | 4-Cl-Ph | H |
| 8-90 | H | H | n-Pr | 4-Cl-Ph | H |
| 8-91 | H | H | CH₂Cl | 4-Cl-Ph | H |
| 8-92 | H | H | CHCl₂ | 4-Cl-Ph | H |
| 8-93 | H | H | CH₂F | 4-Cl-Ph | H |
| 8-94 | H | H | CHF₂ | 4-Cl-Ph | H |
| 8-95 | H | H | Cl | 4-Cl-Ph | H |
| 8-96 | H | H | Et | 4-Me-Ph | H |
| 8-97 | H | H | n-Pr | 4-Me-Ph | H |
| 8-98 | H | H | CH₂Cl | 4-Me-Ph | H |
| 8-99 | H | H | CHCl₂ | 4-Me-Ph | H |
| 8-100 | H | H | CH₂F | 4-Me-Ph | H |
| 8-101 | H | H | CHF₂ | 4-Me-Ph | H |
| 8-102 | H | H | Cl | 4-Me-Ph | H |
| 8-103 | H | H | Et | 2-pyridyl | H |
| 8-104 | H | H | n-Pr | 2-pyridyl | H |
| 8-105 | H | H | CH₂Cl | 2-pyridyl | H |
| 8-106 | H | H | CHCl₂ | 2-pyridyl | H |
| 8-107 | H | H | CH₂F | 2-pyridyl | H |
| 8-108 | H | H | CHF₂ | 2-pyridyl | H |
| 8-109 | H | H | Cl | 2-pyridyl | H |
| 8-110 | H | H | Me | 2-pyridyl | H |
| 8-111 | H | H | Me | 5-Cl-pyridin-2-yl | H |
| 8-112 | H | H | Me | 5-Cl-pyridin-2-yl | 5-Cl |
| 8-113 | H | H | Me | 5-Cl-pyridin-2-yl | 5-Me |
| 8-114 | H | H | Me | 5-Br-pyridin-2-yl | H |
| 8-115 | H | H | Me | 5-Br-pyridin-2-yl | 5-Cl |
| 8-116 | H | H | Me | 5-Br-pyridin-2-yl | 5-Me |
| 8-117 | H | H | Me | 5-F-pyridin-2-yl | H |
| 8-118 | H | H | Me | 5-Me-pyridin-2-yl | H |
| 8-119 | H | H | Me | 5-Me-pyridin-2-yl | 5-Me |
| 8-120 | H | H | Me | 2,4-Cl₂-Ph | H |
| 8-121 | H | H | Me | 4-(CH₂COOH)-Ph | 5-Me |
| 8-122 | H | H | Me | 3,4-Me₂-Ph | 5-Me |
| 8-123 | H | H | Me | 4-Br-Ph | 5-Me |
| 8-124 | H | H | Me | 3,4-Me₂-Ph | H |
| 8-125 | H | H | Me | 3-Me-Ph | H |
| 8-126 | H | H | Me | 4-F-Ph | H |

TABLE 8-continued

Compounds of the formula (Ic''')

| No. | R² | R³ | R⁴ | R⁵ | (R⁶)ₙ |
|---|---|---|---|---|---|
| 8-127 | H | H | Me | 4-(Me-CO)-Ph | H |
| 8-128 | H | H | Me | 4-tBu-Ph | H |
| 8-129 | H | H | Me | 4-Cl-3-Me-Ph | H |
| 8-130 | H | H | n-Pr | 4-Cl-Ph | 5-Me |
| 8-131 | H | H | Me | 3-pyridyl | H |
| 8-132 | H | H | Me | 4-pyridyl | H |
| 8-133 | H | H | C(O)OMe | Ph | H |
| 8-134 | H | H | Me | 6-Me-pyridin-3-yl | H |
| 8-135 | H | H | Me | 4-Cl-Ph | 5-SO₂Me |
| 8-136 | H | H | Me | 3-pyridyl | 5-Me |
| 8-137 | H | H | Me | 2,3-Cl₂-Ph | 5-Me |
| 8-138 | H | H | Me | 2-pyridyl | 5-Me |
| 8-139 | H | H | H | 4-Cl-Ph | 5-Me |
| 8-140 | H | H | Me | 6-Cl-pyridin-3-yl | H |
| 8-141 | H | H | Me | Ph | 5-Me |
| 8-142 | H | H | Me | 4-Me-pyridin-2-yl | H |
| 8-143 | H | H | Me | 4-Me-pyridin-2-yl | 5-Me |
| 8-144 | H | H | Me | 4-Me-pyridin-2-yl | 5-Cl |
| 8-145 | H | H | Me | 4-Me-pyridin-2-yl | 5-F |
| 8-146 | H | H | Me | 4-F-pyridin-2-yl | H |
| 8-147 | H | H | Me | 4-Cl-pyridin-2-yl | H |
| 8-148 | H | H | Me | 4-Br-pyridin-2-yl | H |
| 8-149 | H | H | Me | 4-OMe-pyridin-2-yl | H |
| 8-150 | H | H | Me | 5-CF₃-pyridin-2-yl | H |
| 8-151 | H | H | Me | 6-OMe-pyridin-2-yl | H |
| 8-152 | H | H | cyPr | 4-Cl-Ph | H |
| 8-153 | H | H | CN | 4-Cl-Ph | H |
| 8-154 | H | H | CN | 4-Cl-Ph | 5-Me |
| 8-155 | H | H | CN | 4-Me-Ph | H |
| 8-156 | H | H | CN | 4-Me-Ph | 5-Me |
| 8-157 | H | H | CN | Ph | H |
| 8-158 | H | H | CN | Ph | 5-Me |
| 8-159 | H | H | CN | 2-pyridyl | H |
| 8-160 | H | H | CN | 3-pyridyl | H |
| 8-161 | H | H | CN | 5-Cl-pyridin-2-yl | H |
| 8-162 | H | H | CN | 5-Br-pyridin-2-yl | H |
| 8-163 | H | H | CN | 5-F-pyridin-2-yl | H |
| 8-164 | H | H | CN | 5-Me-pyridin-2-yl | H |
| 8-165 | H | H | CN | 6-Me-pyridin-3-yl | H |
| 8-166 | H | H | CN | 4-Me-pyridin-2-yl | H |
| 8-167 | H | H | CN | 4-F-pyridin-2-yl | H |
| 8-168 | H | H | CN | 4-Cl-pyridin-2-yl | H |
| 8-169 | H | H | CN | 4-Br-pyridin-2-yl | H |
| 8-170 | H | H | CN | 4-OMe-pyridin-2-yl | H |
| 8-171 | H | H | formyl | 4-Cl-Ph | H |
| 8-172 | H | H | formyl | 4-Cl-Ph | 5-Me |
| 8-173 | H | H | formyl | 4-Me-Ph | H |
| 8-174 | H | H | formyl | 4-Me-Ph | 5-Me |
| 8-175 | H | H | formyl | Ph | H |
| 8-176 | H | H | formyl | Ph | 5-Me |
| 8-177 | H | H | formyl | 2-pyridyl | H |
| 8-178 | H | H | formyl | 3-pyridyl | H |
| 8-179 | H | H | formyl | 5-Cl-pyridin-2-yl | H |
| 8-180 | H | H | formyl | 5-Br-pyridin-2-yl | H |
| 8-181 | H | H | formyl | 5-F-pyridin-2-yl | H |
| 8-182 | H | H | formyl | 5-Me-pyridin-2-yl | H |
| 8-183 | H | H | formyl | 6-Me-pyridin-3-yl | H |
| 8-184 | H | H | formyl | 4-Me-pyridin-2-yl | H |
| 8-185 | H | H | formyl | 4-F-pyridin-2-yl | H |
| 8-186 | H | H | formyl | 4-Cl-pyridin-2-yl | H |
| 8-187 | H | H | formyl | 4-Br-pyridin-2-yl | H |
| 8-188 | H | H | formyl | 4-OMe-pyridin-2-yl | H |
| 8-189 | H | H | CH₂OH | 5-Me-pyridin-2-yl | H |
| 8-190 | H | H | CH₂OH | 4-Cl-Ph | H |
| 8-191 | H | H | CH₂OH | 4-Me-pyridin-2-yl | H |
| 8-192 | H | H | CH₂OH | 4-Me-Ph | H |
| 8-193 | H | H | CH₂OH | Ph | H |
| 8-194 | H | H | CH₂OH | 2-pyridyl | H |
| 8-195 | H | H | Me | 2-thiazolyl | H |
| 8-196 | H | H | Me | 2-thiazolyl | 5-Cl |
| 8-197 | H | H | Me | 2-thiazolyl | 5-Me |
| 8-198 | H | H | Me | 4-Me-thiazol-2-yl | H |
| 8-199 | H | H | Me | 4-Me-thiazol-2-yl | 5-Cl |
| 8-200 | H | H | Me | 4-Me-thiazol-2-yl | 5-Me |
| 8-201 | H | H | Me | 5-Me-thiazol-2-yl | H |
| 8-202 | H | H | Me | 5-Br-thiazol-2-yl | H |
| 8-203 | H | H | Me | 5-Br-thiazol-2-yl | 5-Me |
| 8-204 | H | H | Me | 5-Cl-thiazol-2-yl | H |
| 8-205 | H | H | Me | 4,6-Me₂-pyridin-2-yl | H |
| 8-206 | H | H | Me | 4,6-Me₂-pyridin-2-yl | 5-Me |
| 8-207 | H | H | Me | 2-pyridyl | 5-F |
| 8-208 | H | H | Me | 2-pyrazinyl | H |
| 8-209 | H | H | Me | 5-Me-pyrazin-2-yl | H |
| 8-210 | H | H | Me | 2-pyrazinyl | 5-Me |
| 8-211 | H | H | Me | 1,3-benzothiazol-2-yl | H |
| 8-212 | H | H | Me | 1,3-benzothiazol-2-yl | 5-Me |
| 8-213 | H | H | Me | 7-Cl-1,3-benzothiazol-2-yl | H |
| 8-214 | H | H | Me | 1,5-Me₂-pyrazol-3-yl | H |
| 8-215 | H | H | Me | 1,5-Me₂-pyrazol-3-yl | 5-Me |
| 8-216 | H | H | Me | 4,5-Me₂-thiazol-2-yl | H |
| 8-217 | H | H | Me | 4,5-Cl₂-thiazol-2-yl | H |
| 8-218 | H | H | Me | 2-pyrimidinyl | H |
| 8-219 | H | H | Me | 2-pyrimidinyl | 5-Me |
| 8-220 | H | H | Me | 5-F-pyrimidin-2-yl | H |
| 8-221 | H | H | Me | 5-Cl-pyrimidin-2-yl | H |
| 8-222 | H | H | Me | 5-Br-pyrimidin-2-yl | H |
| 8-223 | H | H | Me | 5-Me-pyrimidin-2-yl | H |
| 8-224 | H | H | Me | 5-Me-pyrimidin-2-yl | 5-Me |
| 8-225 | H | H | Me | 4,6-Me₂-pyrimidin-2-yl | H |
| 8-226 | H | H | Me | 4,6-Me₂-pyrimidin-2-yl | 5-Me |
| 8-227 | H | H | Me | 3-pyridazinyl | H |
| 8-228 | H | H | Me | 6-Me-pyridazin-3-yl | H |
| 8-229 | H | H | Me | 3-(1,2,4)-triazinyl | H |
| 8-230 | H | H | Me | 6-Me-(1,2,4)-triazin-3-yl | H |
| 8-231 | H | H | Me | 3,5-Cl₂-Ph | H |
| 8-232 | H | H | Me | isoquinolin-3-yl | H |
| 8-233 | H | H | Me | quinolin-2-yl | H |

TABLE 9

Compounds of the formula (Ic'''')

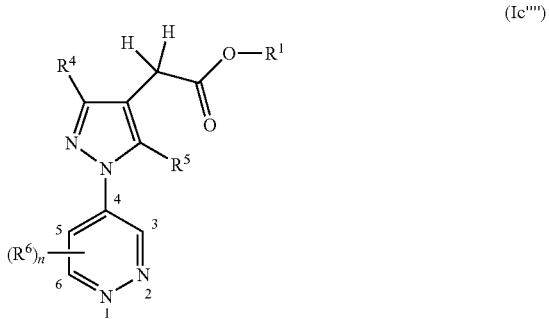

| No. | R¹ | R⁴ | R⁵ | (R⁶)ₙ |
|---|---|---|---|---|
| 9-1 | Et | Me | Ph | H |
| 9-2 | Et | Me | Ph | 5-Me |
| 9-3 | Et | Me | 3-Cl-Ph | H |
| 9-4 | Et | Me | 4-Cl-Ph | H |
| 9-5 | Et | Me | 4-Cl-Ph | 5-Me |
| 9-6 | Et | Me | 2-thienyl | H |
| 9-7 | Et | Me | 3-thienyl | H |
| 9-8 | Et | Me | 3-Me-2-thienyl | H |
| 9-9 | Et | Me | 4-Me-2-thienyl | H |
| 9-10 | Et | Me | 5-Br-2-thienyl | H |
| 9-11 | Et | Me | 5-Br-2-thienyl | 5-Me |
| 9-12 | Et | Me | 5-Cl-2-thienyl | H |
| 9-13 | Et | Me | 5-Cl-2-thienyl | 5-Me |
| 9-14 | Et | Me | 5-I-2-thienyl | H |
| 9-15 | Et | Me | 5-Me-2-thienyl | H |
| 9-16 | Et | Me | 3-pyridyl | H |
| 9-17 | Et | Me | 6-MeO-pyridin-3-yl | H |
| 9-18 | Et | Me | 6-OH-pyridin-3-yl | H |
| 9-19 | Et | Me | 6-Me-pyridin-3-yl | H |
| 9-20 | Et | Me | 4-Me-Ph | H |
| 9-21 | Et | Me | 4-Me-Ph | 5-Me |
| 9-22 | Et | Me | 4-Br-Ph | H |
| 9-23 | Et | Me | 4-F-Ph | H |
| 9-24 | Et | Me | 4-F-Ph | 5-Me |
| 9-25 | Et | Me | 5-Cl-pyridin-2-yl | H |
| 9-26 | Et | Me | 5-Br-pyridin-2-yl | H |
| 9-27 | Et | Me | 5-F-pyridin-2-yl | H |
| 9-28 | Et | Me | 5-F-pyridin-2-yl | 5-Me |
| 9-29 | Et | Me | 5-Cl-pyridin-2-yl | 5-Me |
| 9-30 | Et | Me | 5-Br-pyridin-2-yl | 5-Me |
| 9-31 | Et | Me | 5-Me-pyridin-2-yl | H |
| 9-32 | Et | Me | 5-Me-pyridin-2-yl | 5-Me |
| 9-33 | Et | Me | 2-pyridyl | 5-Me |
| 9-34 | Et | Me | 2-pyridyl | H |
| 9-35 | Et | Me | 4-pyridyl | H |
| 9-36 | Et | Me | 4-Me-pyridin-2-yl | H |
| 9-37 | Et | Me | 4-Me-pyridin-2-yl | 5-Me |
| 9-38 | Et | Me | 2-thiazolyl | H |
| 9-39 | Et | Me | 4-Me-thiazol-2-yl | H |
| 9-40 | Et | Me | 5-Br-thiazol-2-yl | H |
| 9-41 | Et | Me | 5-Cl-thiazol-2-yl | H |
| 9-42 | Et | Me | 5-Me-thiazol-2-yl | H |
| 9-43 | Et | Me | 4,5-Me₂-thiazol-2-yl | H |
| 9-44 | Et | Me | 4,5-Cl₂-thiazol-2-yl | H |
| 9-45 | Et | Me | 4,6-Me₂-pyridin-2-yl | H |
| 9-46 | Et | Me | 2-pyrazinyl | H |
| 9-47 | Et | Me | 2-pyrimidinyl | H |
| 9-48 | Et | Me | 2-pyrimidinyl | 5-Me |
| 9-49 | Et | Me | 5-Cl-pyrimidin-2-yl | H |
| 9-50 | Et | Me | 5-Br-pyrimidin-2-yl | H |
| 9-51 | Et | Me | 5-Me-pyrimidin-2-yl | H |
| 9-52 | Et | Me | 5-Me-pyrimidin-2-yl | 5-Me |
| 9-53 | Et | Me | 4,6-Me₂-pyrimidin-2-yl | H |
| 9-54 | Et | Me | 4,6-Me₂-pyrimidin-2-yl | 5-Me |
| 9-55 | Et | Me | 1,3-benzothiazol-2-yl | H |
| 9-56 | Et | Me | 7-Cl-1,3-benzothiazol-2-yl | H |
| 9-57 | Et | Me | 1,5-Me₂-pyrazol-3-yl | H |
| 9-58 | Et | Me | 5-Me-pyrazin-2-yl | H |
| 9-59 | Et | Me | 5-F-pyrimidin-2-yl | H |

TABLE 9-continued

Compounds of the formula (Ic'''')

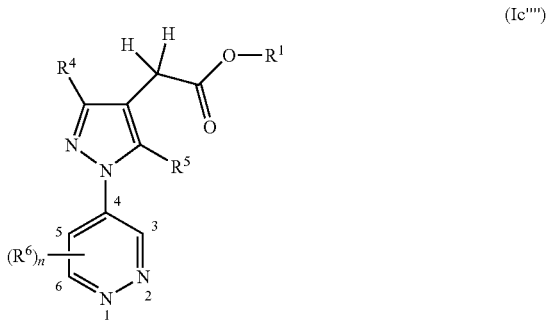

| No. | R¹ | R⁴ | R⁵ | (R⁶)ₙ |
|---|---|---|---|---|
| 9-60 | Et | Me | 4,6-Me₂-pyrimidin-2-yl | H |
| 9-61 | Et | Me | 3-pyridazinyl | H |
| 9-62 | Et | Me | 6-Me-pyridazin-3-yl | H |
| 9-63 | Et | Me | 1,2,4-triazin-3-yl | H |
| 9-64 | Et | Me | 6-Me-1,2,4-triazin-3-yl | H |
| 9-65 | Pr | Me | Ph | H |
| 9-66 | Pr | Me | 4-Cl-Ph | H |
| 9-67 | Pr | Me | 2-thienyl | H |
| 9-68 | Pr | Me | 3-pyridyl | H |
| 9-69 | Pr | Me | 6-Me-pyridin-3-yl | H |
| 9-70 | Pr | Me | 4-Me-Ph | H |
| 9-71 | Pr | Me | 4-Br-Ph | H |
| 9-72 | Pr | Me | 4-F-Ph | H |
| 9-73 | Pr | Me | 5-Cl-pyridin-2-yl | H |
| 9-74 | Pr | Me | 5-Br-pyridin-2-yl | H |
| 9-75 | Pr | Me | 5-F-pyridin-2-yl | H |
| 9-76 | Pr | Me | 5-Me-pyridin-2-yl | H |
| 9-77 | Pr | Me | 2-pyridyl | H |
| 9-78 | Pr | Me | 4-pyridyl | H |
| 9-79 | i-Pr | Me | Ph | H |
| 9-80 | i-Pr | Me | 4-Cl-Ph | H |
| 9-81 | i-Pr | Me | 2-thienyl | H |
| 9-82 | i-Pr | Me | 3-pyridyl | H |
| 9-83 | i-Pr | Me | 6-Me-pyridin-3-yl | H |
| 9-84 | i-Pr | Me | 4-Me-Ph | H |
| 9-85 | i-Pr | Me | 4-Br-Ph | H |
| 9-86 | i-Pr | Me | 4-F-Ph | H |
| 9-87 | i-Pr | Me | 5-Cl-pyridin-2-yl | H |
| 9-88 | i-Pr | Me | 5-Br-pyridin-2-yl | H |
| 9-89 | i-Pr | Me | 5-F-pyridin-2-yl | H |
| 9-90 | i-Pr | Me | 5-Me-pyridin-2-yl | H |
| 9-91 | i-Pr | Me | 2-pyridyl | H |
| 9-92 | i-Pr | Me | 4-pyridyl | H |
| 9-93 | CH₂Ph | Me | Ph | H |
| 9-94 | CH₂Ph | Me | 4-Cl-Ph | H |
| 9-95 | CH₂Ph | Me | 2-thienyl | H |
| 9-96 | CH₂Ph | Me | 2-pyridyl | H |
| 9-97 | prop-2-yn-1-yl | Me | Ph | H |
| 9-98 | prop-2-yn-1-yl | Me | 4-Cl-Ph | H |
| 9-99 | prop-2-yn-1-yl | Me | 2-thienyl | H |
| 9-100 | prop-2-yn-1-yl | Me | 3-thienyl | H |
| 9-101 | prop-2-yn-1-yl | Me | 3-Me-2-thienyl | H |
| 9-102 | prop-2-yn-1-yl | Me | 4-Me-2-thienyl | H |
| 9-103 | prop-2-yn-1-yl | Me | 5-Cl-2-thienyl | H |
| 9-104 | prop-2-yn-1-yl | Me | 5-Me-2-thienyl | H |
| 9-105 | prop-2-yn-1-yl | Me | 3-pyridyl | H |
| 9-106 | prop-2-yn-1-yl | Me | 6-MeO-pyridin-3-yl | H |
| 9-107 | prop-2-yn-1-yl | H | Ph | H |
| 9-108 | prop-2-yn-1-yl | Me | 6-Me-pyridin-3-yl | H |
| 9-109 | prop-2-yn-1-yl | Me | 4-Me-Ph | H |
| 9-110 | prop-2-yn-1-yl | Me | 4-Br-Ph | H |
| 9-111 | prop-2-yn-1-yl | Me | 4-F-Ph | H |
| 9-112 | prop-2-yn-1-yl | Me | 5-Cl-pyridin-2-yl | H |
| 9-113 | prop-2-yn-1-yl | Me | 5-Br-pyridin-2-yl | H |
| 9-114 | prop-2-yn-1-yl | Me | 5-F-pyridin-2-yl | H |
| 9-115 | prop-2-yn-1-yl | Me | 5-Me-pyridin-2-yl | H |
| 9-116 | prop-2-yn-1-yl | Me | 2-pyridyl | H |
| 9-117 | prop-2-yn-1-yl | Me | 4-pyridyl | H |
| 9-118 | prop-2-yn-1-yl | Me | 4-Cl-Ph | 5-Me |

TABLE 9-continued

Compounds of the formula (Ic'''')

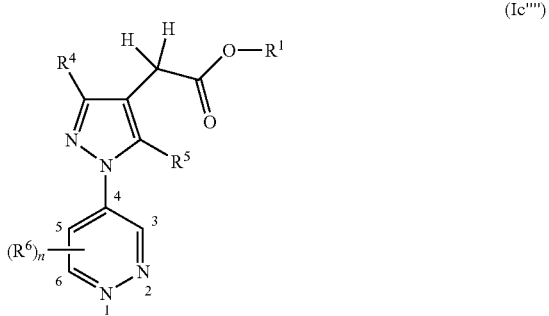

| No. | R¹ | R⁴ | R⁵ | (R⁶)ₙ |
|---|---|---|---|---|
| 9-119 | prop-2-yn-1-yl | Me | Ph | 5-Me |
| 9-120 | cyclopropylmethyl | Me | Ph | H |
| 9-121 | cyclopropylmethyl | Me | 4-Cl-Ph | H |
| 9-122 | cyclopropylmethyl | Me | 2-thienyl | H |
| 9-123 | cyclopropylmethyl | Me | 3-thienyl | H |
| 9-124 | cyclopropylmethyl | Me | 3-Me-2-thienyl | H |
| 9-125 | cyclopropylmethyl | Me | 3-pyridyl | H |
| 9-126 | cyclopropylmethyl | Me | 5-Cl-2-thienyl | H |
| 9-127 | cyclopropylmethyl | Me | 5-Me-2-thienyl | H |
| 9-128 | cyclopropylmethyl | Me | 4-Me-2-thienyl | H |
| 9-129 | cyclopropylmethyl | Me | 6-MeO-pyridin-3-yl | H |
| 9-130 | cyclopropylmethyl | Me | 6-OH-pyridin-3-yl | H |
| 9-131 | cyclopropylmethyl | Me | 6-Me-pyridin-3-yl | H |
| 9-132 | cyclopropylmethyl | Me | 4-Me-Ph | H |
| 9-133 | cyclopropylmethyl | Me | 4-Br-Ph | H |
| 9-134 | cyclopropylmethyl | Me | 4-F-Ph | H |
| 9-135 | cyclopropylmethyl | Me | 5-Cl-pyridin-2-yl | H |
| 9-136 | cyclopropylmethyl | Me | 5-Br-pyridin-2-yl | H |
| 9-137 | cyclopropylmethyl | Me | 5-F-pyridin-2-yl | H |
| 9-138 | cyclopropylmethyl | Me | 5-Me-pyridin-2-yl | H |
| 9-139 | cyclopropylmethyl | Me | 2-pyridyl | H |
| 9-140 | cyclopropylmethyl | Me | 4-pyridyl | H |
| 9-141 | cyclopropylmethyl | Me | 4-Cl-Ph | 5-Me |
| 9-142 | cyclopropylmethyl | Me | Ph | 5-Me |
| 9-143 | cyclopropylmethyl | H | Ph | H |
| 9-144 | 3,3-dichloro-2-fluoroprop-2-en-1-yl | Me | Ph | H |
| 9-145 | 3,3-dichloro-2-fluoroprop-2-en-1-yl | Me | 4-Cl-Ph | H |
| 9-146 | 3,3-dichloro-2-fluoroprop-2-en-1-yl | Me | 2-thienyl | H |
| 9-147 | 3,3-dichloro-2-fluoroprop-2-en-1-yl | Me | 2-pyridyl | H |
| 9-148 | (1-methylcyclopropyl)methyl | Me | Ph | H |
| 9-149 | (1-methylcyclopropyl)methyl | Me | 4-Cl-Ph | H |
| 9-150 | (1-methylcyclopropyl)methyl | Me | 2-thienyl | H |
| 9-151 | (1-methylcyclopropyl)methyl | Me | 2-pyridyl | H |
| 9-152 | 4-chlorobut-2-yn-1-yl | Me | Ph | H |
| 9-153 | 4-chlorobut-2-yn-1-yl | Me | 4-Cl-Ph | H |
| 9-154 | 4-chlorobut-2-yn-1-yl | Me | 2-thienyl | H |
| 9-155 | 4-chlorobut-2-yn-1-yl | Me | 2-pyridyl | H |
| 9-156 | (2,2-dichlorocyclopropyl)methyl | Me | Ph | H |
| 9-157 | (2,2-dichlorocyclopropyl)methyl | Me | 4-Cl-Ph | H |
| 9-158 | (2,2-dichlorocyclopropyl)methyl | Me | 2-thienyl | H |
| 9-159 | (2,2-dichlorocyclopropyl)methyl | Me | 2-pyridyl | H |
| 9-160 | but-2-yn-1-yl | Me | Ph | H |
| 9-161 | but-2-yn-1-yl | Me | 4-Cl-Ph | H |
| 9-162 | but-2-yn-1-yl | Me | 2-thienyl | H |
| 9-163 | but-2-yn-1-yl | Me | 3-thienyl | H |
| 9-164 | but-2-yn-1-yl | Me | 3-Me-2-thienyl | H |
| 9-165 | but-2-yn-1-yl | Me | 4-Me-2-thienyl | H |
| 9-166 | but-2-yn-1-yl | Me | 5-Cl-2-thienyl | H |
| 9-167 | but-2-yn-1-yl | Me | 5-Me-2-thienyl | H |
| 9-168 | but-2-yn-1-yl | Me | 3-pyridyl | H |
| 9-169 | but-2-yn-1-yl | Me | 6-MeO-pyridin-3-yl | H |
| 9-170 | but-2-yn-1-yl | H | Ph | H |
| 9-171 | but-2-yn-1-yl | Me | 6-Me-pyridin-3-yl | H |
| 9-172 | but-2-yn-1-yl | Me | 4-Me-Ph | H |
| 9-173 | but-2-yn-1-yl | Me | 4-Br-Ph | H |
| 9-174 | but-2-yn-1-yl | Me | 4-F-Ph | H |
| 9-175 | but-2-yn-1-yl | Me | 5-Cl-pyridin-2-yl | H |
| 9-176 | but-2-yn-1-yl | Me | 5-Br-pyridin-2-yl | H |
| 9-177 | but-2-yn-1-yl | Me | 5-F-pyridin-2-yl | H |

TABLE 9-continued

Compounds of the formula (Ic'''')

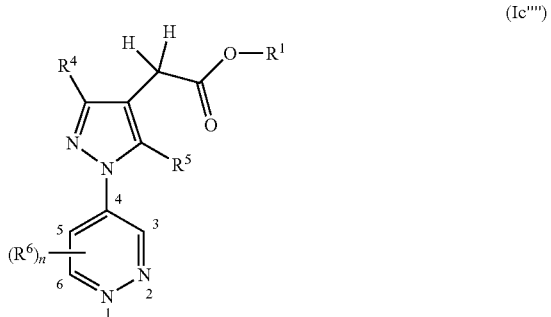

| No. | R¹ | R⁴ | R⁵ | (R⁶)ₙ |
|---|---|---|---|---|
| 9-178 | but-2-yn-1-yl | Me | 5-Me-pyridin-2-yl | H |
| 9-179 | but-2-yn-1-yl | Me | 2-pyridyl | H |
| 9-180 | but-2-yn-1-yl | Me | 4-pyridyl | H |
| 9-181 | but-2-yn-1-yl | Me | 4-Cl-Ph | 5-Me |
| 9-182 | but-2-yn-1-yl | Me | Ph | 5-Me |
| 9-183 | 1-methylprop-2-yn-1-yl | Me | Ph | H |
| 9-184 | 1-methylprop-2-yn-1-yl | Me | 4-Cl-Ph | H |
| 9-185 | 1-methylprop-2-yn-1-yl | Me | 2-thienyl | H |
| 9-186 | 1-methylprop-2-yn-1-yl | Me | 2-pyridyl | H |
| 9-187 | 1-cyclopropylethyl | Me | Ph | H |
| 9-188 | 1-cyclopropylethyl | Me | 4-Cl-Ph | H |
| 9-189 | 1-cyclopropylethyl | Me | 2-thienyl | H |
| 9-190 | 1-cyclopropylethyl | Me | 2-pyridyl | H |
| 9-191 | allyl | Me | Ph | H |
| 9-192 | allyl | Me | 4-Cl-Ph | H |
| 9-193 | allyl | Me | 2-thienyl | H |
| 9-194 | allyl | Me | 2-pyridyl | H |
| 9-195 | 3-methylbut-2-en-1-yl | Me | Ph | H |
| 9-196 | 3-methylbut-2-en-1-yl | Me | 4-Cl-Ph | H |
| 9-197 | 3-methylbut-2-en-1-yl | Me | 2-thienyl | H |
| 9-198 | 3-methylbut-2-en-1-yl | Me | 2-pyridyl | H |
| 9-199 | 2-methylprop-2-en-1-yl | Me | Ph | H |
| 9-200 | 2-methylprop-2-en-1-yl | Me | 4-Cl-Ph | H |
| 9-201 | 2-methylprop-2-en-1-yl | Me | 2-thienyl | H |
| 9-202 | 2-methylprop-2-en-1-yl | Me | 2-pyridyl | H |
| 9-203 | (2E)-1-methylbut-2-en-1-yl | Me | Ph | H |
| 9-204 | (2E)-1-methylbut-2-en-1-yl | Me | 4-Cl-Ph | H |
| 9-205 | (2E)-1-methylbut-2-en-1-yl | Me | 2-thienyl | H |
| 9-206 | (2E)-1-methylbut-2-en-1-yl | Me | 2-pyridyl | H |
| 9-207 | 3-phenylprop-2-yn-1-yl | Me | Ph | H |
| 9-208 | 3-phenylprop-2-yn-1-yl | Me | 4-Cl-Ph | H |
| 9-209 | 3-phenylprop-2-yn-1-yl | Me | 2-thienyl | H |
| 9-210 | 3-phenylprop-2-yn-1-yl | Me | 2-pyridyl | H |
| 9-211 | cyclobutylmethyl | Me | Ph | H |
| 9-212 | cyclobutylmethyl | Me | 4-Cl-Ph | H |
| 9-213 | cyclobutylmethyl | Me | 2-thienyl | H |
| 9-214 | cyclobutylmethyl | Me | 2-pyridyl | H |
| 9-215 | cyclopentylmethyl | Me | Ph | H |
| 9-216 | cyclopentylmethyl | Me | 4-Cl-Ph | H |
| 9-217 | cyclopentylmethyl | Me | 2-thienyl | H |
| 9-218 | cyclopentylmethyl | Me | 2-pyridyl | H |
| 9-219 | cyclohexylmethyl | Me | Ph | H |
| 9-220 | cyclohexylmethyl | Me | 4-Cl-Ph | H |
| 9-221 | cyclohexylmethyl | Me | 2-thienyl | H |
| 9-222 | cyclohexylmethyl | Me | 2-pyridyl | H |
| 9-223 | but-3-en-1-yl | Me | Ph | H |
| 9-224 | but-3-en-1-yl | Me | 4-Cl-Ph | H |
| 9-225 | but-3-en-1-yl | Me | 2-thienyl | H |
| 9-226 | but-3-en-1-yl | Me | 2-pyridyl | H |
| 9-227 | 2-chloroprop-2-en-1-yl | Me | Ph | H |
| 9-228 | 2-chloroprop-2-en-1-yl | Me | 4-Cl-Ph | H |
| 9-229 | 2-chloroprop-2-en-1-yl | Me | 2-thienyl | H |
| 9-230 | 2-chloroprop-2-en-1-yl | Me | 3-thienyl | H |
| 9-231 | 2-chloroprop-2-en-1-yl | Me | 3-Me-2-thienyl | H |
| 9-232 | 2-chloroprop-2-en-1-yl | Me | 4-Me-2-thienyl | H |
| 9-233 | 2-chloroprop-2-en-1-yl | Me | 5-Cl-2-thienyl | H |
| 9-234 | 2-chloroprop-2-en-1-yl | Me | 5-Me-2-thienyl | H |
| 9-235 | 2-chloroprop-2-en-1-yl | Me | 3-pyridyl | H |
| 9-236 | 2-chloroprop-2-en-1-yl | Me | 6-MeO-pyridin-3-yl | H |

TABLE 9-continued

Compounds of the formula (Ic'''')

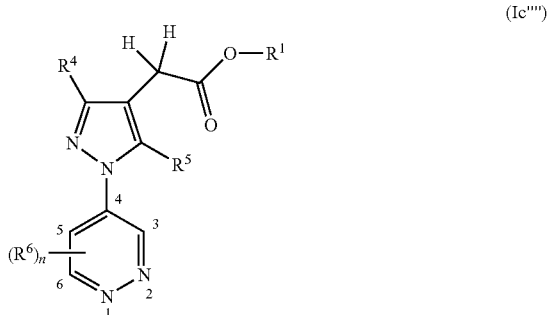

| No. | R¹ | R⁴ | R⁵ | (R⁶)ₙ |
|---|---|---|---|---|
| 9-237 | 2-chloroprop-2-en-1-yl | Me | 6-OH-pyridin-3-yl | H |
| 9-238 | 2-chloroprop-2-en-1-yl | Me | 6-Me-pyridin-3-yl | H |
| 9-239 | 2-chloroprop-2-en-1-yl | Me | 4-Me-Ph | H |
| 9-240 | 2-chloroprop-2-en-1-yl | Me | 4-Br-Ph | H |
| 9-241 | 2-chloroprop-2-en-1-yl | Me | 4-F-Ph | H |
| 9-242 | 2-chloroprop-2-en-1-yl | Me | 5-Cl-pyridin-2-yl | H |
| 9-243 | 2-chloroprop-2-en-1-yl | Me | 5-Br-pyridin-2-yl | H |
| 9-244 | 2-chloroprop-2-en-1-yl | Me | 5-F-pyridin-2-yl | H |
| 9-245 | 2-chloroprop-2-en-1-yl | Me | 5-Me-pyridin-2-yl | H |
| 9-246 | 2-chloroprop-2-en-1-yl | Me | 2-pyridyl | H |
| 9-247 | 2-chloroprop-2-en-1-yl | Me | 4-pyridyl | H |
| 9-248 | 2-chloroprop-2-en-1-yl | Me | 4-Cl-Ph | 5-Me |
| 9-249 | 2-chloroprop-2-en-1-yl | Me | Ph | 5-Me |
| 9-250 | 2-chloroprop-2-en-1-yl | H | Ph | H |
| 9-251 | 2-methoxyethyl | Me | Ph | H |
| 9-252 | 2-methoxyethyl | Me | 4-Cl-Ph | H |
| 9-253 | 2-methoxyethyl | Me | 2-thienyl | H |
| 9-254 | 2-methoxyethyl | Me | 2-pyridyl | H |
| 9-255 | tetrahydrofuran-2-ylmethyl | Me | Ph | H |
| 9-256 | tetrahydrofuran-2-ylmethyl | Me | 4-Cl-Ph | H |
| 9-257 | tetrahydrofuran-2-ylmethyl | Me | 2-thienyl | H |
| 9-258 | tetrahydrofuran-2-ylmethyl | Me | 2-pyridyl | H |
| 9-259 | 2-(dimethylamino)ethyl | Me | Ph | H |
| 9-260 | 2-(dimethylamino)ethyl | Me | 4-Cl-Ph | H |
| 9-261 | 2-(dimethylamino)ethyl | Me | 2-thienyl | H |
| 9-262 | 2-(dimethylamino)ethyl | Me | 2-pyridyl | H |
| 9-263 | oxetan-3-yl | Me | Ph | H |
| 9-264 | oxetan-3-yl | Me | 4-Cl-Ph | H |
| 9-265 | oxetan-3-yl | Me | 2-thienyl | H |
| 9-266 | oxetan-3-yl | Me | 2-pyridyl | H |
| 9-267 | (3-methyloxetan-3-yl)methyl | Me | Ph | H |
| 9-268 | (3-methyloxetan-3-yl)methyl | Me | 4-Cl-Ph | H |
| 9-269 | (3-methyloxetan-3-yl)methyl | Me | 2-thienyl | H |
| 9-270 | (3-methyloxetan-3-yl)methyl | Me | 2-pyridyl | H |
| 9-271 | 2,2,2-trifluoroethyl | Me | Ph | H |
| 9-272 | 2,2,2-trifluoroethyl | Me | 4-Cl-Ph | H |
| 9-273 | 2,2,2-trifluoroethyl | Me | 2-thienyl | H |
| 9-274 | 2,2,2-trifluoroethyl | Me | 3-pyridyl | H |
| 9-275 | 2,2,2-trifluoroethyl | Me | 6-Me-pyridin-3-yl | H |
| 9-276 | 2,2,2-trifluoroethyl | Me | 4-Me-Ph | H |
| 9-277 | 2,2,2-trifluoroethyl | Me | 4-Br-Ph | H |
| 9-278 | 2,2,2-trifluoroethyl | Me | 4-F-Ph | H |
| 9-279 | 2,2,2-trifluoroethyl | Me | 5-Cl-pyridin-2-yl | H |
| 9-280 | 2,2,2-trifluoroethyl | Me | 5-Br-pyridin-2-yl | H |
| 9-281 | 2,2,2-trifluoroethyl | Me | 5-F-pyridin-2-yl | H |
| 9-282 | 2,2,2-trifluoroethyl | Me | 5-Me-pyridin-2-yl | H |
| 9-283 | 2,2,2-trifluoroethyl | Me | 2-pyridyl | H |
| 9-284 | 2,2,2-trifluoroethyl | Me | 4-pyridyl | H |
| 9-285 | CH₂(4-Cl-Ph) | Me | Ph | H |
| 9-286 | CH₂(4-Cl-Ph) | Me | 4-Cl-Ph | H |
| 9-287 | CH₂(4-Cl-Ph) | Me | 2-thienyl | H |
| 9-288 | CH₂(4-Cl-Ph) | Me | 3-pyridyl | H |
| 9-289 | CH₂(4-Cl-Ph) | Me | 6-Me-pyridin-3-yl | H |
| 9-290 | CH₂(4-Cl-Ph) | Me | 4-Me-Ph | H |
| 9-291 | CH₂(4-Cl-Ph) | Me | 4-Br-Ph | H |
| 9-292 | CH₂(4-Cl-Ph) | Me | 4-F-Ph | H |
| 9-293 | CH₂(4-Cl-Ph) | Me | 5-Cl-pyridin-2-yl | H |
| 9-294 | CH₂(4-Cl-Ph) | Me | 5-Br-pyridin-2-yl | H |
| 9-295 | CH₂(4-Cl-Ph) | Me | 5-F-pyridin-2-yl | H |

TABLE 9-continued

Compounds of the formula (Ic'''')

(Ic'''')

| No. | R¹ | R⁴ | R⁵ | (R⁶)ₙ |
|---|---|---|---|---|
| 9-296 | CH₂(4-Cl-Ph) | Me | 5-F-pyridin-2-yl | H |
| 9-296 | CH₂(4-Cl-Ph) | Me | 5-Me-pyridin-2-yl | H |
| 9-297 | CH₂(4-Cl-Ph) | Me | 2-pyridyl | H |
| 9-298 | CH₂(4-Cl-Ph) | Me | 4-pyridyl | H |
| 9-299 | CH₂(4-F-Ph) | Me | Ph | H |
| 9-300 | CH₂(4-F-Ph) | Me | 4-Cl-Ph | H |
| 9-301 | CH₂(4-F-Ph) | Me | 2-thienyl | H |
| 9-302 | CH₂(4-F-Ph) | Me | 3-pyridyl | H |
| 9-303 | CH₂(4-F-Ph) | Me | 6-Me-pyridin-3-yl | H |
| 9-304 | CH₂(4-F-Ph) | Me | 4-Me-Ph | H |
| 9-305 | CH₂(4-F-Ph) | Me | 4-Br-Ph | H |
| 9-306 | CH₂(4-F-Ph) | Me | 4-F-Ph | H |
| 9-307 | CH₂(4-F-Ph) | Me | 5-Cl-pyridin-2-yl | H |
| 9-308 | CH₂(4-F-Ph) | Me | 5-Br-pyridin-2-yl | H |
| 9-309 | CH₂(4-F-Ph) | Me | 5-F-pyridin-2-yl | H |
| 9-310 | CH₂(4-F-Ph) | Me | 5-Me-pyridin-2-yl | H |
| 9-311 | CH₂(4-F-Ph) | Me | 2-pyridyl | H |
| 9-312 | CH₂(4-F-Ph) | Me | 4-pyridyl | H |
| 9-313 | CH₂(4-OMe-Ph) | Me | Ph | H |
| 9-314 | CH₂(4-OMe-Ph) | Me | 4-Cl-Ph | H |
| 9-315 | CH₂(4-OMe-Ph) | Me | 2-thienyl | H |
| 9-316 | CH₂(4-OMe-Ph) | Me | 3-pyridyl | H |
| 9-317 | CH₂(4-OMe-Ph) | Me | 6-Me-pyridin-3-yl | H |
| 9-318 | CH₂(4-OMe-Ph) | Me | 4-Me-Ph | H |
| 9-319 | CH₂(4-OMe-Ph) | Me | 4-Br-Ph | H |
| 9-320 | CH₂(4-OMe-Ph) | Me | 4-F-Ph | H |
| 9-321 | CH₂(4-OMe-Ph) | Me | 5-Cl-pyridin-2-yl | H |
| 9-322 | CH₂(4-OMe-Ph) | Me | 5-Br-pyridin-2-yl | H |
| 9-323 | CH₂(4-OMe-Ph) | Me | 5-F-pyridin-2-yl | H |
| 9-324 | CH₂(4-OMe-Ph) | Me | 5-Me-pyridin-2-yl | H |
| 9-325 | CH₂(4-OMe-Ph) | Me | 2-pyridyl | H |
| 9-326 | CH₂(4-OMe-Ph) | Me | 4-pyridyl | H |
| 9-327 | 2,2-difluoroethyl | Me | Ph | H |
| 9-328 | 2,2-difluoroethyl | Me | 4-Cl-Ph | H |
| 9-329 | 2,2-difluoroethyl | Me | 2-thienyl | H |
| 9-330 | 2,2-difluoroethyl | Me | 2-pyridyl | H |
| 9-331 | Ph | Me | Ph | H |
| 9-332 | Ph | Me | 4-Cl-Ph | H |
| 9-333 | Ph | Me | 2-thienyl | H |
| 9-334 | Ph | Me | 2-pyridyl | H |
| 9-335 | 2-fluoroethyl | Me | Ph | H |
| 9-336 | 2-fluoroethyl | Me | 4-Cl-Ph | H |
| 9-337 | 2-fluoroethyl | Me | 2-thienyl | H |
| 9-338 | 2-fluoroethyl | Me | 2-pyridyl | H |
| 9-339 | 2,2,3,3,3-pentafluoropropyl | Me | Ph | H |
| 9-340 | 2,2,3,3,3-pentafluoropropyl | Me | 4-Cl-Ph | H |
| 9-341 | 2,2,3,3,3-pentafluoropropyl | Me | 2-thienyl | H |
| 9-342 | 2,2,3,3,3-pentafluoropropyl | Me | 2-pyridyl | H |
| 9-343 | 1-ethyl-5-methyl-1H-pyrazol-4-methyl | Me | Ph | H |
| 9-344 | 1-ethyl-5-methyl-1H-pyrazol-4-methyl | Me | 4-Cl-Ph | H |
| 9-345 | 1-ethyl-5-methyl-1H-pyrazol-4-methyl | Me | 2-thienyl | H |
| 9-346 | 1-ethyl-5-methyl-1H-pyrazol-4-methyl | Me | 2-pyridyl | H |
| 9-347 | but-3-yn-2-yl | Me | 5-Cl-pyridin-2-yl | H |
| 9-348 | but-3-yn-2-yl | Me | isoquinolin-3-yl | H |
| 9-349 | but-3-yn-2-yl | Me | quinolin-2-yl | H |
| 9-350 | but-3-yn-2-yl | Me | Ph | H |
| 9-351 | but-3-yn-2-yl | Me | 4-Cl-Ph | H |
| 9-352 | but-3-yn-2-yl | Me | 2-thienyl | H |
| 9-353 | but-3-yn-2-yl | Me | 3-pyridyl | H |

TABLE 9-continued

Compounds of the formula (Ic'''')

(Ic'''')

| No. | R¹ | R⁴ | R⁵ | (R⁶)ₙ |
|---|---|---|---|---|
| 9-354 | but-3-yn-2-yl | Me | 6-Me-pyridin-3-yl | H |
| 9-355 | but-3-yn-2-yl | Me | 4-Me-Ph | H |
| 9-356 | but-3-yn-2-yl | Me | 4-Br-Ph | H |
| 9-357 | but-3-yn-2-yl | Me | 4-F-Ph | H |
| 9-358 | but-3-yn-2-yl | Me | 5-Br-pyridin-2-yl | H |
| 9-359 | but-3-yn-2-yl | Me | 5-F-pyridin-2-yl | H |
| 9-360 | but-3-yn-2-yl | Me | 5-Me-pyridin-2-yl | H |
| 9-361 | but-3-yn-2-yl | Me | 2-pyridyl | H |
| 9-362 | but-3-yn-2-yl | Me | 4-pyridyl | H |
| 9-363 | Et | Me | isoquinolin-3-yl | H |
| 9-364 | Et | Me | quinolin-2-yl | H |

TABLE 10

Compounds of the formula (Id'')

(Id'')

| No. | R² | R³ | R⁴ | R⁵ | (R⁶)ₙ |
|---|---|---|---|---|---|
| 10-1 | H | H | Ph | Ph | H |
| 10-2 | H | H | Me | Ph | H |
| 10-3 | H | H | Me | 5-I-2-thienyl | H |
| 10-4 | H | H | Me | 2-furyl | H |
| 10-5 | H | H | Me | Ph | 3-OMe |
| 10-6 | Me | H | Me | Ph | 5-Me |
| 10-7 | H | H | Me | Ph | 3-Cl |
| 10-8 | H | H | Me | Ph | 5-CF₃ |
| 10-9 | H | H | Me | Ph | 3-CF₃ |
| 10-10 | H | H | Me | Ph | 5-Me |
| 10-11 | H | H | Me | Ph | 3,5-Me₂ |
| 10-12 | H | H | Me | Ph | 3,5-Cl₂ |
| 10-13 | H | H | Me | 4-MeO-Ph | 5-Me |
| 10-14 | H | H | Me | 4-MeO-Ph | H |
| 10-15 | Me | H | Me | Ph | H |
| 10-16 | H | H | Me | 4-Me-Ph | 5-Me |
| 10-17 | H | H | Me | 4-Me-Ph | 5-Cl |
| 10-18 | H | H | Me | 4-Me-Ph | H |
| 10-19 | H | H | Me | 3-Cl-Ph | H |
| 10-20 | H | H | Me | 3-CF₃-Ph | H |
| 10-21 | H | H | Me | 3-CF₃-Ph | 5-Me |
| 10-22 | H | H | Me | 3,4-Cl₂-Ph | 5-Me |
| 10-23 | H | H | Me | 3-Cl-Ph | 5-Me |

TABLE 10-continued

Compounds of the formula (Id")

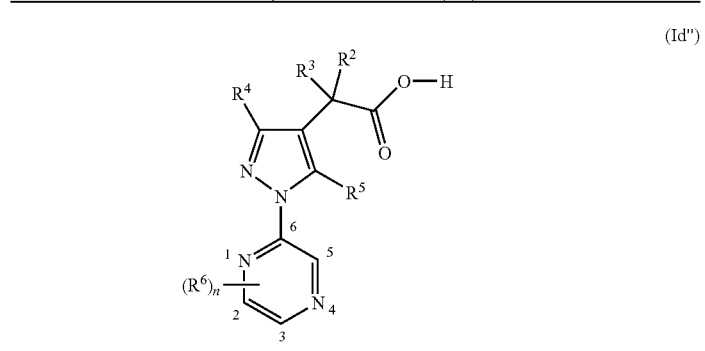

| No. | $R^2$ | $R^3$ | $R^4$ | $R^5$ | $(R^6)_n$ |
|---|---|---|---|---|---|
| 10-24 | H | H | Me | 2-Cl-Ph | 5-Me |
| 10-25 | H | H | Me | 2,4-Cl$_2$-Ph | 5-Me |
| 10-26 | H | H | Me | 4-CF$_3$-Ph | 5-Me |
| 10-27 | H | H | Me | 4-Cl-Ph | 5-Me |
| 10-28 | H | H | Me | 4-Cl-Ph | H |
| 10-29 | H | H | Me | 3,4-Cl$_2$-Ph | H |
| 10-30 | H | H | Me | 4-CF$_3$-Ph | H |
| 10-31 | H | H | Me | 4-Cl-Ph | 5-Cl |
| 10-32 | H | H | Me | Ph | 5-Cl |
| 10-33 | H | H | Me | 2-Cl-Ph | H |
| 10-34 | H | H | Me | 4-tBu-Ph | 5-Me |
| 10-35 | H | H | Me | 3,5-Me$_2$-Ph | 5-Me |
| 10-36 | H | H | Me | Ph | 5-OMe |
| 10-37 | H | H | Me | 4-Cl-Ph | 5-OMe |
| 10-38 | H | H | Me | 4-Me-Ph | 5-Me |
| 10-39 | H | H | Me | 4-F-Ph | 5-Cl |
| 10-40 | H | H | Me | 4-F-Ph | 5-Me |
| 10-41 | H | H | Me | 3-Me-Ph | 5-Me |
| 10-42 | H | H | Me | 4-(COOH)-Ph | 5-Me |
| 10-43 | H | H | Me | 3-Br-Ph | 5-Me |
| 10-44 | H | H | Me | 4-Ph-Ph | 5-Me |
| 10-45 | H | H | Me | 4-(COOH)-Ph | H |
| 10-46 | H | H | Me | 3,5-Me$_2$-Ph | H |
| 10-47 | H | H | Me | Ph | 5-SMe |
| 10-48 | H | H | Me | 4-Cl-Ph | 5-SMe |
| 10-49 | H | H | Me | 3-Cl-4-Me-Ph | H |
| 10-50 | H | H | Me | 3-CF$_3$-4-Cl-Ph | H |
| 10-51 | H | H | Me | 3-CF$_3$-4-Cl-Ph | 5-Me |
| 10-52 | H | H | Me | 3-Cl-4-Me-Ph | 5-Me |
| 10-53 | H | H | Me | 2-pyridyl | 5-Cl |
| 10-54 | H | H | Me | 4-Cl-Ph | 5-F |
| 10-55 | H | H | Me | 2-thienyl | 5-Me |
| 10-56 | H | H | Me | 3-Me-2-thienyl | 5-Me |
| 10-57 | H | H | Me | 4-Me-2-thienyl | 5-Me |
| 10-58 | H | H | Me | 5-Cl-2-thienyl | 5-Me |
| 10-59 | H | H | Me | 5-Cl-2-thienyl | 5-Cl |
| 10-60 | H | H | Me | 3-thienyl | 5-Me |
| 10-61 | H | H | Me | 2-thienyl | H |
| 10-62 | H | H | Me | 3-Me-2-thienyl | H |
| 10-63 | H | H | Me | 4-Me-2-thienyl | H |
| 10-64 | H | H | Me | 5-Cl-2-thienyl | H |
| 10-65 | H | H | Me | 5-Me-2-thienyl | H |
| 10-66 | H | H | Me | 6-MeO-pyridin-3-yl | H |
| 10-67 | H | H | Me | 5-Br-2-thienyl | H |
| 10-68 | H | H | Me | 5-Br-2-thienyl | 5-Me |
| 10-69 | H | H | Me | 3-thienyl | H |
| 10-70 | H | H | Me | 4-Cl-Ph | 5-S(O)Me |
| 10-71 | H | H | Me | 4-Br-Ph | 5-Me |
| 10-72 | H | H | Me | 1,3-benzodioxol-5-yl | 5-Me |
| 10-73 | H | H | Me | 4-I-Ph | 5-Me |
| 10-74 | H | H | Me | 3,5-Cl$_2$-Ph | 5-Me |
| 10-75 | H | H | Me | 4-PhO-Ph | 5-Me |
| 10-76 | H | H | Me | 6-OH-pyridin-3-yl | H |
| 10-77 | H | H | Me | Ph | 5-S(O)Me |
| 10-78 | H | H | H | Ph | H |
| 10-79 | H | H | H | Ph | 5-Me |
| 10-80 | H | H | Et | Ph | H |
| 10-81 | H | H | n-Pr | Ph | H |
| 10-82 | H | H | CH$_2$Cl | Ph | H |

TABLE 10-continued

Compounds of the formula (Id")

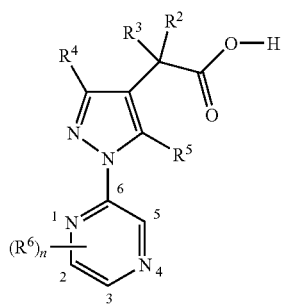

(Id")

| No. | R² | R³ | R⁴ | R⁵ | (R⁶)ₙ |
|---|---|---|---|---|---|
| 10-83 | H | H | CHCl₂ | Ph | H |
| 10-84 | H | H | CH₂F | Ph | H |
| 10-85 | H | H | CHF₂ | Ph | H |
| 10-86 | H | H | Cl | Ph | H |
| 10-87 | H | H | Et | Ph | 5-Me |
| 10-88 | H | H | n-Pr | Ph | 5-Me |
| 10-89 | H | H | CH₂Cl | Ph | 5-Me |
| 10-90 | H | H | CHCl₂ | Ph | 5-Me |
| 10-91 | H | H | CH₂F | Ph | 5-Me |
| 10-92 | H | H | CHF₂ | Ph | 5-Me |
| 10-93 | H | H | Cl | Ph | 5-Me |
| 10-94 | H | H | Et | 4-Cl-Ph | H |
| 10-95 | H | H | n-Pr | 4-Cl-Ph | H |
| 10-96 | H | H | CH₂Cl | 4-Cl-Ph | H |
| 10-97 | H | H | CHCl₂ | 4-Cl-Ph | H |
| 10-98 | H | H | CH₂F | 4-Cl-Ph | H |
| 10-99 | H | H | CHF₂ | 4-Cl-Ph | H |
| 10-100 | H | H | Cl | 4-Cl-Ph | H |
| 10-101 | H | H | Et | 4-Me-Ph | H |
| 10-102 | H | H | n-Pr | 4-Me-Ph | H |
| 10-103 | H | H | CH₂Cl | 4-Me-Ph | H |
| 10-104 | H | H | CHCl₂ | 4-Me-Ph | H |
| 10-105 | H | H | CH₂F | 4-Me-Ph | H |
| 10-106 | H | H | CHF₂ | 4-Me-Ph | H |
| 10-107 | H | H | Cl | 4-Me-Ph | H |
| 10-108 | H | H | Et | 2-pyridyl | H |
| 10-109 | H | H | n-Pr | 2-pyridyl | H |
| 10-110 | H | H | CH₂Cl | 2-pyridyl | H |
| 10-111 | H | H | CHCl₂ | 2-pyridyl | H |
| 10-112 | H | H | CH₂F | 2-pyridyl | H |
| 10-113 | H | H | CHF₂ | 2-pyridyl | H |
| 10-114 | H | H | Cl | 2-pyridyl | H |
| 10-115 | H | H | Me | 2-pyridyl | H |
| 10-116 | H | H | Me | 5-Cl-pyridin-2-yl | H |
| 10-117 | H | H | Me | 5-Cl-pyridin-2-yl | 5-Cl |
| 10-118 | H | H | Me | 5-Cl-pyridin-2-yl | 5-Me |
| 10-119 | H | H | Me | 5-Br-pyridin-2-yl | H |
| 10-120 | H | H | Me | 5-Br-pyridin-2-yl | 5-Cl |
| 10-121 | H | H | Me | 5-Br-pyridin-2-yl | 5-Me |
| 10-122 | H | H | Me | 5-F-pyridin-2-yl | H |
| 10-123 | H | H | Me | 5-Me-pyridin-2-yl | H |
| 10-124 | H | H | Me | 5-Me-pyridin-2-yl | 5-Me |
| 10-125 | H | H | Me | 2,4-Cl₂-Ph | H |
| 10-126 | H | H | Me | 4-CH₂COOH-Ph | 5-Me |
| 10-127 | H | H | Me | 3,4-Me₂-Ph | 5-Me |
| 10-128 | H | H | Me | 4-Br-Ph | H |
| 10-129 | H | H | Me | 3,4-Me₂-Ph | H |
| 10-130 | H | H | Me | 3-Me-Ph | H |
| 10-131 | H | H | Me | 4-F-Ph | H |
| 10-132 | H | H | Me | 4-(Me-CO)-Ph | H |
| 10-133 | H | H | Me | 4-tBu-Ph | H |
| 10-134 | H | H | Me | 4-Cl-3-Me-Ph | H |
| 10-135 | H | H | n-Pr | 4-Cl-Ph | 5-Me |
| 10-136 | H | H | Me | 3-pyridyl | H |
| 10-137 | H | H | Me | 4-pyridyl | H |
| 10-138 | H | H | C(O)OMe | Ph | H |
| 10-139 | H | H | Me | 6-Me-pyridin-3-yl | H |
| 10-140 | H | H | Me | 4-Cl-Ph | 5-SO₂Me |
| 10-141 | H | H | Me | 3-pyridyl | 5-Me |

TABLE 10-continued

Compounds of the formula (Id")

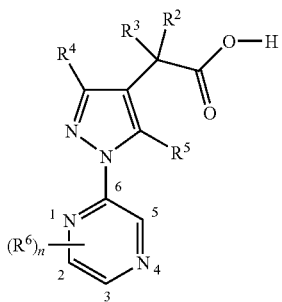

(Id")

| No. | R² | R³ | R⁴ | R⁵ | (R⁶)ₙ |
|---|---|---|---|---|---|
| 10-142 | H | H | Me | 2,3-Cl₂-Ph | 5-Me |
| 10-143 | H | H | Me | 2-pyridyl | 5-Me |
| 10-144 | H | H | H | 4-Cl-Ph | 5-Me |
| 10-145 | H | H | Me | 6-Cl-pyridin-3-yl | H |
| 10-146 | H | H | Me | Ph | 3-Me |
| 10-147 | H | H | Me | 4-Me-pyridin-2-yl | H |
| 10-148 | H | H | Me | 4-Me-pyridin-2-yl | 5-Me |
| 10-149 | H | H | Me | 4-Me-pyridin-2-yl | 5-Cl |
| 10-150 | H | H | Me | 4-Me-pyridin-2-yl | 5-F |
| 10-151 | H | H | Me | 4-F-pyridin-2-yl | H |
| 10-152 | H | H | Me | 4-Cl-pyridin-2-yl | H |
| 10-153 | H | H | Me | 4-Br-pyridin-2-yl | H |
| 10-154 | H | H | Me | 4-OMe-pyridin-2-yl | H |
| 10-155 | H | H | Me | 5-CF₃-pyridin-2-yl | H |
| 10-156 | H | H | Me | 6-OMe-pyridin-2-yl | H |
| 10-157 | H | H | cyPr | 4-Cl-Ph | H |
| 10-158 | H | H | CN | 4-Cl-Ph | H |
| 10-159 | H | H | CN | 4-Cl-Ph | 5-Me |
| 10-160 | H | H | CN | 4-Me-Ph | H |
| 10-161 | H | H | CN | 4-Me-Ph | 5-Me |
| 10-162 | H | H | CN | Ph | H |
| 10-163 | H | H | CN | Ph | 5-Me |
| 10-164 | H | H | CN | 2-pyridyl | H |
| 10-165 | H | H | CN | 3-pyridyl | H |
| 10-166 | H | H | CN | 5-Cl-pyridin-2-yl | H |
| 10-167 | H | H | CN | 5-Br-pyridin-2-yl | H |
| 10-168 | H | H | CN | 5-F-pyridin-2-yl | H |
| 10-169 | H | H | CN | 5-Me-pyridin-2-yl | H |
| 10-170 | H | H | CN | 6-Me-pyridin-3-yl | H |
| 10-171 | H | H | CN | 4-Me-pyridin-2-yl | H |
| 10-172 | H | H | CN | 4-F-pyridin-2-yl | H |
| 10-173 | H | H | CN | 4-Cl-pyridin-2-yl | H |
| 10-174 | H | H | CN | 4-Br-pyridin-2-yl | H |
| 10-175 | H | H | CN | 4-OMe-pyridin-2-yl | H |
| 10-176 | H | H | formyl | 4-Cl-Ph | H |
| 10-177 | H | H | formyl | 4-Cl-Ph | 5-Me |
| 10-178 | H | H | formyl | 4-Me-Ph | H |
| 10-179 | H | H | formyl | 4-Me-Ph | 5-Me |
| 10-180 | H | H | formyl | Ph | H |
| 10-181 | H | H | formyl | Ph | 5-Me |
| 10-182 | H | H | formyl | 2-pyridyl | H |
| 10-183 | H | H | formyl | 3-pyridyl | H |
| 10-184 | H | H | formyl | 5-Cl-pyridin-2-yl | H |
| 10-185 | H | H | formyl | 5-Br-pyridin-2-yl | H |
| 10-186 | H | H | formyl | 5-F-pyridin-2-yl | H |
| 10-187 | H | H | formyl | 5-Me-pyridin-2-yl | H |
| 10-188 | H | H | formyl | 6-Me-pyridin-3-yl | H |
| 10-189 | H | H | formyl | 4-Me-pyridin-2-yl | H |
| 10-190 | H | H | formyl | 4-F-pyridin-2-yl | H |
| 10-191 | H | H | formyl | 4-Cl-pyridin-2-yl | H |
| 10-192 | H | H | formyl | 4-Br-pryidin-2-yl | H |
| 10-193 | H | H | formyl | 4-OMe-pyridin-2-yl | H |
| 10-194 | H | H | CH₂OH | 5-Me-pyridin-2-yl | H |
| 10-195 | H | H | CH₂OH | 4-Cl-Ph | H |
| 10-196 | H | H | CH₂OH | 4-Me-pyridin-2-yl | H |
| 10-197 | H | H | CH₂OH | 4-Me-Ph | H |
| 10-198 | H | H | CH₂OH | Ph | H |
| 10-199 | H | H | CH₂OH | 2-pyridyl | H |
| 10-200 | H | H | Me | 2-thiazolyl | H |

TABLE 10-continued

Compounds of the formula (Id")

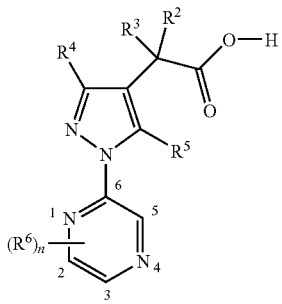

(Id")

| No. | R² | R³ | R⁴ | R⁵ | (R⁶)ₙ |
|---|---|---|---|---|---|
| 10-201 | H | H | Me | 2-thiazolyl | 5-Cl |
| 10-202 | H | H | Me | 2-thiazolyl | 5-Me |
| 10-203 | H | H | Me | 4-Me-thiazol-2-yl | H |
| 10-204 | H | H | Me | 4-Me-thiazol-2-yl | 5-Cl |
| 10-205 | H | H | Me | 4-Me-thiazol-2-yl | 5-Me |
| 10-206 | H | H | Me | 5-Me-thiazol-2-yl | H |
| 10-207 | H | H | Me | 5-Br-thiazol-2-yl | H |
| 10-208 | H | H | Me | 5-Br-thiazol-2-yl | 5-Me |
| 10-209 | H | H | Me | 5-Cl-thiazol-2-yl | H |
| 10-210 | H | H | Me | 4,6-Me₂-pyridin-2-yl | H |
| 10-211 | H | H | Me | 4,6-Me₂-pyridin-2-yl | 5-Me |
| 10-212 | H | H | Me | 2-pyridyl | 5-F |
| 10-213 | H | H | Me | 2-pyrazinyl | H |
| 10-214 | H | H | Me | 5-Me-pyrazin-2-yl | H |
| 10-215 | H | H | Me | 2-pyrazinyl | 5-Me |
| 10-216 | H | H | Me | 1,3-benzothiazol-2-yl | H |
| 10-217 | H | H | Me | 1,3-benzothiazol-2-yl | 5-Me |
| 10-218 | H | H | Me | 7-Cl-1,3-benzothiazol-2-yl | H |
| 10-219 | H | H | Me | 1,5-Me₂-pyrazol-3-yl | H |
| 10-220 | H | H | Me | 1,5-Me₂-pyrazol-3-yl | 5-Me |
| 10-221 | H | H | Me | 4,5-Me₂-thiazol-2-yl | H |
| 10-222 | H | H | Me | 4,5-Cl₂-thiazol-2-yl | H |
| 10-223 | H | H | Me | 2-pyrimidinyl | H |
| 10-224 | H | H | Me | 2-pyrimidinyl | 5-Me |
| 10-225 | H | H | Me | 5-F-pyrimidin-2-yl | H |
| 10-226 | H | H | Me | 5-Cl-pyrimidin-2-yl | H |
| 10-227 | H | H | Me | 5-Br-pyrimidin-2-yl | H |
| 10-228 | H | H | Me | 5-Me-pyrimidin-2-yl | H |
| 10-229 | H | H | Me | 5-Me-pyrimidin-2-yl | 5-Me |
| 10-230 | H | H | Me | 4,6-Me₂-pyrimidin-2-yl | H |
| 10-231 | H | H | Me | 4,6-Me₂-pyrimidin-2-yl | 5-Me |
| 10-232 | H | H | Me | 3-pyridazinyl | H |
| 10-233 | H | H | Me | 6-Me-pyridazin-3-yl | H |
| 10-234 | H | H | Me | 1,2,4-triazin-3-yl | H |
| 10-235 | H | H | Me | 6-Me-1,2,4-triazin-3-yl | H |
| 10-236 | H | H | Me | 4-Cl-Ph | 2-OMe |
| 10-237 | Me | H | Me | 2-pyridyl | 2-OMe |
| 10-238 | Me | H | Me | 4-Cl-Ph | 2-OMe |
| 10-239 | H | H | Me | 3,5-Cl₂-Ph | H |
| 10-240 | H | H | Me | isoquinolin-3-yl | H |
| 10-241 | H | H | Me | quinolin-2-yl | H |

In addition, NMR data of compounds of the general formula (I) according to the invention were generated. The NMR of the exemplary compounds were in each case recorded as ¹H-NMR spectum at 400 MHz (CDCl₃) (¹H nuclear magnetic resonance data). Characteristic chemical shifts δ (ppm) for some exemplary compounds are listed below:

NMR compound 10-236 (CDCl₃, 400 MHz, δ in ppm): 2.39 (s, 3H); 3.23 (s, 3H); 3.39 (s, 2H); 7.24 (d, 2H); 7.38 (d, 2H); 8.01 (d, 1H); 8.63 (d, 1H).m.p.: 169-171° C.

NMR compound 10-237 (CDCl₃, 400 MHz, δ in ppm): 1.51 (d, 3H); 2.49 (s, 3H); 3.29 (s, 3H); 3.72 (q, 1H); 7.30 (m, 1H); 7.46 (m, 1H); 7.82 (m, 1H); 8.10 (d, 1H); 8.64 (d, 1H); 8.70 (m, 1H); 14.32 (brs, 1H).

NMR compound 10-238 (CDCl₃, 400 MHz, δ in ppm):

1.40 (d, 3H); 2.42 (s, 3H); 3.24 (s, 3H); 3.58 (q, 1H); 7.25 (d, 2H); 7.38 (d, 2H); 7.98 (d, 1H); 8.62 (d, 1H). m.p.:176-178° C.

TABLE 11

Compounds of the formula (Id''')

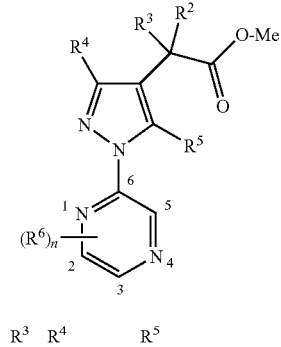

| No. | R² | R³ | R⁴ | R⁵ | (R⁶)ₙ |
|---|---|---|---|---|---|
| 11-1 | H | H | Ph | Ph | H |
| 11-2 | H | H | Me | Ph | H |
| 11-3 | H | H | Me | 5-I-2-thienyl | H |
| 11-4 | H | H | Me | 2-furyl | H |
| 11-5 | H | H | Me | Ph | 3-OMe |
| 11-6 | Me | H | Me | Ph | 5-Me |
| 11-7 | H | H | Me | Ph | 3-Cl |
| 11-8 | H | H | Me | Ph | 5-CF₃ |
| 11-9 | H | H | Me | Ph | 3-CF₃ |
| 11-10 | H | H | Me | Ph | 5-Me |
| 11-11 | H | H | Me | Ph | 3,5-Me₂ |
| 11-12 | H | H | Me | Ph | 3,5-Cl₂ |
| 11-13 | H | H | Me | 4-MeO-Ph | 5-Me |
| 11-14 | H | H | Me | 4-MeO-Ph | H |
| 11-15 | Me | H | Me | Ph | H |
| 11-16 | H | H | Me | 4-Me-Ph | H |
| 11-17 | H | H | Me | 4-Me-Ph | 5-Me |
| 11-18 | H | H | Me | 4-Me-Ph | 5-Cl |
| 11-19 | H | H | Me | 3-Cl-Ph | H |
| 11-20 | H | H | Me | 3-CF₃-Ph | H |
| 11-21 | H | H | Me | 3-CF₃-Ph | 5-Me |
| 11-22 | H | H | Me | 3,4-Cl₂-Ph | 5-Me |
| 11-23 | H | H | Me | 3-Cl-Ph | 5-Me |
| 11-24 | H | H | Me | 2-Cl-Ph | 5-Me |
| 11-25 | H | H | Me | 2,4-Cl₂-Ph | 5-Me |
| 11-26 | H | H | Me | 4-CF₃-Ph | 5-Me |
| 11-27 | H | H | Me | 4-Cl-Ph | 5-Me |
| 11-28 | H | H | Me | 4-Cl-Ph | H |
| 11-29 | H | H | Me | 3,4-Cl₂-Ph | H |
| 11-30 | H | H | Me | 4-CF₃-Ph | H |
| 11-31 | H | H | Me | 4-Cl-Ph | 5-Cl |
| 11-32 | H | H | Me | Ph | 5-Cl |
| 11-33 | H | H | Me | 2-Cl-Ph | H |
| 11-34 | H | H | Me | 4-tBu-Ph | 5-Me |
| 11-35 | H | H | Me | 3,5-Me₂-Ph | 5-Me |
| 11-36 | H | H | Me | Ph | 5-OMe |
| 11-37 | H | H | Me | 4-Cl-Ph | 5-OMe |
| 11-38 | H | H | Me | 4-Me-Ph | 5-Me |
| 11-39 | H | H | Me | 4-F-Ph | 5-Me |
| 11-40 | H | H | Me | 4-F-Ph | 5-Cl |
| 11-41 | H | H | Me | 3-Me-Ph | 5-Me |
| 11-42 | H | H | Me | 4-COOH-Ph | 5-Me |
| 11-43 | H | H | Me | 3-Br-Ph | 5-Me |
| 11-44 | H | H | Me | 4-Ph-Ph | 5-Me |
| 11-45 | H | H | Me | 4-COOH-Ph | H |
| 11-46 | H | H | Me | 3,5-Me₂-Ph | H |
| 11-47 | H | H | Me | Ph | 5-SMe |
| 11-48 | H | H | Me | 4-Cl-Ph | 5-SMe |
| 11-49 | H | H | Me | 3-Cl-4-Me-Ph | H |
| 11-50 | H | H | Me | 3-CF₃-4-Cl-Ph | H |
| 11-51 | H | H | Me | 3-CF₃-4-Cl-Ph | 5-Me |
| 11-52 | H | H | Me | 3-Cl-4-Me-Ph | 5-Me |
| 11-53 | H | H | Me | 2-pyridyl | 5-Cl |
| 11-54 | H | H | Me | 4-Cl-Ph | 5-F |
| 11-55 | H | H | Me | 2-thienyl | 5-Me |
| 11-56 | H | H | Me | 3-Me-2-thienyl | 5-Me |
| 11-57 | H | H | Me | 4-Me-2-thienyl | 5-Me |
| 11-58 | H | H | Me | 5-Cl-2-thienyl | 5-Me |
| 11-59 | H | H | Me | 5-Cl-2-thienyl | 5-Cl |
| 11-60 | H | H | Me | 3-thienyl | 5-Me |
| 11-61 | H | H | Me | 2-thienyl | H |
| 11-62 | H | H | Me | 3-Me-2-thienyl | H |
| 11-63 | H | H | Me | 4-Me-2-thienyl | H |
| 11-64 | H | H | Me | 5-Cl-2-thienyl | H |
| 11-65 | H | H | Me | 5-Me-2-thienyl | H |
| 11-66 | H | H | Me | 6-MeO-pyridin-3-yl | H |
| 11-67 | H | H | Me | 5-Br-2-thienyl | H |
| 11-68 | H | H | Me | 5-Br-2-thienyl | 5-Me |
| 11-69 | H | H | Me | 3-thienyl | H |
| 11-70 | H | H | Me | 4-Cl-Ph | 5-S(O)Me |
| 11-71 | H | H | Me | 4-Br-Ph | 5-Me |
| 11-72 | H | H | Me | 1,3-benzodioxol-5-yl | 5-Me |
| 11-73 | H | H | Me | 4-I-Ph | 5-Me |
| 11-74 | H | H | Me | 3,5-Cl₂-Ph | 5-Me |
| 11-75 | H | H | Me | 4-PhO-Ph | 5-Me |
| 11-76 | H | H | Me | 6-OH-pyridin-3-yl | H |
| 11-77 | H | H | Me | Ph | 5-S(O)Me |
| 11-78 | H | H | H | Ph | H |
| 11-79 | H | H | H | Ph | 5-Me |
| 11-80 | H | H | Et | Ph | H |
| 11-81 | H | H | n-Pr | Ph | H |
| 11-82 | H | H | CH₂Cl | Ph | H |
| 11-83 | H | H | CHCl₂ | Ph | H |
| 11-84 | H | H | CH₂F | Ph | H |
| 11-85 | H | H | CHF₂ | Ph | H |
| 11-86 | H | H | Cl | Ph | H |
| 11-87 | H | H | Et | Ph | 5-Me |
| 11-88 | H | H | n-Pr | Ph | 5-Me |
| 11-89 | H | H | CH₂Cl | Ph | 5-Me |
| 11-90 | H | H | CHCl₂ | Ph | 5-Me |
| 11-91 | H | H | CH₂F | Ph | 5-Me |
| 11-92 | H | H | CHF₂ | Ph | 5-Me |
| 11-93 | H | H | Cl | Ph | 5-Me |
| 11-94 | H | H | Et | 4-Cl-Ph | H |
| 11-95 | H | H | n-Pr | 4-Cl-Ph | H |
| 11-96 | H | H | CH₂Cl | 4-Cl-Ph | H |
| 11-97 | H | H | CHCl₂ | 4-Cl-Ph | H |
| 11-98 | H | H | CH₂F | 4-Cl-Ph | H |
| 11-99 | H | H | CHF₂ | 4-Cl-Ph | H |
| 11-100 | H | H | Cl | 4-Cl-Ph | H |
| 11-101 | H | H | Et | 4-Me-Ph | H |
| 11-102 | H | H | n-Pr | 4-Me-Ph | H |
| 11-103 | H | H | CH₂Cl | 4-Me-Ph | H |
| 11-104 | H | H | CHCl₂ | 4-Me-Ph | H |
| 11-105 | H | H | CH₂F | 4-Me-Ph | H |
| 11-106 | H | H | CHF₂ | 4-Me-Ph | H |
| 11-107 | H | H | Cl | 4-Me-Ph | H |
| 11-108 | H | H | Et | 2-pyridyl | H |

TABLE 11-continued

Compounds of the formula (Id''')

| No. | R² | R³ | R⁴ | R⁵ | (R⁶)ₙ |
|---|---|---|---|---|---|
| 11-109 | H | H | n-Pr | 2-pyridyl | H |
| 11-110 | H | H | CH₂Cl | 2-pyridyl | H |
| 11-111 | H | H | CHCl₂ | 2-pyridyl | H |
| 11-112 | H | H | CH₂F | 2-pyridyl | H |
| 11-113 | H | H | CHF₂ | 2-pyridyl | H |
| 11-114 | H | H | Cl | 2-pyridyl | H |
| 11-115 | H | H | Me | 2-pyridyl | H |
| 11-116 | H | H | Me | 5-Cl-pyridin-2-yl | H |
| 11-117 | H | H | Me | 5-Cl-pyridin-2-yl | 5-Cl |
| 11-118 | H | H | Me⁻ | 5-Cl-pyridin-2-yl | 5-Me |
| 11-119 | H | H | Me | 5-Br-pyridin-2-yl | H |
| 11-120 | H | H | Me | 5-Br-pyridin-2-yl | 5-Cl |
| 11-121 | H | H | Me | 5-Br-pyridin-2-yl | 5-Me |
| 11-122 | H | H | Me | 5-F-pyridin-2-yl | H |
| 11-123 | H | H | Me | 5-Me-pyridin-2-yl | H |
| 11-124 | H | H | Me | 5-Me-pyridin-2-yl | 5-Me |
| 11-125 | H | H | Me | 2,4-Cl₂-Ph | H |
| 11-126 | H | H | Me | 4-(CH₂COOH)-Ph | 5-Me |
| 11-127 | H | H | Me | 3,4-Me₂-Ph | 5-Me |
| 11-128 | H | H | Me | 4-Br-Ph | 5-Me |
| 11-129 | H | H | Me | 3,4-Me₂-Ph | H |
| 11-130 | H | H | Me | 3-Me-Ph | H |
| 11-131 | H | H | Me | 4-F-Ph | H |
| 11-132 | H | H | Me | 4-(Me-CO)-Ph | H |
| 11-133 | H | H | Me | 4-tBu-Ph | H |
| 11-134 | H | H | Me | 4-Cl-3-Me-Ph | H |
| 11-135 | H | H | n-Pr | 4-Cl-Ph | 5-Me |
| 11-136 | H | H | Me | 3-pyridyl | H |
| 11-137 | H | H | Me | 4-pyridyl | H |
| 11-138 | H | H | C(O)OMe | Ph | H |
| 11-139 | H | H | Me | 6-Me-pyridin-3-yl | H |
| 11-140 | H | H | Me | 4-Cl-Ph | 5-SO₂Me |
| 11-141 | H | H | Me | 3-pyridyl | 5-Me |
| 11-142 | H | H | Me | 2,3-Cl₂-Ph | 5-Me |
| 11-143 | H | H | Me | 2-pyridyl | 5-Me |
| 11-144 | H | H | H | 4-Cl-Ph | 5-Me |
| 11-145 | H | H | Me | 6-Cl-pyridin-3-yl | H |
| 11-146 | H | H | Me | Ph | 5-Me |
| 11-147 | H | H | Me | 4-Me-pyridin-2-yl | H |
| 11-148 | H | H | Me | 4-Me-pyridin-2-yl | 5-Me |
| 11-149 | H | H | Me | 4-Me-pyridin-2-yl | 5-Cl |
| 11-150 | H | H | Me | 4-Me-pyridin-2-yl | 5-F |
| 11-151 | H | H | Me | 4-F-pyridin-2-yl | H |
| 11-152 | H | H | Me | 4-Cl-pyridin-2-yl | H |
| 11-153 | H | H | Me | 4-Br-pyridin-2-yl | H |
| 11-154 | H | H | Me | 4-OMe-pyridin-2-yl | H |
| 11-155 | H | H | Me | 5-CF₃-pyridin-2-yl | H |
| 11-156 | H | H | Me | 6-OMe-pyridin-2-yl | H |
| 11-157 | H | H | cyPr | 4-Cl-Ph | H |
| 11-158 | H | H | CN | 4-Cl-Ph | H |
| 11-159 | H | H | CN | 4-Cl-Ph | 5-Me |
| 11-160 | H | H | CN | 4-Me-Ph | H |
| 11-161 | H | H | CN | 4-Me-Ph | 5-Me |
| 11-162 | H | H | CN | Ph | H |
| 11-163 | H | H | CN | Ph | 5-Me |
| 11-164 | H | H | CN | 2-pyridyl | H |
| 11-165 | H | H | CN | 3-pyridyl | H |
| 11-166 | H | H | CN | 5-Cl-pyridin-2-yl | H |
| 11-167 | H | H | CN | 5-Br-pyridin-2-yl | H |
| 11-168 | H | H | CN | 5-F-pyridin-2-yl | H |
| 11-169 | H | H | CN | 5-Me-pyridin-2-yl | H |
| 11-170 | H | H | CN | 6-Me-pyridin-3-yl | H |
| 11-171 | H | H | CN | 4-Me-pyridin-2-yl | H |
| 11-172 | H | H | CN | 4-F-pyridin-2-yl | H |
| 11-173 | H | H | CN | 4-Cl-pyridin-2-yl | H |
| 11-174 | H | H | CN | 4-Br-pyridin-2-yl | H |
| 11-175 | H | H | CN | 4-OMe-pyridin-2-yl | H |
| 11-176 | H | H | formyl | 4-Cl-Ph | H |
| 11-177 | H | H | formyl | 4-Cl-Ph | 5-Me |
| 11-178 | H | H | formyl | 4-Me-Ph | H |
| 11-179 | H | H | formyl | 4-Me-Ph | 5-Me |
| 11-180 | H | H | formyl | Ph | H |
| 11-181 | H | H | formyl | Ph | 5-Me |
| 11-182 | H | H | formyl | 2-pyridyl | H |
| 11-183 | H | H | formyl | 3-pyridyl | H |
| 11-184 | H | H | formyl | 5-Cl-pyridin-2-yl | H |
| 11-185 | H | H | formyl | 5-Br-pyridin-2-yl | H |
| 11-186 | H | H | formyl | 5-F-pyridin-2-yl | H |
| 11-187 | H | H | formyl | 5-Me-pyridin-2-yl | H |
| 11-188 | H | H | formyl | 6-Me-pyridin-3-yl | H |
| 11-189 | H | H | formyl | 4-Me-pyridin-2-yl | H |
| 11-190 | H | H | formyl | 4-F-pyridin-2-yl | H |
| 11-191 | H | H | formyl | 4-Cl-pyridin-2-yl | H |
| 11-192 | H | H | formyl | 4-Br-pyridin-2-yl | H |
| 11-193 | H | H | formyl | 4-OMe-pyridin-2-yl | H |
| 11-194 | H | H | CH₂OH | 5-Me-pyridin-2-yl | H |
| 11-195 | H | H | CH₂OH | 4-Cl-Ph | H |
| 11-196 | H | H | CH₂OH | 4-Me-pyridin-2-yl | H |
| 11-197 | H | H | CH₂OH | 4-Me-Ph | H |
| 11-198 | H | H | CH₂OH | Ph | H |
| 11-199 | H | H | CH₂OH | 2-pyridyl | H |
| 11-200 | H | H | Me | 2-thiazolyl | H |
| 11-201 | H | H | Me | 2-thiazolyl | 5-Cl |
| 11-202 | H | H | Me | 2-thiazolyl | 5-Me |
| 11-203 | H | H | Me | 4-Me-thiazol-2-yl | H |
| 11-204 | H | H | Me | 4-Me-thiazol-2-yl | 5-Cl |
| 11-205 | H | H | Me | 4-Me-thiazol-2-yl | 5-Me |
| 11-206 | H | H | Me | 5-Me-thiazol-2-yl | H |
| 11-207 | H | H | Me | 5-Br-thiazol-2-yl | H |
| 11-208 | H | H | Me | 5-Br-thiazol-2-yl | 5-Me |
| 11-209 | H | H | Me | 5-Cl-thiazol-2-yl | H |
| 11-210 | H | H | Me | 4,6-Me₂-pyridin-2-yl | H |
| 11-211 | H | H | Me | 4,6-Me₂-pyridin-2-yl | 5-Me |
| 11-212 | H | H | Me | 2-pyridyl | 5-F |
| 11-213 | H | H | Me | 2-pyrazinyl | H |
| 11-214 | H | H | Me | 5-Me-pyrazin-2-yl | H |
| 11-215 | H | H | Me | 2-pyrazinyl | 5-Me |
| 11-216 | H | H | Me | 1,3-benzothiazol-2-yl | H |
| 11-217 | H | H | Me | 1,3-benzothiazol-2-yl | 5-Me |
| 11-218 | H | H | Me | 7-Cl-1,3-benzothiazol-2-yl | H |
| 11-219 | H | H | Me | 1,5-Me₂-pyrazol-3-yl | H |
| 11-220 | H | H | Me | 1,5-Me₂-pyrazol-3-yl | 5-Me |
| 11-221 | H | H | Me | 4,5-Me₂-thiazol-2-yl | H |
| 11-222 | H | H | Me | 4,5-Cl₂-thiazol-2-yl | H |

TABLE 11-continued

Compounds of the formula (Id''')

(Id''')

| No. | R² | R³ | R⁴ | R⁵ | (R⁶)ₙ |
|---|---|---|---|---|---|
| 11-223 | H | H | Me | 2-pyrimidinyl | H |
| 11-224 | H | H | Me | 2-pyrimidinyl | 5-Me |
| 11-225 | H | H | Me | 5-F-pyrimidin-2-yl | H |
| 11-226 | H | H | Me | 5-Cl-pyrimidin-2-yl | H |
| 11-227 | H | H | Me | 5-Br-pyrimidin-2-yl | H |
| 11-228 | H | H | Me | 5-Me-pyrimidin-2-yl | H |
| 11-229 | H | H | Me | 5-Me-pyrimidin-2-yl | 5-Me |
| 11-230 | H | H | Me | 4,6-Me₂-pyrimidin-2-yl | H |
| 11-231 | H | H | Me | 4,6-Me₂-pyrimidin-2-yl | 5-Me |
| 11-232 | H | H | Me | 3-pyridazinyl | H |
| 11-233 | H | H | Me | 6-Me-pyridazin-3-yl | H |
| 11-234 | H | H | Me | 1,2,4-triazin-3-yl | H |
| 11-235 | H | H | Me | 6-Me-1,2,4-triazin-3-yl | H |
| 11-236 | Me | H | Me | 2-pyridyl | 2-Cl |
| 11-237 | H | H | Me | 4-Cl-Ph | 2-Cl |
| 11-238 | Me | H | Me | 4-Cl-Ph | 2-Cl |
| 11-239 | H | H | Me | 3,5-Cl₂-Ph | H |
| 11-240 | H | H | Me | isoquinolin-3-yl | H |
| 11-241 | H | H | Me | quinolin-2-yl | H |

In addition, NMR data of compounds of the general formula (I) according to the invention were generated. The NMR of the exemplary compounds were in each case recorded as ¹H-NMR spectrum at 400 MHz (CDCl₃) (¹H nuclear magnetic resonance data). Characteristic chemical shifts δ (ppm) for some exemplary compounds are listed below:

NMR compound 11-236 (CDCl₃, 400 MHz, δ in ppm):

1.42 (d, 3H); 2.39 (s, 3H); 3.65 (s, 3H); 3.72 (q, 1H); 7.35 (m, 1H); 7.44 (m, 1H); 7.80 (m, 1H); 8.31 (m, 1H); 8.61 (m, 1H); 8.98 (m, 1H).

NMR compound 11-28 (CDCl₃, 400 MHz, δ in ppm):

2.37 (s, 3H); 3.38 (s, 2H); 3.70 (s, 3H); 7.20 (d, 2H); 7.36 (d, 2H); 8.17 (dd, 1H); 8.38 (d, 1H); 8.86 (d, 1H).

NMR compound 11-237 (CDCl₃, 400 MHz, δ in ppm):

2.36 (s, 3H); 3.36 (s, 2H); 3.69 (s, 3H); 7.22 (d, 2H); 7.39 (d, 2H); 8.34 (d, 1H); 8.85 (d, 1H).m.p.:126-128° C.

NMR compound 11-238 (CDCl₃, 400 MHz, δ in ppm):

1.40 (d, 3H); 2.37 (s, 3H); 3.56 (q, 1H); 3.68 (s, 3H); 7.22 (d, 2H); 7.40 (d, 2H); 8.33 (d, 1H); 8.82 (d, 1H).

TABLE 12

Compounds of the formula (Id'''')

(Id'''')

| No. | R¹ | R⁴ | R⁵ | (R⁶)ₙ |
|---|---|---|---|---|
| 12-1 | Et | Me | Ph | H |
| 12-2 | Et | Me | Ph | 5-Me |
| 12-3 | Et | Me | 3-Cl-Ph | H |
| 12-4 | Et | Me | 4-Cl-Ph | H |
| 12-5 | Et | Me | 4-Cl-Ph | 5-Me |
| 12-6 | Et | Me | 2-thienyl | H |
| 12-7 | Et | Me | 3-thienyl | H |
| 12-8 | Et | Me | 3-Me-2-thienyl | H |
| 12-9 | Et | Me | 4-Me-2-thienyl | H |
| 12-10 | Et | Me | 5-Br-2-thienyl | H |
| 12-11 | Et | Me | 5-Br-2-thienyl | 5-Me |
| 12-12 | Et | Me | 5-Cl-2-thienyl | H |
| 12-13 | Et | Me | 5-Cl-2-thienyl | 5-Me |
| 12-14 | Et | Me | 5-I-2-thienyl | H |
| 12-15 | Et | Me | 5-Me-2-thienyl | H |
| 12-16 | Et | Me | 3-pyridyl | H |
| 12-17 | Et | Me | 6-MeO-pyridin-3-yl | H |
| 12-18 | Et | Me | 6-OH-pyridin-3-yl | H |
| 12-19 | Et | Me | 6-Me-pyridin-3-yl | H |
| 12-20 | Et | Me | 4-Me-Ph | H |
| 12-21 | Et | Me | 4-Me-Ph | 5-Me |
| 12-22 | Et | Me | 4-Br-Ph | H |
| 12-23 | Et | Me | 4-F-Ph | H |
| 12-24 | Et | Me | 4-F-Ph | 5-Me |
| 12-25 | Et | Me | 5-Cl-pyridin-2-yl | H |
| 12-26 | Et | Me | 5-Br-pyridin-2-yl | H |
| 12-27 | Et | Me | 5-F-pyridin-2-yl | H |
| 12-28 | Et | Me | 5-F-pyridin-2-yl | 5-Me |
| 12-29 | Et | Me | 5-Cl-pyridin-2-yl | 5-Me |
| 12-30 | Et | Me | 5-Br-pyridin-2-yl | 5-Me |
| 12-31 | Et | Me | 5-Me-pyridin-2-yl | H |
| 12-32 | Et | Me | 5-Me-pyridin-2-yl | 5-Me |
| 12-33 | Et | Me | 2-pyridyl | 5-Me |
| 12-34 | Et | Me | 2-pyridyl | H |
| 12-35 | Et | Me | 4-pyridyl | H |
| 12-36 | Et | Me | 4-Me-pyridin-2-yl | H |
| 12-37 | Et | Me | 4-Me-pyridin-2-yl | 5-Me |
| 12-38 | Et | Me | 2-thiazolyl | H |
| 12-39 | Et | Me | 4-Me-thiazol-2-yl | H |
| 12-40 | Et | Me | 5-Br-thiazol-2-yl | H |
| 12-41 | Et | Me | 5-Cl-thiazol-2-yl | H |
| 12-42 | Et | Me | 5-Me-thiazol-2-yl | H |
| 12-43 | Et | Me | 4,5-Me₂-thiazol-2-yl | H |
| 12-44 | Et | Me | 4,5-Cl₂-thiazol-2-yl | H |
| 12-45 | Et | Me | 4,6 Me₂-pyridin-2-yl | H |
| 12-46 | Et | Me | 2-pyrazinyl | H |
| 12-47 | Et | Me | 2-pyrimidinyl | H |
| 12-48 | Et | Me | 2-pyrimidinyl | 5-Me |
| 12-49 | Et | Me | 5-Cl-pyrimidin-2-yl | H |
| 12-50 | Et | Me | 5-Br-pyrimidin-2-yl | H |

TABLE 12-continued

Compounds of the formula (Id'''')

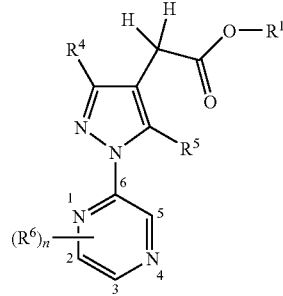

| No. | R¹ | R⁴ | R⁵ | (R⁶)ₙ |
|---|---|---|---|---|
| 12-51 | Et | Me | 5-Me-pyrimidin-2-yl | H |
| 12-52 | Et | Me | 5-Me-pyrimidin-2-yl | 5-Me |
| 12-53 | Et | Me | 4,6-Me₂-pyrimidin-2-yl | H |
| 12-54 | Et | Me | 4,6-Me₂-pyrimidin-2-yl | 5-Me |
| 12-55 | Et | Me | 1,3-benzothiazol-2-yl | H |
| 12-56 | Et | Me | 7-Cl-1,3-benzothiazol-2-yl | H |
| 12-57 | Et | Me | 1,5-Me₂-pyrazol-3-yl | H |
| 12-58 | Et | Me | 5-Me-pyrazin-2-yl | H |
| 12-59 | Et | Me | 5-F-pyrimidin-2-yl | H |
| 12-60 | Et | Me | 4,6-Me₂-pyrimidin-2-yl | H |
| 12-61 | Et | Me | 3-pyridazinyl | H |
| 12-62 | Et | Me | 6-Me-pyridazin-3-yl | H |
| 12-63 | Et | Me | 1,2,4-triazin-3-yl | H |
| 12-64 | Et | Me | 6-Me-1,2,4-triazin-3-yl | H |
| 12-65 | Pr | Me | Ph | H |
| 12-66 | Pr | Me | 4-Cl-Ph | H |
| 12-67 | Pr | Me | 2-thienyl | H |
| 12-68 | Pr | Me | 3-pyridyl | H |
| 12-69 | Pr | Me | 6-Me-pyridin-3-yl | H |
| 12-70 | Pr | Me | 4-Me-Ph | H |
| 12-71 | Pr | Me | 4-Br-Ph | H |
| 12-72 | Pr | Me | 4-F-Ph | H |
| 12-73 | Pr | Me | 5-Cl-pyridin-2-yl | H |
| 12-74 | Pr | Me | 5-Br-pyridin-2-yl | H |
| 12-75 | Pr | Me | 5-F-pyridin-2-yl | H |
| 12-76 | Pr | Me | 5-Me-pyridin-2-yl | H |
| 12-77 | Pr | Me | 2-pyridyl | H |
| 12-78 | Pr | Me | 4-pyridyl | H |
| 12-79 | i-Pr | Me | Ph | H |
| 12-80 | i-Pr | Me | 4-Cl-Ph | H |
| 12-81 | i-Pr | Me | 2-thienyl | H |
| 12-82 | i-Pr | Me | 3-pyridyl | H |
| 12-83 | i-Pr | Me | 6-Me-pyridin-3-yl | H |
| 12-84 | i-Pr | Me | 4-Me-Ph | H |
| 12-85 | i-Pr | Me | 4-Br-Ph | H |
| 12-86 | i-Pr | Me | 4-F-Ph | H |
| 12-87 | i-Pr | Me | 5-Cl-pyridin-2-yl | H |
| 12-88 | i-Pr | Me | 5-Br-pyridin-2-yl | H |
| 12-89 | i-Pr | Me | 5-F-pyridin-2-yl | H |
| 12-90 | i-Pr | Me | 5-Me-pyridin-2-yl | H |
| 12-91 | i-Pr | Me | 2-pyridyl | H |
| 12-92 | i-Pr | Me | 4-pyridyl | H |
| 12-93 | CH₂Ph | Me | Ph | H |
| 12-94 | CH₂Ph | Me | 4-Cl-Ph | H |
| 12-95 | CH₂Ph | Me | 2-thienyl | H |
| 12-96 | CH₂Ph | Me | 2-pyridyl | H |
| 12-97 | prop-2-yn-1-yl | Me | Ph | H |
| 12-98 | prop-2-yn-1-yl | Me | 4-Cl-Ph | H |
| 12-99 | prop-2-yn-1-yl | Me | 2-thienyl | H |
| 12-100 | prop-2-yn-1-yl | Me | 3-thienyl | H |
| 12-101 | prop-2-yn-1-yl | Me | 3-Me-2-thienyl | H |
| 12-102 | prop-2-yn-1-yl | Me | 4-Me-2-thienyl | H |
| 12-103 | prop-2-yn-1-yl | Me | 5-Cl-2-thienyl | H |
| 12-104 | prop-2-yn-1-yl | Me | 5-Me-2-thienyl | H |
| 12-105 | prop-2-yn-1-yl | Me | 3-pyridyl | H |
| 12-106 | prop-2-yn-1-yl | Me | 6-MeO-pyridin-3-yl | H |
| 12-107 | prop-2-yn-1-yl | H | Ph | H |
| 12-108 | prop-2-yn-1-yl | Me | 6-Me-pyridin-3-yl | H |
| 12-109 | prop-2-yn-1-yl | Me | 4-Me-Ph | H |
| 12-110 | prop-2-yn-1-yl | Me | 4-Br-Ph | H |
| 12-111 | prop-2-yn-1-yl | Me | 4-F-Ph | H |
| 12-112 | prop-2-yn-1-yl | Me | 5-Cl-pyridin-2-yl | H |
| 12-113 | prop-2-yn-1-yl | Me | 5-Br-pyridin-2-yl | H |
| 12-114 | prop-2-yn-1-yl | Me | 5-F-pyridin-2-yl | H |
| 12-115 | prop-2-yn-1-yl | Me | 5-Me-pyridin-2-yl | H |
| 12-116 | prop-2-yn-1-yl | Me | 2-pyridyl | H |
| 12-117 | prop-2-yn-1-yl | Me | 4-pyridyl | H |
| 12-118 | prop-2-yn-1-yl | Me | 4-Cl-Ph | 5-Me |
| 12-119 | prop-2-yn-1-yl | Me | Ph | 5-Me |
| 12-120 | cyclopropylmethyl | Me | Ph | H |
| 12-121 | cyclopropylmethyl | Me | 4-Cl-Ph | H |
| 12-122 | cyclopropylmethyl | Me | 2-thienyl | H |
| 12-123 | cyclopropylmethyl | Me | 3-thienyl | H |
| 12-124 | cyclopropylmethyl | Me | 3-Me-2-thienyl | H |
| 12-125 | cyclopropylmethyl | Me | 3-pyridyl | H |
| 12-126 | cyclopropylmethyl | Me | 5-Cl-2-thienyl | H |
| 12-127 | cyclopropylmethyl | Me | 5-Me-2-thienyl | H |
| 12-128 | cyclopropylmethyl | Me | 4-Me-2-thienyl | H |
| 12-129 | cyclopropylmethyl | Me | 6-MeO-pyridin-3-yl | H |
| 12-130 | cyclopropylmethyl | Me | 6-OH-pyridin-3-yl | H |
| 12-131 | cyclopropylmethyl | Me | 6-Me-pyridin-3-yl | H |
| 12-132 | cyclopropylmethyl | Me | 4-Me-Ph | H |
| 12-133 | cyclopropylmethyl | Me | 4-Br-Ph | H |
| 12-134 | cyclopropylmethyl | Me | 4-F-Ph | H |
| 12-135 | cyclopropylmethyl | Me | 5-Cl-pyridin-2-yl | H |
| 12-136 | cyclopropylmethyl | Me | 5-Br-pyridin-2-yl | H |
| 12-137 | cyclopropylmethyl | Me | 5-F-pyridin-2-yl | H |
| 12-138 | cyclopropylmethyl | Me | 5-Me-pyridin-2-yl | H |
| 12-139 | cyclopropylmethyl | Me | 2-pyridyl | H |
| 12-140 | cyclopropylmethyl | Me | 4-pyridyl | H |
| 12-141 | cyclopropylmethyl | Me | 4-Cl-Ph | 5-Me |
| 12-142 | cyclopropylmethyl | Me | Ph | 5-Me |
| 12-143 | cyclopropylmethyl | H | Ph | H |
| 12-144 | 3,3-dichloro-2-fluoroprop-2-en-1-yl | Me | Ph | H |
| 12-145 | 3,3-dichloro-2-fluoroprop-2-en-1-yl | Me | 4-Cl-Ph | H |

TABLE 12-continued

Compounds of the formula (Id'''')

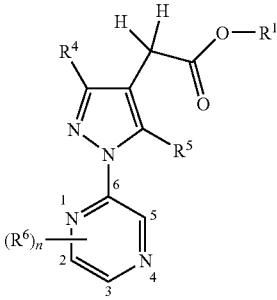

| No. | R¹ | R⁴ | R⁵ | (R⁶)ₙ |
|---|---|---|---|---|
| 12-146 | 3,3-dichloro-2-fluoroprop-2-en-1-yl | Me | 2-thienyl | H |
| 12-147 | 3,3-dichloro-2-fluoroprop-2-en-1-yl | Me | 2-pyridyl | H |
| 12-148 | (1-methylcyclopropyl)methyl | Me | Ph | H |
| 12-149 | (1-methylcyclopropyl)methyl | Me | 4-Cl-Ph | H |
| 12-150 | (1-methylcyclopropyl)methyl | Me | 2-thienyl | H |
| 12-151 | (1-methylcyclopropyl)methyl | Me | 2-pyridyl | H |
| 12-152 | 4-chlorobut-2-yn-1-yl | Me | Ph | H |
| 12-153 | 4-chlorobut-2-yn-1-yl | Me | 4-Cl-Ph | H |
| 12-154 | 4-chlorobut-2-yn-1-yl | Me | 2-thienyl | H |
| 12-155 | 4-chlorobut-2-yn-1-yl | Me | 2-pyridyl | H |
| 12-156 | (2,2-dichlorocyclopropyl)methyl | Me | Ph | H |
| 12-157 | (2,2-dichlorocyclopropyl)methyl | Me | 4-Cl-Ph | H |
| 12-158 | (2,2-dichlorocyclopropyl)methyl | Me | 2-thienyl | H |
| 12-159 | (2,2-dichlorocyclopropyl)methyl | Me | 2-pyridyl | H |
| 12-160 | but-2-yn-1-yl | Me | Ph | H |
| 12-161 | but-2-yn-1-yl | Me | 4-Cl-Ph | H |
| 12-162 | but-2-yn-1-yl | Me | 2-thienyl | H |
| 12-163 | but-2-yn-1-yl | Me | 3-thienyl | H |
| 12-164 | but-2-yn-1-yl | Me | 3-Me-2-thienyl | H |
| 12-165 | but-2-yn-1-yl | Me | 4-Me-2-thienyl | H |
| 12-166 | but-2-yn-1-yl | Me | 5-Cl-2-thienyl | H |
| 12-167 | but-2-yn-1-yl | Me | 5-Me-2-thienyl | H |
| 12-168 | but-2-yn-1-yl | Me | 3-pyridyl | H |
| 12-169 | but-2-yn-1-yl | Me | 6-MeO-pyridin-3-yl | H |
| 12-170 | but-2-yn-1-yl | H | Ph | H |
| 12-171 | but-2-yn-1-yl | Me | 6-Me-pyridin-3-yl | H |
| 12-172 | but-2-yn-1-yl | Me | 4-Me-Ph | H |
| 12-173 | but-2-yn-1-yl | Me | 4-Br-Ph | H |
| 12-174 | but-2-yn-1-yl | Me | 4-F-Ph | H |
| 12-175 | but-2-yn-1-yl | Me | 5-Cl-pyridin-2-yl | H |
| 12-176 | but-2-yn-1-yl | Me | 5-Br-pyridin-2-yl | H |
| 12-177 | but-2-yn-1-yl | Me | 5-F-pyridin-2-yl | H |
| 12-178 | but-2-yn-1-yl | Me | 5-Me-pyridin-2-yl | H |
| 12-179 | but-2-yn-1-yl | Me | 2-pyridyl | H |
| 12-180 | but-2-yn-1-yl | Me | 4-pyridyl | H |
| 12-181 | but-2-yn-1-yl | Me | 4-Cl-Ph | 5-Me |
| 12-182 | but-2-yn-1-yl | Me | Ph | 5-Me |
| 12-183 | 1-methylprop-2-yn-1-yl | Me | Ph | H |
| 12-184 | 1-methylprop-2-yn-1-yl | Me | 4-Cl-Ph | H |
| 12-185 | 1-methylprop-2-yn-1-yl | Me | 2-thienyl | H |
| 12-186 | 1-methylprop-2-yn-1-yl | Me | 2-pyridyl | H |
| 12-187 | 1-cyclopropylethyl | Me | Ph | H |
| 12-188 | 1-cyclopropylethyl | Me | 4-Cl-Ph | H |
| 12-189 | 1-cyclopropylethyl | Me | 2-thienyl | H |
| 12-190 | 1-cyclopropylethyl | Me | 2-pyridyl | H |
| 12-191 | allyl | Me | Ph | H |
| 12-192 | allyl | Me | 4-Cl-Ph | H |
| 12-193 | allyl | Me | 2-thienyl | H |
| 12-194 | allyl | Me | 2-pyridyl | H |
| 12-195 | 3-methylbut-2-en-1-yl | Me | Ph | H |
| 12-196 | 3-methylbut-2-en-1-yl | Me | 4-Cl-Ph | H |
| 12-197 | 3-methylbut-2-en-1-yl | Me | 2-thienyl | H |
| 12-198 | 3-methylbut-2-en-1-yl | Me | 2-pyridyl | H |
| 12-199 | 2-methylprop-2-en-1-yl | Me | Ph | H |

TABLE 12-continued

Compounds of the formula (Id'''')

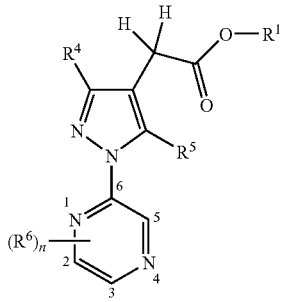

| No. | R¹ | R⁴ | R⁵ | (R⁶)ₙ |
|---|---|---|---|---|
| 12-200 | 2-methylprop-2-en-1-yl | Me | 4-Cl-Ph | H |
| 12-201 | 2-methylprop-2-en-1-yl | Me | 2-thienyl | H |
| 12-202 | 2-methylprop-2-en-1-yl | Me | 2-pyridyl | H |
| 12-203 | (2E)-1-methylbut-2-en-1-yl | Me | Ph | H |
| 12-204 | (2E)-1-methylbut-2-en-1-yl | Me | 4-Cl-Ph | H |
| 12-205 | (2E)-1-methylbut-2-en-1-yl | Me | 2-thienyl | H |
| 12-206 | (2E)-1-methylbut-2-en-1-yl | Me | 2-pyridyl | H |
| 12-207 | 3-phenylprop-2-yn-1-yl | Me | Ph | H |
| 12-208 | 3-phenylprop-2-yn-1-yl | Me | 4-Cl-Ph | H |
| 12-209 | 3-phenylprop-2-yn-1-yl | Me | 2-thienyl | H |
| 12-210 | 3-phenylprop-2-yn-1-yl | Me | 2-pyridyl | H |
| 12-211 | cyclobutylmethyl | Me | Ph | H |
| 12-212 | cyclobutylmethyl | Me | 4-Cl-Ph | H |
| 12-213 | cyclobutylmethyl | Me | 2-thienyl | H |
| 12-214 | cyclobutylmethyl | Me | 2-pyridyl | H |
| 12-215 | cyclopentylmethyl | Me | Ph | H |
| 12-216 | cyclopentylmethyl | Me | 4-Cl-Ph | H |
| 12-217 | cyclopentylmethyl | Me | 2-thienyl | H |
| 12-218 | cyclopentylmethyl | Me | 2-pyridyl | H |
| 12-219 | cyclohexylmethyl | Me | Ph | H |
| 12-220 | cyclohexylmethyl | Me | 4-Cl-Ph | H |
| 12-221 | cyclohexylmethyl | Me | 2-thienyl | H |
| 12-222 | cyclohexylmethyl | Me | 2-pyridyl | H |
| 12-223 | but-3-en-1-yl | Me | Ph | H |
| 12-224 | but-3-en-1-yl | Me | 4-Cl-Ph | H |
| 12-225 | but-3-en-1-yl | Me | 2-thienyl | H |
| 12-226 | but-3-en-1-yl | Me | 2-pyridyl | H |
| 12-227 | 2-chloroprop-2-en-1-yl | Me | Ph | H |
| 12-228 | 2-chloroprop-2-en-1-yl | Me | 4-Cl-Ph | H |
| 12-229 | 2-chloroprop-2-en-1-yl | Me | 2-thienyl | H |
| 12-230 | 2-chloroprop-2-en-1-yl | Me | 3-thienyl | H |
| 12-231 | 2-chloroprop-2-en-1-yl | Me | 3-Me-2-thienyl | H |
| 12-232 | 2-chloroprop-2-en-1-yl | Me | 4-Me-2-thienyl | H |
| 12-233 | 2-chloroprop-2-en-1-yl | Me | 5-Cl-2-thienyl | H |
| 12-234 | 2-chloroprop-2-en-1-yl | Me | 5-Me-2-thienyl | H |
| 12-235 | 2-chloroprop-2-en-1-yl | Me | 3-pyridyl | H |
| 12-236 | 2-chloroprop-2-en-1-yl | Me | 6-MeO-pyridin-3-yl | H |
| 12-237 | 2-chloroprop-2-en-1-yl | Me | 6-OH-pyridin-3-yl | H |
| 12-238 | 2-chloroprop-2-en-1-yl | Me | 6-Me-pyridin-3-yl | H |
| 12-239 | 2-chloroprop-2-en-1-yl | Me | 4-Me-Ph | H |
| 12-240 | 2-chloroprop-2-en-1-yl | Me | 4-Br-Ph | H |
| 12-241 | 2-chloroprop-2-en-1-yl | Me | 4-F-Ph | H |
| 12-242 | 2-chloroprop-2-en-1-yl | Me | 5-Cl-pyridin-2-yl | H |
| 12-243 | 2-chloroprop-2-en-1-yl | Me | 5-Br-pyridin-2-yl | H |
| 12-244 | 2-chloroprop-2-en-1-yl | Me | 5-F-pyridin-2-yl | H |
| 12-245 | 2-chloroprop-2-en-1-yl | Me | 5-Me-pyridin-2-yl | H |
| 12-246 | 2-chloroprop-2-en-1-yl | Me | 2-pyridyl | H |
| 12-247 | 2-chloroprop-2-en-1-yl | Me | 4-pyridyl | H |
| 12-248 | 2-chloroprop-2-en-1-yl | Me | 4-Cl-Ph | 5-Me |
| 12-249 | 2-chloroprop-2-en-1-yl | Me | Ph | 5-Me |
| 12-250 | 2-chloroprop-2-en-1-yl | H | Ph | H |
| 12-251 | 2-methoxyethyl | Me | Ph | H |
| 12-252 | 2-methoxyethyl | Me | 4-Cl-Ph | H |

TABLE 12-continued

Compounds of the formula (Id'''')

(Id'''')

| No. | R¹ | R⁴ | R⁵ | (R⁶)ₙ |
|---|---|---|---|---|
| 12-253 | 2-methoxyethyl | Me | 2-thienyl | H |
| 12-254 | 2-methoxyethyl | Me | 2-pyridyl | H |
| 12-255 | tetrahydrofuran-2-ylmethyl | Me | Ph | H |
| 12-256 | tetrahydrofuran-2-ylmethyl | Me | 4-Cl-Ph | H |
| 12-257 | tetrahydrofuran-2-ylmethyl | Me | 2-thienyl | H |
| 12-258 | tetrahydrofuran-2-ylmethyl | Me | 2-pyridyl | H |
| 12-259 | 2-(dimethylamino)ethyl | Me | Ph | H |
| 12-260 | 2-(dimethylamino)ethyl | Me | 4-Cl-Ph | H |
| 12-261 | 2-(dimethylamino)ethyl | Me | 2-thienyl | H |
| 12-262 | 2-(dimethylamino)ethyl | Me | 2-pyridyl | H |
| 12-263 | oxetan-3-yl | Me | Ph | H |
| 12-264 | oxetan-3-yl | Me | 4-Cl-Ph | H |
| 12-265 | oxetan-3-yl | Me | 2-thienyl | H |
| 12-266 | oxetan-3-yl | Me | 2-pyridyl | H |
| 12-267 | (3-methyloxetan-3-yl)methyl | Me | Ph | H |
| 12-268 | (3-methyloxetan-3-yl)methyl | Me | 4-Cl-Ph | H |
| 12-269 | (3-methyloxetan-3-yl)methyl | Me | 2-thienyl | H |
| 12-270 | (3-methyloxetan-3-yl)methyl | Me | 2-pyridyl | H |
| 12-271 | 2,2,2-trifluoroethyl | Me | Ph | H |
| 12-272 | 2,2,2-trifluoroethyl | Me | 4-Cl-Ph | H |
| 12-273 | 2,2,2-trifluoroethyl | Me | 2-thienyl | H |
| 12-274 | 2,2,2-trifluoroethyl | Me | 3-pyridyl | H |
| 12-275 | 2,2,2-trifluoroethyl | Me | 6-Me-pyridin-3-yl | H |
| 12-276 | 2,2,2-trifluoroethyl | Me | 4-Me-Ph | H |
| 12-277 | 2,2,2-trifluoroethyl | Me | 4-Br-Ph | H |
| 12-278 | 2,2,2-trifluoroethyl | Me | 4-F-Ph | H |
| 12-279 | 2,2,2-trifluoroethyl | Me | 5-Cl-pyridin-2-yl | H |
| 12-280 | 2,2,2-trifluoroethyl | Me | 5-Br-pyridin-2-yl | H |
| 12-281 | 2,2,2-trifluoroethyl | Me | 5-F-pyridin-2-yl | H |
| 12-282 | 2,2,2-trifluoroethyl | Me | 5-Me-pyridin-2-yl | H |
| 12-283 | 2,2,2-trifluoroethyl | Me | 2-pyridyl | H |
| 12-284 | 2,2,2-trifluoroethyl | Me | 4-pyridyl | H |
| 12-285 | CH₂(4-Cl-Ph) | Me | Ph | H |
| 12-286 | CH₂(4-Cl-Ph) | Me | 4-Cl-Ph | H |
| 12-287 | CH₂(4-Cl-Ph) | Me | 2-thienyl | H |
| 12-288 | CH₂(4-Cl-Ph) | Me | 3-pyridyl | H |
| 12-289 | CH₂(4-Cl-Ph) | Me | 6-Me-pyridin-3-yl | H |
| 12-290 | CH₂(4-Cl-Ph) | Me | 4-Me-Ph | H |
| 12-291 | CH₂(4-Cl-Ph) | Me | 4-Br-Ph | H |
| 12-292 | CH₂(4-Cl-Ph) | Me | 4-F-Ph | H |
| 12-293 | CH₂(4-Cl-Ph) | Me | 5-Cl-pyridin-2-yl | H |
| 12-294 | CH₂(4-Cl-Ph) | Me | 5-Br-pyridin-2-yl | H |
| 12-295 | CH₂(4-Cl-Ph) | Me | 5-F-pyridin-2-yl | H |
| 12-296 | CH₂(4-Cl-Ph) | Me | 5-Me-pyridin-2-yl | H |
| 12-297 | CH₂(4-Cl-Ph) | Me | 2-pyridyl | H |
| 12-298 | CH₂(4-Cl-Ph) | Me | 4-pyridyl | H |
| 12-299 | CH₂(4-F-Ph) | Me | Ph | H |
| 12-300 | CH₂(4-F-Ph) | Me | 4-Cl-Ph | H |
| 12-301 | CH₂(4-F-Ph) | Me | 2-thienyl | H |
| 12-302 | CH₂(4-F-Ph) | Me | 3-pyridyl | H |
| 12-303 | CH₂(4-F-Ph) | Me | 6-Me-pyridin-3-yl | H |
| 12-304 | CH₂(4-F-Ph) | Me | 4-Me-Ph | H |
| 12-305 | CH₂(4-F-Ph) | Me | 4-Br-Ph | H |
| 12-306 | CH₂(4-F-Ph) | Me | 4-F-Ph | H |
| 12-307 | CH₂(4-F-Ph) | Me | 5-Cl-pyridin-2-yl | H |
| 12-308 | CH₂(4-F-Ph) | Me | 5-Br-pyridin-2-yl | H |
| 12-309 | CH₂(4-F-Ph) | Me | 5-F-pyridin-2-yl | H |
| 12-310 | CH₂(4-F-Ph) | Me | 5-Me-pyridin-2-yl | H |
| 12-311 | CH₂(4-F-Ph) | Me | 2-pyridyl | H |
| 12-312 | CH₂(4-F-Ph) | Me | 4-pyridyl | H |
| 12-313 | CH₂(4-OMe-Ph) | Me | Ph | H |
| 12-314 | CH₂(4-OMe-Ph) | Me | 4-Cl-Ph | H |
| 12-315 | CH₂(4-OMe-Ph) | Me | 2-thienyl | H |
| 12-316 | CH₂(4-OMe-Ph) | Me | 3-pyridyl | H |
| 12-317 | CH₂(4-OMe-Ph) | Me | 6-Me-pyridyl | H |
| 12-318 | CH₂(4-OMe-Ph) | Me | 4-Me-Ph | H |
| 12-319 | CH₂(4-OMe-Ph) | Me | 4-Br-Ph | H |
| 12-320 | CH₂(4-OMe-Ph) | Me | 4-F-Ph | H |
| 12-321 | CH₂(4-OMe-Ph) | Me | 5-Cl-pyridin-2-yl | H |
| 12-322 | CH₂(4-OMe-Ph) | Me | 5-Br-pyridin-2-yl | H |
| 12-323 | CH₂(4-OMe-Ph) | Me | 5-F-pyridin-2-yl | H |
| 12-324 | CH₂(4-OMe-Ph) | Me | 5-Me-pyridin-2-yl | H |
| 12-325 | CH₂(4-OMe-Ph) | Me | 2-pyridyl | H |
| 12-326 | CH₂(4-OMe-Ph) | Me | 4-pyridyl | H |
| 12-327 | 2,2-difluoroethyl | Me | Ph | H |
| 12-328 | 2,2-difluoroethyl | Me | 4-Cl-Ph | H |
| 12-329 | 2,2-difluoroethyl | Me | 2-thienyl | H |
| 12-330 | 2,2-difluoroethyl | Me | 2-pyridyl | H |
| 12-331 | Ph | Me | Ph | H |
| 12-332 | Ph | Me | 4-Cl-Ph | H |
| 12-333 | Ph | Me | 2-thienyl | H |
| 12-334 | Ph | Me | 2-pyridyl | H |
| 12-335 | 2-fluoroethyl | Me | Ph | H |
| 12-336 | 2-fluoroethyl | Me | 4-Cl-Ph | H |
| 12-337 | 2-fluoroethyl | Me | 2-thienyl | H |
| 12-338 | 2-fluoroethyl | Me | 2-pyridyl | H |
| 12-339 | 2,2,3,3,3-pentafluoropropyl | Me | Ph | H |
| 12-340 | 2,2,3,3,3-pentafluoropropyl | Me | 4-Cl-Ph | H |
| 12-341 | 2,2,3,3,3-pentafluoropropyl | Me | 2-thienyl | H |
| 12-342 | 2,2,3,3,3-pentafluoropropyl | Me | 2-pyridyl | H |
| 12-343 | 1-ethyl-5-methyl-1H-pyrazole-4-methyl | Me | Ph | H |
| 12-344 | 1-ethyl-5-methyl-1H-pyrazole-4-methyl | Me | 4-Cl-Ph | H |
| 12-345 | 1-ethyl-5-methyl-1H-pyrazole-4-methyl | Me | 2-thienyl | H |
| 12-346 | 1-ethyl-5-methyl-1H-pyrazole-4-methyl | Me | 2-pyridyl | H |
| 12-347 | but-3-yn-2-yl | Me | 5-Cl-pyridin-2-yl | H |
| 12-348 | but-3-yn-2-yl | Me | isoquinolin-3-yl | H |
| 12-349 | but-3-yn-2-yl | Me | quinolin-2-yl | H |
| 12-350 | but-3-yn-2-yl | Me | Ph | H |
| 12-351 | but-3-yn-2-yl | Me | 4-Cl-Ph | H |
| 12-352 | but-3-yn-2-yl | Me | 2-thienyl | H |
| 12-353 | but-3-yn-2-yl | Me | 3-pyridyl | H |
| 12-354 | but-3-yn-2-yl | Me | 6-Me-pyridin-3-yl | H |
| 12-355 | but-3-yn-2-yl | Me | 4-Me-Ph | H |
| 12-356 | but-3-yn-2-yl | Me | 4-Br-Ph | H |
| 12-357 | but-3-yn-2-yl | Me | 4-F-Ph | H |
| 12-358 | but-3-yn-2-yl | Me | 5-Br-pyridin-2-yl | H |
| 12-359 | but-3-yn-2-yl | Me | 5-F-pyridin-2-yl | H |
| 12-360 | but-3-yn-2-yl | Me | 5-Me-pyridin-2-yl | H |
| 12-361 | but-3-yn-2-yl | Me | 2-pyridyl | H |
| 12-362 | but-3-yn-2-yl | Me | 4-pyridyl | H |
| 12-363 | Et | Me | isoquinolin-3-yl | H |
| 12-364 | Et | Me | quinolin-2-yl | H |

TABLE 13

Compounds of the formula (III) (intermediates)

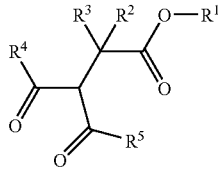

(III)

| No. | R¹ | R² | R³ | R⁴ | R⁵ |
|---|---|---|---|---|---|
| 13-1 | Me | H | H | Ph | Ph |
| 13-2 | Me | H | H | Me | Ph |
| 13-3 | Me | H | H | Me | 2-furyl |
| 13-4 | Me | Me | H | Me | Ph |
| 13-5 | Me | H | H | Me | 4-MeO-Ph |
| 13-6 | Me | H | H | Me | 4-Me-Ph |
| 13-7 | Me | H | H | Me | 3-CF₃-Ph |
| 13-8 | Me | H | H | Me | 3,4-Cl₂-Ph |
| 13-9 | Me | H | H | Me | 3-Cl-Ph |
| 13-10 | Me | H | H | Me | 2-Cl-Ph |
| 13-11 | Me | H | H | Me | 2,4-Cl₂-Ph |
| 13-12 | Me | H | H | Me | 4-CF₃-Ph |
| 13-13 | Me | H | H | Me | 4-Cl-Ph |
| 13-14 | Me | H | H | Me | 4-CF₃-Ph |
| 13-15 | Me | H | H | Me | 4-tBu-Ph |
| 13-16 | Me | H | H | Me | 3,5-Me₂-Ph |
| 13-17 | Me | H | H | Me | 4-Me-Ph |
| 13-18 | Me | H | H | Me | 4-F-Ph |
| 13-19 | Me | H | H | Me | 3-Me-Ph |
| 13-20 | Me | H | H | Me | 4-COOH-Ph |
| 13-21 | Me | H | H | Me | 3-Br-Ph |
| 13-22 | Me | H | H | Me | 4-Ph-Ph |
| 13-23 | Me | H | H | Me | 3-Cl-4-Me-Ph |
| 13-24 | Me | H | H | Me | 3-CF₃-4-Cl-Ph |
| 13-25 | Me | H | H | Me | 2-thienyl |
| 13-26 | Me | H | H | Me | 3-Me-2-thienyl |
| 13-27 | Me | H | H | Me | 4-Me-2-thienyl |
| 13-28 | Me | H | H | Me | 5-Cl-2-thienyl |
| 13-29 | Me | H | H | Me | 5-I-2-thienyl |
| 13-30 | Me | H | H | Me | 3-thienyl |
| 13-31 | Me | H | H | Me | 3-pyridyl |
| 13-32 | Me | H | H | Me | 5-Me-2-thienyl |
| 13-33 | Me | H | H | Me | 6-MeO-pyridin-3-yl |
| 13-34 | Me | H | H | Me | 5-Br-2-thienyl |
| 13-35 | Me | H | H | Me | 4-Br-Ph |
| 13-36 | Me | H | H | Me | 1,3-benzodioxol-5-yl |
| 13-37 | Me | H | H | Me | 4-I-Ph |
| 13-38 | Me | H | H | Me | 4-PhO-Ph |
| 13-39 | Me | H | H | Me | 6-OH-pyridin-3-yl |
| 13-40 | Me | H | H | H | Ph |
| 13-41 | Me | H | H | Et | Ph |
| 13-42 | Me | H | H | n-Pr | Ph |
| 13-43 | Me | H | H | CH₂Cl | Ph |
| 13-44 | Me | H | H | CHCl₂ | Ph |
| 13-45 | Me | H | H | CH₂F | Ph |
| 13-46 | Me | H | H | CHF₂ | Ph |
| 13-47 | Me | H | H | Cl | Ph |
| 13-48 | Me | H | H | n-Pr | 4-Cl-Ph |
| 13-49 | Me | H | H | CH₂Cl | 4-Cl-Ph |
| 13-50 | Me | H | H | CHCl₂ | 4-Cl-Ph |
| 13-51 | Me | H | H | CH₂F | 4-Cl-Ph |
| 13-52 | Me | H | H | CHF₂ | 4-Cl-Ph |
| 13-53 | Me | H | H | Cl | 4-Cl-Ph |
| 13-54 | Me | H | H | Et | 4-Me-Ph |
| 13-55 | Me | H | H | n-Pr | 4-Me-Ph |
| 13-56 | Me | H | H | CH₂Cl | 4-Me-Ph |
| 13-57 | Me | H | H | CHCl₂ | 4-Me-Ph |
| 13-58 | Me | H | H | CH₂F | 4-Me-Ph |
| 13-59 | Me | H | H | CHF₂ | 4-Me-Ph |
| 13-60 | Me | H | H | Cl | 4-Me-Ph |
| 13-61 | Me | H | H | Et | 2-pyridyl |
| 13-62 | Me | H | H | n-Pr | 2-pyridyl |
| 13-63 | Me | H | H | CH₂Cl | 2-pyridyl |
| 13-64 | Me | H | H | CHCl₂ | 2-pyridyl |
| 13-65 | Me | H | H | CH₂F | 2-pyridyl |
| 13-66 | Me | H | H | CHF₂ | 2-pyridyl |
| 13-67 | Me | H | H | Cl | 2-pyridyl |
| 13-68 | Me | H | H | Me | 2-pyridyl |
| 13-69 | Me | H | H | Me | 5-Cl-pyridin-2-yl |
| 13-70 | Me | H | H | Me | 5-Br-pyridin-2-yl |
| 13-71 | Me | H | H | Me | 5-F-pyridin-2-yl |
| 13-72 | Me | H | H | Me | 5-Me-pyridin-2-yl |
| 13-73 | Me | H | H | Me | 4-Me-pyridin-2-yl |
| 13-74 | Me | H | H | Me | 2,4-Cl₂-Ph |
| 13-75 | Me | H | H | Me | 4-CH₂COOH-Ph |
| 13-76 | Me | H | H | Me | 4-(MeCO)-Ph |
| 13-77 | Me | H | H | Me | 4-tBu-Ph |
| 13-78 | Me | H | H | Me | 4-Cl-3-Me-Ph |
| 13-79 | Me | H | H | n-Pr | 4-Cl-Ph |
| 13-80 | Me | H | H | Me | 3-pyridyl |
| 13-81 | Me | H | H | Me | 4-pyridyl |
| 13-82 | Me | H | H | C(O)OMe | Ph |
| 13-83 | Me | H | H | Me | 6-Me-pyridin-3-yl |
| 13-84 | Me | H | H | Me | 2,3-Cl₂-Ph |
| 13-85 | Me | H | H | H | 4-Cl-Ph |
| 13-86 | Me | H | H | Me | 6-Cl-pyridin-3-yl |
| 13-87 | Me | H | H | Me | 2-thiazolyl |
| 13-88 | Me | H | H | Me | 4-Me-thiazol-2-yl |
| 13-89 | Me | H | H | Me | 5-Br-thiazol-2-yl |
| 13-90 | Me | H | H | Me | 5-Cl-thiazol-2-yl |
| 13-91 | Me | H | H | Me | 5-Me-thiazol-2-yl |
| 13-92 | Me | H | H | Me | 4,5-Me₂-thiazol-2-yl |
| 13-93 | Me | H | H | Me | 4,5-Cl₂-thiazol-2-yl |
| 13-94 | Me | H | H | Me | 4,6-Me₂-pyridin-2-yl |
| 13-95 | Me | H | H | Me | 2-pyrazinyl |
| 13-96 | Me | H | H | Me | 2-pyrimidinyl |
| 13-97 | Me | H | H | Me | 5-Cl-pyrimidin-2-yl |
| 13-98 | Me | H | H | Me | 5-Br-pyrimidin-2-yl |
| 13-99 | Me | H | H | Me | 5-Me-pyrimidin-2-yl |
| 13-100 | Me | H | H | Me | 4,6-Me₂-pyrimidin-2-yl |
| 13-101 | Me | H | H | Me | 1,3-benzothiazol-2-yl |
| 13-102 | Me | H | H | Me | 7-Cl-1,3-benzothiazol-2-yl |
| 13-103 | Me | H | H | Me | 1,5-Me₂-pyrazol-3-yl |
| 13-104 | Me | H | H | Me | 5-Me-pyrazin-2-yl |
| 13-105 | Me | H | H | Me | 5-F-pyrimidin-2-yl |
| 13-106 | Me | H | H | Me | 4,6-Me₂-pyrimidin-2-yl |
| 13-107 | Me | H | H | Me | 3-pyridazinyl |
| 13-108 | Me | H | H | Me | 6-Me-pyridazin-3-yl |
| 13-109 | Me | H | H | Me | 1,2,4-triazin-3-yl |
| 13-110 | Me | H | H | Me | 6-Me-1,2,4-triazin-3-yl |
| 13-111 | Et | H | H | Ph | Ph |
| 13-112 | Et | H | H | Me | Ph |
| 13-113 | Et | H | H | Me | 2-furyl |
| 13-114 | Et | Me | H | Me | Ph |
| 13-115 | Et | H | H | Me | 4-MeO-Ph |
| 13-116 | Et | H | H | Me | 4-Me-Ph |
| 13-117 | Et | H | H | Me | 3-CF₃Ph |
| 13-118 | Et | H | H | Me | 3,4-Cl₂-Ph |
| 13-119 | Et | H | H | Me | 3-Cl-Ph |
| 13-120 | Et | H | H | Me | 2-Cl-Ph |
| 13-121 | Et | H | H | Me | 2,4-Cl₂-Ph |
| 13-122 | Et | H | H | Me | 4-CF₃-Ph |
| 13-123 | Et | H | H | Me | 4-Cl-Ph |
| 13-124 | Et | H | H | Me | 4-CF₃-Ph |
| 13-125 | Et | H | H | Me | 4-tBu-Ph |
| 13-126 | Et | H | H | Me | 3,5-Me₂-Ph |
| 13-127 | Et | H | H | Me | 4-Me-Ph |
| 13-128 | Et | H | H | Me | 4-F-Ph |
| 13-129 | Et | H | H | Me | 3-Me-Ph |
| 13-130 | Et | H | H | Me | 4-COOH-Ph |
| 13-131 | Et | H | H | Me | 3-Br-Ph |
| 13-132 | Et | H | H | Me | 4-Ph-Ph |

TABLE 13-continued

Compounds of the formula (III) (intermediates)

$$\text{(III)}$$

| No. | R¹ | R² | R³ | R⁴ | R⁵ |
|---|---|---|---|---|---|
| 13-133 | Et | H | H | Me | 3-Cl-4-Me-Ph |
| 13-134 | Et | H | H | Me | 3-CF₃-4-Me-Ph |
| 13-135 | Et | H | H | Me | 2-thienyl |
| 13-136 | Et | H | H | Me | 3-Me-2-thienyl |
| 13-137 | Et | H | H | Me | 4-Me-2-thienyl |
| 13-138 | Et | H | H | Me | 5-Cl-2-thienyl |
| 13-139 | Et | H | H | Me | 5-I-2-thienyl |
| 13-140 | Et | H | H | Me | 3-thienyl |
| 13-141 | Et | H | H | Me | 3-pyridyl |
| 13-142 | Et | H | H | Me | 5-Me-2-thienyl |
| 13-143 | Et | H | H | Me | 6-MeO-pyridin-3-yl |
| 13-144 | Et | H | H | Me | 5-Br-2-thienyl |
| 13-145 | Et | H | H | Me | 4-Br-Ph |
| 13-146 | Et | H | H | Me | 1,3-benzodioxol-5-yl |
| 13-147 | Et | H | H | Me | 4-I-Ph |
| 13-148 | Et | H | H | Me | 4-PhO-Ph |
| 13-149 | Et | H | H | Me | 6-OH-pyridin-3-yl |
| 13-150 | Et | H | H | H | Ph |
| 13-151 | Et | H | H | Et | Ph |
| 13-152 | Et | H | H | n-Pr | Ph |
| 13-153 | Et | H | H | CH₂Cl | Ph |
| 13-154 | Et | H | H | CHCl₂ | Ph |
| 13-155 | Et | H | H | CH₂F | Ph |
| 13-156 | Et | H | H | CHF₂ | Ph |
| 13-157 | Et | H | H | Cl | Ph |
| 13-158 | Et | H | H | n-Pr | 4-Cl-Ph |
| 13-159 | Et | H | H | CH₂Cl | 4-Cl-Ph |
| 13-160 | Et | H | H | CHCl₂ | 4-Cl-Ph |
| 13-161 | Et | H | H | CH₂F | 4-Cl-Ph |
| 13-162 | Et | H | H | CHF₂ | 4-Cl-Ph |
| 13-163 | Et | H | H | Cl | 4-Cl-Ph |
| 13-164 | Et | H | H | Et | 4-Me-Ph |
| 13-165 | Et | H | H | n-Pr | 4-Me-Ph |
| 13-166 | Et | H | H | CH₂Cl | 4-Me-Ph |
| 13-167 | Et | H | H | CHCl₂ | 4-Me-Ph |
| 13-168 | Et | H | H | CH₂F | 4-Me-Ph |
| 13-169 | Et | H | H | CHF₂ | 4-Me-Ph |
| 13-170 | Et | H | H | Cl | 4-Me-Ph |
| 13-171 | Et | H | H | Et | 2-pyridyl |
| 13-172 | Et | H | H | n-Pr | 2-pyridyl |
| 13-173 | Et | H | H | CH₂Cl | 2-pyridyl |
| 13-174 | Et | H | H | CHCl₂ | 2-pyridyl |
| 13-175 | Et | H | H | CH₂F | 2-pyridyl |
| 13-176 | Et | H | H | CHF₂ | 2-pyridyl |
| 13-177 | Et | H | H | Cl | 2-pyridyl |
| 13-178 | Et | H | H | Me | 2-pyridyl |
| 13-179 | Et | H | H | Me | 5-Cl-pyridin-2-yl |
| 13-180 | Et | H | H | Me | 5-Br-pyridin-2-yl |
| 13-181 | Et | H | H | Me | 5-F-pyridin-2-yl |
| 13-182 | Et | H | H | Me | 5-Me-pyridin-2-yl |
| 13-183 | Et | H | H | Me | 4-Me-pyridin-2-yl |
| 13-184 | Et | H | H | Me | 2,4-Cl₂-Ph |
| 13-185 | Et | H | H | Me | 4-CH₂COOH-Ph |
| 13-186 | Et | H | H | Me | 4-(MeCO)-Ph |
| 13-187 | Et | H | H | Me | 4-tBu-Ph |
| 13-188 | Et | H | H | Me | 4-Cl-3-Me-Ph |
| 13-189 | Et | H | H | n-Pr | 4-Cl-Ph |
| 13-190 | Et | H | H | Me | 3-pyridyl |
| 13-191 | Et | H | H | Me | 4-pyridyl |
| 13-192 | Et | H | H | C(O)OMe | Ph |
| 13-193 | Et | H | H | Me | 6-Me-pyridin-3-yl |
| 13-194 | Et | H | H | Me | 2,3-Cl₂-Ph |
| 13-195 | Et | H | H | H | 4-Cl-Ph |
| 13-196 | Et | H | H | Me | 6-Cl-pyridin-3-yl |
| 13-197 | Et | H | H | Me | 2-thiazolyl |
| 13-198 | Et | H | H | Me | 4-Me-thiazol-2-yl |
| 13-199 | Et | H | H | Me | 5-Br-thiazol-2-yl |
| 13-200 | Et | H | H | Me | 5-Cl-thiazol-2-yl |
| 13-201 | Et | H | H | Me | 5-Me-thiazol-2-yl |
| 13-202 | Et | H | H | Me | 4,5-Me₂-thiazol-2-yl |
| 13-203 | Et | H | H | Me | 4,5-Cl₂-thiazol-2-yl |
| 13-204 | Et | H | H | Me | 4,6-Me₂-pyridin-2-yl |
| 13-205 | Et | H | H | Me | 2-pyrazinyl |
| 13-206 | Et | H | H | Me | 2-pyrimidinyl |
| 13-207 | Et | H | H | Me | 5-Cl-pyrimidin-2-yl |
| 13-208 | Et | H | H | Me | 5-Br-pyrimidin-2-yl |
| 13-209 | Et | H | H | Me | 5-Me-pyrimidin-2-yl |
| 13-210 | Et | H | H | Me | 4,6-Me₂-pyrimidin-2-yl |
| 13-211 | Et | H | H | Me | 1,3-benzothiazol-2-yl |
| 13-212 | Et | H | H | Me | 7-Cl-1,3-benzothiazol-2-yl |
| 13-213 | Et | H | H | Me | 1,5-Me₂-pyrazol-3-yl |
| 13-214 | Et | H | H | Me | 5-Me-pyrazin-2-yl |
| 13-215 | Et | H | H | Me | 5-F-pyrimidin-2-yl |
| 13-216 | Et | H | H | Me | 4,6-Me₂-pyrimidin-2-yl |
| 13-217 | Et | H | H | Me | 3-pyridazinyl |
| 13-218 | Et | H | H | Me | 6-Me-pyridazin-3-yl |
| 13-219 | Et | H | H | Me | 1,2,4-triazin-3-yl |
| 13-220 | Et | H | H | Me | 6-Me-1,2,4-triazin-3-yl |
| 13-221 | Me | H | H | Me | 5-Cl-pyridin-3-yl |
| 13-222 | Me | H | H | Me | 4-Br-3-Me-Ph |
| 13-223 | Me | H | H | Me | 4-Cl-6-Me-pyridin-2-yl |
| 13-224 | Me | H | H | Me | 2-Me-pyridin-4-yl |
| 13-225 | Me | H | H | Me | 3,5-Cl₂-Ph |
| 13-226 | Me | H | H | Me | quinolin-2-yl |
| 13-227 | Me | H | H | Me | isoquinolin-3-yl |
| 13-228 | Me | H | H | Me | 5-CF₃-pyridin-2-yl |
| 13-229 | Me | H | H | Me | 6-OMe-pyridin-2-yl |
| 13-230 | Me | H | H | Me | 4-OMe-pyridin-2-yl |
| 13-231 | Me | H | H | Me | 4-Br-pyridin-2-yl |
| 13-232 | Me | H | H | Me | 4-Cl-pyridin-2-yl |
| 13-233 | Me | H | H | Me | 4-F-pyridin-2-yl |
| 13-234 | Me | H | H | Me | 3,4-Me₂-Ph |
| 13-235 | Me | Me | H | Me | 4-Cl-Ph |
| 13-236 | Me | Me | H | Me | 5-Cl-pyridin-2-yl |
| 13-237 | Me | Me | H | Me | 5-Br-pyridin-2-yl |
| 13-238 | Me | Me | H | Me | 5-Br-pyrimidin-2-yl |
| 13-239 | Me | Me | H | Me | 5-Cl-pyrimidin-2-yl |
| 13-240 | Me | H | H | Me | 4-NO₂-Ph |
| 13-241 | Me | Me | H | Me | 2-pyridinyl |
| 13-242 | Me | H | H | Me | 5-allylpyridin-2-yl |
| 13-243 | Me | H | H | Me | 5-cyclopropylpyridin-2-yl |
| 13-244 | Me | H | H | Me | 5-ethynylpyridin-2-yl |
| 13-245 | Me | H | H | Me | 5-Ph-pyridin-2-yl |
| 13-246 | Me | H | H | Me | 3-Br-Ph |
| 13-247 | Me | H | H | Me | 4-thiazolyl |
| 13-248 | Me | H | H | Me | 2-Cl-thiazol-4-yl |
| 13-249 | Me | H | H | Me | 2-Br-thiazol-4-yl |
| 13-250 | Me | H | H | Me | 5-OSO₂Me-pyridin-2-yl |
| 13-251 | Me | H | H | Me | 6-Cl-1,3-benzothiazol-2-yl |
| 13-252 | Me | H | H | Me | 6-Br-1,3-benzothiazol-2-yl |
| 13-253 | Me | H | H | Me | 1,3-benzoxazol-2-yl |
| 13-254 | Me | H | H | Me | 6-Cl-1,3-benzoxazol-2-yl |
| 13-255 | Me | H | H | Me | 6-Br-1,3-benzoxazol-2-yl |
| 13-256 | Me | H | H | Me | 7-Cl-1,3-benzoxazol-2-yl |
| 13-257 | Me | H | H | Me | 5-NH₂-pyridin-2-yl |
| 13-258 | Me | H | H | Me | 5-OH-pyridin-2-yl |
| 13-259 | Me | H | H | Me | 5-OCHF₂-pyridin-2-yl |
| 13-260 | Me | H | H | Me | 5-MeO-pyridin-2-yl |
| 13-261 | Me | H | H | Me | 5-MeS-pyridin-2-yl |
| 13-262 | Me | H | H | Me | 5-NHMe-pyridin-2-yl |
| 13-263 | Me | H | H | Me | 5-NMe₂-pyridin-2-yl |

(B) FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255 up to over 277° C.) and grinding the mixture in an attrition ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
75 parts by weight of a compound of the formula (I),
10 parts by weight of calcium lignosulfonate,
5 parts by weight of sodium lauryl sulfate,
3 parts by weight of polyvinyl alcohol and
7 parts by weight of kaolin,
grinding the mixture in a pinned-disk mill and granulating the powder in a fluidized bed by spraying on water as granulation liquid.

f) Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
subsequently grinding the mixture in a bead mill, and atomizing and drying the resulting suspension in a spray tower by means of a single-substance nozzle.

(C) BIOLOGICAL EXAMPLES

1. Pre-emergence Herbicidal Effect and Crop Plant Compatibility

Seeds of monocotyledonous or dicotyledonous weeds or crop plants are placed in sandy loam soil in wood-fiber pots and covered with soil. The compounds (I) according to the invention, formulated in the form of wettable powders (WP), are then applied to the surface of the soil cover in the form of an aqueous suspension or emulsion at a water application rate of 600 I/ha (converted), with addition of 0.2% wetting agent.

Following the treatment, the pots are placed in the greenhouse and kept under good growth conditions for the test plants. After about 3 weeks, the activity of the preparations is scored visually in comparison to untreated controls (herbicidal activity in percent (%): 100% activity=the plants have died, 0% activity=like control plants).

The compounds (I) according to the invention have good herbicidal pre-emergence activity against a number of harmful plants at an application rate of 0.32 kg or less of active substance per hectare. For example, the compound Nos. 1-28, 1-154, 2-2, 2-16, 2-28, 2-116, 2-120, 2-132, 2-117, 1-116, 1-119, 1-210, 1-214, 1-236, 2-47, 2-64, 2-65, 2-124, 2-135, 2-148, 2-155, 2-215, 2-217, 2-224, 2-241, 2-240, 2-243, 2-249, 3-4, 3-25, 3-26, 3-112, 3-121, 3-135, 3-36, 3-161, 3-176, 3-353 and other compounds from Tables 1 to 12 have good herbicidal activity against harmful plants such as *Alopecurus myosuroides, Echinochloa crus galli, Setaria viridis* and *Veronica persica* when applied by the pre-emergence method at an application rate of 0.32 kg of active substance per hectare.

At the same time, when applied by the pre-emergence method, the compounds according to the invention do not damage dicotyledonous crops such as oilseed rape even at high active compound dosages, and in addition, they spare graminaceous crops such as wheat and rice. Some of the compounds according to the invention have high selectivity, and they are therefore suitable for controlling unwanted vegetation in agricultural crops by the pre-emergence method.

2. Post-emergence Herbicidal Effect and Crop Plant Compatibility

Seeds of monocotyledonous and dicotyledonous weeds and crop plants are placed in sandy loam soil in wood-fiber pots, covered with soil, and cultivated in a greenhouse under good growth conditions. 2 to 3 weeks after sowing, the test plants are treated at the one-leaf stage. The compounds (I) according to the invention, formulated as wettable powders (WP), are then sprayed onto the green parts of the plants as an aqueous suspension or emulsion at a water application rate of 600 I/ha (converted), with addition of 0.2% wetting agent. The test plants are allowed to stand in a greenhouse for about 3 weeks under optimum growth conditions, and the effect of the preparations is then scored visually by comparison with untreated controls (herbicidal activity in percent (%): 100% activity=the plants have died, 0% activity=like control plants).

As evident from the results, the compounds (I) according to the invention have good post-emergence herbicidal activity against a broad spectrum of weed grasses and broad-leaved weeds at an application rate of 0.32 kg or less of active substance per hectare. For example, the compounds Nos. 1-28, 1-154, 2-2, 2-16, 2-28, 2-116, 2-120, 2-132, 2-117, 1-116, 1-119, 1-210, 1-214, 1-236, 2-47, 2-64, 2-65, 2-124, 2-135, 2-148, 2-155, 2-215, 2-217, 2-224, 2-241, 2-240, 2-243, 2-249, 3-4, 3-25, 3-26, 3-112, 3-121, 3-161, 3-135, 3-136, 3-176, 3-353 and other compounds from Tables 1 to 12 have good herbicidal activity against harmful plants such as *Avena fatua, Echinochloa crus galli, Lolium multiflorum, Setaria viridis, Veronica persica, Viola tricolor* and *Alopecurus myosuroides* when applied by the post-emergence method at an application rate of 0.32 kg or less of active substance per hectare.

The invention claimed is:
1. A compound of the formula (I) or a salt thereof

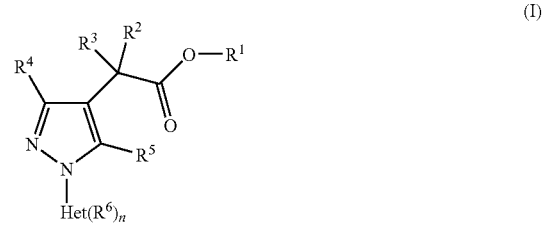

wherein Het is a six-membered heteroaromatic radical having two heteroatoms as ring atoms, where the heteroatoms in the ring are nitrogen atoms and at least one nitrogen atom in the ring is located in the 1,3-position to the ring carbon atom which is attached to the pyrazole radical;

wherein $R^1$ is hydrogen or a hydrolyzable radical;

wherein:

$R^2$ and $R^3$ are as follows:

$R^2$ is hydrogen, halogen, or $(C_1-C_6)$-alkyl which is unsubstituted or substituted by one or more radicals selected from the group consisting of halogen, $(C_1-C_4)$-alkoxy, $(C_1-C_4)$-alkylthio, and $(C_1-C_4)$-haloalkoxy; and $R^3$ is hydrogen, halogen, or $(C_1-C_6)$-alkyl which is unsubstituted or substituted by one or more radicals selected from the group consisting of halogen, $(C_1-C_4)$-alkoxy, $(C_1-C_4)$-alkylthio, and $(C_1-C_4)$-haloalkoxy; or $R^2$ and $R^3$ together with the carbon atom to which they are attached are a carbocyclic saturated or partially unsaturated ring having 3 to 6 carbon atoms which is unsubstituted or substituted by one or more radicals selected from the group consisting of halogen and $(C_1-C_4)$-alkyl; and wherein $R^4$ is:

hydrogen, halogen, or cyano; or $(C_1-C_6)$-alkyl, $(C_2-C_6)$-alkenyl, or $(C_2-C_6)$-alkynyl, where each of the three last-mentioned radicals independently is unsubstituted or substituted by one or more radicals selected from the group consisting of:

halogen, cyano, hydroxyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio and optionally halogen-, cyano-, $(C_1-C_4)$-alkyl-, and $(C_1-C_4)$-haloalkyl-substituted $(C_3-C_9)$-cycloalkyl; or $(C_3-C_9)$-cycloalkyl, $(C_5-C_9)$-cycloalkenyl, or $(C_5-C_9)$-cycloalkynyl, where each of the 3 last-mentioned radicals independently is unsubstituted or substituted by one or more radicals selected from the group consisting of:

halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, and $(C_1-C_4)$-alkylthio; or phenyl which is unsubstituted or substituted by one or more radicals selected from the group consisting of halogen, cyano, nitro, carboxy, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $(C_1-C_4)$-alkanoyl, $(C_1-C_4)$-haloalkanoyl, $[(C_1-C_4)$-alkoxy]carbonyl, and $[(C_1-C_4)$-haloalkoxy]carbonyl; or $(C_1-C_6)$-alkanoyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, and optionally $(C_1-C_4)$-alkyl- or $(C_1-C_4)$-haloalkyl-substituted $(C_3-C_6)$-cycloalkyl; or $[(C_1-C_4)$-alkoxy]carbonyl which is unsubstituted or substituted by one or more radicals selected from the group consisting of halogen, cyano, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, and optionally $(C_1-C_4)$-alkyl- or $(C_1-C_4)$-haloalkyl-substituted $(C_3-C_6)$-cycloalkyl; or $[(C_3-C_9)$-cycloalkoxy]carbonyl which is unsubstituted or substituted by one or more radicals selected from the group consisting of halogen, $(C_1-C_4)$-alkyl, $(C_1-C_4)$-haloalkyl, $(C_2-C_4)$-alkenyl, $(C_2-C_4)$-alkynyl, $(C_1-C_4)$-alkoxy, $(C_1-C_4)$-haloalkoxy, and $(C_1-C_4)$-alkylthio;

wherein $R^5$ is:

an aryl radical which is unsubstituted or substituted and, including substituents, has 6 to 30 carbon atoms; or a heteroaromatic radical having 1 to 4 ring heteroatoms selected from the group consisting of N, O, and S, which is unsubstituted or substituted and, including substituents, has 1 to 30 carbon atoms; and wherein $(R^6)_n$ are n substituents $R^6$, where $R^6$, in the case that n=1, or each of the substituents $R^6$ independently of the others, in the case that n is greater than 1, is:

a radical halogen, hydroxyl, amino, nitro, carboxy, cyano, carbamoyl, $(C_1-C_6)$-alkyl, $(C_1-C_6)$ haloalkyl, $(C_1-C_4)$-alkoxy-$(C_1-C_4)$-alkyl, $(C_1-C_4)$-akylthio-$(C_1-C_4)$-alkyl, mono- or di-$[(C_1-C_4)$-alkyl]aminoalkyl, hydroxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_1-C_6)$-haloalkoxy, $(C_1-C_4)$-alkoxy-$(C_1-C_4)$-alkoxy, $(C_1-C_6)$-alkylthio, $(C_1-C_6)$-haloalkylthio, $[(C_1-C_6)$-alkoxy]carbonyl, $[(C_1-C_6)$-haloalkoxy]carbonyl, $(C_1-C_6)$-alkanoyl, $(C_1-C_6)$-haloalkanoyl, mono- or di-$[(C_1-C_4)$-alkyl]aminocarbonyl, mono- or di-$[(C_1-C_6)$-acyl]amino, mono- or di-$[(C_1-C_4)$-alkyl]amino, N—$[(C_1-C_6)$-acyl]-N—$[(C_1-C_6)$-alkyl]amino, $(C_1-C_6)$-alkylsulfinyl, $(C_1-C_6)$-haloalkylsulfinyl, $(C_1-C_6)$-alkylsulfonyl, or $(C_1-C_6)$-haloalkylsulfonyl; or $(C_3-C_9)$-cycloalkyl or $(C_5-C_9)$-cycloalkenyl, where each of the two last-mentioned radicals independently is unsubstituted or substituted by one or more radicals selected from the group consisting of halogen, $(C_1-C_4)$-alkyl, and $(C_1-C_4)$-haloalkyl; and wherein n is 0, 1, 2 or 3.

2. The compound of the formula (I) or its salt as claimed in claim 1;

wherein $R^1$ is:

H; or $(C_1-C_{18})$-alkyl, $(C_2-C_{18})$-alkenyl, $(C_2-C_{18})$-alkynyl, $(C_3-C_9)$-cycloalkyl, $(C_5-C_9)$-cycloalkenyl, $(C_5-C_9)$-cycloalkynyl, or phenyl, where each of the 7 last-mentioned radicals independently is unsubstituted or substituted by one or more radicals selected from the group consisting of:

halogen, cyano, thio, nitro, hydroxyl, also carboxy, $(C_1-C_8)$-alkyl, $(C_1-C_8)$-haloalkyl, $(C_1-C_4)$-alkoxy-$(C_1-C_4)$-alkyl, $(C_2-C_8)$-alkenyl, $(C_2-C_8)$-haloalkenyl, $(C_2-C_8)$-alkynyl, $(C_2-C_8)$-haloalkynyl, the 7 last-mentioned radicals only in the case of cyclic base radicals, $(C_1-C_8)$-alkoxy, $(C_2-C_8)$-alkenyloxy, $(C_2-C_8)$-alkynyloxy, $(C_1-C_8)$-haloalkoxy, $(C_1-C_4)$-alkoxy-$(C_1-C_4)$-alkoxy, $(C_1-C_8)$-alkylthio, $(C_2-C_8)$-alkenylthio, and $(C_2-C_8)$-alkynylthio; and radicals of the formulae —NR*R**, —CO—NR*R**, and —O—CO—NR*R**;

where each of the radicals and R* and R** in the 3 last-mentioned formulae independently of the others is H, $(C_1-C_8)$-alkyl, $(C_2-C_8)$-alkenyl, $(C_2-C_8)$-alkynyl, benzyl, substituted benzyl, phenyl, or substituted phenyl; or where the radicals R* and R** together with the nitrogen atom is a 3- to 8-membered heterocycle which, in addition to the nitrogen atom, may contain one or two further ring heteroatoms selected from the group consisting of N, O, and S, and which is unsubstituted or substituted by one or more radicals selected from the group consisting of $(C_1-C_4)$-alkyl and $(C_1-C_4)$-haloalkyl; and

[$(C_1-C_8)$-alkoxy]carbonyl, [$(C_1-C_8)$-alkoxy]thiocarbonyl, [$(C_2-C_8)$-alkenyloxy]carbonyl, [$(C_2-C_8)$-alkynyloxy]carbonyl, [$(C_1-C_8)$-alkylthio]carbonyl, [$(C_2-C_8)$-alkenylthio]carbonyl, [$(C_2-C_8)$-alkynylthio]carbonyl, $(C_1-C_8)$-alkanoyl, [$(C_2-C_8)$-alkenyl]carbonyl, [$(C_2-C_8)$-alkynyl]carbonyl, $(C_1-C_4)$-alkylimino, $(C_1-C_4)$-alkoxyimino, [$(C_1-C_8)$-alkyl]carbonylamino, [$(C_2-C_8)$-alkenyl]carbonylamino, [$(C_2-C_8)$-alkynyl]carbonylamino, [$(C_1-C_8)$-alkoxy]carbonylamino, [$(C_2-C_8)$-alkenyloxy]carbonylamino, [$(C_2-C_8)$-alkynyloxy]carbonylamino, [$(C_1-C_8)$-alkylamino]carbonylamino, [$(C_1-C_6)$-alkyl]carbonyloxy, [$(C_2-C_6)$-alkenyl]carbonyloxy, [$(C_2-C_6)$-alkynyl]carbonyloxy, [$(C_1-C_8)$-alkoxy]carbonyloxy, [$(C_2-C_8)$-alkenyloxy]carbonyloxy, [$(C_2-C_8)$-alkynyloxy]carbonyloxy, $(C_1-C_8)$-alkylsulfinyl, and $(C_1-C_8)$-alkylsulfonyl;

where each of the 27 last-mentioned radicals independently is unsubstituted or substituted by one or more radicals selected from the group consisting of halogen, $NO_2$, $(C_1-C_4)$-alkoxy, and optionally substituted phenyl; and phenyl, phenyl-$(C_1-C_6)$-alkoxy, phenyl-[$(C_1-C_6)$-alkoxy]carbonyl, phenoxy, phenoxy-$(C_1-C_6)$-alkoxy, phenoxy-[$(C_1-C_6)$-alkoxy]carbonyl, phenoxycarbonyl, phenylcarbonyloxy, also phenoxycarbonyloxy, phenylcarbonylamino, phenyl-[$(C_1-C_6)$-alkyl]carbonylamino, phenyl-[$(C_1-C_6)$-alkyl]carbonyloxy, also phenyl-[$(C_1-C_6)$-alkoxy]carbonyloxy, $(C_3-C_7)$-cycloalkyl, $(C_3-C_7)$-cycloalkoxy, also $(C_3-C_6)$-cycloalkyl-$(C_1-C_6)$-alkoxy, also $(C_3-C_6)$-cycloalkyl-[$(C_1-C_6)$-alkoxy]carbonyl, also $(C_3-C_6)$-cycloalkoxy-$(C_1-C_6)$-alkoxy, also $(C_3-C_6)$-cycloalkoxy-[$(C_1-C_6)$-alkoxy]carbonyl, also $(C_3-C_6)$-cycloalkoxycarbonyl, also $(C_3-C_6)$-cycloalkylcarbonyloxy, also $(C_3-C_6)$-cycloalkoxycarbonyloxy, also $(C_3-C_6)$-cycloalkyl-[$(C_1-C_6)$-alkoxy]carbonyloxy, also $(C_3-C_6)$-cycloalkylcarbonylamino, also $(C_3-C_6)$-cycloalkyl-[$(C_1-C_6)$-alkyl]carbonylamino, and also $(C_3-C_6)$-cycloalkyl-[$(C_1-C_6)$-alkyl]carbonyloxy;

where each of the 26 last-mentioned radicals independently is optionally also fused to a carbocyclic or heterocyclic ring and is, in the ring or in the polycyclic system, unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, and nitro; and radicals of the formulae —$SiR'_3$, —O—$SiR'_3$, $(R')_3Si$—$(C_1-C_6)$-alkoxy, —CO—O—$NR'_2$, —O—N=$CR'_2$, —N=$CR'_2$, —CH$(OR')_2$, and —O—$(CH_2)_m$—CH$(OR')_2$;

where each of the radicals R' independently of the others is H, or $(C_1-C_4)$-alkyl or phenyl which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, and nitro, or which is substituted in two adjacent positions by a $(C_2-C_6)$-alkylene bridge; and where m is an integer of from 0 to 6; and radicals of the formula R"O—CHR'"CH(OR")—$(C_1-C_6)$-alkoxy;

where each of the radicals R" independently of the others is H or $(C_1-C_4)$-alkyl, or the radicals R" together are a $(C_1-C_6)$-alkylene group; and where R'" is H or $(C_1-C_4)$-alkyl; and radicals of the formula $Het^1$, where $Het^1$ is in each case independently of the others a saturated, partially unsaturated, or heteroaromatic heterocyclyl radical having 3 to 9 ring atoms;

where the heterocyclic radical in question contains 1 to 4 heteroatoms, from the group consisting of N, O, and S; and where the heterocyclic radical in question is optionally also fused to a carbocyclic or heterocyclic ring and is, in the ring or in the polycyclic system, unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl, and oxo; or wherein $R^1$ is a polycyclic radical based on $(C_3-C_9)$-cycloalkyl, $(C_5-C_9)$-cycloalkenyl, $(C_5-C_9)$-cycloalkynyl, or phenyl;

where the base ring is fused to a carbocyclic or heterocyclic ring; and where the base ring or the polycyclic system is unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl, and oxo; or wherein $R^1$ is a saturated, partially unsaturated or heteroaromatic heterocyclyl radical having 3 to 9 ring atoms;

where the heterocyclic radical in question contains 1 to 4 heteroatoms, from the group consisting of N, O, and S; and where the heterocyclic radical in question is optionally fused to a carbocyclic or heterocyclic ring and which is, in the ring or in the polycyclic system, unsubstituted or substituted by one or more radicals selected from the group consisting of halogen, cyano, thio, nitro, hydroxyl, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_1-C_6)$-haloalkynyl, $(C_1-C_6)$-alkoxy, $(C_2C_6)$-alkenyloxy, $(C_2C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, [$(C_1-C_8)$-alkoxy]carbonyl, [$(C_1-C_6)$-haloalkoxy]carbonyl, and oxo.

3. The compound of the formula (I) or its salt as claimed in claim 1;

wherein $R^1$ is:

H; or ($C_1$-$C_{18}$)-alkyl, ($C_2$-$C_{18}$)-alkenyl, ($C_2$-$C_{18}$)-alkynyl, ($C_3$-$C_9$)-cycloalkyl, ($C_5$-$C_9$)-cycloalkenyl, ($C_5$-$C_9$)-cycloalkynyl, or phenyl, where each of the 7 last-mentioned radicals independently is unsubstituted or substituted by one or more radicals selected from the group consisting of:

halogen, cyano, thio, nitro, hydroxyl, also carboxy, ($C_1$-$C_8$)-alkyl, ($C_1$-$C_8$)-haloalkyl, ($C_1$-$C_4$)-alkoxy-($C_1$-$C_4$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, the 7 last-mentioned radicals only in the case of cyclic base radicals, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, and ($C_2$-$C_8$)-alkynylthio; and radicals of the formulae —NR*R**, —CO—NR*R**, and —O—CO—NR*R**;

where each of the radicals R* and R** in the 3 last-mentioned formulae independently of the others is H, ($C_1$-$C_8$)-alkyl, ($C_2$-$C_8$)-alkenyl, ($C_2$-$C_8$)-alkynyl, benzyl, substituted benzyl, phenyl or substituted phenyl; or where the radicals R* and R** together with the nitrogen atom is a 3- to 8-membered heterocycle which, in addition to the nitrogen atom, may contain one or two further ring heteroatoms selected from the group consisting of N, O, and S, and which is unsubstituted or substituted by one or more radicals selected from the group consisting of ($C_1$-$C_4$)-alkyl and ($C_1$-$C_4$)-haloalkyl; and

[($C_1$-$C_8$)-alkoxy]carbonyl, [($C_1$-$C_8$)-alkoxy]thiocarbonyl, [($C_2$-$C_8$)-alkenyloxy]carbonyl, [($C_2$-$C_8$)-alkynyloxy]carbonyl, [($C_1$-$C_8$)-alkylthio]carbonyl, [($C_2$-$C_8$)-alkenylthio]carbonyl, [($C_2$-$C_8$)-alkynylthio]carbonyl, ($C_1$-$C_8$)-alkanoyl, [($C_2$-$C_8$)-alkenyl]carbonyl, [($C_2$-$C_8$)-alkynyl]carbonyl, ($C_1$-$C_4$)-alkylimino, ($C_1$-$C_4$)-alkoxyimino, [($C_1$-$C_8$)-alkyl]carbonylamino, [($C_2$-$C_8$)-alkenyl]carbonylamino, [($C_2$-$C_8$)-alkynyl]carbonylamino, [($C_1$-$C_8$)-alkoxy]carbonylamino, [($C_2$-$C_8$)-alkenyloxy]carbonylamino, [($C_2$-$C_8$)-alkynyloxy]carbonylamino, [($C_1$-$C_8$)-alkylamino]carbonylamino, [($C_1$-$C_6$)-alkyl]carbonyloxy, [($C_2$-$C_6$)-alkenyl]carbonyloxy, [($C_2$-$C_6$)-alkynyl]carbonyloxy, [($C_1$-$C_8$)-alkoxy]carbonyloxy, [($C_2$-$C_8$)-alkenyloxy]carbonyloxy, [($C_2$-$C_8$)-alkynyloxy]carbonyloxy, ($C_1$-$C_8$)-alkylsulfinyl, and ($C_1$-$C_8$)-alkylsulfony;

where each of the 27 last-mentioned radicals independently is unsubstituted or substituted by one or more radicals selected from the group consisting of halogen, $NO_2$, ($C_1$-$C_4$)-alkoxy, and optionally substituted phenyl; and phenyl, phenyl-($C_1$-$C_6$)-alkoxy, phenyl-[($C_1$-$C_6$)-alkoxy]carbonyl, phenoxy, phenoxy-($C_1$-$C_6$)-alkoxy, phenoxy-[($C_1$-$C_6$)-alkoxy]carbonyl, phenoxycarbonyl, phenylcarbonyloxy, also phenoxycarbonyloxy, also phenyl-[($C_1$-$C_6$)-alkoxy]carbonyloxy, phenylcarbonylamino, phenyl-[($C_1$-$C_6$)-alkyl]carbonylamino, phenyl-[($C_1$-$C_6$)-alkyl]carbonyloxy, ($C_3$-$C_7$)-cycloalkyl, and ($C_3$-$C_7$)-cycloalkoxy, also ($C_3$-$C_6$)-cycloalkoxycarbonyl, also ($C_3$-$C_6$)-cycloalkylcarbonyloxy, also ($C_3$-$C_6$)-cycloalkoxycarbonyloxy, also ($C_3$-$C_6$)-cycloalkyl-[($C_1$-$C_6$)-alkyl]carbonyloxy, and also ($C_3$-$C_6$)-cycloalkyl-[($C_1$-$C_6$)-alkoxy]carbonyloxy;

where each of the 20 last-mentioned radicals independently is, in the ring, unsubstituted or substituted by one or more radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy, and nitro; and radicals of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$, and —O—$(CH_2)_m$—CH(OR')$_2$;

where each of the radicals R' independently of the others is H, or ($C_1$-$C_4$)-alkyl or phenyl which is unsubstituted or substituted by one or more radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy, and nitro, or which is substituted at two adjacent positions by a ($C_2$-$C_6$)-alkylene bridge; and where m is an integer from 0 to 6; and radicals of the formula R"O—CHR'"CH(OR")—($C_1$-$C_6$)-alkoxy;

where:

each of the radicals R" independently of the others is H or ($C_1$-$C_4$)-alkyl; or the radicals R" together are a ($C_1$-$C_6$)-alkylene group; and where R'" is H or ($C_1$-$C_4$)-alkyl; and radicals of the formula Het$^1$, where Het$^1$ is in each case independently of the others a saturated, partially unsaturated or heteroaromatic heterocyclyl radical having 5 or 6 ring atoms;

where the respective heterocyclic radical contains 1 to 3 ring heteroatoms selected from the group consisting of N, O, and S; and where the respective heterocyclic radical is optionally fused to a carbocyclic or heterocyclic 5- or 6-membered ring having 0 or 1 to 3 ring heteroatoms selected from the group consisting of N, O, and S; and where the respective heterocyclic radical, in the ring or in the polycyclic system, is unsubstituted or substituted by one or more radicals selected from the group consisting of halogen, hydroxyl, ($C_1$-$C_4$)-alkyl, ($C_1$-$C_4$)-alkoxy, ($C_1$-$C_4$)-haloalkyl, and ($C_1$-$C_4$)-haloalkoxy.

4. The compound of the formula (I) or its salt as claimed in claim 1;

wherein $R^1$ is:

H; or ($C_1$-$C_{18}$)-alkyl, ($C_2$-$C_{18}$)-alkenyl, ($C_2$-$C_{18}$)-alkynyl, ($C_3$-$C_9$)-cycloalkyl, ($C_5$-$C_9$)-cycloalkenyl, ($C_5$-$C_9$)-cycloalkynyl, or phenyl, where each of the 7 last-mentioned radicals independently is unsubstituted or substituted by one or more radicals selected from the group consisting of:

halogen, cyano, thio, nitro, hydroxyl, also carboxy, ($C_1$-$C_8$)-alkyl, ($C_1$-$C_8$)-haloalkyl, ($C_1$-$C_4$)-alkoxy-($C_1$-$C_4$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, the 7 last-mentioned radicals only in the case of cyclic base radicals, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)- alkoxy-$(C_1-C_4)$-alkoxy, $(C_1-C_8)$-alkylthio, $(C_2-C_8)$-alkenylthio, and $(C_2-C_8)$-alkynylthio; and radicals of the formulae —NR*R**, —CO—NR*R**, and —O—CO—NR*R**;

where each of the radicals R* and R** in the 3 last-mentioned formulae independently of the others is H, $(C_1-C_8)$-alkyl, $(C_2-C_8)$-alkenyl, $(C_2-C_8)$-alkenyl, benzyl, substituted benzyl, phenyl or substituted phenyl; or where the radicals R* and R** together with the nitrogen atom is a 3- to 8-membered heterocycle which, in addition to the nitrogen atom, may contain one or two further ring heteroatoms selected from the group consisting of N, O, and S, and which is unsubstituted or substituted by one or more radicals selected from the group consisting of $(C_1-C_4)$-alkyl and $(C_1-C_4)$-haloalkyl; and $[(C_1-C_8)$-alkoxy]carbonyl, $[(C_1-C_8)$-alkoxy]thiocarbonyl, $[(C_2-C_8)$-alkenyloxy]carbonyl, $[(C_2-C_8)$-alkynyloxy]carbonyl, $[(C_1-C_8)$-alkylthio]carbonyl, $[(C_2-C_8)$-alkenylthio]carbonyl, $[(C_2-C_8)$-alkynylthio]carbonyl, $(C_1-C_8)$-alkanoyl, $[(C_2-C_8)$-alkenyl]carbonyl, $[(C_2-C_8)$-alkynyl]carbonyl, $(C_1-C_4)$-alkylimino, $(C_1-C_4)$-alkoxyimino, $[(C_1-C_8)$-alkyl]carbonylamino, $[(C_2-C_8)$-alkenyl]carbonylamino, $[(C_2-C_8)$-alkynyl]carbonylamino, $[(C_1-C_8)$-alkoxy]carbonylamino, $[(C_2-C_8)$-alkenyloxy]carbonylamino, $[(C_2-C_8)$-alkynyloxy]carbonylamino, $[(C_1-C_8)$-alkylamino]carbonylamino, $[(C_1-C_6)$-alkyl]carbonyloxy, $[(C_2-C_6)$-alkenyl]carbonyloxy, $[(C_2-C_6)$-alkynyl]carbonyloxy, $[(C_1-C_8)$-alkoxy]carbonyloxy, $[(C_2-C_8)$-alkenyloxy]carbonyloxy, $[(C_2-C_8)$- alkynyloxy]carbonyloxy, $(C_1-C_8)$-alkylsulfinyl, and $(C_1-C_8)$-alkylsulfonyl;

where each of the 27 last-mentioned radicals independently is unsubstituted or substituted by one or more radicals selected from the group consisting of halogen, $NO_2$, $(C_1-C_4)$-alkoxy and optionally substituted phenyl; and phenyl, phenyl-$(C_1-C_6)$-alkoxy, phenyl-$[(C_1-C_6)$-alkoxy]carbonyl, phenoxy, phenoxy-$(C_1-C_6)$-alkoxy, phenoxy-$[(C_1-C_6)$-alkoxy]carbonyl, phenoxycarbonyl, phenylcarbonyloxy, also phenoxycarbonyloxy, also phenyl-$[(C_1-C_6)$-alkoxy]carbonyloxy, phenylcarbonylamino, phenyl-$[(C_1-C_6)$-alkyl]carbonylamino, phenyl-$[(C_1-C_6)$-alkyl]carbonyloxy, $(C_3-C_7)$-cycloalkyl, and $(C_3-C_7)$-cycloalkoxy, also $(C_3-C_6)$-cycloalkoxycarbonyl, also $(C_3-C_6)$-cycloalkylcarbonyloxy, also $(C_3-C_6)$-cycloalkoxycarbonyloxy, also $(C_3-C_6)$-cycloalkyl-$[(C_1-C_6)$-alkyl]carbonyloxy, and also $(C_3-C_6)$-cycloalkyl-$[(C_1-C_6)$-alkoxy]carbonyloxy;

where each of the 20 last-mentioned radicals independently is, in the ring, unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, and nitro; and radicals of the formulae —SiR'$_3$, —O—SiR'$_3$, (R')$_3$Si—$(C_1-C_6)$-alkoxy, —CO—O—NR'$_2$, —O—N=CR'$_2$, —N=CR'$_2$, —O—NR'$_2$, —CH(OR')$_2$ and —O—$(CH_2)_m$—CH(OR')$_2$;

where each of the radicals R' independendy of the others is H, or $(C_1-C_4)$-alkyl or phenyl which is unsubstituted or substituted by one or more radicals selected from the group consisting of halogen, $(C_1-C_4)$-alkyl, $(C_1-C_4)$-alkoxy, $(C_1-C_4)$-haloalkyl, $(C_1-C_4)$-haloalkoxy, and nitro, or which is substituted at two adjacent positions by a $(C_2-C_6)$-alkylene bridge; and where m is an integer from 0 to 6; and radicals of the formula R"O—CHR'"(OR")—$(C_1-C_6)$-alkoxy;

where each of the radicals R" independently of the others is H or $(C_1-C_4)$-alkyl, or the radicals R" together are a $(C_1-C_6)$-alkylene group; and where R'" is H or $(C_1-C_4)$-alkyl; and radicals of the formula Het$^1$, where Het$^1$ is in each case independently of the others a saturated, partially unsaturated or heteroaromatic heterocyclyl radical having 5 or 6 ring atoms;

where the respective heterocyclic radical contains 1 to 3 ring heteroatoms selected from the group consisting of N, O, and S; and where the respective heterocyclic radical is optionally also fused to a carbocyclic or heterocyclic 5- or 6-membered ring having 0 or 1 to 3 ring heteroatoms selected from the group consisting of N, O, and S; and where the respective heterocyclic radical, in the ring or in the polycyclic system, is unsubstituted or substituted by one or more radicals selected from the group consisting of halogen, hydroxyl, $(C_1-C_4)$-alkyl, $(C_1-C_4)$-alkoxy, $(C_1-C_4)$-haloalkyl, and $(C_1-C_4)$-haloalkoxy.

5. The compound of the formula (I) or its salt as claimed in claim 1;

wherein:

$R^2$ is hydrogen, halogen, or $(C_1-C_4)$-alkyl which is unsubstituted or substituted by one or more radicals selected from the group consisting of halogen; and $R^3$ is hydrogen, halogen, or $(C_1-C_4)$-alkyl which is unsubstituted or substituted by one or more radicals selected from the group consisting of halogen; or wherein $R^2$ and $R^3$ together with the carbon atom to which they are attached are $(C_3-C_6)$-cycloalkyl or $(C_5-C_6)$-cycloalkenyl, where each of the 2 last-mentioned radicals independently is unsubstituted or substituted by one or more radicals selected from the group consisting of halogen and $(C_1-C_4)$-alkyl.

6. The compound of the formula (I) or its salt as claimed in claim 1;

wherein $R^4$ is:

hydrogen, halogen, or cyano; or $(C_1-C_4)$-alkyl, $(C_2-C_4)$-alkenyl, or $(C_2-C_4)$-alkynyl, where each of the three last-mentioned radicals independently is unsubstituted or substituted by one or more radicals selected from the group consisting of halogen and hydroxyl; or $(C_3-C_6)$-cycloalkyl which is unsubstituted or substituted by one or more radicals selected from the group consisting of halogen and $(C_1-C_4)$-alkyl; or phenyl which is unsubstituted or substituted by one or more radicals selected from the group consisting of halogen, nitro, $(C_1-C_4)$-alkyl, $(C_1-C_4)$-haloalkyl, $(C_1-C_4)$-alkoxy, $(C_1-C_4)$-haloalkoxy, $(C_1-C_4)$-alkoxy-$(C_1-C_4)$-alkoxy, $(C_1-C_4)$-alkylthio, $[(C_1-C_4)$-alkoxy]carbonyl, and $[(C_1-C_4)$-haloalkoxy]carbonyl; or $(C_1-C_4)$-alkanoyl which is unsubstituted or substituted by one or more radicals selected from the group consisting of halogen, cyano, $(C_1-C_4)$-alkoxy, $(C_1-C_4)$-haloalkoxy and $(C_1-C_2)$-alkoxy-$(C_1-C_2)$-alkoxy; or

[($C_1$-$C_4$)-alkoxy]carbonyl which is unsubstituted or substituted by one or more radicals selected from the group consisting of halogen; or

[($C_3$-$C_6$)-cycloalkoxy]carbonyl which is unsubstituted or substituted by one or more radicals selected from the group consisting of halogen and ($C_1$-$C_4$)-alkyl.

7. The compound of the formula (I) or its salt as claimed in claim 1;
wherein $R^5$ is a phenyl radical or a 5- or 6-membered heteroaromatic radical having 1 to 3 ring heteroatoms selected from the group consisting of N, O and S;
where the phenyl radical or the heterocyclic radical is unsubstituted or substituted by one or more radicals selected from the group consisting of the radicals:
(a) halogen, hydroxyl, amino, nitro, carboxy, cyano, and carbamoyl;
(b) ($C_1$-$C_6$)-alkyl, ($C_2$-$C_6$)-alkenyl, ($C_2$-$C_6$)-alkynyl, ($C_1$-$C_6$)-alkoxy, ($C_1$-$C_6$)-alkenyloxy, and ($C_1$-$C_6$)-alkynyloxy, where each of the 6 last-mentioned radicals independently is unsubstituted or substituted by one or more radicals selected from the group consisting of halogen, ($C_1$-$C_4$)-alkoxy, ($C_1$-$C_6$)-haloalkoxy, ($C_1$-$C_4$)-alkylthio, mono- and di-[($C_1$-$C_4$)-alkyl]amino, hydroxyl, carboxy, [($C_1$-$C_4$)-alkoxy]carbonyl, [($C_1$-$C_4$)-haloalkoxy]carbonyl, mono- and di-[($C_1$-$C_4$)-alkyl]aminocarbonyl, and cyano;
(c) ($C_1$-$C_6$)-alkylthio, [($C_1$-$C_6$)-alkoxy]carbonyl, [($C_1$-$C_6$)-haloalkoxy]carbonyl, ($C_1$-$C_6$)-alkanoyl, ($C_1$-$C_6$)-haloalkanoyl, mono- and di-[($C_1$-$C_4$)-alkyl]aminocarbonyl, mono- and di-[($C_1$-$C_6$)-acyl]amino, mono- and di-[($C_1$-$C_4$)-alkyl]amino, N—[($C_1$-$C_6$)-acyl]N—[($C_1$-$C_6$)-alkyl]amino, ($C_1$-$C_6$)-alkylsulfinyl, ($C_1$-$C_6$)-haloalkylsulfinyl, ($C_1$-$C_6$)-alkylsulfonyl, ($C_1$-$C_6$)-haloalkylsulfonyl, ($C_1$-$C_6$)-alkylsulfinyloxy, ($C_1$-$C_6$)-haloalkylsulfinyloxy, ($C_1$-$C_6$)-alkylsulfonyloxy, ($C_1$-$C_6$)-haloalkylsulfonyloxy, and ($C_1$-$C_6$)-alkylsulfato, ($C_1$-$C_6$)-haloalkylsulfato; and
(d) ($C_3$-$C_6$)-cycloalkyl, ($C_3$-$C_6$)-cycloalkyloxy, phenyl, and phenoxy, where each of the 4 last-mentioned radicals independently is unsubstituted or substituted by one or more radicals selected from the group consisting of halogen, ($C_1$-$C_4$)-alkyl, ($C_1$-$C_4$)-haloalkyl, ($C_1$-$C_4$)-alkoxy, ($C_1$-$C_6$)-haloalkoxy, and ($C_1$-$C_4$)-alkylthio; and
where two adjacent substituents may form a fused-on 5- or 6-membered ring which is carbocyclic or may contain another 1 to 3 ring heteroatoms selected from the group consisting of N, O, and S, and which is unsubstituted or substituted by one or more radicals selected from the group consisting of halogen, ($C_1$-$C_4$)-alkyl, ($C_1$-$C_4$)-haloalkyl, ($C_1$-$C_4$)-alkoxy, ($C_1$-$C_6$)-haloalkoxy, and ($C_1$-$C_4$)-alkylthio.

8. The compound of the formula (I) or its salt as claimed in claim 1;
wherein ($R^6$)$_n$ is n substituents $R^6$, where $R^6$, if n=1, or each of the substituents $R^6$ independently of the others, if n is greater than 1, is a radical halogen, cyano, ($C_1$-$C_4$)-alkyl, ($C_1$-$C_4$)-haloalkyl, ($C_1$-$C_4$)-alkoxy, ($C_1$-$C_4$)-alkylthio, ($C_1$-$C_4$)-alkylsulfinyl, ($C_1$-$C_4$)-haloalkylsulfinyl, ($C_1$-$C_4$)-alkylsulfonyl, or ($C_1$-$C_4$)-haloalkylsulfonyl; and
wherein n is 0, 1, 2 or 3.

9. A process for preparing a compound of the formula (I) as defined in claim 1 or a salt thereof, wherein:
(a) a compound of the formula (II), $H_2N$—NH-Het($R^6$)$_n$            (II)

where Het and ($R^6$)$_n$ are as defined for formula (I), is reacted with a compound of the formula (III),

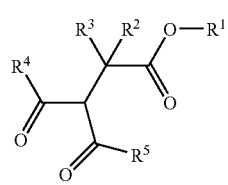

(III)

where $R^1$, $R^2$, $R^3$, $R^4$ and $R^5$ are as defined for formula (I), to give the compound of the formula (I) or its salt; or (b) if $R^1$ in formula (I) is different from hydrogen, a compound of the formula (I'),

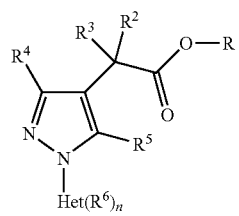

(I')

where Het, $R^2$, $R^3$, $R^4$, $R^5$ and $R^6$ are as defined for formula (I), and
where R is a radical which is different from the radical $R^1$ and different from hydrogen selected from the group of radicals as defined for $R^1$, or an anhydride, acid halide or an activated ester of the compound of the formula (I') in which R=H,
is reacted with a compound of the formula (IV), $R^1$—OH            (IV)

where $R^1$ is as defined for formula (I), to give the compound of the formula (I); or (c) if $R^1$ in formula (I) is different from hydrogen, a compound of the formula (I"),

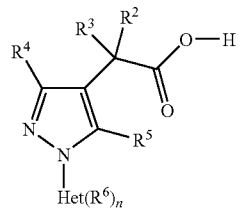

(I")

where Het, $R^2$, $R^3$, $R^4$, $R^5$ and $R^6$ are as defined for formula (I), is, if appropriate after activation of the acid group, reacted (esterified) with a compound of the formula (IV), $R^1$—OH            (IV)

where $R^1$ is as defined for formula (I), to give the compound of the formula (I); or (d) if the compound of the formula (I) in which R=H or its salt is prepared, a compound of the formula (I') [see definition in variant (b)] is hydrolyzed to give the compound of the formula (I) or its salt; or g) a compound of the general formula (XI) is reacted with a boron derivative of the formula (XII) in the presence of a Cu(I) or Cu(II) salt and an organic base, if appropriate in a solvent,

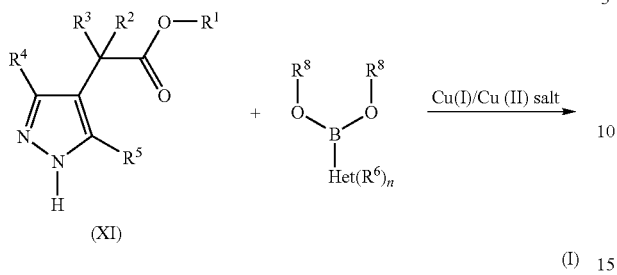

(I)

where, in the formulae (XI) and (XII), Het, $R^1$, $R^2$, $R^3$, $R^4$, $R^5$, and $R^6$ have the meanings given above for formula (I), and where $R^8$ is H or $(C_1$-$C_6)$-alkyl, or the two alkyl radicals $R^8$ are linked cyclically; or h) a compound of the general formula (XV) is reacted with a compound of the general formula (III) in the presence of an acid, if appropriate in a solvent, to give the compound of the formula (I) or its salt,

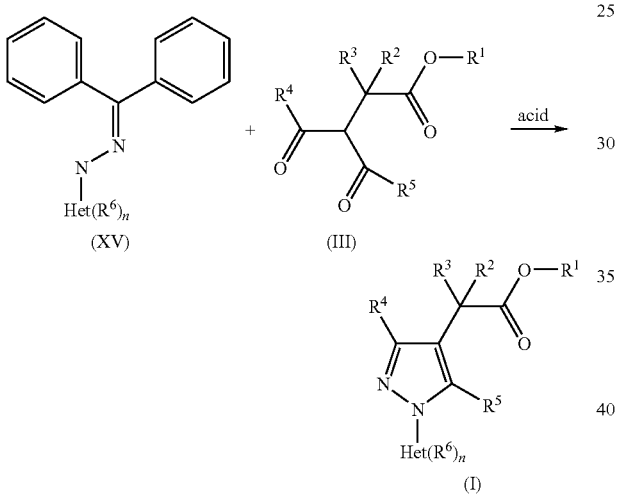

where in the formulae (XV) and (III) Het, $R^1$, $R^2$, $R^3$, $R^4$, $R^5$, and $R^6$ are as defined for formula (I), and LG is a leaving group; or i) a compound of the general formula (XVI), where $R^6$ is as defined for formula (I), is reacted with di-tert-butyl azodicarboxylate (DBAD, XVII) in the presence of a copper salt, optionally in a solvent, to give a compound of the formula (XVIII) in which $R^6$ is as defined for formula (I), which is then, via compounds of the formula (II) or salts thereof, in which $R^6$ is as defined for formula (I), and the process according to process a), converted into compounds of the formula (I):

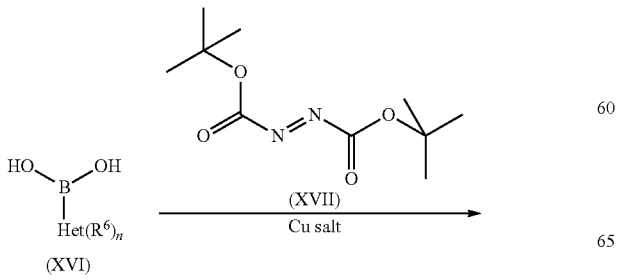

-continued

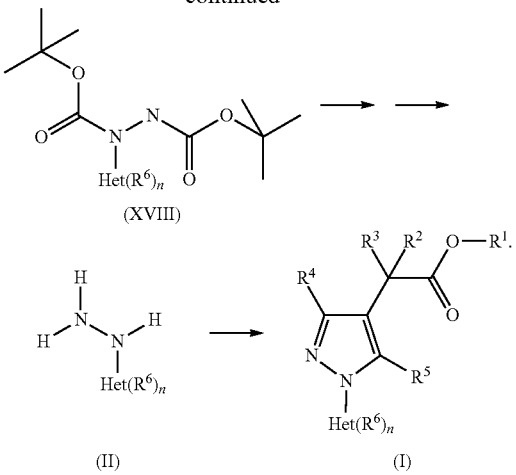

10. An herbicidal or plant growth-regulating composition comprising:
    one or more compounds of the formula (I) or salts thereof as claimed in claim 1; and
    formulation auxiliaries customary in crop protection.

11. A method for controlling harmful plants or for regulating the growth of plants, comprising:
    applying an effective amount of one or more compounds of the formula (I) or salts thereof as claimed in claim 1 onto the plants, plant seeds or the area under cultivation.

12. The method as claimed in claim 11;
    wherein the compounds of the formula (I) or salts thereof are employed for controlling harmful plants or for regulating the growth in crops of useful plants or ornamental plants.

13. The method as claimed in claim 12;
    wherein the crop plants are transgenic crop plants.

14. The compound of the formula (I) or its salt as claimed in claim 1;
    wherein $R^1$ is:
    hydrogen; or
    an optionally substituted hydrocarbon radical or an optionally substituted heterocyclyl radical, where each of the two last-mentioned carbon-containing radicals independently has, including substituents, 1 to 30 carbon atoms; or
    a radical of the formula $SiR^aR^bR^c$, $-NR^aR^b$, or $-N=CR^cR^d$, where in the 3 last-mentioned formulae:
    the radicals $R^a$ and $R^b$ are as follows:
        each of the radicals $R^a$ and $R^b$ independently of the others is hydrogen or an optionally substituted hydrocarbon radical; or
        $R^a$ and $R^b$ together with the nitrogen atom are a 3- to 9-membered heterocycle which, in addition to the nitrogen atom, may contain one or two further ring heteroatoms selected from the group consisting of N, O and S and which is unsubstituted or substituted; and
    the radicals $R^c$ and $R^d$ are as follows:
        each of the radicals $R^c$ and $R^d$ independently of the others is hydrogen or an optionally substituted hydrocarbon radical; or $R^c$ and $R^d$ together with the carbon atom are a 3- to 9-membered carbocyclic radical or a heterocyclic radical which may contain 1 to 3 ring heteroatoms selected from the group consisting of N, O and S, where the carbocyclic or heterocyclic radical is unsubstituted or substituted;

where each of the radicals $R^a$, $R^b$, $R^c$, and $R^d$ independently, including substituents, has up to 30 carbon atoms.

\* \* \* \* \*